United States Patent
Orentas et al.

(10) Patent No.: US 10,543,263 B2
(45) Date of Patent: Jan. 28, 2020

(54) COMPOSITIONS AND METHODS FOR TREATING CANCER WITH ANTI-CD22 IMMUNOTHERAPY

(71) Applicants: LentigenTechnology, Inc., Gaithersburg, MD (US); The U.S.A., as represented by the Secretary, Department of Health and Human Services, Bethesda, MD (US)

(72) Inventors: Rimas J. Orentas, Seattle, WA (US); Dina Schneider, Potomac, MD (US); Boro Dropulic, Ellicott City, MD (US); Dimiter S. Dimitrov, Frederick, MD (US); Zhongyu Zhu, Frederick, MD (US)

(73) Assignees: Lentigen Technology Inc., Gaithersburg, MD (US); The U.S.A., as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/161,542

(22) Filed: Oct. 16, 2018

(65) Prior Publication Data
US 2019/0099476 A1    Apr. 4, 2019

Related U.S. Application Data

(60) Provisional application No. 62/572,926, filed on Oct. 16, 2017.

(51) Int. Cl.
| | |
|---|---|
| C12N 15/63 | (2006.01) |
| C12N 15/13 | (2006.01) |
| C07K 14/47 | (2006.01) |
| A61K 39/395 | (2006.01) |
| A61K 39/00 | (2006.01) |
| C07K 16/28 | (2006.01) |
| C07K 14/705 | (2006.01) |
| C07K 14/725 | (2006.01) |
| A61P 35/00 | (2006.01) |

(52) U.S. Cl.
CPC ....... *A61K 39/001113* (2018.08); *A61P 35/00* (2018.01); *C07K 14/7051* (2013.01); *C07K 14/70517* (2013.01); *C07K 16/2803* (2013.01); *A61K 2039/5156* (2013.01); *C07K 2317/622* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 2003/0059937 A1 | 3/2003 | Ruben et al. |
| 2005/0215770 A1 | 9/2005 | Bell et al. |

FOREIGN PATENT DOCUMENTS

| | | |
|---|---|---|
| WO | 2016/102965 | 6/2016 |

OTHER PUBLICATIONS

Mirzaei et al, Chimeric Antigen Receptors T Cell Therapy in Solid Tumor: Challenges and Clinical Applications, Frontiers in Immuology, 2017, pp. 1-13.*
Newick et al, Chimeric antigen receptor T-cell therapy for solid tumors, Molecular Therapy—Oncolytics (2016) 3, pp. 1-7.*

* cited by examiner

*Primary Examiner* — Maria Marvich
(74) *Attorney, Agent, or Firm* — Serge Sira, Esq.; Fish & Richardson P.C.

(57) ABSTRACT

Chimeric antigen receptors (CARs) containing CD22 antigen binding domains are disclosed. Nucleic acids, recombinant expression vectors, host cells, antigen binding fragments, and pharmaceutical compositions, relating to the CARs are also disclosed. Methods of treating or preventing cancer in a subject, and methods of making CAR T cells are also disclosed.

12 Claims, 28 Drawing Sheets

Specification includes a Sequence Listing.

FIGURE 2A

LTG2202: LP-16P-CD8 TM-41BB-CD3zeta nucleic acid sequence (SEQ ID NO: 3)

ATGCTTCTCCTGGTGACAAGCCTTCTGCTCTGTGAGTTACCACACCCAGCA
TTCCTCCTGATCCCACAAGTACAACTCCAGCAAAGCGGGCCTGGTCTGGT
GAAGCCGTCACAGACGCTTTCACTTACGTGTGCGATCTCCGGTGACTCCGT
GAGTTCTAATAGCGCGGCTTGGAACTGGATTAGGCAGTCTCCATCCCGAG
GATTGGAATGGCTCGGCAGGACTTATTATAGAAGTAAGTGGTACAACGAT
TATGCAGTCTCTGTGAAATCTCGCATCACCATTAACCCAGACACGTCTAAG
AATCAGTTCAGTCTTCAACTCAACTCTGTAACCCCCGAAGATACAGCGGT
CTACTACTGTGCTCAGGAGGTGCAACCCCACGATGCTTTTGATATCTGGGG
CCAGGGTACCATGGTTACGGTGTCTTCTGGGGGAGGGGGGTCCGGTGGGG
GAGGATCAGGGGGTGGGGGCAGCGACATACAAATGACGCAATCCCCGTC
TTCTGTTTCTGCGTCTGTCGGAGATAAAGTAACAATAACCTGTCGAGCGTC
ACAGGACGTTAGTGGCTGGCTTGCGTGGTATCAGCAAAAACCGGGGCTCG
CCCCGCAATTGCTTATATTTGGAGCGAGTACTCTTCAGGGCGAGGTACCTA
GCAGATTTTCTGGGTCCGGCTCAGGTACGGACTTCACCCTGACCATATCTA
GCTTGCAGCCTGAAGATTTCGCCACCTACTATTGTCAACAGGCGAAGAAC
TTTCCATATACGTTCGGGCAGGGTACGAAATTGGAGATAAAAGCGGCCGC
AACTACCACCCCTGCCCCTCGGCCGCCGACTCCGGCCCCAACCATCGCAA
GCCAACCCCTCTCCTTGCGCCCCGAAGCTTGCCGCCCGGCCGCGGGTGGA
GCCGTGCATACCCGGGGGCTGGACTTTGCCTGCGATATCTACATTTGGGCC
CCGCTGGCCGGCACTTGCGGCGTGCTCCTGCTGTCGCTGGTCATCACCCTT
TACTGCAAGAGGGGCCGGAAGAAGCTGCTTTACATCTTCAAGCAGCCGTT
CATGCGGCCCGTGCAGACGACTCAGGAAGAGGACGGATGCTCGTGCAGA
TTCCCTGAGGAGGAAGAGGGGGGATGCGAACTGCGCGTCAAGTTCTCACG
GTCCGCCGACGCCCCCGCATATCAACAGGGCCAGAATCAGCTCTACAACG
AGCTGAACCTGGGAAGGAGAGAGGAGTACGACGTGCTGGACAAGCGACG
CGGACGCGACCCGGAGATGGGGGGGAAACCACGGCGGAAAAACCCTCAG
GAAGGACTGTACAACGAACTCCAGAAAGACAAGATGGCGGAAGCCTACT
CAGAAATCGGGATGAAGGGAGAGCGGAGGAGGGGAAAGGGTCACGACG
GGCTGTACCAGGGACTGAGCACCGCCACTAAGGATACCTACGATGCCTTG
CATATGCAAGCACTCCCACCCCGG

LTG2202: LP-16P-CD8 TM-41BB-CD3zeta amino acid sequence (SEQ ID NO: 4)

MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAQEVQPHDAFDIWGQGTMVTVSSGGGGSGGGGSGG
GGSDIQMTQSPSSVSASVGDKVTITCRASQDVSGWLAWYQQKPGLAPQLLIF
GASTLQGEVPSRFSGSGSGTDFTLTISSLQPEDFATYYCQQAKNFPYTFGQGT
KLEIKAAATTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSC
RFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGL
YQGLSTATKDTYDALHMQALPPR

FIGURE 2B

LTG2246: LP-24P-CD8 TM-41BB-CD3zeta nucleic acid sequence (SEQ ID NO: 13)
ATGCTGCTGTTGGTGACATCACTTCTGCTCTGTGAACTCCCCCATCCAGCC
TTTCTGCTTATACCGCAAGTACAGCTGCAACAATCTGGCCCTGGGCTTGTG
AAACCCTCTCAGACTTTGTCCTTGACGTGCGCGATAAGTGGCGATTCAGTT
AGTTCTAACAGCGCCGCTTGGAACTGGATTAGACAGAGCCCCAGTCGGGG
ACTCGAATGGCTTGGCCGGACTTATTATCGCAGTAAATGGTATAATGATTA
TGCTGTGAGTGTGAAAAGTAGGATCACAATCAACCCCGATACGAGCAAGA
ATCAATTCTCATTGCAACTGAACAGCGTCACTCCCGAGGATACAGCTGTA
TATTATTGTGCAAGAGAAGGTGGGTGGTATGGCGAGATGGATGTATGGGG
GAAAGGAACTACGGTAACTGTGTCCAGTGGCGGAGGCGGTTCAGGTGGTG
GAGGCTCTGGAGGAGGAGGGTCCGAAATCGTGCTTACCCAGTCTCCGGCT
ACTCTGAGCGTTAGTCCGGGTGAAAGGGCCTCACTCTCTTGTCGAGCTTCA
CAGTCAGTCTCTTCCTACTTGGCTTGGTATCAGCAGAAGCCAGGTCAGGC
GCCCCGCTTGCTCATTTACGACGCAAGCACACGAGCGACAGGCATTCCAG
ACAGATTTTCTGGTTCTGGTTCTGGCACGGACTTTACTCTTACTATAAACT
CACTTGAGGCAGAGGATGCTGCGACTTACTATTGTCACCAATCAAGCTCT
CTGCCTTACACCTTTGGGCAAGGCACCAAACTCGAAATCAAGGTTACGGT
ATCATCTGCGGCCGCAACTACCACCCCTGCCCCTCGGCCGCCGACTCCGG
CCCCAACCATCGCAAGCCAACCCCTCTCCTTGCGCCCCGAAGCTTGCCGCC
CGGCCGCGGGTGGAGCCGTGCATACCCGGGGGCTGGACTTTGCCTGCGAT
ATCTACATTTGGGCCCCGCTGGCCGGCACTTGCGGCGTGCTCCTGCTGTCG
CTGGTCATCACCCTTTACTGCAAGAGGGGCCGGAAGAAGCTGCTTTACAT
CTTCAAGCAGCCGTTCATGCGGCCCGTGCAGACGACTCAGGAAGAGGACG
GATGCTCGTGCAGATTCCCTGAGGAGGAAGAGGGGGGATGCGAACTGCG
CGTCAAGTTCTCACGGTCCGCCGACGCCCCGCATATCAACAGGGCCAGA
ATCAGCTCTACAACGAGCTGAACCTGGGAAGGAGAGAGGAGTACGACGT
GCTGGACAAGCGACGCGGACGCGACCCGGAGATGGGGGGGAAACCACGG
CGGAAAAACCCTCAGGAAGGACTGTACAACGAACTCCAGAAAGACAAGA
TGGCGGAAGCCTACTCAGAAATCGGGATGAAGGGAGAGCGGAGGAGGGG
AAAGGGTCACGACGGGCTGTACCAGGGACTGAGCACCGCCACTAAGGAT
ACCTACGATGCCTTGCATATGCAAGCACTCCCACCCCGG LTG2246: LP-24P-CD8 TM-41BB-CD3 zeta amino acid sequence (SEQ ID NO: 14)

MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAREGGWYGEMDVWGKGTTVTVSSGGGGSGGGGSG
GGGSEIVLTQSPATLSVSPGERASLSCRASQSVSSYLAWYQQKPGQAPRLLIY
DASTRATGIPDRFSGSGSGTDFTLTINSLEAEDAATYYCHQSSSLPYTFGQGTK
LEIKVTVSSAAATTTPAPRPPTPAPTIASQPLSLRPEACRPAAGGAVHTRGLDF
ACDIYIWAPLAGTCGVLLLSLVITLYCKRGRKKLLYIFKQPFMRPVQTTQEED
GCSCRFPEEEEGGCELRVKFSRSADAPAYQQGQNQLYNELNLGRREEYDVLD
KRRGRDPEMGGKPRRKNPQEGLYNELQKDKMAEAYSEIGMKGERRRGKGH
DGLYQGLSTATKDTYDALHMQALPPR

FIGURE 2C

LTG2247: LP-25P-CD8 TM-41BB-CD3zeta nucleic acid sequence (SEQ ID NO: 23)

ATGCTTCTCCTGGTGACAAGCCTTCTGCTCTGTGAGTTACCACACCCAGCA
TTCCTCCTGATCCCACAAGTACAGCTCCAACAGAGTGGACCTGGTCTCGTT
AAGCCGTCCCAAACACTGTCTTTGACGTGCGCTATTAGTGGCGACAGCGT
ATCATCCAATTCTGCTGCTTGGAACTGGATTAGACAGTCACCGTCCAGAG
GCTTGGAATGGCTGGGCAGGACGTACTACCGCTCAAAATGGTATAACGAT
TACGCGGTTAGTGTCAAATCCAGGATTACCATTAACCCTGACACAAGTAA
GAATCAGTTTTCTCTTCAGCTGAATTCCCTGACTCCTGAGGATACGGCCGT
TTACTACTGTGCCCGAGAACACCAGAATGAGGCGGCTTTTGATATTTGGG
GGCAAGGAACAATGGTCACAGTTAGCAGTGGGGGGGGTGGCTCCGGGGG
AGGTGGTTCCGGCGGCGGTGGTTCTCAATCCGTCCTGACACAACCTCCCTC
AGCGAGCGGGACTCCCGGTCAAAGGGTGACCATCTCTTGTTCTGGGGGAG
GTAGTAACATCGGGACAAATACTGCGTCCTGGTATCAGCAACTCCCTGGG
ACCGCTCCCAAGTTGTTGATATATCGCAATACGCAACGACCTAGTGGGAT
ACCTGATAGATTCAGCGGAAGCAAAAGTGGTACGAGTGCGTCTTTGGCAA
TATCTGGCCTCCAGTCCGAGGACGAAGCGGATTACTATTGTGCGGCCTGG
GATGACTCACTGAATGGTTATGTGTTCGGTGCAGGTACTCAACTCACCGTA
CTTGGTGCGGCCGCAACTACCACCCCTGCCCCTCGGCCGCCGACTCCGGC
CCCAACCATCGCAAGCCAACCCCTCTCCTTGCGCCCCGAAGCTTGCCGCCC
GGCCGCGGGTGGAGCCGTGCATACCCGGGGCTGGACTTTGCCTGCGATA
TCTACATTTGGGCCCCGCTGGCCGGCACTTGCGGCGTGCTCCTGCTGTCGC
TGGTCATCACCCTTTACTGCAAGAGGGGCCGGAAGAAGCTGCTTTACATC
TTCAAGCAGCCGTTCATGCGGCCCGTGCAGACGACTCAGGAAGAGGACGG
ATGCTCGTGCAGATTCCCTGAGGAGGAAGAGGGGGGATGCGAACTGCGC
GTCAAGTTCTCACGGTCCGCCGACGCCCCGCATATCAACAGGGCCAGAA
TCAGCTCTACAACGAGCTGAACCTGGGAAGGAGAGAGGAGTACGACGTG
CTGGACAAGCGACGCGGACGCGACCCGGAGATGGGGGGGAAACCACGGC
GGAAAAACCCTCAGGAAGGACTGTACAACGAACTCCAGAAAGACAAGAT
GGCGGAAGCCTACTCAGAAATCGGGATGAAGGGAGAGCGGAGGAGGGA
AAGGGTCACGACGGGCTGTACCAGGGACTGAGCACCGCCACTAAGGATA
CCTACGATGCCTTGCATATGCAAGCACTCCCACCCCGG

LTG2247: LP-25P-CD8 TM-41BB-CD3zeta amino acid sequence (SEQ ID NO: 24)

MLLLVTSLLLCELPHPAFLLIPQVQLQQSGPGLVKPSQTLSLTCAISGDSVSSNSAAW
NWIRQSPSRGLEWLGRTYYRSKWYNDYAVSVKSRITINPDTSKNQFSLQLNSLTPED
TAVYYCAREHQNEAAFDIWGQGTMVTVSSGGGGSGGGGSGGGGSQSVLTQPPSAS
GTPGQRVTISCSGGGSNIGTNTASWYQQLPGTAPKLLIYRNTQRPSGIPDRFSGSKSGT
SASLAISGLQSEDEADYYCAAWDDSLNGYVFGAGTQLTVLGAAATTTPAPRPPTPAP
TIASQPLSLRPEACRPAAGGAVHTRGLDFACDIYIWAPLAGTCGVLLLSLVITLYCKR
GRKKLLYIFKQPFMRPVQTTQEEDGCSCRFPEEEEGGCELRVKFSRSADAPAYQQGQ
NQLYNELNLGRREEYDVLDKRRGRDPEMGGKPRRKNPQEGLYNELQKDKMAEAYS
EIGMKGERRRGKGHDGLYQGLSTATKDTYDALHMQALPPR

FIGURE 2D

LTG2248: LP-11s-CD8 TM-41BB-CD3zeta nucleic acid sequence (SEQ ID NO: 33)
ATGCTTCTCCTGGTGACAAGCCTTCTGCTCTGTGAGTTACCACACCCAGCA
TTCCTCCTGATCCCACAAGTCCAGTTGCAACAGTCCGGGCCAGGTCTGGTT
AAGCCATCCCAAACTCTGAGTTTGACGTGCGCTATTAGCGGAGATTCCGT
GTCCAGCAATTCTGCAACCTGGAATTGGATCCGGCAGAGTCCGAGTGGCG
GTTTGGAATGGCTCGGACGCACTTACTACAGGAGCAAATGGTACGATGAT
TATGCTGTTTCTGTGCGCTCGAATCACCATGAATCCTGATACTTCTAAG
AACCAATTTTCTTTGCAGTTGAACTCCGTCACGCCTGAAGATACTGCGGTC
TACTATTGCGCACGCGAAGGCGTAGCCGGCGATTTTGATTACTGGGGGCA
AGGAACATTGGTCACGGTCTCCTCTGGTGGAGGAGGATCAGGAGGCGGG
GGTTCAGGTGGAGGTGGGAGCGATATTCAACTTACGCAGTCTCCGAGCAG
TCTTTCTGCTTCCGTGGGAGACCGAGTGACGATTACTTGTAGGGCATCTCA
GTCAATAAGTTCCTATCTTAACTGGTATCAGCAGAAGCCTGGAAAGGCTC
CAAAACTTCTTATTTATGCCGCATCCTCATTGCAATCCGGCGTGCCTTCCC
GATTTCCGGATCTGGCTCAGGCACTGACTTTACCTTGACTATTAGTTCCC
TTCAACCAGAAGATTTTGCTACCTATTACTGCCAACAATCATACAGTACCC
CATATACATTCGGCCAAGGCACGAAATTGGAGATTAAAGCGGCCGCAACT
ACCACCCCTGCCCCTCGGCCGCCGACTCCGGCCCCAACCATCGCAAGCCA
ACCCCTCTCCTTGCGCCCCGAAGCTTGCCGCCCGGCCGCGGGTGGAGCCG
TGCATACCCGGGGGCTGGACTTTGCCTGCGATATCTACATTTGGGCCCCGC
TGGCCGGCACTTGCGGCGTGCTCCTGCTGTCGCTGGTCATCACCCTTTACT
GCAAGAGGGGCCGGAAGAAGCTGCTTTACATCTTCAAGCAGCCGTTCATG
CGGCCCGTGCAGACGACTCAGGAAGAGGACGGATGCTCGTGCAGATTCCC
TGAGGAGGAAGAGGGGGGATGCGAACTGCGCGTCAAGTTCTCACGGTCC
GCCGACGCCCCCGCATATCAACAGGGCCAGAATCAGCTCTACAACGAGCT
GAACCTGGGAAGGAGAGAGGAGTACGACGTGCTGGACAAGCGACGCGGA
CGCGACCCGGAGATGGGGGGGAAACCACGGCGGAAAAACCCTCAGGAAG
GACTGTACAACGAACTCCAGAAAGACAAGATGGCGGAAGCCTACTCAGA
AATCGGGATGAAGGGAGAGCGGAGGAGGGGAAAGGGTCACGACGGGCT
GTACCAGGGACTGAGCACCGCCACTAAGGATACCTACGATGCCTTGCATA
TGCAAGCACTCCCACCCCGG LTG2248: LP-11s-CD8 TM-41BB-CD3zeta amino acid sequence (SEQ ID NO : 34)

MLLLVTSLLLCELPHPAFLLIPQVQLQQSGPGLVKPSQTLSLTCAISGDSVSSNSATW
NWIRQSPSGGLEWLGRTYYRSKWYDDYAVSVRSRITMNPDTSKNQFSLQLNSVTPE
DTAVYYCAREGVAGDFDYWGQGTLVTVSSGGGGSGGGGSGGGGSDIQLTQSPSSLS
ASVGDRVTITCRASQSISSYLNWYQQKPGKAPKLLIYAASSLQSGVPSRFSGSGSGTD
FTLTISSLQPEDFATYYCQQSYSTPYTFGQGTKLEIKAAATTTPAPRPPTPAPTIASQPL
SLRPEACRPAAGGAVHTRGLDFACDIYIWAPLAGTCGVLLLSLVITLYCKRGRKKLL
YIFKQPFMRPVQTTQEEDGCSCRFPEEEEGGCELRVKFSRSADAPAYQQGQNQLYNE
LNLGRREEYDVLDKRRGRDPEMGGKPRRKNPQEGLYNELQKDKMAEAYSEIGMKG
ERRRGKGHDGLYQGLSTATKDTYDALHMQALPPR

FIGURE 2E

LTG2249: LP-12S-CD8 TM-41BB-CD3zeta nucleic acid sequence (SEQ ID NO: 43)
ATGCTTCTCCTGGTGACAAGCCTTCTGCTCTGTGAGTTACCACACCCAGCA
TTCCTCCTGATCCCACAAGTTCAGTTGCAGCAGAGTGGCCCTGGGCTTGTT
AAACCATCACAGACGCTCTCACTGACCTGTGCCATCTCTGGAGACAGTGT
AAGTTCTAACTCAGCCGCGTGGAATTGGATTAGACAATCACCAAGCCGGG
GACTTGAATGGCTTGGTCGGACGTACTATAGATCTAAGTGGTATAATGAC
TACGCAGTGTCAGTGAAATCACGGATAACCATAAACCCTGACACCAGCAA
AAACCAATTTTCTCTTCAGCTTAATTCCGTCACGCCAGAAGATACGGCCGT
TTACTACTGTGCGAGGGAAGGTGATGACGCATTGGACATCTGGGGTCAGG
GGACCATGGTGACTGTCTCTTCCGGCGGGGGGGTAGTGGAGGGGGTGGC
TCAGGTGGTGGCGGGTCAGATATACAAATGACACAGAGCCCTAGTAGTCT
GAGTGCTTCAGTGGGCGACCGCGTAACTATAACCTGTAGAGCATCCCAAA
GCATTTCCCACTTCCTTAATTGGTACCAGCAGAAGCCGGGCACAGCGCCC
AAACTCCTGATCACCACTGCGAGCGGACTTGGTTCAGGTGTTCCTAGCCG
GTTTAGTGGGTCAGGTAGCGGTACAGATTTCACTCTCACGATAAACTCCCT
TCAGCCTGAGGACCTGGCGACATATTACTGTCAACAATCCTATACCACCC
CACTGACATTCGGAGGGGGCACAAAACTGGAGATCAAAGCGGCCGCAAC
TACCACCCCTGCCCCTCGGCCGCCGACTCCGGCCCCAACCATCGCAAGCC
AACCCCTCTCCTTGCGCCCCGAAGCTTGCCGCCCGGCCGCGGGTGGAGCC
GTGCATACCCGGGGGCTGGACTTTGCCTGCGATATCTACATTTGGGCCCCG
CTGGCCGGCACTTGCGGCGTGCTCCTGCTGTCGCTGGTCATCACCCTTTAC
TGCAAGAGGGGCCGGAAGAAGCTGCTTTACATCTTCAAGCAGCCGTTCAT
GCGGCCCGTGCAGACGACTCAGGAAGAGGACGGATGCTCGTGCAGATTCC
CTGAGGAGGAAGAGGGGGGATGCGAACTGCGCGTCAAGTTCTCACGGTC
CGCCGACGCCCCCGCATATCAACAGGGCCAGAATCAGCTCTACAACGAGC
TGAACCTGGGAAGGAGAGAGGAGTACGACGTGCTGGACAAGCGACGCGG
ACGCGACCCGGAGATGGGGGGGAAACCACGGCGGAAAAACCCTCAGGAA
GGACTGTACAACGAACTCCAGAAAGACAAGATGGCGGAAGCCTACTCAG
AAATCGGGATGAAGGGAGAGCGGAGGAGGGGAAAGGGTCACGACGGGC
TGTACCAGGGACTGAGCACCGCCACTAAGGATACCTACGATGCCTTGCAT
ATGCAAGCACTCCCACCCCGG LTG2249: LP-12S-CD8 TM-41BB-CD3zeta amino acid sequence (SEQ ID NO: 44)

MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAREGDDALDIWGQGTMVTVSSGGGGSGGGGSGGGG
SDIQMTQSPSSLSASVGDRVTITCRASQSISHFLNWYQQKPGTAPKLLITTASG
LGSGVPSRFSGSGSGTDFTLTINSLQPEDLATYYCQQSYTTPLTFGGGTKLEIK
AAATTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEE
EEGGCELRVKFSRSADAPAYQQGQNQLYNELNLGRREEYDVLDKRRGRDPE
MGGKPRRKNPQEGLYNELQKDKMAEAYSEIGMKGERRRGKGHDGLYQGLS
TATKDTYDALHMQALPPR

FIGURE 2F

LTG2203: LP-16P3-CD8 TM-41BB-CD3zeta nucleic acid sequence (SEQ ID NO: 53)

ATGTTGTTGCTTGTCACAAGCCTTCTTCTCTGTGAGCTTCCGCACCCGGCTTTCCT
GCTGATCCCGCAGATACAGCTTCAGCAGTCCGGCCCCGGTCTGGTAAAGCCGTCC
CAAACGCTTTCACTCACATGCGCGATCTCTGGTGATTCTGTGTCATCCAACAGCG
CAGCATGGAATTGGATCCGCCAATCACCCAGTAGAGGCTTGGAGTGGTTGGGCC
GGACTTATTATCGAAGTAAGTGGTACAATGATTATGCAGTCTCAGTTAAATCCAG
GATCACTATTAACCCAGATACAAGTAAAAACCAGTTCTCATTGCAACTTAATTCC
GTAACTCCGGAGGACACTGCAGTATATTACTGCGCTCAGGAGGTGCAGCCTGAT
GATGCTCTGGACATTTGGGGACAAGGCACGATGGTCACGGTTAGTTCCGGGGGG
GGAGGTTCTGGCGGAGGTGGTAGTGGGGGGGGCGGCAGTGACATCCAGATGACA
CAGAGTCCCAGCAGCGTGTCTGCGTCAGTCGGGGATAAGGTAACAATTACGTGT
AGAGCGAGCCAGGACGTTTCCGGGTGGCTGGCGTGGTACCAACAAAAACCCGGT
CTCGCTCCGCAGTTGCTCATCTCTGGAGCGTCCACCCTTCAGGGAGAGGTGCCTA
GCAGATTTTCTGGGTCTGGATCCGGCACGGATTTTACACTTACGATTTCCTCTCTT
CAACCCGAAGATTTTGCTACTTACTATTGCCAGCAGGCCAAAAACTTCCCGTACA
CGTTTGGACAGGGCACAAAGTTGGAAATTAAGGCGGCCGCAACTACCACCCCTG
CCCCTCGGCCGCCGACTCCGGCCCCAACCATCGCAAGCCAACCCCTCTCCTTGCG
CCCCGAAGCTTGCCGCCGGCCGCGGGTGGAGCCGTGCATACCCGGGGCTGGA
CTTTGCCTGCGATATCTACATTTGGGCCCCGCTGGCCGGCACTTGCGGCGTGCTC
CTGCTGTCGCTGGTCATCACCCTTTACTGCAAGAGGGGCCGGAAGAAGCTGCTTT
ACATCTTCAAGCAGCCGTTCATGCGGCCCGTGCAGACGACTCAGGAAGAGGACG
GATGCTCGTGCAGATTCCCTGAGGAGGAAGAGGGGGGATGCGAACTGCGCGTCA
AGTTCTCACGGTCCGCCGACGCCCCCGCATATCAACAGGGCCAGAATCAGCTCTA
CAACGAGCTGAACCTGGGAAGGAGAGAGGAGTACGACGTGCTGGACAAGCGAC
GCGGACGCGACCCGGAGATGGGGGGGAAACCACGGCGGAAAAACCCTCAGGAA
GGACTGTACAACGAACTCCAGAAAGACAAGATGGCGGAAGCCTACTCAGAAATC
GGGATGAAGGGAGAGCGGAGGAGGGGAAAGGGTCACGACGGGCTGTACCAGGG
ACTGAGCACCGCCACTAAGGATACCTACGATGCCTTGCATATGCAAGCACTCCCA
CCCCGG

LTG2203: LP-16P3-CD8 TM-41BB-CD3zeta amino acid sequence (SEQ ID NO: 54)

MLLLVTSLLLCELPHPAFLLIPQIQLQQSGPGLVKPSQTLSLTCAISGDSVSSNS
AAWNWIRQSPSRGLEWLGRTYYRSKWYNDYAVSVKSRITINPDTSKNQFSLQLNSV
TPEDTAVYYCAQEVQPDDALDIWGQGTMVTVSSGGGGSGGGGSGGGGSDIQMTQS
PSSVSASVGDKVTITCRASQDVSGWLAWYQQKPGLAPQLLISGASTLQGEVPSRFSG
SGSGTDFTLTISSLQPEDFATYYCQQAKNFPYTFGQGTKLEIKAAATTTPAPRPPTPAP
TIASQPLSLRPEACRPAAGGAVHTRGLDFACDIYIWAPLAGTCGVLLLSLVITLYCKR
GRKKLLYIFKQPFMRPVQTTQEEDGCSCRFPEEEEGGCELRVKFSRSADAPAYQQGQ
NQLYNELNLGRREEYDVLDKRRGRDPEMGGKPRRKNPQEGLYNELQKDKMAEAYS
EIGMKGERRRGKGHDGLYQGLSTATKDTYDALHMQALPPR

FIGURE 2G

LTG2204: LP-16P16-CD8 TM-41BB-CD3zeta nucleic acid sequence (SEQ ID NO: 63)
ATGCTGCTTTTGGTAACTTCCCTCCTTTTGTGCGAGCTGCCCCATCCAGCG
TTCCTCCTCATCCCTCAAGTACAGTTGCAGCAGTCAGGACCTGGCCTTGTG
AAACCATCCCAAACTCTCAGCCTCACGTGTGCTATTTCTGGTGACTCAGTA
AGTAGCAATAGCGCTGCTTGGAACTGGATCAGACAATCTCCCTCCAGGGG
TCTCGAATGGCTGGGGCGAACCTATTACCGATCTAAATGGTATAACGATT
ATGCAGTATCCGTGAAATCCAGGATTACAATCAACCCAGATACGTTCAAG
AATCAATTCTCTCTTCAGCTCAACTCCGTAACTCCAGAGGACACTGCGGTA
TATTATTGCGCCCAAGAAGTCGAGCCACACGATGCCCTCGATATCTGGGG
TCAAGGTACCATGGTTACAGTTAGTAGTGGGGGTGGGGGAAGCGGGGGC
GGTGGGTCCGGTGGCGGGGGTTCAGACATCAAGATGACCCAATCCCCAAG
CTCTGTTTCAGCATCCGTGGGCGATAAGGTAACCATTACATGCAGAGCGA
GTCAGGACGTTTCAGGGTGGCTGGCTTGGTACCAGCAAAAACCGGGACTC
GCACCGCAGCTGTTGATTTTCGGCGCCAGTACGCTTCAGGGCGAAGTACC
GTCCAGGTTCAGTGGGTCAGGTTCTGGCACCGATTTTACGCTCACGATATC
CAGTCTCCAACCGGAGGATTTTGCTACTTATTACTGCCAGCAGGCTAAGTA
TTTTCCATACACATTTGGCCAGGGGACAAAGTTGGAGATCAAAGCGGCCG
CAACTACCACCCCTGCCCCTCGGCCGCCGACTCCGGCCCCAACCATCGCA
AGCCAACCCCTCTCCTTGCGCCCCGAAGCTTGCCGCCCGGCCGCGGGTGG
AGCCGTGCATACCCGGGGGCTGGACTTTGCCTGCGATATCTACATTTGGG
CCCCGCTGGCCGGCACTTGCGGCGTGCTCCTGCTGTCGCTGGTCATCACCC
TTTACTGCAAGAGGGGCCGGAAGAAGCTGCTTTACATCTTCAAGCAGCCG
TTCATGCGGCCCGTGCAGACGACTCAGGAAGAGGACGGATGCTCGTGCAG
ATTCCCTGAGGAGGAAGAGGGGGGATGCGAACTGCGCGTCAAGTTCTCAC
GGTCCGCCGACGCCCCGCATATCAACAGGGCCAGAATCAGCTCTACAAC
GAGCTGAACCTGGGAAGGAGAGAGGAGTACGACGTGCTGGACAAGCGAC
GCGGACGCGACCCGGAGATGGGGGGGAAACCACGGCGGAAAAACCCTCA
GGAAGGACTGTACAACGAACTCCAGAAAGACAAGATGGCGGAAGCCTAC
TCAGAAATCGGGATGAAGGGAGAGCGGAGGAGGGGAAAGGGTCACGAC
GGGCTGTACCAGGGACTGAGCACCGCCACTAAGGATACCTACGATGCCTT
GCATATGCAAGCACTCCCACCCCGG LTG2204: LP-16P16-CD8 TM-41BB-CD3zeta amino acid sequence (SEQ ID NO: 64)

MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTFKNQFSL
QLNSVTPEDTAVYYCAQEVEPHDALDIWGQGTMVTVSSGGGGSGGGGSGG
GGSDIKMTQSPSSVSASVGDKVTITCRASQDVSGWLAWYQQKPGLAPQLLIF
GASTLQGEVPSRFSGSGSGTDFTLTISSLQPEDFATYYCQQAKYFPYTFGQGT
KLEIKAAATTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSC
RFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGL
YQGLSTATKDTYDALHMQALPPR

FIGURE 2H

LTG2205: LP-16P20-CD8 TM-41BB-CD3zeta nucleic acid sequence (SEQ ID NO: 73)

ATGCTGCTCCTCGTAACCTCTCTTCTTCTTTGTGAGTTGCCACATCCAGCAT
TTCTTCTGATACCTCAAGTTCAACTCCAGCAGAGTGGTCCAGGTTTGGTAA
AACCCAGCCAGACTCTCTCATTGACGTGTGCCATATCAGGTGATTCAGTTT
CCTCTAATAGCGCGGCATGGAATTGGATCAGGCAAAGCCCTAGTCGCGGG
CTGGAGTGGCTCGGCCGGACATACTACCGCTCAAAGTGGTACAACGACTA
CGCCGTCAGCGTAAAATCTCGGATTACCATTAACCCGGATACTTCCAAAA
ACCAATTCTCCCTGCAGCTTAACAGTGTCACGCCGGAAGATACGGCCGTT
TATTACTGCGCACAAGAGGTGGAACCGCACGACGCCCTCGATATCTGGGG
CCAAGGCACTATGGTGACCGTCAGTAGCGGAGGGGGGGGTTCCGGAGGA
GGCGGCTCTGGTGGCGGAGGATCTGATATCCAAATGACCCAATCACCGTC
TTCAGTATCAGCTTCTGTTGGTGACAAAGTTACGATTACCTGTCGAGCGTC
ACAGGACGTTTCTGGTTGGTTGGCTTGGTATCAGCAAAAACCAGGGCTTG
CGCCTCAGTTGCTTATTTTGGGGCATCTACTTTGCAGGGAGAGGTGCCCT
CCCGGTTCTCCGGCAGTGGGAGCGGCACCGATTTTACACTTACCATCTCTT
CCTTGCAACCCGAAGACTTTGCGACGTACTATTGCCAGCAGGCAAAGTAT
TTTCCCTACACTTTTGGACAAGGGACTAAACTTGAAATCAAGGCGGCCGC
AACTACCACCCTGCCCCTCGGCCGCCGACTCCGGCCCCAACCATCGCAA
GCCAACCCCTCTCCTTGCGCCCCGAAGCTTGCCGCCCGGCCGCGGGTGGA
GCCGTGCATACCCGGGGGCTGGACTTTGCCTGCGATATCTACATTTGGGCC
CCGCTGGCCGGCACTTGCGGCGTGCTCCTGCTGTCGCTGGTCATCACCCTT
TACTGCAAGAGGGGCCGGAAGAAGCTGCTTTACATCTTCAAGCAGCCGTT
CATGCGGCCCGTGCAGACGACTCAGGAAGAGGACGGATGCTCGTGCAGA
TTCCCTGAGGAGGAAGAGGGGGGATGCGAACTGCGCGTCAAGTTCTCACG
GTCCGCCGACGCCCCGCATATCAACAGGGCCAGAATCAGCTCTACAACG
AGCTGAACCTGGGAAGGAGAGAGGAGTACGACGTGCTGGACAAGCGACG
CGGACGCGACCCGGAGATGGGGGGGAAACCACGGCGGAAAAACCCTCAG
GAAGGACTGTACAACGAACTCCAGAAAGACAAGATGGCGGAAGCCTACT
CAGAAATCGGGATGAAGGGAGAGCGGAGGAGGGGAAAGGGTCACGACG
GGCTGTACCAGGGACTGAGCACCGCCACTAAGGATACCTACGATGCCTTG
CATATGCAAGCACTCCCACCCCGG

LTG2205: LP-16P20-CD8 TM-41BB-CD3zeta amino acid sequence (SEQ ID NO: 74)

MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAQEVEPHDALDIWGQGTMVTVSSGGGGSGGGGSGG
GGSDIQMTQSPSSVSASVGDKVTITCRASQDVSGWLAWYQQKPGLAPQLLIF
GASTLQGEVPSRFSGSGSGTDFTLTISSLQPEDFATYYCQQAKYFPYTFGQGT
KLEIKAAATTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSC
RFPEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGL
YQGLSTATKDTYDALHMQALPPR

FIGURE 2I

LTG2206: LP-16P2-CD8 TM-41BB-CD3zeta nucleic acid sequence (SEQ ID NO: 83)

ATGCTTCTTTTGGTGACTTCCCTTTTGCTGTGCGAGTTGCCACACCCCGCCT
TCCTGCTTATTCCCCAAGTCCAGCTCCAACAATCCGGACCCGGACTTGTTA
AGCCGTCTCAGACGTTGTCACTCACATGCGCCATCAGTGGCGATAGCGTG
TCCAGCAACAGTGCCGCATGGAATTGGATACGACAGAGCCCTTCCCGAGG
ATTGGAATGGCTGGGACGAACGTACTATAGGTCCAAGTGGTATAACGACT
ACGCGGTGTCAGTTAAATCTCGGATTACTATAAATCCCGACACTTTTAAGA
ATCAGTTTTCCCTGCAACTCAATTCAGTCACACCGGAAGATACGGCAGTG
TACTATTGCGCTCAAGAAGTTGAGCCACATGATGCGCTGGATATTTGGGG
TCAGGGGACTATGGTGACGGTAAGCAGTGGGGGCGGGGGCAGTGGCGGA
GGTGGCAGCGGGGGCGGTGGAAGCGACATTAAGATGACTCAGTCTCCGTC
TTCAGTTTCCGCCTCCGTAGGGACAAGGTTACAATTACTTGTCGCGCATC
TCAGGATGTCTCAGGTTGGCTGGCTTGGTATCAACAGAAGCCTGGCCTCG
CCCCTCAGCTTCTCATATTCGGGGCTAGTACCCTGCAAGGAGAAGTCCCG
AGCAGGTTTTCCGGTTCAGGGTCCGGGACAGACTTTACCTTGACCATCAG
CTCCCTGCAACCGGAGGACTTCGCGACCTACTATTGTCAACAGGCGAAGT
ACTTCCCCTACACGTTCGGGCAAGGGACTAAGCTCGAAATCAAGGCGGCC
GCAACTACCACCCCTGCCCCTCGGCCGCCGACTCCGGCCCCAACCATCGC
AAGCCAACCCCTCTCCTTGCGCCCCGAAGCTTGCCGCCCGGCCGCGGGTG
GAGCCGTGCATACCCGGGGGCTGGACTTTGCCTGCGATATCTACATTTGG
GCCCCGCTGGCCGGCACTTGCGGCGTGCTCCTGCTGTCGCTGGTCATCACC
CTTTACTGCAAGAGGGGCCGGAAGAAGCTGCTTTACATCTTCAAGCAGCC
GTTCATGCGGCCCGTGCAGACGACTCAGGAAGAGGACGGATGCTCGTGCA
GATTCCCTGAGGAGGAAGAGGGGGGATGCGAACTGCGCGTCAAGTTCTCA
CGGTCCGCCGACGCCCCCGCATATCAACAGGGCCAGAATCAGCTCTACAA
CGAGCTGAACCTGGGAAGGAGAGAGGAGTACGACGTGCTGGACAAGCGA
CGCGGACGCGACCCGGAGATGGGGGGGAAACCACGGCGGAAAAACCCTC
AGGAAGGACTGTACAACGAACTCCAGAAAGACAAGATGGCGGAAGCCTA
CTCAGAAATCGGGATGAAGGGAGAGCGGAGGAGGGGAAAGGGTCACGAC
GGGCTGTACCAGGGACTGAGCACCGCCACTAAGGATACCTACGATGCCTT
GCATATGCAAGCACTCCCACCCCGG

LTG2206: LP-16P2-CD8 TM-41BB-CD3zeta amino acid sequence (SEQ ID NO: 84)

MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTFKNQFSL
QLNSVTPEDTAVYYCAQEVEPHDALDIWGQGTMVTVSSGGGGSGGGGSGG
GGSDIKMTQSPSSVSASVGDKVTITCRASQDVSGWLAWYQQKPGLAPQLLIF
GASTLQGEVPSRFSGSGSGTDFTLTISSLQPEDFATYYCQQAKYFPYTFGQGT
KLEIKAAATTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSC
RFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGL
YQGLSTATKDTYDALHMQALPPR

FIGURE 2J

LTG2207: LP-16P6-CD8 TM-41BB-CD3zeta nucleic acid sequence (SEQ ID NO: 93)
ATGCTTCTTTTGGTGACTTCCCTTTTGCTGTGCGAGTTGCCACACCCCGCCT
TCCTGCTTATTCCCCAAGTACAACTCCAGCAATCAGGGCCTGGCCTTGTCA
AGCCGAGTCAAACCTTGAGTTTGACGTGTGCCATCAGCGGTGACTCTGTC
AGTTCAAACTCCGCAGCTTGGAACTGGATTCGGCAGTCCCCTCCAGGGG
CCTCGAATGGCTTGGACGGACGTACTACAGATCAAAATGGTACAACGACT
ACGCAGTCAGTGTAAAATCAAGGATTACGATAAACCCTGATACGAGTAAA
AACCAGTTCTCTCTCCAACTGAACAGCGTCACACCGGAAGATACAGCCGT
GTATTACTGTGCTCAGGAAGTGCAACCTGACGACGCATTTGACATCTGGG
GTCAGGGCACGATGATCACCGTGAGTAGTGGAGGAGGAGGCAGTGGGGG
AGGCGGTTCTGGCGGGGTGGGTCTGATATACAGATGACACAGAGTCCCT
CCTCAGTTTCCGCCTCTGTTGGAGATAAGGTGACAATTACATGCAGGGCG
TCCCAAGATGTTTCTGGATGGCTCGCATGGTACCAACAGAAGCCAGGACT
CGCCCCTCAGCTCCTCATTAGCGGCGCTAGCACTCTCCAAGGGGGAGTAC
CGAGCAGGTTCTCTGGGTCCGGAAGTGGGACGGACTTTACCCTGACAATA
TCCTCCCTTCAGCCAGAAGACTTCGCAACCTACTATTGCCAACAGGCGAA
AAATTTCCCTTACACGTTCGGCCAAGGAACTAAACTTGAAATCAAGGCGG
CCGCAACTACCACCCCTGCCCCTCGGCCGCCGACTCCGGCCCCAACCATC
GCAAGCCAACCCCTCCTTGCGCCCCGAAGCTTGCCGCCCGGCCGCGGG
TGGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGC
AGATTCCCTGAGGAGGAAGAGGGGGGATGCGAACTGCGCGTCAAGTTCTC
ACGGTCCGCCGACGCCCCGCATATCAACAGGGCCAGAATCAGCTCTACA
ACGAGCTGAACCTGGGAAGGAGAGAGGAGTACGACGTGCTGGACAAGCG
ACGCGGACGCGACCCGGAGATGGGGGGGAAACCACGGCGGAAAAACCCT
CAGGAAGGACTGTACAACGAACTCCAGAAAGACAAGATGGCGGAAGCCT
ACTCAGAAATCGGGATGAAGGGAGAGCGGAGGAGGGGAAAGGGTCACG
ACGGGCTGTACCAGGGACTGAGCACCGCCACTAAGGATACCTACGATGCC
TTGCATATGCAAGCACTCCCACCCCGG LTG2207: LP-16P6-CD8 TM-41BB-CD3zeta amino acid sequence (SEQ ID NO: 94)

MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAQEVQPDDAFDIWGQGTMITVSSGGGGSGGGGSGGG
GSDIQMTQSPSSVSASVGDKVTITCRASQDVSGWLAWYQQKPGLAPQLLISG
ASTLQGGVPSRFSGSGSGTDFTLTISSLQPEDFATYYCQQAKNFPYTFGQGTK
LEIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGHDGLYQ
GLSTATKDTYDALHMQALPPR

FIGURE 2K

LTG2208: LP-16P10-CD8 TM-41BB-CD3zeta nucleic acid sequence (SEQ ID NO: 103)

ATGCTTCTTTTGGTGACTTCCCTTTTGCTGTGCGAGTTGCCACACCCCGCCT
TCCTGCTTATTCCCCAAGTGCAGTTGCAACAGTCTGGACCAGGCCTCGTAA
AACCTTCTCAAACTTTGTCACTCACTTGTGCCATCTCAGGGGACAGTGTCA
GTTCCAACAGTGCGGCATGGAATTGGATTAGGCAATCCCCCTCTCGAGGT
CTGGAATGGCTTGGGCGGACTTACTACCGAAGTAAGTGGTACAACGATTA
TGCAGTTTCTGTAAAATCACGAATCACTATAAATCCGGACACTTCTAAGA
ATCAGTTCTCTTTGCAGCTTAACTCTGTTACTCCTGAAGACACAGCCGTAT
ATTACTGTGCTCAAGAGGTAGAGCCGCAAGATGCCTTCGACATCTGGGGC
CAAGGGACTATGGTGACAGTAAGCTCCGGAGGTGGGGGATCAGGGGGAG
GTGGGTCCGGTGGTGGTGGCTCTGACATACAGATGACACAGTCCCCTAGC
TCTGTGTCAGCAAGTGTCGGTGACAAGGTTACGATAACGTGCAGGGCCAG
TCAAGATGTGTCAGGATGGTTGGCGTGGTACCAACAGAAACCCGGCTTGG
CACCGCAGCTTTTGATATTCGGCGCGTCCACACTCCAAGGCGAAGTGCCTT
CTCGGTTTTCTGGAAGCGGCAGCGGGACGGACTTTACTTTGACAATATCCT
CCCTCCAACCCGAGGATTTCGCGACGTATTATTGCCAGCAAGCAAAATAC
TTCCCATACACCTTCGGGCCTGGGACCAAACTGGAGATCAAAGCGGCCGC
AACTACCACCCCTGCCCCTCGGCCGCCGACTCCGGCCCCAACCATCGCAA
GCCAACCCCTCTCCTTGCGCCCCGAAGCTTGCCGCCCGGCCGCGGGTGGA
GCCGTGCATACCCGGGGCTGGACTTTGCCTGCGATATCTACATTTGGGCC
CCGCTGGCCGGCACTTGCGGCGTGCTCCTGCTGTCGCTGGTCATCACCCTT
TACTGCAAGAGGGGCCGGAAGAAGCTGCTTTACATCTTCAAGCAGCCGTT
CATGCGGCCCGTGCAGACGACTCAGGAAGAGGACGGATGCTCGTGCAGA
TTCCCTGAGGAGGAAGAGGGGGGATGCGAACTGCGCGTCAAGTTCTCACG
GTCCGCCGACGCCCCCGCATATCAACAGGGCCAGAATCAGCTCTACAACG
AGCTGAACCTGGGAAGGAGAGAGGAGTACGACGTGCTGGACAAGCGACG
CGGACGCGACCCGGAGATGGGGGGGAAACCACGGCGGAAAAACCCTCAG
GAAGGACTGTACAACGAACTCCAGAAAGACAAGATGGCGGAAGCCTACT
CAGAAATCGGGATGAAGGGAGAGCGGAGGAGGGGAAAGGGTCACGACG
GGCTGTACCAGGGACTGAGCACCGCCACTAAGGATACCTACGATGCCTTG
CATATGCAAGCACTCCCACCCCGG

LTG2208: LP-16P10-CD8 TM-41BB-CD3zeta amino acid sequence (SEQ ID NO: 104)

MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAQEVEPQDAFDIWGQGTMVTVSSGGGGSGGGGSGGG
GSDIQMTQSPSSVSASVGDKVTITCRASQDVSGWLAWYQQKPGLAPQLLIFG
ASTLQGEVPSRFSGSGSGTDFTLTISSLQPEDFATYYCQQAKYFPYTFGPGTKL
EIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGHDGLYQ
GLSTATKDTYDALHMQALPPR

FIGURE 2L

LTG2209: LP-16P17-CD8 TM-41BB-CD3zeta nucleic acid sequence (SEQ ID NO: 113)

ATGCTTCTTTTGGTGACTTCCCTTTTGCTGTGCGAGTTGCCACACCCCGCCT
TCCTGCTTATTCCCCAGGTACAGCTTCAACAGAGTGGGCCGGGACTGGTG
AAACACTCCCAAACACTTTCTCTGACGTGCGCTATATCAGGTGACTCTGTT
TCATCTAATTCTGCTGCGTGGAACTGGATTCGACAATCTCCCAGTCGCGGG
TTGGAATGGCTGGGACGAACATATTATCGGTCTAAGTGGTATAACGATTA
TGCTGTATCTGTTAAATCTCGAATTACGATTAATCCTGACACCTCCAAGAA
CCAGTTCTCCTCCAGTTGAACTCAGTCACACCGGAAGACACTGCGGTCT
ACTATTGCGCTCAAGAAGTCGAGCCACATGATGCATTCGACATCTGGGGC
CAGGGAACGATGGTCACCGTCAGCAGTGGCGGCGGCGGATCTGGGGGTG
GCGGTTCTGGCGGTGGAGGATCAGACATACAAATGACGCAGAGTCCCTCA
AGTGTGTACGCGAGTGTGGGGGATAAGGTAACTATTACGTGCAGAGCGTC
ACAGGATGTTAGTGGATGGCTTGCCTGGTATCAGCAGAAGCCAGGCCTTG
CTCCACAGCTCCTTATCAGTGGTGCTTCTACACTTCAGGGCGAGGTTCCGA
GTAGATTCTCTGGTTCTGGATCTGGTACTGACTTCACTCTTACAATTTCTTC
TTTGCAACCAGAAGACTTTGCGACTTATTACTGCCAACAGGCCAAATACTT
CCCTTATACATTTGGCCAAGGTACCAAGTTGGAGATAAAGGCGGCCGCAA
CTACCACCCCTGCCCCTCGGCCGCCGACTCCGGCCCCAACCATCGCAAGC
CAACCCCTCTCCTTGCGCCCCGAAGCTTGCCGCCCGGCCGCGGGTGGAGC
CGTGCATACCCGGGGGCTGGACTTTGCCTGCGATATCTACATTTGGGCCCC
GCTGGCCGGCACTTGCGGCGTGCTCCTGCTGTCGCTGGTCATCACCCTTTA
CTGCAAGAGGGGCCGGAAGAAGCTGCTTTACATCTTCAAGCAGCCGTTCA
TGCGGCCCGTGCAGACGACTCAGGAAGAGGACGGATGCTCGTGCAGATTC
CCTGAGGAGGAAGAGGGGGGATGCGAACTGCGCGTCAAGTTCTCACGGT
CCGCCGACGCCCCCGCATATCAACAGGGCCAGAATCAGCTCTACAACGAG
CTGAACCTGGGAAGGAGAGAGGAGTACGACGTGCTGGACAAGCGACGCG
GACGCGACCCGGAGATGGGGGGGAAACCACGGCGGAAAAACCCTCAGGA
AGGACTGTACAACGAACTCCAGAAAGACAAGATGGCGGAAGCCTACTCA
GAAATCGGGATGAAGGGAGAGCGGAGGAGGGGAAAGGGTCACGACGGG
CTGTACCAGGGACTGAGCACCGCCACTAAGGATACCTACGATGCCTTGCA
TATGCAAGCACTCCCACCCCGG

LTG2209: LP-16P17-CD8 TM-41BB-CD3zeta amino acid sequence (SEQ ID NO: 114)

MLLLVTSLLLCELPHPAFLLIPQVQLQQSGPGLVKHSQTLSLTCAISGDSVSSN
SAAWNWIRQSPSRGLEWLGRTYYRSKWYNDYAVSVKSRITINPDTSKNQFSL
QLNSVTPEDTAVYYCAQEVEPHDAFDIWGQGTMVTVSSGGGGSGGGGSGGG
GSDIQMTQSPSSVYASVGDKVTITCRASQDVSGWLAWYQQKPGLAPQLLISG
ASTLQGEVPSRFSGSGSGTDFTLTISSLQPEDFATYYCQQAKYFPYTFGQGTKL
EIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGHDGLYQ
GLSTATKDTYDALHMQALPPR

FIGURE 2M

LTG2210: LP-16P20v2-CD8 TM-41BB-CD3zeta nucleic acid sequence (SEQ ID NO: 123)
ATGCTTCTTTTGGTGACTTCCCTTTTGCTGTGCGAGTTGCCACACCCCGCCT
TCCTGCTTATTCCCCAAGTACAACTTCAACAGTCTGGGCCTGGGCTTGTAA
AACCTAGCCAAACTCTGTCCCTCACGTGCGCGATTTCAGGGGACAGTGTA
AGTTCCAACTCAGCCGCATGGAACTGGATCAGGCAGTCACCTTCAAGGGG
GCTCGAATGGCTTGGCCGAACGTACTACAGGAGTAAGTGGTACAACGATT
ATGCAGTGTCTGTGAAATCACGGATTACTATCAATCCCGACACGTCCAAG
AACCAGTTCTCTCTGCAACTCAACTCAGTGACACCAGAGGATACGGCCGT
TTACTATTGTGCACAGGAAGTGCAACCTGATGATGCCTTTGACATTTGGGG
TCAGGGCACGATGGTTACGGTAAGCTCTGGGGGAGGCGGCAGTGGAGGG
GGAGGTAGTGGGGGAGGGGGATCTGATATACAGATGACACAAAGCCCGT
CATCCGTCAGTGCTTCAGTTGGTGATAAAGTAACCATTACGTGCCGCGCTT
CCCAAGACGTTAGCGGATGGTTGGCTTGGTATCAACAAAAACCGGGGTTG
GCTCCGCAACTCCTCATATCCGGTGCGAGTACGCTCCAAGGCGAAGTCCC
TAGCAGATTTTCCGGGAGCGGTTCCGGTACAGATTTCACGTTGACCATTAG
CTCTCTCCAGCCCGAAGATTTTGCAACCTACTATTGCCAACAGGCCAAAA
ATTTTCCATATACATTTGGTCAAGGCACTAAGCTCGAAATCAAAGCGGCC
GCAACTACCACCCCTGCCCCTCGGCCGCCGACTCCGGCCCCAACCATCGC
AAGCCAACCCCTCTCCTTGCGCCCCGAAGCTTGCCGCCCGGCCGCGGGTG
GAGCCGTGCATACCCGGGGCTGGACTTTGCCTGCGATATCTACATTTGG
GCCCCGCTGGCCGGCACTTGCGGCGTGCTCCTGCTGTCGCTGGTCATCACC
CTTTACTGCAAGAGGGGCCGGAAGAAGCTGCTTTACATCTTCAAGCAGCC
GTTCATGCGGCCCGTGCAGACGACTCAGGAAGAGGACGGATGCTCGTGCA
GATTCCCTGAGGAGGAAGAGGGGGGATGCGAACTGCGCGTCAAGTTCTCA
CGGTCCGCCGACGCCCCCGCATATCAACAGGGCCAGAATCAGCTCTACAA
CGAGCTGAACCTGGGAAGGAGAGAGGAGTACGACGTGCTGGACAAGCGA
CGCGGACGCGACCCGGAGATGGGGGGGAAACCACGGCGGAAAAACCCTC
AGGAAGGACTGTACAACGAACTCCAGAAAGACAAGATGGCGGAAGCCTA
CTCAGAAATCGGGATGAAGGGAGAGCGGAGGAGGGGAAAGGGTCACGAC
GGGCTGTACCAGGGACTGAGCACCGCCACTAAGGATACCTACGATGCCTT
GCATATGCAAGCACTCCCACCCCGG LTG2210: LP-16P20v2-CD8 TM-41BB-CD3zeta amino acid sequence (SEQ ID NO: 124)

MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAQEVQPDDAFDIWGQGTMVTVSSGGGGSGGGGSGG
GGSDIQMTQSPSSVSASVGDKVTITCRASQDVSGWLAWYQQKPGLAPQLLIS
GASTLQGEVPSRFSGSGSGTDFTLTISSLQPEDFATYYCQQAKNFPYTFGQGT
KLEIKAAATTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSC
RFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGL
YQGLSTATKDTYDALHMQALPPR

FIGURE 2N

LTG2216: LP-16P1-CD8 TM-41BB-CD3zeta nucleic acid sequence (SEQ ID NO: 133)

ATGTTGCTGCTCGTGACCTCGCTCCTTCTGTGCGAGCTGCCCCATCCGGCT
TTTCTGCTCATCCCTCAAGTGCAGCTGCAGCAGTCCGGTCCTGGACTGGTC
AAGCCGTCCCAGACTCTGAGCCTGACTTGCGATATTAGCGGGGACTCAGT
CTCGTCCAATTCGGCGGCCTGGAACTGGATCCGGCAGTCACCATCAAGGG
GCCTGGAATGGCTCGGGCGCACTTACTACCGGTCCAAATGGTATAACGAC
TACGCCGTGTCCGTGAAGTCCCGGATCACCATTAACCCCGACACCTCGAA
GAACCAGTTCTCACTCCAACTGAACAGCGTGACCCCCGAGGATACCGCGG
TGTACTACTGCGCACAAGAAATCGAACCGCACGACGCCTTCGACATTTGG
GACCAGGGAACGATGGTCACAGTGTCGTCCGGTGGAGGAGGTTCCGGAG
GCGGTGGATCTGGAGGCGGAGGTTCGGTGATCCAGATGACCCAGAGCCCC
TCCTCGGTGTCCGCATCCGTGGGCGATAAGGTCACCATTACCTGTAGAGC
GTCCCAGGACGTGTCCGGATGGCTGGCCTGGTACCAGCAGAAGCCAGGCT
TGGCTCCTCAACTGCTGATCTCCGGCGCCAGCTCACTTCAGGGGGGGGTG
CCATCACGCTTCTCCGGATCCGGTTCCGGCACCGACTTCACCCTGACCATC
AGCAGCCTCCAGCCTGAGGACTTCGCCACTTACTACTGCCAACAGGCCAA
GTACTTCCCCTATACCTTCGGACAAGGCACTAAGCTGGAAATCAAGGCGG
CCGCAACTACCACCCCTGCCCCTCGGCCGCCGACTCCGGCCCCAACCATC
GCAAGCCAACCCCTCCTTGCGCCCCGAAGCTTGCCGCCCGGCCGCGGG
TGGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGC
AGATTCCCTGAGGAGGAAGAGGGGGGATGCGAACTGCGCGTCAAGTTCTC
ACGGTCCGCCGACGCCCCCGCATATCAACAGGGCCAGAATCAGCTCTACA
ACGAGCTGAACCTGGGAAGGAGAGAGGAGTACGACGTGCTGGACAAGCG
ACGCGGACGCGACCCGGAGATGGGGGGGAAACCACGGCGGAAAAACCCT
CAGGAAGGACTGTACAACGAACTCCAGAAAGACAAGATGGCGGAAGCCT
ACTCAGAAATCGGGATGAAGGGAGAGCGGAGGAGGGGAAAGGGTCACG
ACGGGCTGTACCAGGGACTGAGCACCGCCACTAAGGATACCTACGATGCC
TTGCATATGCAAGCACTCCCACCCCGG

LTG2216: LP-16P1-CD8 TM-41BB-CD3zeta amino acid sequence (SEQ ID NO: 134)

MLLLVTSLLLCELPHPAFLLIPQVQLQQSGPGLVKPSQTLSLTCDISGDSVSSN
SAAWNWIRQSPSRGLEWLGRTYYRSKWYNDYAVSVKSRITINPDTSKNQFSL
QLNSVTPEDTAVYYCAQEIEPHDAFDIWDQGTMVTVSSGGGGSGGGGSGGG
GSVIQMTQSPSSVSASVGDKVTITCRASQDVSGWLAWYQQKPGLAPQLLISG
ASSLQGGVPSRFSGSGSGTDFTLTISSLQPEDFATYYCQQAKYFPYTFGQGTK
LEIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGHDGLYQ
GLSTATKDTYDALHMQALPPR

FIGURE 20

LTG2217: LP-16P3v2-CD8 TM-41BB-CD3zeta nucleic acid sequence (SEQ ID NO: 143)
ATGTTGCTGCTCGTGACCTCGCTCCTTCTGTGCGAGCTGCCCCATCCGGCT
TTTCTGCTCATCCCTCAAGTGCAGCTGCAGCAGTCCGGTCCTGGACTGGTC
AAGCACTCCCAGACTCTGAGCCTGGCCTGCGCGATTAGCGGGGACTCAGT
CTCGTCCAATTCGGCGGCCTGGAACTGGATCCGGCAGTCACCATCAAGGG
GCCTGGAATGGCTCGGGCGCACTTACTACCGGTCCAAATGGTATAACGAC
TACGCCGTGTCCGTGAAGTCCCGGATCACCATTAACCCCGACACCTCGAA
GAACCAGTTCTCACTCCAACTGAACAGCGTGACCCCCGAGGATACCGCGG
TGTACTACTGCGCACAAGAAGTGCAGCCGCAGGACGCCCTGGACATTTGG
GGGCAGGGAACGATGGTCACAGTGTCGTCCGGTGGAGGAGGTTCCGGAG
GCGGTGGATCTGGAGGCGGAGGTTCGGATATCCAGATGACCCAGAGCCCC
TCCTTCGTGTCCGCATCCGTGGGCGATAAGGTCATTATTACCTGTAGAGCG
TCCCAGGACGTGTCCGGATGGCTGGCCTGGTACCAGCAGAAGCCAGGCTT
GGCTCCTCAACTGCTGATCTCCGGCGCCAGCACTCTTCAGGGGGAAGTGC
CATCACGCTTCTCCGGATCCGGTTCCGGCACCGACTTCACCCTGACCATCA
GCAGCCTCCAGCCTGAGGACTTCGCCACTTACTACTGCCAACAGGCCAAG
TACTTCCCCTATACCTTCGGACAAGGCACTAAGCTGGAAATCAAGGCGGC
CGCAACTACCACCCCTGCCCCTCGGCCGCCGACTCCGGCCCCAACCATCG
CAAGCCAACCCCTCTCCTTGCGCCCCGAAGCTTGCCGCCCGGCCGCGGGT
GGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGC
AGATTCCCTGAGGAGGAAGAGGGGGGATGCGAACTGCGCGTCAAGTTCTC
ACGGTCCGCCGACGCCCCCGCATATCAACAGGGCCAGAATCAGCTCTACA
ACGAGCTGAACCTGGGAAGGAGAGAGGAGTACGACGTGCTGGACAAGCG
ACGCGGACGCGACCCGGAGATGGGGGGAAACCACGGCGGAAAAACCCT
CAGGAAGGACTGTACAACGAACTCCAGAAAGACAAGATGGCGGAAGCCT
ACTCAGAAATCGGGATGAAGGGAGAGCGGAGGAGGGGAAAGGGTCACG
ACGGGCTGTACCAGGGACTGAGCACCGCCACTAAGGATACCTACGATGCC
TTGCATATGCAAGCACTCCCACCCCGG LTG2217: LP-16P3v2-CD8 TM-41BB-CD3zeta amino acid sequence (SEQ ID NO: 144)

MLLLVTSLLLCELPHPAFLLIPQVQLQQSGPGLVKHSQTLSLACAISGDSVSSN
SAAWNWIRQSPSRGLEWLGRTYYRSKWYNDYAVSVKSRITINPDTSKNQFSL
QLNSVTPEDTAVYYCAQEVQPQDALDIWGQGTMVTVSSGGGGSGGGGSGG
GGSDIQMTQSPSFVSASVGDKVIITCRASQDVSGWLAWYQQKPGLAPQLLISG
ASTLQGEVPSRFSGSGSGTDFTLTISSLQPEDFATYYCQQAKYFPYTFGQGTKL
EIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGHDGLYQ
GLSTATKDTYDALHMQALPPR

FIGURE 2P

LTG2218: LP-16P8-CD8 TM-41BB-CD3zeta nucleic acid sequence (SEQ ID NO: 153)
ATGTTGCTGCTCGTGACCTCGCTCCTTCTGTGCGAGCTGCCCCATCCGGCT
TTTCTGCTCATCCCTCAAGTGCAGCTGCAGCAGTCCGGTCCTGGACTGGTC
AAGCCGTCCCAGACTCTGAGCCTGACTTGCGCAATTAGCGGGGACTCAGT
CTCGTCCAATTCGGCGGCCTGGAACTGGATCCGGCAGTCACCATCAAGGG
GCCTGGAATGGCTCGGGCGCACTTACTACCGGTCCAAATGGTATACCGAC
TACGCCGTGTCCGTGAAGAATCGGATCACCATTAACCCCGACACCTCGAA
GAACCAGTTCTCACTCCAACTGAACAGCGTGACCCCCGAGGATACCGCGG
TGTACTACTGCGCACAAGAAGTGGAACCGCAGGACGCCTTCGACATTTGG
GGACAGGGAACGATGGTCACAGTGTCGTCCGGTGGAGGAGGTTCCGGAG
GCGGTGGATCTGGAGGCGGAGGTTCGGATATCCAGATGACCCAGAGCCCC
TCCTCGGTGTCCGCATCCGTGGGCGATAAGGTCACCATTACCTGTAGAGC
GTCCCAGGACGTGTCCGGATGGCTGGCCTGGTACCAGCAGAAGCCAGGCT
TGGCTCCTCAACTGCTGATCTTCGGCGCCAGCACTCTTCAGGGGGAAGTG
CCATCACGCTTCTCCGGATCCGGTTCCGGCACCGACTTCACCCTGACCATC
AGCAGCCTCCAGCCTGAGGACTTCGCCACTTACTACTGCCAACAGGCCAA
GTACTTCCCCTATACCTTCGGAAGAGGCACTAAGCTGGAAATCAAGGCGG
CCGCAACTACCACCCCTGCCCCTCGGCCGCCGACTCCGGCCCCAACCATC
GCAAGCCAACCCCTCCTTGCGCCCCGAAGCTTGCCGCCCGGCCGCGGG
TGGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGC
AGATTCCCTGAGGAGGAAGAGGGGGGATGCGAACTGCGCGTCAAGTTCTC
ACGGTCCGCCGACGCCCCCGCATATCAACAGGGCCAGAATCAGCTCTACA
ACGAGCTGAACCTGGGAAGGAGAGAGGAGTACGACGTGCTGGACAAGCG
ACGCGGACGCGACCCGGAGATGGGGGGGAAACCACGGCGGAAAAACCCT
CAGGAAGGACTGTACAACGAACTCCAGAAAGACAAGATGGCGGAAGCCT
ACTCAGAAATCGGGATGAAGGGAGAGCGGAGGAGGGGAAAGGGTCACG
ACGGGCTGTACCAGGGACTGAGCACCGCCACTAAGGATACCTACGATGCC
TTGCATATGCAAGCACTCCCACCCCGG LTG2218: LP-16P8-CD8 TM-41BB-CD3zeta amino acid sequence (SEQ ID NO: 154)

MLLLVTSLLLCELPHPAFLLIPQVQLQQSGPGLVKPSQTLSLTCAISGDSVSSN
SAAWNWIRQSPSRGLEWLGRTYYRSKWYTDYAVSVKNRITINPDTSKNQFSL
QLNSVTPEDTAVYYCAQEVEPQDAFDIWGQGTMVTVSSGGGGSGGGGSGGG
GSDIQMTQSPSSVSASVGDKVTITCRASQDVSGWLAWYQQKPGLAPQLLIFG
ASTLQGEVPSRFSGSGSGTDFTLTISSLQPEDFATYYCQQAKYFPYTFGRGTKL
EIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGHDGLYQ
GLSTATKDTYDALHMQALPPR

FIGURE 2Q

LTG2219: LP-16P13-CD8 TM-41BB-CD3zeta nucleic acid sequence (SEQ ID NO: 163)
ATGTTGCTGCTCGTGACCTCGCTCCTTCTGTGCGAGCTGCCCCATCCGGCT
TTTCTGCTCATCCCTCAAGTGCAGCTGCAGCAGTCCGGTCCTGGACTGGTC
AAGCCGTCCCAGACTCTGAGCCTGACTTGCGCCATTAGCGGGAACTCAGT
CTCGTCCAATTCGGCGGCCTGGAACTGGATCCGGCAGTCACCATCAAGGG
GCCTGGAATGGCTCGGGCGCACTTACTACCGGTCCAAATGGTATAACGAC
TACGCCGTGTCCGTGAAGTCCCGGATCACCATTAACCCCGACACCTCGAA
GAACCAGTTCTCACTCCAACTGAACAGCGTGACCCCCGAGGATACCGCGG
TGTACTACTGCGCACAAGAAGTGGAACCGCAGGACGCCTTCGACATTTGG
GGACAGGGAACGATGGTCACAGTGTCGTCCGGTGGAGGAGGTTCCGGAG
GCGGTGGATCTGGAGGCGGAGGTTCGGATATCCAGATGACCCAGAGCCCC
TCCTCGGTGTCCGCATCCGTGGGCGATAAGGTCACCATTACCTGTAGAGC
GTCCCAGGACGTGTCCGGATGGCTGGCCTGGTACCAGCAGAAGCCAGGCT
TGGCTCCTCAACTGCTGATCTTTGGCGCCAGCACTCTTCAGGGGGAGGTGC
CATCACGCTTCTCCGGAGGTGGTTCCGGCACCGACTTCACCCTGACCATCA
GCAGCCTCCAGCCTGAGGACTTCGCCACTTACTACTGCCAACAGGCCAAG
TACTTCCCCTATACCTTCGGACAAGGCACTAAGCTGGAAATCAAGGCGGC
CGCAACTACCACCCCTGCCCCTCGGCCGCCGACTCCGGCCCCAACCATCG
CAAGCCAACCCCTCTCCTTGCGCCCCGAAGCTTGCCGCCCGGCCGCGGGT
GGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGC
AGATTCCCTGAGGAGGAAGAGGGGGGATGCGAACTGCGCGTCAAGTTCTC
ACGGTCCGCCGACGCCCCCGCATATCAACAGGGCCAGAATCAGCTCTACA
ACGAGCTGAACCTGGGAAGGAGAGAGGAGTACGACGTGCTGGACAAGCG
ACGCGGACGCGACCCGGAGATGGGGGGGAAACCACGGCGGAAAAACCCT
CAGGAAGGACTGTACAACGAACTCCAGAAAGACAAGATGGCGGAAGCCT
ACTCAGAAATCGGGATGAAGGGAGAGCGGAGGAGGGGAAAGGGTCACG
ACGGGCTGTACCAGGGACTGAGCACCGCCACTAAGGATACCTACGATGCC
TTGCATATGCAAGCACTCCCACCCCGG LTG2219: LP-16P13-CD8 TM-41BB-CD3zeta amino acid sequence (SEQ ID NO: 164)

MLLLVTSLLLCELPHPAFLLIPQVQLQQSGPGLVKPSQTLSLTCAISGNSVSSN
SAAWNWIRQSPSRGLEWLGRTYYRSKWYNDYAVSVKSRITINPDTSKNQFSL
QLNSVTPEDTAVYYCAQEVEPQDAFDIWGQGTMVTVSSGGGGSGGGGSGGG
GSDIQMTQSPSSVSASVGDKVTITCRASQDVSGWLAWYQQKPGLAPQLLIFG
ASTLQGEVPSRFSGGGSGTDFTLTISSLQPEDFATYYCQQAKYFPYTFGQGTK
LEIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGHDGLYQ
GLSTATKDTYDALHMQALPPR

FIGURE 2R

LTG2220: LP-16P15-CD8 TM-41BB-CD3zeta nucleic acid sequence (SEQ ID NO: 173)

ATGTTGCTGCTCGTGACCTCGCTCCTTCTGTGCGAGCTGCCCCATCCGGCT
TTTCTGCTCATCCCTCAAGTGCAGCTGCAGCAGTCCGGTCCTGGACTGGTC
AAGCCGTCCCAGACTCTGAGCCTGACTTGCGCGATTAGCGGGGACTCAGT
CTCGTCCAATTCGGCGGCCTGGAACTGGATCCGGCAGTCACCATCAAGGG
GCCTGGAATGGCTCGGGCGCACTTACTACCGGTCCAAATGGTATAACGAC
TACGCCGTGTCCGTGAAGTCCCGGATCACCATTAACCCCGACACCTCGAA
GAACCAGTTCTCACTCCAACTGAACAGCGTGACCCCCGAGGATACCGCGG
TGTACTACTGCGCACAAGAAGTGGAACCGCACGACGCCCTGGACATTTGG
GGTCAGGGAACGATGGTCACAGTGTCGTCCGGTGGAGGAGGTTCCGGAG
GCGGTGGATCTGGAGGCGGAGGTTCGGATATCCAGATGACCCAGAGCCCC
TCCTCGGTGTCCGCATCCGTGGGCGATAAGGTCACCATTACCTGTAGAGC
GTCCCAGGACGTGTCCGGATGGCTGGCCTGGTACCAGCAGAAGCCAGGCT
TGGCTCCTCAACTGCTGATCTTCGGCGCCAGCACACTTCAGGGGGAGGTG
CCATCACGCTTCTCCGGATCCGGTTCCGGCACCGACTTCACCCTGACCATC
AGCAGCCTCCAGCCTGAGGACTTCGCCACTTACTACTGCCAACAGGCCAA
GTACTTCCCCTATACCTTCGGACAAGGCACTAAGCTGGAAATCAAGGCGG
CCGCAACTACCACCCCTGCCCCTCGGCCGCCGACTCCGGCCCCAACCATC
GCAAGCCAACCCCTCTCCTTGCGCCCCGAAGCTTGCCGCCCGGCCGCGGG
TGGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGC
AGATTCCCTGAGGAGGAAGAGGGGGGATGCGAACTGCGCGTCAAGTTCTC
ACGGTCCGCCGACGCCCCCGCATATCAACAGGGCCAGAATCAGCTCTACA
ACGAGCTGAACCTGGGAAGGAGAGAGGAGTACGACGTGCTGGACAAGCG
ACGCGGACGCGACCCGGAGATGGGGGGGAAACCACGGCGGAAAAACCCT
CAGGAAGGACTGTACAACGAACTCCAGAAAGACAAGATGGCGGAAGCCT
ACTCAGAAATCGGGATGAAGGGAGAGCGGAGGAGGGGAAAGGGTCACG
ACGGGCTGTACCAGGGACTGAGCACCGCCACTAAGGATACCTACGATGCC
TTGCATATGCAAGCACTCCCACCCCGG

LTG2220: LP-16P15-CD8 TM-41BB-CD3zeta amino acid sequence (SEQ ID NO: 174)

MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAQEVEPHDALDIWGQGTMVTVSSGGGGSGGGGSGG
GGSDIQMTQSPSSVSASVGDKVTITCRASQDVSGWLAWYQQKPGLAPQLLIF
GASTLQGEVPSRFSGSGSGTDFTLTISSLQPEDFATYYCQQAKYFPYTFGQGT
KLEIKAAATTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSC
RFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGL
YQGLSTATKDTYDALHMQALPPR

FIGURE 7A
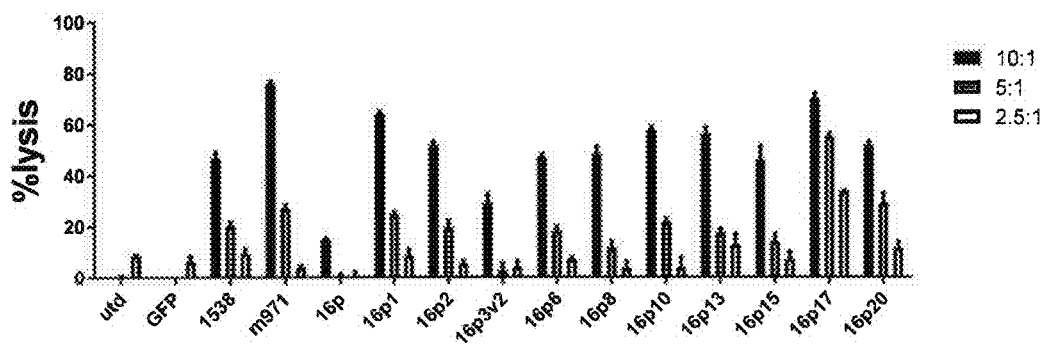
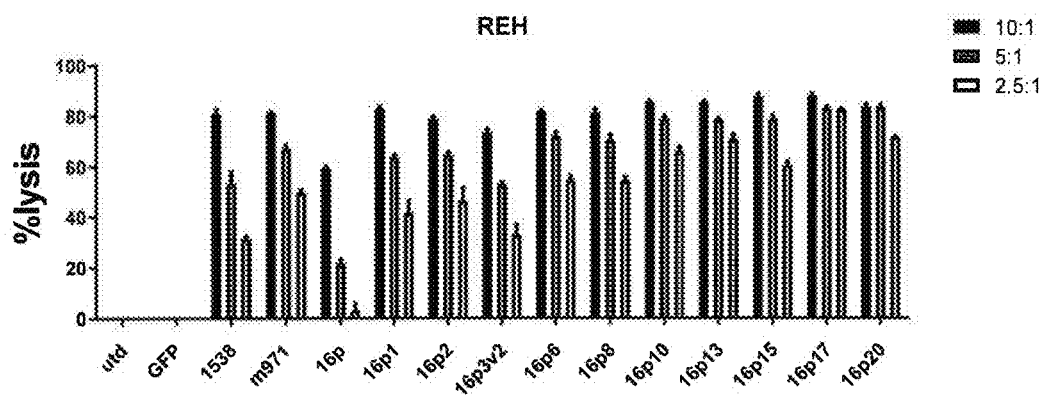
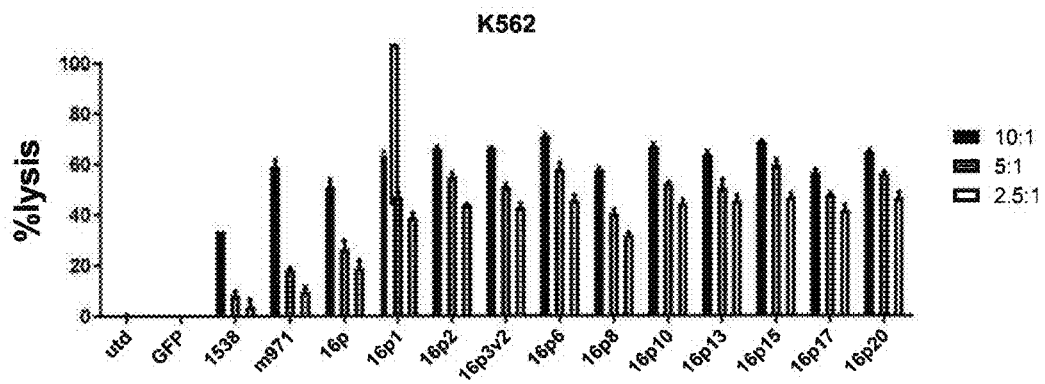

SEQUENCE LISTING

<160> NUMBER OF SEQ ID NOS: 206

<210> SEQ ID NO 1
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caagtacaac tccagcaaag cgggcctggt ctggtgaagc cgtcacagac gctttcactt     60
acgtgtgcga tctccggtga ctccgtgagt tctaatagcg cggcttggaa ctggattagg    120
cagtctccat cccgaggatt ggaatggctc ggcaggactt attatagaag taagtggtac    180
aacgattatg cagtctctgt gaaatctcgc atcaccatta cccagacac gtctaagaat     240 cagttcagtc ttcaactcaa ctctgtaacc cccgaagata cagcggtcta ctactgtgct    300
caggaggtgc aacccacga tgcttttgat atctggggcc agggtaccat ggttacggtg     360
tcttctgggg gaggggggtc cggtggggga ggatcagggg gtggggcag cgacatacaa     420 atgacgcaat ccccgtcttc tgtttctgcg tctgtcggag ataaagtaac aataacctgt    480
cgagcgtcac aggacgttag tggctggctt gcgtggtatc agcaaaaacc ggggctcgcc    540
ccgcaattgc ttatatttgg agcgagtact cttcagggcg aggtacctag cagattttct    600
gggtccggct caggtacgga cttcaccctg accatatcta gcttgcagcc tgaagatttc    660
gccacctact attgtcaaca ggcgaagaac tttccatata cgttcgggca gggtacgaaa    720
ttggagataa aa                                                        732

<210> SEQ ID NO 2
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Gln Val Gln Leu Gln Gln Ser Gly Pro Gly Leu Val Lys Pro Ser Gln
1               5                   10                  15
Thr Leu Ser Leu Thr Cys Ala Ile Ser Gly Asp Ser Val Ser Ser Asn
            20                  25                  30
Ser Ala Ala Trp Asn Trp Ile Arg Gln Ser Pro Ser Arg Gly Leu Glu
        35                  40                  45
Trp Leu Gly Arg Thr Tyr Tyr Arg Ser Lys Trp Tyr Asn Asp Tyr Ala
    50                  55                  60
Val Ser Val Lys Ser Arg Ile Thr Ile Asn Pro Asp Thr Ser Lys Asn
65                  70                  75                  80
Gln Phe Ser Leu Gln Leu Asn Ser Val Thr Pro Glu Asp Thr Ala Val
                85                  90                  95
Tyr Tyr Cys Ala Gln Glu Val Gln Pro His Asp Ala Phe Asp Ile Trp
            100                 105                 110
Gly Gln Gly Thr Met Val Thr Val Ser Ser Gly Gly Gly Gly Ser Gly
        115                 120                 125
Gly Gly Gly Ser Gly Gly Gly Ser Asp Ile Gln Met Thr Gln Ser
    130                 135                 140
Pro Ser Ser Val Ser Ala Ser Val Gly Asp Lys Val Thr Ile Thr Cys
145                 150                 155                 160
Arg Ala Ser Gln Asp Val Ser Gly Trp Leu Ala Trp Tyr Gln Gln Lys
                165                 170                 175
Pro Gly Leu Ala Pro Gln Leu Leu Ile Phe Gly Ala Ser Thr Leu Gln
            180                 185                 190
Gly Glu Val Pro Ser Arg Phe Ser Gly Ser Gly Ser Gly Thr Asp Phe
        195                 200                 205
Thr Leu Thr Ile Ser Ser Leu Gln Pro Glu Asp Phe Ala Thr Tyr Tyr
    210                 215                 220
Cys Gln Gln Ala Lys Asn Phe Pro Tyr Thr Phe Gly Gln Gly Thr Lys
225                 230                 235                 240
Leu Glu Ile Lys Arg
                245
```

<210> SEQ ID NO 3
<211> LENGTH: 1476
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
atgcttctcc tggtgacaag ccttctgctc tgtgagttac cacacccagc attcctcctg      60
atcccacaag tacaactcca gcaaagcggg cctggtctgg tgaagccgtc acagacgctt     120
tcacttacgt gtgcgatctc cggtgactcc gtgagttcta atagcgcggc ttggaactgg     180
attaggcagt ctccatcccg aggattggaa tggctcggca ggacttatta tagaagtaag     240
tggtacaacg attatgcagt ctctgtgaaa tctcgcatca ccattaaccc agacacgtct     300
aagaatcagt tcagtcttca actcaactct gtaaccccccg aagatacagc ggtctactac     360
tgtgctcagg aggtgcaacc ccacgatgct tttgatatct ggggccaggg taccatggtt     420
acggtgtctt ctgggggagg ggggtccggt ggggaggat cagggggtgg gggcagcgac     480
atacaaatga cgcaatcccc cgtcttctgt tctgcgtctg tcggagataa agtaacaata     540
```

-continued

```
acctgtcgag cgtcacagga cgttagtggc tggcttgcgt ggtatcagca aaaaccgggg    600
ctcgccccgc aattgcttat atttggagcg agtactcttc agggcgaggt acctagcaga    660
ttttctgggt ccggctcagg tacggacttc accctgacca tatctagctt gcagcctgaa    720
gatttcgcca cctactattg tcaacaggcg aagaactttc catatacgtt cgggcagggt    780
acgaaattgg agataaaagc ggccgcaact accacccctg cccctcggcc gccgactccg    840
gccccaacca tcgcaagcca acccctctcc ttgcgcccccg aagcttgccg cccggccgcg    900
ggtggagccg tgcatacccg ggggctggac tttgcctgcg atatctacat ttgggccccg    960
ctggccggca cttgcggcgt gctcctgctg tcgctggtca tcacccttta ctgcaagagg   1020
ggccggaaga agctgcttta catcttcaag cagccgttca tgcggcccgt gcagacgact   1080
caggaagagg acggatgctc gtgcagattc cctgaggagg aagagggggg atgcgaactg   1140
cgcgtcaagt tctcacggtc cgccgacgcc cccgcatatc aacagggcca gaatcagctc   1200
tacaacgagc tgaacctggg aaggagagag gagtacgacg tgctggacaa gcgacgcgga   1260
cgcgacccgg agatggggg gaaaccacg cggaaaaacc ctcaggaagg actgtacaac   1320
gaactccaga aagacaagat ggcggaagcc tactcagaaa tcgggatgaa gggagagcgg   1380
aggagggaa agggtcacga cgggctgtac cagggactga gcaccgccac taaggatacc   1440
tacgatgcct tgcatatgca agcactccca ccccgg                              1476
```

<210> SEQ ID NO 4
<211> LENGTH: 492
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Met Leu Leu Leu Val Thr Ser Leu Leu Cys Glu Leu Pro His Pro
 1               5                  10                  15

Ala Phe Leu Leu Ile Pro Gln Val Gln Leu Gln Gln Ser Gly Pro Gly
                20                  25                  30

Leu Val Lys Pro Ser Gln Thr Leu Ser Leu Thr Cys Ala Ile Ser Gly
            35                  40                  45

Asp Ser Val Ser Ser Asn Ser Ala Ala Trp Asn Trp Ile Arg Gln Ser
        50                  55                  60

Pro Ser Arg Gly Leu Glu Trp Leu Gly Arg Thr Tyr Tyr Arg Ser Lys
    65                  70                  75                  80

Trp Tyr Asn Asp Tyr Ala Val Ser Val Lys Ser Arg Ile Thr Ile Asn
                    85                  90                  95

Pro Asp Thr Ser Lys Asn Gln Phe Ser Leu Gln Leu Asn Ser Val Thr
                100                 105                 110

Pro Glu Asp Thr Ala Val Tyr Tyr Cys Ala Gln Glu Val Gln Pro His
            115                 120                 125

Asp Ala Phe Asp Ile Trp Gly Gln Gly Thr Met Val Thr Val Ser Ser
        130                 135                 140

Gly Gly Gly Gly Ser Gly Gly Gly Ser Gly Gly Gly Ser Asp
145                 150                 155                 160

Ile Gln Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190
```

Ala Trp Tyr Gln Gln Lys Pro Gly Leu Ala Pro Gln Leu Leu Ile Phe
            195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Asn Phe Pro Tyr Thr
                245                 250                 255

Phe Gly Gln Gly Thr Lys Leu Glu Ile Lys Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Asp Val Ser Gly Trp
1               5

<210> SEQ ID NO 6
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ala Ser
1

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gln Ala Lys Asn Phe Pro Tyr Thr
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Asp Ser Val Ser Ser Asn Ser Ala Ala
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Tyr Tyr Arg Ser Lys Trp Tyr Asn
1               5

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Gln Glu Val Gln Pro His Asp Ala Phe Asp Ile
1               5                   10

<210> SEQ ID NO 11
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
caagtacagc tgcaacaatc tggccctggg cttgtgaaac cctctcagac tttgtccttg    60
acgtgcgcga taagtggcga ttcagttagt tctaacagcg ccgcttggaa ctggattaga   120
cagagcccca gtcggggact cgaatggctt ggccggactt attatcgcag taaatggtat   180

-continued

```
aatgattatg ctgtgagtgt gaaaagtagg atcacaatca accccgatac gagcaagaat    240
caattctcat tgcaactgaa cagcgtcact cccgaggata cagctgtata ttattgtgca    300
agagaaggtg ggtggtatgg cgagatggat gtatggggga aaggaactac ggtaactgtg    360
tccagtggcg gaggcggttc aggtggtgga ggctctggag gaggagggtc cgaaatcgtg    420
cttacccagt ctccggctac tctgagcgtt agtccgggtg aaagggcctc actctcttgt    480
cgagcttcac agtcagtctc ttcctacttg gcttggtatc agcagaagcc aggtcaggcg    540
ccccgcttgc tcatttacga cgcaagcaca cgagcgacag gcattccaga cagatttttct   600 ggttctggtt ctggcacgga ctttactctt actataaact cacttgaggc agaggatgct    660
gcgacttact attgtcacca atcaagctct ctgccttaca cctttgggca aggcaccaaa    720
ctcgaaatca ag                                                        732
```

```
<210> SEQ ID NO 12
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Gly Gly Trp Tyr Gly Glu Met Asp Val Trp
            100                 105                 110

Gly Lys Gly Thr Thr Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Ala Thr Leu Ser Val Ser Pro Gly Glu Arg Ala Ser Leu Ser Cys
145                 150                 155                 160

Arg Ala Ser Gln Ser Val Ser Ser Tyr Leu Ala Trp Tyr Gln Gln Lys
                165                 170                 175

Pro Gly Gln Ala Pro Arg Leu Leu Ile Tyr Asp Ala Ser Thr Arg Ala
            180                 185                 190

Thr Gly Ile Pro Asp Arg Phe Ser Gly Ser Gly Ser Gly Thr Asp Phe
        195                 200                 205

Thr Leu Thr Ile Asn Ser Leu Glu Ala Glu Asp Ala Ala Thr Tyr Tyr
    210                 215                 220

Cys His Gln Ser Ser Ser Leu Pro Tyr Thr Phe Gly Gln Gly Thr Lys
225                 230                 235                 240

Leu Glu Ile Lys Arg
                245
```

<210> SEQ ID NO 13
<211> LENGTH: 1491
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
atgctgctgt tggtgacatc acttctgctc tgtgaactcc cccatccagc ctttctgctt      60
ataccgcaag tacagctgca acaatctggc cctgggcttg tgaaaccctc tcagactttg     120
tccttgacgt gcgcgataag tggcgattca gttagttcta acagcgccgc ttggaactgg     180
attagacaga gccccagtcg gggactcgaa tggcttggcc ggacttatta tcgcagtaaa     240
tggtataatg attatgctgt gagtgtgaaa agtaggatca caatcaaccc cgatacgagc     300
aagaatcaat tctcattgca actgaacagc gtcactcccg aggatacagc tgtatattat     360
tgtgcaagag aaggtgggtg gtatggcgag atggatgtat gggggaaagg aactacggta     420
actgtgtcca gtggcggagg cggttcaggt ggtggaggct ctggaggagg agggtccgaa     480
atcgtgctta cccagtctcc ggctactctg agcgttagtc cgggtgaaag gcctcactc     540
tcttgtcgag cttcacagtc agtctcttcc tacttggctt ggtatcagca aagccaggt     600
caggcgcccc gcttgctcat ttacgacgca agcacgagg cgacaggcat tccagacaga     660
ttttctggtt ctggttctgg cacggacttt actcttacta taaactcact tgaggcagag     720
gatgctgcga cttactattg tcaccaatca agctctctgc ttacaccctt tgggcaaggc     780
accaaactcg aaatcaaggt tacggtatca tctgcggccg caactaccac ccctgcccct     840
cggccgccga ctccggcccc aaccatcgca agccaacccc tctccttgcg ccccgaagct     900
tgccgcccgg ccgcgggtgg agccgtgcat acccggggggc tggactttgc ctgcgatatc     960
tacatttggg cccccgctgcc cggcacttgc ggcgtgctcc tgctgtcgct ggtcatcacc    1020
ctttactgca agaggggccg gaagaagctg ctttacatct tcaagcagcc gttcatgcgg    1080
cccgtgcaga cgactcagga agaggacgga tgctcgtgca gattccctga ggaggaagag    1140
gggggatgcg aactgcgcgt caagttctca cggtccgccg acgccccgcc atatcaacag    1200
ggccagaatc agctctacaa cgagctgaac ctgggaagga gaggagta cgacgtgctg    1260
gacaagcgac gcggacgcga cccggagatg gggggaaac cacggcggaa aaaccctcag    1320
gaaggactgt acaacgaact ccagaaagac aagatggcgg aagcctactc agaaatcggg    1380
atgaagggag agcggaggag gggaaagggt cacgacgggc tgtaccaggg actgagcacc    1440
gccactaagg ataccacgga tgccttgcat atgcaagcac tcccacccccg g            1491
```

<210> SEQ ID NO 14
<211> LENGTH: 497
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
```

```
            35                  40                  45
Asp Ser Val Ser Ser Asn Ser Ala Ala Trp Asn Trp Ile Arg Gln Ser
 50                  55                  60

Pro Ser Arg Gly Leu Glu Trp Leu Gly Arg Thr Tyr Tyr Arg Ser Lys
65                   70                  75                  80

Trp Tyr Asn Asp Tyr Ala Val Ser Val Lys Ser Arg Ile Thr Ile Asn
                 85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Gly Gly Trp Tyr
        115                 120                 125

Gly Glu Met Asp Val Trp Gly Lys Gly Thr Thr Val Thr Val Ser Ser
    130                 135                 140

Gly Gly Gly Gly Ser Gly Gly Gly Ser Gly Gly Gly Gly Ser Glu
145                 150                 155                 160

Ile Val Leu Thr Gln Ser Pro Ala Thr Leu Ser Val Ser Pro Gly Glu
                165                 170                 175

Arg Ala Ser Leu Ser Cys Arg Ala Ser Gln Ser Val Ser Ser Tyr Leu
            180                 185                 190

Ala Trp Tyr Gln Gln Lys Pro Gly Gln Ala Pro Arg Leu Leu Ile Tyr
        195                 200                 205

Asp Ala Ser Thr Arg Ala Thr Gly Ile Pro Asp Arg Phe Ser Gly Ser
    210                 215                 220

Gly Ser Gly Thr Asp Phe Thr Leu Thr Ile Asn Ser Leu Glu Ala Glu
225                 230                 235                 240

Asp Ala Ala Thr Tyr Tyr Cys His Gln Ser Ser Ser Leu Pro Tyr Thr
                245                 250                 255

Phe Gly Gln Gly Thr Lys Leu Glu Ile Lys Val Thr Val Ser Ser Ala
            260                 265                 270

Ala Ala Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Gly Gly Cys Glu
    370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460
```

```
Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Ser Val Ser Ser Tyr
1               5

<210> SEQ ID NO 16
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Ala Ser
1

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

His Gln Ser Ser Ser Leu Pro Tyr Thr
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Asp Ser Val Ser Ser Asn Ser Ala Ala
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Tyr Tyr Arg Ser Lys Trp Tyr Asn
1               5
```

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Ala Arg Glu Gly Gly Trp Tyr Gly Glu Met Asp Val
1               5                   10

<210> SEQ ID NO 21
<211> LENGTH: 744
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
caagtacagc tccaacagag tggacctggt ctcgttaagc cgtcccaaac actgtctttg      60
acgtgcgcta ttagtggcga cagcgtatca tccaattctg ctgcttggaa ctggattaga     120
cagtcaccgt ccagaggctt ggaatggctg gcaggacgt actaccgctc aaaatggtat     180
aacgattacg cggttagtgt caaatccagg attaccatta accctgacac aagtaagaat     240
cagttttctc ttcagctgaa ttccctgact cctgaggata cggccgttta ctactgtgcc     300
cgagaacacc agaatgaggc ggcttttgat atttgggggc aaggaacaat ggtcacagtt     360
agcagtgggg ggggtggctc cggggaggt ggttccggcg gcggtggttc tcaatccgtc     420
ctgacacaac ctccctcagc gagcgggact cccggtcaaa gggtgaccat ctcttgttct     480
gggggaggta gtaacatcgg gacaaatact gcgtcctggt atcagcaact ccctgggacc     540
gctcccaagt tgttgatata tcgcaatacg caacgaccta gtgggatacc tgatagattc     600
agcggaagca aaagtggtac gagtgcgtct ttggcaatat ctggcctcca gtccgaggac     660
gaagcggatt actattgtgc ggcctgggat gactcactga atggttatgt gttcggtgca     720
ggtactcaac tcaccgtact tggt                                             744
```

<210> SEQ ID NO 22
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Leu Thr Pro Glu Asp Thr Ala Val
                85                  90                  95

```
Tyr Tyr Cys Ala Arg Glu His Gln Asn Glu Ala Ala Phe Asp Ile Trp
            100                 105                 110
Gly Gln Gly Thr Met Val Thr Val Ser Ser Gly Gly Gly Ser Gly
        115                 120                 125
Gly Gly Gly Ser Gly Gly Gly Ser Gln Ser Val Leu Thr Gln Pro
    130                 135                 140
Pro Ser Ala Ser Gly Thr Pro Gly Gln Arg Val Thr Ile Ser Cys Ser
145                 150                 155                 160
Gly Gly Gly Ser Asn Ile Gly Thr Asn Thr Ala Ser Trp Tyr Gln Gln
                165                 170                 175
Leu Pro Gly Thr Ala Pro Lys Leu Leu Ile Tyr Arg Asn Thr Gln Arg
            180                 185                 190
Pro Ser Gly Ile Pro Asp Arg Phe Ser Gly Ser Lys Ser Gly Thr Ser
        195                 200                 205
Ala Ser Leu Ala Ile Ser Gly Leu Gln Ser Glu Asp Glu Ala Asp Tyr
    210                 215                 220
Tyr Cys Ala Ala Trp Asp Asp Ser Leu Asn Gly Tyr Val Phe Gly Ala
225                 230                 235                 240
Gly Thr Gln Leu Thr Val Leu Gly
                245

<210> SEQ ID NO 23
<211> LENGTH: 1488
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
atgcttctcc tggtgacaag ccttctgctc tgtgagttac cacacccagc attcctcctg      60
atcccacaag tacagctcca acagagtgga cctggtctcg ttaagccgtc ccaaacactg     120
tctttgacgt gcgctattag tggcgacagc gtatcatcca attctgctgc ttggaactgg     180
attagacagt caccgtccag aggcttggaa tggctgggca ggacgtacta ccgctcaaaa     240
tggtataacg attacgcggt tagtgtcaaa tccaggatta ccattaaccc tgacacaagt     300
aagaatcagt tttctcttca gctgaattcc ctgactcctg aggatacggc cgtttactac     360
tgtgcccgag aacaccagaa tgaggcggct tttgatattt gggggcaagg aacaatggtc     420
acagttagca gtggggggg tggctccggg ggaggtggtt ccggcggcgg tggttctcaa     480
tccgtcctga cacaacctcc ctcagcgagc gggactcccg gtcaaagggt gaccatctct     540
tgttctgggg gaggtagtaa catcgggaca aatactgcgt cctggtatca gcaactccct     600
gggaccgctc ccaagttgtt gatatatcgc aatacgcaac gacctagtgg gatacctgat     660
agattcagcg gaagcaaaag tggtacgagt gcgtctttgg caatatctgg cctccagtcc     720
gaggacgaag cggattacta ttgtgcggcc tgggatgact cactgaatgg ttatgtgttc     780
ggtgcaggta ctcaactcac cgtacttggt gcggccgcaa ctaccacccc tgcccctcgg     840
ccgccgactc cggccccaac catcgcaagc aacccctct ccttgcgccc gaagcttgc     900 cgcccggccg cgggtggagc cgtgcatacc cgggggctgg actttgcctg cgatatctac     960
atttgggccc cgctggccgg cacttgcggc gtgctcctgc tgtcgctggt catcaccctt    1020
tactgcaaga gggccggaa gaagctgctt tacatcttca gcagccgtt catgcggccc    1080 gtgcagacga ctcaggaaga ggacggatgc tcgtgcagat ccctgagga ggaagagggg    1140
```

-continued

```
ggatgcgaac tgcgcgtcaa gttctcacgg tccgccgacg cccccgcata tcaacagggc    1200
cagaatcagc tctacaacga gctgaacctg gaaggagag aggagtacga cgtgctggac     1260
aagcgacgcg gacgcgaccc ggagatgggg gggaaaccac ggcggaaaaa ccctcaggaa    1320
ggactgtaca cgaactcca gaaagacaag atggcggaag cctactcaga aatcgggatg     1380
aagggagagc ggaggagggg aaagggtcac gacgggctgt accagggact gagcaccgcc   1440
actaaggata cctacgatgc cttgcatatg caagcactcc accccgg                   1488
```

<210> SEQ ID NO 24
<211> LENGTH: 496
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Leu Thr
            100                 105                 110

Pro Glu Asp Thr Ala Val Tyr Tyr Cys Ala Arg Glu His Gln Asn Glu
        115                 120                 125

Ala Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Gln
145                 150                 155                 160

Ser Val Leu Thr Gln Pro Pro Ser Ala Ser Gly Thr Pro Gly Gln Arg
                165                 170                 175

Val Thr Ile Ser Cys Ser Gly Gly Ser Asn Ile Gly Thr Asn Thr
            180                 185                 190

Ala Ser Trp Tyr Gln Gln Leu Pro Gly Thr Ala Pro Lys Leu Leu Ile
        195                 200                 205

Tyr Arg Asn Thr Gln Arg Pro Ser Gly Ile Pro Asp Arg Phe Ser Gly
    210                 215                 220

Ser Lys Ser Gly Thr Ser Ala Ser Leu Ala Ile Ser Gly Leu Gln Ser
225                 230                 235                 240

Glu Asp Glu Ala Asp Tyr Tyr Cys Ala Ala Trp Asp Asp Ser Leu Asn
                245                 250                 255

Gly Tyr Val Phe Gly Ala Gly Thr Gln Leu Thr Val Leu Gly Ala Ala
            260                 265                 270

Ala Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
```

```
                    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Ser Leu
                325                 330                 335

Val Ile Thr Leu Tyr Cys Lys Arg Gly Arg Lys Leu Leu Tyr Ile
                340                 345                 350

Phe Lys Gln Pro Phe Met Arg Pro Val Gln Thr Thr Gln Glu Glu Asp
                355                 360                 365

Gly Cys Ser Cys Arg Phe Pro Glu Glu Glu Gly Gly Cys Glu Leu
            370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
                420                 425                 430

Pro Arg Arg Lys Asn Pro Gln Glu Gly Leu Tyr Asn Glu Leu Gln Lys
                435                 440                 445

Asp Lys Met Ala Glu Ala Tyr Ser Glu Ile Gly Met Lys Gly Glu Arg
                450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Ser Asn Ile Gly Thr Asn Thr
1               5

<210> SEQ ID NO 26
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Asn Thr
1

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Ala Trp Asp Asp Ser Leu Asn Gly Tyr Val
1               5                   10
```

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Asp Ser Val Ser Ser Asn Ser Ala Ala
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Tyr Tyr Arg Ser Lys Trp Tyr Asn
1               5

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Arg Glu His Gln Asn Glu Ala Ala Phe Asp Ile
1               5                   10

<210> SEQ ID NO 31
<211> LENGTH: 729
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
caagtccagt tgcaacagtc cgggccaggt ctggttaagc catcccaaac tctgagtttg     60
acgtgcgcta ttagcggaga ttccgtgtcc agcaattctg caacctggaa ttggatccgg    120
cagagtccga gtggcggttt ggaatggctc ggacgcactt actacaggag caaatggtac    180
gatgattatg ctgtttctgt gcgctctcga atcaccatga atcctgatac ttctaagaac    240
caattttctt tgcagttgaa ctccgtcacg cctgaagata ctgcggtcta ctattgcgca    300
cgcgaaggcg tagccggcga ttttgattac tgggggcaag aacattggt cacggtctcc    360 tctggtggag gaggatcagg aggcgggggt tcaggtggag gtgggagcga tattcaactt    420
acgcagtctc cgagcagtct ttctgcttcc gtgggagacc gagtgacgat tacttgtagg    480
gcatctcagt caataagttc ctatcttaac tggtatcagc agaagcctgg aaaggctcca    540
aaacttctta tttatgccgc atcctcattg caatccggcg tgccttcccg attttccgga    600
tctggctcag gcactgactt taccttgact attagttccc ttcaaccaga agattttgct    660
acctattact gccaacaatc atacagtacc ccatatacat tcggccaagg cacgaaattg    720
gagattaaa                                                            729

<210> SEQ ID NO 32
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Gly Gly Leu Glu
        35                  40                  45

Trp Leu Gly Arg Thr Tyr Tyr Arg Ser Lys Trp Tyr Asp Asp Tyr Ala
    50                  55                  60

Val Ser Val Arg Ser Arg Ile Thr Met Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Gly Val Ala Gly Asp Phe Asp Tyr Trp Gly
            100                 105                 110

Gln Gly Thr Leu Val Thr Val Ser Gly Gly Gly Gly Ser Gly Gly
            115                 120                 125

Gly Gly Ser Gly Gly Gly Ser Asp Ile Gln Leu Thr Gln Ser Pro
130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Tyr Ala Ala Ser Ser Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Thr Pro Tyr Thr Phe Gly Gln Gly Thr Lys Leu
225                 230                 235                 240

Glu Ile Lys Arg

<210> SEQ ID NO 33
<211> LENGTH: 1473
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
atgcttctcc tggtgacaag ccttctgctc tgtgagttac cacacccagc attcctcctg      60
atcccacaag tccagttgca acagtccggg ccaggtctgg ttaagccatc ccaaactctg     120
agtttgacgt gcgctattag cggagattcc gtgtccagca attctgcaac ctggaattgg     180
atccggcaga gtccgagtgg cggtttggaa tggctcggac gcacttacta caggagcaaa     240
tggtacgatg attatgctgt ttctgtgcgc tctcgaatca ccatgaatcc tgatacttct     300

```
aagaaccaat tttctttgca gttgaactcc gtcacgcctg aagatactgc ggtctactat      360
tgcgcacgcg aaggcgtagc cggcgatttt gattactggg ggcaaggaac attggtcacg      420
gtctcctctg gtggaggagg atcaggaggc gggggttcag gtggaggtgg gagcgatatt      480
caacttacgc agtctccgag cagtctttct gcttccgtgg gagaccgagt gacgattact      540
tgtagggcat ctcagtcaat aagttcctat cttaactggt atcagcagaa gcctggaaag      600
gctccaaaac ttcttattta tgccgcatcc tcattgcaat ccggcgtgcc ttccgatttt      660
tccggatctg gctcaggcac tgactttacc ttgactatta gttcccttca accagaagat      720
tttgctacct attactgcca acaatcatac agtaccccat atacattcgg ccaaggcacg      780
aaattggaga ttaaagcggc cgcaactacc accctgccc ctcggccgcc gactccggcc       840
ccaaccatcg caagccaacc cctctccttg cgccccgaag cttgccgccc ggccgcgggt      900
ggagccgtgc atacccgggg gctggacttt gcctgcgata tctacatttg gccccgctg       960 gccggcactt gcggcgtgct cctgctgtcg ctggtcatca cccttactg caagaggggc      1020 cggaagaagc tgctttacat cttcaagcag ccgttcatgc ggcccgtgca gacgactcag     1080
gaagaggacg gatgctcgtg cagattccct gaggaggaag agggggatg cgaactgcgc      1140 gtcaagttct cacggtccgc cgacgccccc gcatatcaac agggccagaa tcagctctac     1200
aacgagctga acctgggaag agagaggag tacgacgtgc tggacaagcg acgcggacgc      1260
gacccggaga tggggggaa accacggcgg aaaaaccctc aggaaggact gtacaacgaa      1320
ctccagaaag acaagatggc ggaagcctac tcagaaatcg ggatgaaggg agagcggagg     1380
aggggaaagg gtcacgacgg gctgtaccag ggactgagca ccgccactaa ggatacctac     1440
gatgccttgc atatgcaagc actcccaccc cgg                                 1473
```

<210> SEQ ID NO 34
<211> LENGTH: 491
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 34

Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Thr Trp Asn Trp Ile Arg Gln Ser
50                  55                  60

Pro Ser Gly Gly Leu Glu Trp Leu Gly Arg Thr Tyr Tyr Arg Ser Lys
65                  70                  75                  80

Trp Tyr Asp Asp Tyr Ala Val Ser Val Arg Ser Arg Ile Thr Met Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Gly Val Ala Gly
        115                 120                 125

Asp Phe Asp Tyr Trp Gly Gln Gly Thr Leu Val Thr Val Ser Ser Gly
    130                 135                 140

Gly Gly Gly Ser Gly Gly Gly Ser Gly Gly Gly Ser Asp Ile
145                 150                 155                 160

Gln Leu Thr Gln Ser Pro Ser Ser Leu Ser Ala Ser Val Gly Asp Arg
                165                 170                 175

Val Thr Ile Thr Cys Arg Ala Ser Gln Ser Ile Ser Ser Tyr Leu Asn
            180                 185                 190

Trp Tyr Gln Gln Lys Pro Gly Lys Ala Pro Lys Leu Leu Ile Tyr Ala
        195                 200                 205

Ala Ser Ser Leu Gln Ser Gly Val Pro Ser Arg Phe Ser Gly Ser Gly
    210                 215                 220

Ser Gly Thr Asp Phe Thr Leu Thr Ile Ser Ser Leu Gln Pro Glu Asp
225                 230                 235                 240

Phe Ala Thr Tyr Tyr Cys Gln Gln Ser Tyr Ser Thr Pro Tyr Thr Phe
                245                 250                 255

Gly Gln Gly Thr Lys Leu Glu Ile Lys Ala Ala Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ser Ile Ser Ser Tyr
1               5

<210> SEQ ID NO 36
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Ala Ser
1

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Gln Ser Tyr Ser Thr Pro Tyr Thr
1               5

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Asp Ser Val Ser Ser Asn Ser Ala Thr
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Tyr Tyr Arg Ser Lys Trp Tyr Asp
1               5

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Arg Glu Gly Val Ala Gly Asp Phe Asp Tyr
1               5                   10

<210> SEQ ID NO 41
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
caagttcagt tgcagcagag tggccctggg cttgttaaac catcacagac gctctcactg      60
acctgtgcca tctctggaga cagtgtaagt tctaactcag ccgcgtggaa ttggattaga     120
caatcaccaa gccggggact tgaatggctt ggtcggacgt actatagatc taagtggtat     180
aatgactacg cagtgtcagt gaaatcacgg ataaccataa accctgacac cagcaaaaac     240
caatttctc ttcagcttaa ttccgtcacg ccagaagata cggccgttta ctactgtgcg      300
agggaaggtg atgacgcatt ggacatctgg ggtcagggga ccatggtgac tgtctcttcc     360
ggcgggggg gtagtggagg gggtggctca ggtggtggcg ggtcagatat acaaatgaca      420
cagagcccta gtagtctgag tgcttcagtg ggcgaccgcg taactataac ctgtagagca     480
tcccaaagca tttcccactt ccttaattgg taccagcaga agccgggcac agcgcccaaa     540
ctcctgatca ccactgcgag cggacttggt tcaggtgttc ctagccggtt tagtgggtca     600
ggtagcggta cagatttcac tctcacgata aactcccttc agcctgagga cctggcgaca     660
tattactgtc aacaatccta taccacccca ctgacattcg gaggggcac aaaactggag      720
atcaaa                                                                 726
```

<210> SEQ ID NO 42
<211> LENGTH: 243
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Gly Asp Asp Ala Leu Asp Ile Trp Gly Gln
            100                 105                 110

Gly Thr Met Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Ser His Phe Leu Asn Trp Tyr Gln Gln Lys Pro Gly
                165                 170                 175

Thr Ala Pro Lys Leu Leu Ile Thr Thr Ala Ser Gly Leu Gly Ser Gly
            180                 185                 190

Val Pro Ser Arg Phe Ser Gly Ser Gly Ser Gly Thr Asp Phe Thr Leu
        195                 200                 205
```

Thr Ile Asn Ser Leu Gln Pro Glu Asp Leu Ala Thr Tyr Tyr Cys Gln
    210                 215                 220

Gln Ser Tyr Thr Thr Pro Leu Thr Phe Gly Gly Gly Thr Lys Leu Glu
225                 230                 235                 240

Ile Lys Arg

<210> SEQ ID NO 43
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

| | | | | |
|---|---|---|---|---|
| atgcttctcc | tggtgacaag | ccttctgctc | tgtgagttac | cacacccagc attcctcctg | 60 |
| atcccacaag | ttcagttgca | gcagagtggc | cctgggcttg | ttaaaccatc acagacgctc | 120 |
| tcactgacct | gtgccatctc | tggagacagt | gtaagttcta | actcagccgc gtggaattgg | 180 |
| attagacaat | caccaagccg | ggacttgaa | tggcttggtc | ggacgtacta tagatctaag | 240 |
| tggtataatg | actacgcagt | gtcagtgaaa | tcacggataa | ccataaaccc tgacaccagc | 300 |
| aaaaaccaat | tttctcttca | gcttaattcc | gtcacgccag | aagatacggc cgtttactac | 360 |
| tgtgcgaggg | aaggtgatga | cgcattggac | atctggggtc | aggggaccat ggtgactgtc | 420 |
| tcttccggcg | ggggggtag | tggaggggt | ggctcaggtg | gtggcgggtc agatatacaa | 480 |
| atgacacaga | gccctagtag | tctgagtgct | tcagtgggcg | accgcgtaac tataacctgt | 540 |
| agagcatccc | aaagcatttc | ccacttcctt | aattggtacc | agcagaagcc gggcacagcg | 600 |
| cccaaactcc | tgatcaccac | tgcgagcgga | cttggttcag | tgttcctag ccggtttagt | 660 |
| gggtcaggta | gcggtacaga | tttcactctc | acgataaact | cccttcagcc tgaggacctg | 720 |
| gcgacatatt | actgtcaaca | atcctatacc | accccactga | cattcggagg ggcacaaaa | 780 |
| ctggagatca | agcggccgc | aactaccacc | cctgcccctc | ggccgccgac tccggcccca | 840 |
| accatcgcaa | gccaaccccct | ctccttgcgc | cccgaagctt | gccgccggc cgcgggtgga | 900 |
| gccgtgcata | cccgggggct | ggactttgcc | tgcgatatct | catttgggc cccgctggcc | 960 |
| ggcacttgcg | gcgtgctcct | gctgtcgctg | gtcatcaccc | tttactgcaa gaggggccgg | 1020 |
| aagaagctgc | tttacatctt | caagcagccg | ttcatgcggc | ccgtgcagac gactcaggaa | 1080 |
| gaggacggat | gctcgtgcag | attccctgag | gaggaagagg | ggggatgcga actgcgcgtc | 1140 |
| aagttctcac | ggtccgccga | cgcccccgca | tatcaacagg | gccagaatca gctctacaac | 1200 |
| gagctgaacc | tgggaaggag | agaggagtac | gacgtgctgg | acaagcgacg cggacgcgac | 1260 |
| ccggagatgg | ggggaaacc | acggcggaaa | aaccctcagg | aaggactgta caacgaactc | 1320 |
| cagaaagaca | gatggcgga | agcctactca | gaaatcggga | tgaagggaga gcggaggagg | 1380 |
| ggaaagggtc | acgacgggct | gtaccaggga | ctgagcaccg | ccactaagga tacctacgat | 1440 |
| gccttgcata | tgcaagcact | cccacccccgg | | | 1470 |

<210> SEQ ID NO 44
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
            35                  40                  45

Asp Ser Val Ser Ser Asn Ser Ala Ala Trp Asn Trp Ile Arg Gln Ser
        50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Gly Asp Asp Ala
            115                 120                 125

Leu Asp Ile Trp Gly Gln Gly Thr Met Val Thr Val Ser Ser Gly Gly
        130                 135                 140

Gly Gly Ser Gly Gly Gly Gly Ser Gly Gly Gly Gly Ser Asp Ile Gln
145                 150                 155                 160

Met Thr Gln Ser Pro Ser Ser Leu Ser Ala Ser Val Gly Asp Arg Val
            165                 170                 175

Thr Ile Thr Cys Arg Ala Ser Gln Ser Ile Ser His Phe Leu Asn Trp
            180                 185                 190

Tyr Gln Gln Lys Pro Gly Thr Ala Pro Lys Leu Leu Ile Thr Thr Ala
            195                 200                 205

Ser Gly Leu Gly Ser Gly Val Pro Ser Arg Phe Ser Gly Ser Gly Ser
210                 215                 220

Gly Thr Asp Phe Thr Leu Thr Ile Asn Ser Leu Gln Pro Glu Asp Leu
225                 230                 235                 240

Ala Thr Tyr Tyr Cys Gln Gln Ser Tyr Thr Thr Pro Leu Thr Phe Gly
            245                 250                 255

Gly Gly Thr Lys Leu Glu Ile Lys Ala Ala Ala Thr Thr Thr Pro Ala
            260                 265                 270

Pro Arg Pro Pro Thr Pro Ala Pro Thr Ile Ala Ser Gln Pro Leu Ser
            275                 280                 285

Leu Arg Pro Glu Ala Cys Arg Pro Ala Ala Gly Gly Ala Val His Thr
        290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
            325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
            355                 360                 365

Pro Glu Glu Glu Glu Gly Gly Cys Glu Leu Arg Val Lys Phe Ser Arg
            370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

```
Arg Gly Arg Asp Pro Glu Met Gly Gly Lys Pro Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ser Ile Ser His Phe
1               5

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Ala Ser
1

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Gln Ser Tyr Thr Thr Pro Leu Thr
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Asp Ser Val Ser Ser Asn Ser Ala Ala
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 49

Thr Tyr Tyr Arg Ser Lys Trp Tyr Asn
1               5

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Arg Glu Gly Asp Asp Ala Leu Asp Ile
1               5                   10

<210> SEQ ID NO 51
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
cagatacagt tgcagcagtc aggtccagga ctagtgaagc cctcgcagac cctctcactc      60
acctgtgcca tctccgggga cagtgtctct agcaacagtg ctgcttggaa ctggatcagg     120
cagtccccat cgagaggcct tgagtggctg gaaggacat actacaggtc aagtggtat      180
aatgattatg cagtatctgt gaaaagtcga ataaccatca cccagacac atccaagaac     240
cagttctccc tgcagctgaa ctctgtgact cccgaggaca cggctgtgta ttactgtgcc     300
caagaggtac aacctgatga tgctttagat atctggggcc aagggacaat ggtcaccgtc     360
tcttcaggag gtggcgggtc tggcggtgga ggtagcggtg gtggcggatc cgacatccag     420
atgacccagt ctccatcttc cgtgtctgca tctgtaggag acaaagtcac catcacttgt     480
cgggcgagtc aggatgttag cggctggtta gcctggtatc agcagaaacc agggctagcc     540
cctcagctcc tgatctctgg tgcatccact ttgcaaggtg aagtcccatc aaggttcagc     600
ggcagtggat ctgggacaga ttttactctc accatcagca gcctgcagcc tgaagatttt     660
gccacttatt attgtcaaca ggctaaaaat ttcccttaca cttttggcca ggggaccaag     720
ctggaaatca aa                                                        732
```

<210> SEQ ID NO 52
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Ile Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

```
Val Ser Val Lys Ser Arg Ile Thr Ile Asn Pro Asp Thr Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Gln Glu Val Gln Pro Asp Asp Ala Leu Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Ser Asp Ile Gln Met Thr Gln Ser
130                 135                 140

Pro Ser Ser Val Ser Ala Ser Val Gly Asp Lys Val Thr Ile Thr Cys
145                 150                 155                 160

Arg Ala Ser Gln Asp Val Ser Gly Trp Leu Ala Trp Tyr Gln Gln Lys
                165                 170                 175

Pro Gly Leu Ala Pro Gln Leu Leu Ile Ser Gly Ala Ser Thr Leu Gln
            180                 185                 190

Gly Glu Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ala Lys Asn Phe Pro Tyr Thr Phe Gly Gln Gly Thr Lys
225                 230                 235                 240

Leu Glu Ile Lys
```

<210> SEQ ID NO 53
<211> LENGTH: 1476
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

| | | | | | |
|---|---|---|---|---|---|
| atgttgttgc | ttgtcacaag | ccttcttctc | tgtgagcttc | cgcacccggc | tttcctgctg | 60 |
| atcccgcaga | tacagcttca | gcagtccggc | cccggtctgg | taaagccgtc | ccaaacgctt | 120 |
| tcactcacat | gcgcgatctc | tggtgattct | gtgtcatcca | acagcgcagc | atggaattgg | 180 |
| atccgccaat | cacccagtag | aggcttggag | tggttgggcc | ggactattta | tcgaagtaag | 240 |
| tggtacaatg | attatgcagt | ctcagttaaa | tccaggatca | ctattaaccc | agatacaagt | 300 |
| aaaaaccagt | tctcattgca | acttaattcc | gtaactccgg | aggacactgc | agtatattac | 360 |
| tgcgctcagg | aggtgcagcc | tgatgatgct | ctggacattt | ggggacaagg | cacgatggtc | 420 |
| acggttagtt | ccggggggg | aggttctggc | ggaggtggta | gtgggggggg | cggcagtgac | 480 |
| atccagatga | cacagagtcc | cagcagcgtg | tctgcgtcag | tcgggataa | ggtaacaatt | 540 |
| acgtgtagag | cgagccagga | cgtttccggg | tggctggcgt | ggtaccaaca | aaaacccggt | 600 |
| ctcgctccgc | agttgctcat | ctctggagcg | tccacccttc | agggagaggt | gcctagcaga | 660 |
| ttttctgggt | ctggatccgg | cacggatttt | acacttacga | tttcctctct | tcaacccgaa | 720 |
| gattttgcta | cttactattg | ccagcaggcc | aaaaacttcc | cgtacacgtt | tggacagggc | 780 |
| acaaagttgg | aaattaaggc | ggccgcaact | accacccctg | cccctcggcc | gccgactccg | 840 |
| gccccaacca | tcgcaagcca | accctctcc | ttgcgccccg | aagcttgccg | cccgccgcg | 900 |
| ggtggagccg | tgcatacccg | ggggctggac | tttgcctgcg | atatctacat | ttgggcccg | 960 |

```
ctggccggca cttgcggcgt gctcctgctg tcgctggtca tcacccttta ctgcaagagg      1020
ggccggaaga agctgcttta catcttcaag cagccgttca tgcggcccgt gcagacgact      1080
caggaagagg acggatgctc gtgcagattc cctgaggagg aagaggggg atgcgaactg       1140 cgcgtcaagt tctcacggtc cgccgacgcc cccgcatatc aacagggcca gaatcagctc      1200
tacaacgagc tgaacctggg aaggagagag gagtacgacg tgctggacaa gcgacgcgga      1260
cgcgacccgg agatggggg gaaaccacgg cggaaaaacc ctcaggaagg actgtacaac       1320
gaactccaga agacaagat ggcggaagcc tactcagaaa tcgggatgaa gggagagcgg       1380
aggaggggaa agggtcacga cgggctgtac cagggactga gcaccgccac taaggatacc      1440
tacgatgcct tgcatatgca agcactccca ccccgg                                1476
```

<210> SEQ ID NO 54
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Met Leu Leu Leu Val Thr Ser Leu Leu Leu Cys Glu Leu Pro His Pro
1               5                   10                  15

Ala Phe Leu Leu Ile Pro Gln Ile Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Gln Pro Asp
        115                 120                 125

Asp Ala Leu Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Asn Phe Pro Tyr Thr
                245                 250                 255

Phe Gly Gln Gly Thr Lys Leu Glu Ile Lys Ala Ala Ala Thr Thr Thr
            260                 265                 270
```

```
Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
        290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Ser Leu Val Ile Thr Leu
                325                 330                 335

Tyr Cys Lys Arg Gly Arg Lys Leu Leu Tyr Ile Phe Lys Gln Pro
                340                 345                 350

Phe Met Arg Pro Val Gln Thr Thr Gln Glu Asp Gly Cys Ser Cys
                355                 360                 365

Arg Phe Pro Glu Glu Glu Gly Cys Glu Leu Arg Val Lys Phe
                370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Asp Val Ser Gly Trp
1               5

<210> SEQ ID NO 56
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Ala Ser
1

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 57

Gln Gln Ala Lys Asn Phe Pro Tyr Thr
1               5

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Asp Ser Val Ser Ser Asn Ser Ala Ala
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Tyr Tyr Arg Ser Lys Trp Tyr Asn
1               5

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Gln Glu Val Gln Pro Asp Asp Ala Leu Asp Ile
1               5                   10

<210> SEQ ID NO 61
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
caagtacagt tgcagcagtc aggacctggc cttgtgaaac catcccaaac tctcagcctc        60
acgtgtgcta tttctggtga ctcagtaagt agcaatagcg ctgcttggaa ctggatcaga       120
caatctccct ccagggggtct cgaatggctg ggcgaacct attaccgatc taaatggtat       180
aacgattatg cagtatccgt gaaatccagg attacaatca acccagatac gttcaagaat       240
caattctctc ttcagctcaa ctccgtaact ccagaggaca ctgcggtata ttattgcgcc       300
caagaagtcg agccacacga tgccctcgat atctggggtc aaggtaccat ggttacagtt       360
agtagtgggg gtgggggaag cggggggcggt gggtccggtg gcgggggttc agacatcaag       420
atgacccaat ccccaagctc tgtttcagca tccgtgggcg ataaggtaac cattacatgc       480
agagcgagtc aggacgtttc agggtggctg gcttggtacc agcaaaaacc gggactcgca       540
ccgcagctgt tgattttcgg cgccagtacg cttcagggcg aagtaccgtc caggttcagt       600

```
gggtcaggtt ctggcaccga ttttacgctc acgatatcca gtctccaacc ggaggatttt      660
gctacttatt actgccagca ggctaagtat tttccataca catttggcca ggggacaaag      720
ttggagatca aa                                                          732
```

<210> SEQ ID NO 62
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Phe Lys Asn
65                  70                  75                  80

Gln Phe Ser Leu Gln Leu Asn Ser Val Thr Pro Glu Asp Thr Ala Val
                85                  90                  95

Tyr Tyr Cys Ala Gln Glu Val Glu Pro His Asp Ala Leu Asp Ile Trp
            100                 105                 110

Gly Gln Gly Thr Met Val Thr Val Ser Ser Gly Gly Gly Ser Gly
        115                 120                 125

Gly Gly Gly Ser Gly Gly Gly Ser Asp Ile Lys Met Thr Gln Ser
    130                 135                 140

Pro Ser Ser Val Ser Ala Ser Val Gly Asp Lys Val Thr Ile Thr Cys
145                 150                 155                 160

Arg Ala Ser Gln Asp Val Ser Gly Trp Leu Ala Trp Tyr Gln Gln Lys
                165                 170                 175

Pro Gly Leu Ala Pro Gln Leu Leu Ile Phe Gly Ala Ser Thr Leu Gln
            180                 185                 190

Gly Glu Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ala Lys Tyr Phe Pro Tyr Thr Phe Gly Gln Gly Thr Lys
225                 230                 235                 240

Leu Glu Ile Lys
```

<210> SEQ ID NO 63
<211> LENGTH: 1476
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

```
atgctgcttt tggtaacttc cctccttttg tgcgagctgc cccatccagc gttcctcctc       60
atccctcaag tacagttgca gcagtcagga cctggccttg tgaaaccatc ccaaactctc      120
```

```
agcctcacgt gtgctatttc tggtgactca gtaagtagca atagcgctgc ttggaactgg    180
atcagacaat ctccctccag gggtctcgaa tggctggggc gaacctatta ccgatctaaa    240
tggtataacg attatgcagt atccgtgaaa tccaggatta caatcaaccc agatacgttc    300
aagaatcaat tctctcttca gctcaactcc gtaactccag aggacactgc ggtatattat    360
tgcgcccaag aagtcgagcc acacgatgcc ctcgatatct ggggtcaagg taccatggtt    420
acagttagta gtgggggtgg gggaagcggg ggcggtgggt ccggtggcgg gggttcagac    480
atcaagatga cccaatcccc aagctctgtt tcagcatccg tgggcgataa ggtaaccatt    540
acatgcagag cgagtcagga cgtttcaggg tggctggctt ggtaccagca aaaaccggga    600
ctcgcaccgc agctgttgat tttcggcgcc agtacgcttc agggcgaagt accgtccagg    660
ttcagtgggt caggttctgg caccgatttt acgctcacga tatccagtct ccaaccggag    720
gattttgcta cttattactg ccagcaggct aagtatttc catacacatt tggccagggg    780
acaaagttgg agatcaaagc ggccgcaact accacccctg ccctcggcc gccgactccg    840 gccccaacca tcgcaagcca accctctcc ttgcccccg aagcttgccg cccggccgcg    900
ggtggagccg tgcatacccg ggggctggac tttgcctgcg atatctacat ttgggccccg    960
ctggccggca cttgcggcgt gctcctgctg tcgctggtca tcaccctta ctgcaagagg    1020 ggccggaaga agctgctta catcttcaag cagccgttca tgcggccgt gcagacgact    1080 caggaagagg acgatgctc gtgcagattc cctgaggagg aagaggggg atgcgaactg    1140 cgcgtcaagt tctcacggtc cgccgacgcc cccgcatatc aacagggcca gaatcagctc    1200
tacaacgagc tgaacctggg aaggagagag gagtacgacg tgctggacaa gcgacgcgga    1260
cgcgacccgg agatgggggg gaaaccacgg cggaaaaacc ctcaggaagg actgtacaac    1320
gaactccaga aagacaagat ggcggaagcc tactcagaaa tcgggatgaa gggagagcgg    1380 aggagggaa agggtcacga cgggctgtac cagggactga gcaccgccac taaggatacc    1440
tacgatgcct tgcatatgca agcactccca ccccgg                              1476
```

<210> SEQ ID NO 64
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Phe Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His

```
            115                 120                 125
Asp Ala Leu Asp Ile Trp Gly Gln Gly Thr Met Val Thr Val Ser Ser
130                 135                 140

Gly Gly Gly Gly Ser Gly Gly Gly Ser Gly Gly Gly Ser Asp
145                 150                 155                 160

Ile Lys Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Phe
        195                 200                 205

Gly Ala Ser Thr Leu Gln Gly Glu Val Pro Ser Arg Phe Ser Gly Ser
210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
        370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
        450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 65

Gln Asp Val Ser Gly Trp
1               5

<210> SEQ ID NO 66
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Ala Ser
1

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Gln Ala Lys Tyr Phe Pro Tyr Thr
1               5

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Asp Ser Val Ser Ser Asn Ser Ala Ala
1               5                   10

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Tyr Tyr Arg Ser Lys Trp Tyr Asn
1               5

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Gln Glu Val Glu Pro His Asp Ala Leu Asp Ile
1               5                   10

<210> SEQ ID NO 71
<211> LENGTH: 732
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg gaaggacat actacaggtc caagtggtat      180
aatgattatg cagtatctgt gaaaagtcga ataaccatca acccagacac atccaagaac     240
cagttctccc tgcagctgaa ctctgtgact cccgaggaca cggctgtgta ttactgtgcc     300
caagaggtag aacctcatga tgctcttgat atctggggcc aagggacaat ggtcaccgtc     360
tcttcaggag gtggcgggtc tggcggaggc ggtagcggtg gtggcggatc cgacatccag     420
atgacgcagt ctccatcatc cgtgtctgca tctgtaggag acaaagtcac catcacttgt     480
cgggcgagtc aggatgttag cggctggtta gcctggtatc aacagaaacc agggctagcc     540
cctcagctcc tgatctttgg tgcatccact ttgcaaggtg aagtcccatc aaggttcagc     600
ggcagtggat ctgggacaga ttttactctc accatcagca gcctgcagcc tgaagatttt     660
gccacttatt attgtcaaca ggctaaatat ttcccttaca cttttggcca ggggaccaag     720
ctggagatca aa                                                        732

<210> SEQ ID NO 72
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Gln Glu Val Glu Pro His Asp Ala Leu Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Val Ser Ala Ser Val Gly Asp Lys Val Thr Ile Thr Cys
145                 150                 155                 160

Arg Ala Ser Gln Asp Val Ser Gly Trp Leu Ala Trp Tyr Gln Gln Lys
                165                 170                 175

Pro Gly Leu Ala Pro Gln Leu Leu Ile Phe Gly Ala Ser Thr Leu Gln
```

```
                    180                 185                 190
Gly Glu Val Pro Ser Arg Phe Ser Gly Ser Gly Ser Gly Thr Asp Phe
            195                 200                 205

Thr Leu Thr Ile Ser Ser Leu Gln Pro Glu Asp Phe Ala Thr Tyr Tyr
        210                 215                 220

Cys Gln Gln Ala Lys Tyr Phe Pro Tyr Thr Phe Gly Gln Gly Thr Lys
225                 230                 235                 240

Leu Glu Ile Lys

<210> SEQ ID NO 73
<211> LENGTH: 1476
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
atgctgctcc tcgtaacctc tcttcttctt tgtgagttgc cacatccagc atttcttctg      60
atacctcaag ttcaactcca gcagagtggt ccaggtttgg taaaacccag ccagactctc     120
tcattgacgt gtgccatatc aggtgattca gtttcctcta atagcgcggc atggaattgg     180
atcaggcaaa gccctagtcg cgggctggag tggctcggcc ggacatacta ccgctcaaag     240
tggtacaacg actacgccgt cagcgtaaaa tctcggatta ccattaaccc ggatacttcc     300
aaaaaccaat tctccctgca gcttaacagt gtcacgccgg aagatacggc cgtttattac     360
tgcgcacaag aggtggaacc gcacgacgcc ctcgatatct ggggccaagg cactatggtg     420
accgtcagta gcggaggggg gggttccgga ggaggcggct ctggtggcgg aggatctgat     480
atccaaatga cccaatcacc gtcttcagta tcagcttctg ttggtgacaa agttacgatt     540
acctgtcgag cgtcacagga cgtttctggt tggttggctt ggtatcagca aaaaccaggg     600
cttgcgcctc agttgcttat ttttggggca tctactttgc agggagaggt gccctcccgg     660
ttctccggca gtgggagcgg caccgatttt acacttacca tctcttcctt gcaacccgaa     720
gactttgcga cgtactattg ccagcaggca agtatttttc cctacacttt tggacaaggg     780
actaaacttg aaatcaaggc ggccgcaact accacccctg cccctcggcc gccgactccg     840
gccccaacca tcgcaagcca acccctctcc ttgcgcccog aagcttgccg ccggccgcg      900 ggtggagccg tgcatacccg ggggctggac tttgcctgcg atatctacat ttgggccccg     960
ctggccggca cttgcggcgt gctcctgctg tcgctggtca tcacccttta ctgcaagagg    1020
ggccggaaga gctgctttta catcttcaag cagccgttca tgcggcccgt gcagacgact    1080
caggaagagg acggatgctc gtgcagattc cctgaggagg aagaggggggg atgcgaactg    1140 cgcgtcaagt tctcacggtc cgccgacgcc cccgcatatc aacagggcca gaatcagctc    1200
tacaacgagc tgaacctggg aaggagagag gagtacgacg tgctggacaa gcgacgcgga    1260
cgcgacccgg agatgggggg gaaaccacgg cggaaaaacc ctcaggaagg actgtacaac    1320
gaactccaga agacaagat ggcggaagcc tactcagaaa tcgggatgaa gggagagcgg    1380 aggagggggaa agggtcacga cgggctgtac cagggactga gcaccgccac taaggatacc    1440
tacgatgcct tgcatatgca agcactccca ccccgg                              1476

<210> SEQ ID NO 74
<211> LENGTH: 492
<212> TYPE: PRT
<213> ORGANISM: Artificial Sequence
```

<220> FEATURE:
<223> OTHER INFORMATION: Description of Artificial Sequence: Synthetic polypeptide

<400> SEQUENCE: 74

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Leu Asp Ile Trp Gly Gln Gly Thr Met Val Thr Val Ser Ser
130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Phe
        195                 200                 205

Gly Ala Ser Thr Leu Gln Gly Glu Val Pro Ser Arg Phe Ser Gly Ser
210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
370                 375                 380

Ser Arg Ser Ala Asp Ala Pro Ala Tyr Gln Gln Gly Gln Asn Gln Leu
```

```
              385                 390                 395                 400
Tyr Asn Glu Leu Asn Leu Gly Arg Arg Glu Glu Tyr Asp Val Leu Asp
                    405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
        450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Asp Val Ser Gly Trp
1               5

<210> SEQ ID NO 76
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Ala Ser
1

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Gln Ala Lys Tyr Phe Pro Tyr Thr
1               5

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Asp Ser Val Ser Ser Asn Ser Ala Ala
1               5                   10

<210> SEQ ID NO 79
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Tyr Tyr Arg Ser Lys Trp Tyr Asn
1               5

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Gln Glu Val Glu Pro His Asp Ala Leu Asp Ile
1               5                   10

<210> SEQ ID NO 81
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg gaaggacat actacaggtc caagtggtat      180
aatgattatg cagtatctgt gaaaagtcga ataaccatca acccagacac attcaagaac     240
cagttctccc tgcagctgaa ctctgtgact cccgaggaca cggctgtgta ttactgtgcc     300
caagaggtag aacctcatga tgctcttgat atctggggcc aagggacaat ggtcaccgtc     360
tcttcaggag gtggcgggtc tggcggtgga ggtagcggtg gtggcggatc cgacatcaag     420
atgacccagt ctccatcttc cgtgtctgca tctgtaggag acaaagtcac catcacttgt     480
cgggcgagtc aggatgttag cggctggtta gcctggtatc agcagaaacc agggctagcc     540
cctcagctcc tgatctttgg tgcatccact ttgcaaggtg aagtcccatc aaggttcagc     600
ggcagtggat ctgggacaga ttttactctc accatcagca gcctgcagcc tgaagatttt     660
gccacttatt attgtcaaca ggctaaatat ttcccttaca cttttggcca ggggaccaag     720
ctggaaatca aa                                                         732

<210> SEQ ID NO 82
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30
```

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
 50                  55                  60

Val Ser Val Lys Ser Arg Ile Thr Ile Asn Pro Asp Thr Phe Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Gln Glu Val Glu Pro His Asp Ala Leu Asp Ile Trp
            100                 105                 110

Gly Gln Gly Thr Met Val Thr Val Ser Gly Gly Gly Gly Ser Gly
            115                 120                 125

Gly Gly Gly Ser Gly Gly Gly Ser Asp Ile Lys Met Thr Gln Ser
            130                 135                 140

Pro Ser Ser Val Ser Ala Ser Val Gly Asp Lys Val Thr Ile Thr Cys
145                 150                 155                 160

Arg Ala Ser Gln Asp Val Ser Gly Trp Leu Ala Trp Tyr Gln Gln Lys
                165                 170                 175

Pro Gly Leu Ala Pro Gln Leu Leu Ile Phe Gly Ala Ser Thr Leu Gln
            180                 185                 190

Gly Glu Val Pro Ser Arg Phe Ser Gly Ser Gly Ser Gly Thr Asp Phe
            195                 200                 205

Thr Leu Thr Ile Ser Ser Leu Gln Pro Glu Asp Phe Ala Thr Tyr Tyr
            210                 215                 220

Cys Gln Gln Ala Lys Tyr Phe Pro Tyr Thr Phe Gly Gln Gly Thr Lys
225                 230                 235                 240

Leu Glu Ile Lys

<210> SEQ ID NO 83
<211> LENGTH: 1476
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
atgcttcttt tggtgacttc ccttttgctg tgcgagttgc cacacccgc cttcctgctt        60 attccccaag tccagctcca acaatccgga cccggacttg ttaagccgtc tcagacgttg      120
tcactcacat gcgccatcag tggcgatagc gtgtccagca acagtgccgc atggaattgg      180
atacgacaga gcccttcccg aggattggaa tggctgggac gaacgtacta taggtccaag      240
tggtataacg actacgcggt gtcagttaaa tctcggatta ctataaatcc cgacactttt      300
aagaatcagt tttccctgca actcaattca gtcacaccgg aagatacggc agtgtactat      360
tgcgctcaag aagttgagcc acatgatgcg ctggatattt ggggtcaggg gactatggtg      420
acggtaagca gtgggggcgg gggcagtggc ggaggtggca gcggggggcg ggtggaagcgac     480 attaagatga ctcagtctcc gtcttcagtt tccgcctccg tagggacaa ggttacaatt       540 acttgtcgcg catctcagga tgtctcaggt tggctggctt ggtatcaaca gaagcctggc     600
ctcgcccctc agcttctcat attcggggct agtaccctgc aaggagaagt cccgagcagg     660
ttttccggtt cagggtccgg gacagacttt accttgacca tcagctccct gcaaccggag     720
gacttcgcga cctactattg tcaacaggcg aagtacttcc cctacacgtt cgggcaaggg     780
actaagctcg aaatcaaggc ggccgcaact accaccccctg cccctcggcc gccgactccg     840

-continued

```
gccccaacca tcgcaagcca accoctctcc ttgcgcccg aagcttgccg cccggccgcg    900
ggtggagccg tgcatacccg ggggctggac tttgcctgcg atatctacat ttgggccccg   960
ctggccggca cttgcggcgt gctcctgctg tcgctggtca tcacccttta ctgcaagagg  1020
ggccggaaga agctgcttta catcttcaag cagccgttca tgcggcccgt gcagacgact  1080
caggaagagg acggatgctc gtgcagattc cctgaggagg aagagggggg atgcgaactg  1140
cgcgtcaagt tctcacggtc cgccgacgcc cccgcatatc aacagggcca gaatcagctc  1200
tacaacgagc tgaacctggg aaggagagag gagtacgacg tgctggacaa gcgacgcgga  1260 cgcgaccgg agatggggg gaaaccacgg cggaaaaacc ctcaggaagg actgtacaac   1320
gaactccaga aagacaagat ggcggaagcc tactcagaaa tcgggatgaa gggagagcgg  1380
aggaggggaa agggtcacga cgggctgtac cagggactga gcaccgccac taaggatacc  1440
tacgatgcct tgcatatgca agcactccca ccccgg                            1476
```

<210> SEQ ID NO 84
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Phe Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Leu Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Lys Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Phe
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240
```

-continued

```
Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Asp Val Ser Gly Trp
1               5

<210> SEQ ID NO 86
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Ala Ser
1

<210> SEQ ID NO 87
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gln Gln Ala Lys Tyr Phe Pro Tyr Thr
1               5

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Asp Ser Val Ser Ser Asn Ser Ala Ala
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Thr Tyr Tyr Arg Ser Lys Trp Tyr Asn
1               5

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Gln Glu Val Glu Pro His Asp Ala Leu Asp Ile
1               5                   10

<210> SEQ ID NO 91
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
caggtacagc tgcagcagtc aggtccagga ctggtgaagc cctcgcagac cctctcactc     60
acctgtgcca tctccgggga cagtgtctct agcaacagtg ctgcttggaa ctggatcagg    120
cagtccccat cgagaggcct tgagtggctg ggaaggacat actacaggtc caagtggtat    180
aatgattatg cagtatctgt gaaaagtcga ataaccatca cccagacac atccaagaac    240 cagttctccc tgcagctgaa ctctgtgact cccgaggata cggctgtgta ttactgtgcc    300
caagaggtac aacctgatga tgcttttgat atctggggcc aaggacaat gatcaccgtc    360 tcttcaggag gtggcgggtc tggcggtgga ggtagcggtg gtgcggatc cgacatccag    420 atgacccagt ctccatcttc cgtgtctgca tctgtaggag acaaagtcac catcacttgt    480
```

```
cgggcgagtc aggatgttag cggctggtta gcctggtatc agcagaaacc agggctagcc    540
cctcagctcc tgatctctgg tgcatccact ttgcaaggtg agtcccatc aaggttcagc     600 ggcagtggat ctgggacaga ttttactctc accatcagca gcctgcagcc tgaagatttt    660
gccacttatt attgtcaaca ggctaaaaat ttcccttaca cttttggtca ggggaccaag    720
ctggaaatca aa                                                        732
```

<210> SEQ ID NO 92
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Gln Glu Val Gln Pro Asp Asp Ala Phe Asp Ile Trp
            100                 105                 110

Gly Gln Gly Thr Met Ile Thr Val Ser Ser Gly Gly Gly Gly Ser Gly
        115                 120                 125

Gly Gly Gly Ser Gly Gly Gly Ser Asp Ile Gln Met Thr Gln Ser
    130                 135                 140

Pro Ser Ser Val Ser Ala Ser Val Gly Asp Lys Val Thr Ile Thr Cys
145                 150                 155                 160

Arg Ala Ser Gln Asp Val Ser Gly Trp Leu Ala Trp Tyr Gln Gln Lys
                165                 170                 175

Pro Gly Leu Ala Pro Gln Leu Leu Ile Ser Gly Ala Ser Thr Leu Gln
            180                 185                 190

Gly Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ala Lys Asn Phe Pro Tyr Thr Phe Gly Gln Gly Thr Lys
225                 230                 235                 240

Leu Glu Ile Lys
```

<210> SEQ ID NO 93
<211> LENGTH: 1476
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

```
atgcttcttt tggtgacttc ccttttgctg tgcgagttgc cacaccccgc cttcctgctt      60
attccccaag tacaactcca gcaatcaggg cctggccttg tcaagccgag tcaaaccttg     120
agtttgacgt gtgccatcag cggtgactct gtcagttcaa actccgcagc ttggaactgg     180
attcggcagt cccctccag gggcctcgaa tggcttggac ggacgtacta cagatcaaaa     240
tggtacaacg actacgcagt cagtgtaaaa tcaaggatta cgataaaccc tgatacgagt     300
aaaaaccagt tctctctcca actgaacagc gtcacaccgg aagatacagc cgtgtattac     360
tgtgctcagg aagtgcaacc tgacgacgca tttgacatct ggggtcaggg cacgatgatc     420
accgtgagta gtggaggagg aggcagtggg ggaggcggtt ctggcggggg tgggtctgat     480
atacagatga cacagagtcc ctcctcagtt tccgcctctg ttggagataa ggtgacaatt     540
acatgcaggg cgtcccaaga tgtttctgga tggctcgcat ggtaccaaca gaagccagga     600
ctcgcccctc agctcctcat tagcggcgct agcactctcc aagggggagt accgagcagg     660
ttctctgggt ccggaagtgg gacggacttt accctgacaa tatcctccct tcagccagaa     720
gacttcgcaa cctactattg ccaacaggcg aaaaatttcc cttacacgtt cggccaagga     780
actaaacttg aaatcaaggc ggccgcaact accaccctg cccctcggcc gccgactccg     840
gccccaacca tcgcaagcca acccctctcc ttgcgccccg aagcttgccg cccggccgcg     900
ggtggagccg tgcataccg ggggctggac tttgcctgcg atatctacat ttgggccccg     960
ctggccggca cttgcggcgt gctcctgctg tcgctggtca tcacccttta ctgcaagagg    1020
ggccggaaga agctgcttta catcttcaag cagccgttca tgcggcccgt gcagacgact    1080
caggaagagg acggatgctc gtgcagattc cctgaggagg aagaggggg atgcgaactg    1140
cgcgtcaagt tctcacggtc cgccgacgcc cccgcatatc aacagggcca gaatcagctc    1200
tacaacgagc tgaacctggg aaggagagag gagtacgacg tgctggacaa gcgacgcgga    1260
cgcgacccgg agatggggg gaaaccacg cggaaaaacc ctcaggaagg actgtacaac    1320
gaactccaga aagacaagat ggcggaagcc tactcagaaa tcgggatgaa gggagagcgg    1380
aggagggga agggtcacga cgggctgtac cagggactga gcaccgccac taaggatacc    1440
tacgatgcct tgcatatgca agcactccca ccccgg                              1476
```

<210> SEQ ID NO 94
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

-continued

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Gln Pro Asp
        115                 120                 125

Asp Ala Phe Asp Ile Trp Gly Gln Gly Thr Met Ile Thr Val Ser Ser
130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Asn Phe Pro Tyr Thr
                245                 250                 255

Phe Gly Gln Gly Thr Lys Leu Glu Ile Lys Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 95
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Asp Val Ser Gly Trp
1               5

<210> SEQ ID NO 96
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Ala Ser
1

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Gln Ala Lys Asn Phe Pro Tyr Thr
1               5

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Asp Ser Val Ser Ser Asn Ser Ala Ala
1               5                   10

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Tyr Tyr Arg Ser Lys Trp Tyr Asn
1               5

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Gln Glu Val Gln Pro Asp Asp Ala Phe Asp Ile
```

<210> SEQ ID NO 101
<211> LENGTH: 732
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 101

```
caggtacagc tgcagcagtc aggtccagga ctggtgaagc cctcgcagac cctctcactc    60
acctgtgcca tctccgggga cagtgtctct agcaacagtg ctgcttggaa ctggatcagg   120
cagtccccat cgagaggcct tgagtggctg ggaaggacat actacaggtc caagtggtat   180
aatgattatg cagtatctgt gaaaagtcga ataaccatca acccagacac atccaagaac   240
cagttctccc tgcagctgaa ctctgtgact cccgaggaca cggctgtgta ttactgtgcc   300
caagaggtag aacctcagga tgcttttgat atctggggcc aagggacaat ggtcaccgtc   360
tcttcaggag gtggcgggtc tggtggtggc ggtagcggtg gtggcggatc cgacatccag   420
atgacccagt ctccatcttc cgtgtctgca tctgtaggag acaaagtcac catcacttgt   480
cgggcgagtc aggatgttag cggctggtta gcctggtatc agcagaaacc agggctagcc   540
cctcagctcc tgatctttgg tgcatccact ctgcaaggtg aagtcccatc aaggttcagt   600
ggcagtggat ctgggacaga ttttactctc accatcagca gcctgcagcc tgaagatttt   660
gccacttatt attgtcaaca ggctaaatat ttcccttaca cttttggccc ggggaccaag   720
ctggaaatca aa                                                       732
```

<210> SEQ ID NO 102
<211> LENGTH: 244
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 102

```
Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Gln Glu Val Glu Pro Gln Asp Ala Phe Asp Ile Trp
            100                 105                 110

Gly Gln Gly Thr Met Val Thr Val Ser Gly Gly Gly Gly Ser Gly
        115                 120                 125

Gly Gly Gly Ser Gly Gly Gly Ser Asp Ile Gln Met Thr Gln Ser
    130                 135                 140

Pro Ser Ser Val Ser Ala Ser Val Gly Asp Lys Val Thr Ile Thr Cys
145                 150                 155                 160
```

Arg Ala Ser Gln Asp Val Ser Gly Trp Leu Ala Trp Tyr Gln Gln Lys
                165                 170                 175

Pro Gly Leu Ala Pro Gln Leu Leu Ile Phe Gly Ala Ser Thr Leu Gln
            180                 185                 190

Gly Glu Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ala Lys Tyr Phe Pro Tyr Thr Phe Gly Pro Gly Thr Lys
225                 230                 235                 240

Leu Glu Ile Lys

<210> SEQ ID NO 103
<211> LENGTH: 1476
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
atgcttcttt tggtgacttc ccttttgctg tgcgagttgc cacacccgc cttcctgctt        60
attccccaag tgcagttgca acagtctgga ccaggcctcg taaaaccttc tcaaactttg      120
tcactcactt gtgccatctc aggggacagt gtcagttcca acagtgcggc atggaattgg      180
attaggcaat ccccctctcg aggtctggaa tggcttgggc ggacttacta ccgaagtaag      240
tggtacaacg attatgcagt ttctgtaaaa tcacgaatca ctataaatcc ggacacttct      300
aagaatcagt tctcttttgca gcttaactct gttactcctg aagacacagc cgtatattac      360
tgtgctcaag aggtagagcc gcaagatgcc ttcgacatct ggggccaagg gactatggtg      420
acagtaagct ccggaggtgg gggatcaggg ggaggtgggt ccggtggtgg tggctctgac      480
atacagatga cacagtcccc tagctctgtg tcagcaagtg tcggtgacaa ggttacgata      540
acgtgcaggg ccagtcaaga tgtgtcagga tggttggcgt ggtaccaaca gaaacccggc      600
ttggcaccgc agcttttgat attcggcgcg tccacactcc aaggcgaagt gccttctcgg      660
ttttctggaa gcggcagcgg gacggacttt actttgacaa tatcctccct ccaacccgag      720
gatttcgcga cgtattattg ccagcaagca aaatacttcc catacacctt cgggcctggg      780
accaaactgg agatcaaagc ggccgcaact accacccctg cccctcggcc gccgactccg      840
gcccaacca tcgcaagcca ccccctctcc ttgcgccccg aagcttgccg cccggccgcg      900
ggtggagccg tgcataccg ggggctggac tttgcctgcg atatctacat ttgggccccg      960
ctggccggca cttgcggcgt gctcctgctg tcgctggtca tcacccttta ctgcaagagg     1020
ggccggaaga agctgcttta catcttcaag cagccgttca tgcggcccgt gcagacgact     1080
caggaagagg acggatgctc gtgcagattc cctgaggagg aagagggggg atgcgaactg     1140
cgcgtcaagt tctcacggtc cgccgacgcc cccgcatatc aacagggcca gaatcagctc     1200
tacaacgagc tgaacctggg aaggagagag gagtacgacg tgctggacaa gcgacgcgga     1260
cgcgaccccg agatggggg gaaaccacg cggaaaaacc ctcaggaagg actgtacaac     1320
gaactccaga agacaagat ggcggaagcc tactcagaaa tcgggatgaa gggagagcgg     1380
aggagggaa aggtcacga cgggctgtac cagggactga gcaccgccac taaggatacc     1440
tacgatgcct tgcatatgca agcactccca ccccgg                             1476
```

<210> SEQ ID NO 104
<211> LENGTH: 492
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

```
Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro Gln
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Phe
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Pro Gly Thr Lys Leu Glu Ile Lys Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365
```

Arg Phe Pro Glu Glu Glu Gly Gly Cys Glu Leu Arg Val Lys Phe
          370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
              405                 410                 415

Lys Arg Arg Gly Arg Asp Pro Glu Met Gly Gly Lys Pro Arg Arg Lys
              420                 425                 430

Asn Pro Gln Glu Gly Leu Tyr Asn Glu Leu Gln Lys Asp Lys Met Ala
          435                 440                 445

Glu Ala Tyr Ser Glu Ile Gly Met Lys Gly Glu Arg Arg Arg Gly Lys
          450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
              485                 490

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gln Asp Val Ser Gly Trp
1               5

<210> SEQ ID NO 106
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Ala Ser
1

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Gln Ala Lys Tyr Phe Pro Tyr Thr
1               5

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Asp Ser Val Ser Ser Asn Ser Ala Ala

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Thr Tyr Tyr Arg Ser Lys Trp Tyr Asn
1               5

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Gln Glu Val Glu Pro Gln Asp Ala Phe Asp Ile
1               5                   10

<210> SEQ ID NO 111
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
caggtacagc tgcagcagtc aggtccagga ctggtgaagc actcgcagac cctctcactc      60
acctgtgcca tctccgggga cagtgtctct agcaacagtg ctgcttggaa ctggatcagg     120
cagtccccat cgagaggcct tgagtggctg gaaggacat actacaggtc caagtggtat      180
aatgattatg cagtatctgt gaaaagtcga ataaccatca cccagacac atccaagaac      240 cagttctccc tgcagttgaa ctctgtgact cccgaggaca cggctgtgta ttactgtgcc     300
caagaggtag aacctcatga tgcttttgat atctggggcc aagggacaat ggtcaccgtc     360
tcttcaggag gtggcgggtc tggcggtgga ggtagcggtg gtggcggatc cgacatccag     420
atgacccagt ctccatcttc cgtgtatgca tctgtaggag acaaagtcac catcacttgt     480
cgggcgagtc aggatgttag cggctggtta gcctggtatc agcagaaacc agggctagcc     540
cctcagctcc tgatctctgg tgcatccact ttgcaaggtg aagtcccatc aaggttcagc     600
ggcagtggat ctgggacaga ttttactctc accatcagca gcctgcagcc tgaagatttt     660
gccacttatt attgtcaaca ggctaaatat ttcccttaca cttttggcca ggggaccaag     720
ctggaaatca aa                                                         732

<210> SEQ ID NO 112
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Gln Leu Gln Gln Ser Gly Pro Gly Leu Val Lys His Ser Gln

```
  1               5                  10                 15
Thr Leu Ser Leu Thr Cys Ala Ile Ser Gly Asp Ser Val Ser Ser Asn
             20                  25                 30

Ser Ala Ala Trp Asn Trp Ile Arg Gln Ser Pro Ser Arg Gly Leu Glu
         35                  40                 45

Trp Leu Gly Arg Thr Tyr Tyr Arg Ser Lys Trp Tyr Asn Asp Tyr Ala
     50                  55                 60

Val Ser Val Lys Ser Arg Ile Thr Ile Asn Pro Asp Thr Ser Lys Asn
 65                  70                  75                 80

Gln Phe Ser Leu Gln Leu Asn Ser Val Thr Pro Glu Asp Thr Ala Val
                 85                  90                 95

Tyr Tyr Cys Ala Gln Glu Val Glu Pro His Asp Ala Phe Asp Ile Trp
             100                 105                110

Gly Gln Gly Thr Met Val Thr Val Ser Ser Gly Gly Gly Gly Ser Gly
         115                 120                125

Gly Gly Ser Gly Gly Gly Ser Asp Ile Gln Met Thr Gln Ser
     130                 135                 140

Pro Ser Ser Val Tyr Ala Ser Val Gly Asp Lys Val Thr Ile Thr Cys
145                 150                 155                160

Arg Ala Ser Gln Asp Val Ser Gly Trp Leu Ala Trp Tyr Gln Gln Lys
                 165                 170                175

Pro Gly Leu Ala Pro Gln Leu Leu Ile Ser Gly Ala Ser Thr Leu Gln
             180                 185                190

Gly Glu Val Pro Ser Arg Phe Ser Gly Ser Gly Ser Gly Thr Asp Phe
         195                 200                205

Thr Leu Thr Ile Ser Ser Leu Gln Pro Glu Asp Phe Ala Thr Tyr Tyr
     210                 215                 220

Cys Gln Gln Ala Lys Tyr Phe Pro Tyr Thr Phe Gly Gln Gly Thr Lys
225                 230                 235                240

Leu Glu Ile Lys

<210> SEQ ID NO 113
<211> LENGTH: 1476
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
atgcttcttt tggtgacttc ccttttgctg tgcgagttgc cacacccgc cttcctgctt      60 attccccagg tacagcttca acagagtggg ccgggactgg tgaaacactc ccaaacactt    120
tctctgacgt gcgctatatc aggtgactct gtttcatcta attctgctgc gtggaactgg    180
attcgacaat ctcccagtcg cgggttggaa tggctgggac gaacatatta tcggtctaag    240
tggtataacg attatgctgt atctgttaaa tctcgaatta cgattaatcc tgacacctcc    300
aagaaccagt tctcccctcca gttgaactca gtcacaccgg aagacactgc ggtctactat    360
tgcgctcaag aagtcgagcc acatgatgca ttcgacatct ggggccaggg aacgatggtc    420
accgtcagca gtggcggcgg cggatctggg ggtggcggtt ctggcggtgg aggatcagac    480
atacaaatga cgcagagtcc ctcaagtgtg tacgcgagtg tgggggataa ggtaactatt    540
acgtgcagag cgtcacagga tgttagtgga tggcttgcct ggtatcagca gaagccaggc    600
cttgctccac agctccttat cagtggtgct tctacacttc agggcgaggt tccgagtaga    660
```

```
ttctctggtt ctggatctgg tactgacttc actcttacaa tttcttcttt gcaaccagaa    720
gactttgcga cttattactg ccaacaggcc aaatacttcc cttatacatt tggccaaggt    780
accaagttgg agataaaggc ggccgcaact accacccctg cccctcggcc gccgactccg    840
gccccaacca tcgcaagcca acccctctcc ttgcgcccg aagcttgccg cccggccgcg     900
ggtggagccg tgcatacccg ggggctggac tttgcctgcg atatctacat ttgggccccg   960
ctggccggca cttgcggcgt gctcctgctg tcgctggtca tcacccttta ctgcaagagg   1020
ggccggaaga agctgcttta catcttcaag cagccgttca tgcggcccgt gcagacgact   1080
caggaagagg acggatgctc gtgcagattc cctgaggagg aagagggggg atgcgaactg   1140
cgcgtcaagt tctcacggtc cgccgacgcc cccgcatatc aacagggcca gaatcagctc   1200
tacaacgagc tgaacctggg aaggagagag gagtacgacg tgctggacaa gcgacgcgga   1260
cgcgacccgg agatgggggg gaaaccacgg cggaaaaacc ctcaggaagg actgtacaac   1320
gaactccaga agacaagat ggcggaagcc tactcagaaa tcgggatgaa gggagagcgg    1380
aggagggaa agggtcacga cgggctgtac cagggactga gcaccgccac taaggatacc    1440
tacgatgcct tgcatatgca agcactccca ccccgg                            1476
```

<210> SEQ ID NO 114
<211> LENGTH: 492
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

```
Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
```

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
            245                 250                 255

Phe Gly Gln Gly Thr Lys Leu Glu Ile Lys Ala Ala Ala Thr Thr Thr
        260                 265                 270

Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
        290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
            325                 330                 335

Tyr Cys Lys Arg Gly Arg Lys Lys Leu Leu Tyr Ile Phe Lys Gln Pro
        340                 345                 350

Phe Met Arg Pro Val Gln Thr Thr Gln Glu Glu Asp Gly Cys Ser Cys
        355                 360                 365

Arg Phe Pro Glu Glu Glu Gly Gly Cys Glu Leu Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
            405                 410                 415

Lys Arg Arg Gly Arg Asp Pro Glu Met Gly Gly Lys Pro Arg Arg Lys
        420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
        450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
            485                 490

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gln Asp Val Ser Gly Trp
1               5

<210> SEQ ID NO 116
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Ala Ser

```
<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Gln Ala Lys Tyr Phe Pro Tyr Thr
1               5

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Asp Ser Val Ser Ser Asn Ser Ala Ala
1               5                   10

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Thr Tyr Tyr Arg Ser Lys Trp Tyr Asn
1               5

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Gln Glu Val Glu Pro His Asp Ala Phe Asp Ile
1               5                   10

<210> SEQ ID NO 121
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
caagtacaac ttcaacagtc tgggcctggg cttgtaaaac ctagccaaac tctgtccctc     60
acgtgcgcga tttcagggga cagtgtaagt tccaactcag ccgcatggaa ctggatcagg    120
cagtcacctt caagggggct cgaatggctt ggccgaacgt actacaggag taagtggtac    180
aacgattatg cagtgtctgt gaaatcacgg attactatca atcccgacac gtccaagaac    240
cagttctctc tgcaactcaa ctcagtgaca ccagaggata cggccgttta ctattgtgca    300
```

```
caggaagtgc aacctgatga tgcctttgac atttggggtc agggcacgat ggttacggta    360
agctctgggg gaggcggcag tggagggga ggtagtgggg gagggggatc tgatatacag     420
atgacacaaa gcccgtcatc cgtcagtgct tcagttggtg ataaagtaac cattacgtgc    480
cgcgcttccc aagacgttag cggatggttg gcttggtatc aacaaaaacc ggggttggct    540
ccgcaactcc tcatatccgg tgcgagtacg ctccaaggcg aagtccctag cagattttcc    600
gggagcggtt ccggtacaga tttcacgttg accattagct ctctccagcc cgaagatttt    660
gcaacctact attgccaaca ggccaaaaat tttccatata catttggtca aggcactaag    720
ctcgaaatca aa                                                        732
```

<210> SEQ ID NO 122
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Gln Glu Val Gln Pro Asp Asp Ala Phe Asp Ile Trp
            100                 105                 110

Gly Gln Gly Thr Met Val Thr Val Ser Ser Gly Gly Gly Ser Gly
        115                 120                 125

Gly Gly Gly Ser Gly Gly Gly Ser Asp Ile Gln Met Thr Gln Ser
    130                 135                 140

Pro Ser Ser Val Ser Ala Ser Val Gly Asp Lys Val Thr Ile Thr Cys
145                 150                 155                 160

Arg Ala Ser Gln Asp Val Ser Gly Trp Leu Ala Trp Tyr Gln Gln Lys
                165                 170                 175

Pro Gly Leu Ala Pro Gln Leu Leu Ile Ser Gly Ala Ser Thr Leu Gln
            180                 185                 190

Gly Glu Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ala Lys Asn Phe Pro Tyr Thr Phe Gly Gln Gly Thr Lys
225                 230                 235                 240

Leu Glu Ile Lys
```

<210> SEQ ID NO 123
<211> LENGTH: 1476
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 123
atgcttcttt tggtgacttc ccttttgctg tgcgagttgc cacaccccgc cttcctgctt      60
attccccaag tacaacttca acagtctggg cctgggcttg taaaacctag ccaaactctg     120
tccctcacgt gcgcgatttc aggggacagt gtaagttcca actcagccgc atggaactgg     180
atcaggcagt caccttcaag ggggctcgaa tggcttggcc gaacgtacta caggagtaag     240
tggtacaacg attatgcagt gtctgtgaaa tcacggatta ctatcaatcc cgacacgtcc     300
aagaaccagt tctctctgca actcaactca gtgacaccag aggatacggc cgtttactat     360
tgtgcacagg aagtgcaacc tgatgatgcc tttgacattt ggggtcaggg cacgatggtt     420
acggtaagct ctgggggagg cggcagtgga gggggaggta gtggggagg gggatctgat      480
atacagatga cacaaagccc gtcatccgtc agtgcttcag ttggtgataa agtaaccatt     540
acgtgccgcg cttcccaaga cgttagcgga tggttggctt ggtatcaaca aaaaccgggg     600
ttggctccgc aactcctcat atccggtgcg agtacgctcc aaggcgaagt ccctagcaga     660
ttttccggga gcggttccgg tacagatttc acgttgacca ttagctctct ccagcccgaa     720
gattttgcaa cctactattg ccaacaggcc aaaaattttc catatacatt tggtcaaggc     780
actaagctcg aaatcaaagc ggccgcaact accaccccctg cccctcggcc gccgactccg     840
gccccaacca tcgcaagcca acccctctcc ttgcgccccg aagcttgccg cccggccgcg     900
ggtggagccg tgcatacccg ggggctggac tttgcctgcg atatctacat ttgggccccg     960
ctggccggca cttgcggcgt gctcctgctg tcgctggtca tcacccttta ctgcaagagg    1020
ggccggaaga agctgcttta catcttcaag cagccgttca tgcggcccgt gcagacgact    1080
caggaagagg acggatgctc gtgcagattc cctgaggagg aagaggggg atgcgaactg     1140
cgcgtcaagt tctcacggtc cgccgacgcc cccgcatatc aacagggcca gaatcagctc    1200
tacaacgagc tgaacctggg aaggagagag gagtacgacg tgctggacaa gcgacgcgga    1260
cgcgacccgg agatggggg gaaaccacg cggaaaaacc ctcaggaagg actgtacaac      1320
gaactccaga aagacaagat ggcggaagcc tactcagaaa tcgggatgaa gggagagcgg    1380
aggagggga aggtcacga cgggctgtac cagggactga gcaccgccac taaggatacc    1440
tacgatgcct tgcatatgca agcactccca ccccgg                               1476
```

```
<210> SEQ ID NO 124
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60
```

```
Pro Ser Arg Gly Leu Glu Trp Leu Gly Arg Thr Tyr Arg Ser Lys
 65                  70                  75                  80

Trp Tyr Asn Asp Tyr Ala Val Ser Val Lys Ser Arg Ile Thr Ile Asn
                 85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Gln Pro Asp
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Asn Phe Pro Tyr Thr
                245                 250                 255

Phe Gly Gln Gly Thr Lys Leu Glu Ile Lys Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
```

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Asp Val Ser Gly Trp
1               5

<210> SEQ ID NO 126
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Ala Ser
1

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gln Gln Ala Lys Asn Phe Pro Tyr Thr
1               5

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Asp Ser Val Ser Ser Asn Ser Ala Ala
1               5                   10

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Thr Tyr Tyr Arg Ser Lys Trp Tyr Asn
1               5

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Ala Gln Glu Val Gln Pro Asp Asp Ala Phe Asp Ile
1               5                   10

<210> SEQ ID NO 131
<211> LENGTH: 732
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 131

```
caggtacagc tgcagcagtc aggtccagga ctggtgaagc cctcgcagac cctctcactc      60
acctgtgaca tctccgggga cagtgtctct agcaacagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca cccagacac atccaagaac     240
cagttctccc tgcagctgaa ctctgtgact cccgaggaca cggctgtgta ttactgtgcc     300
caagagatag aacctcatga tgcttttgat atctgggacc aagggacaat ggtcaccgtc     360
tcttcaggag gtggcgggtc tggcggtgga ggtagcggtg gtggcggatc cgtcatccag     420
atgacccagt ctccatcttc cgtgtctgca tctgtaggag acaaagtcac catcacttgt     480
cgggcgagtc aggatgttag cggctggtta gcctggtatc agcagaaacc agggctagcc     540
cctcagctcc tgatctctgg tgcatcctct ttgcaaggtg gagtcccatc aaggttcagc     600
ggcagtggat ctgggacaga ttttactctc accatcagca gcctgcagcc tgaagatttt     660
gccacttatt attgtcaaca ggctaaatat ttcccttaca cttttggcca ggggaccaag     720
ctggaaatca aa                                                         732
```

<210> SEQ ID NO 132
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 132

Gln Val Gln Leu Gln Gln Ser Gly Pro Gly Leu Val Lys Pro Ser Gln
1               5                   10                  15

Thr Leu Ser Leu Thr Cys Asp Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Gln Glu Ile Glu Pro His Asp Ala Phe Asp Ile Trp
            100                 105                 110

Asp Gln Gly Thr Met Val Thr Val Ser Ser Gly Gly Gly Gly Ser Gly
        115                 120                 125

Gly Gly Gly Ser Gly Gly Gly Ser Val Ile Gln Met Thr Gln Ser
            130                 135                 140

Pro Ser Ser Val Ser Ala Ser Val Gly Asp Lys Val Thr Ile Thr Cys
145                 150                 155                 160

Arg Ala Ser Gln Asp Val Ser Gly Trp Leu Ala Trp Tyr Gln Gln Lys
                165                 170                 175

Pro Gly Leu Ala Pro Gln Leu Leu Ile Ser Gly Ala Ser Ser Leu Gln
            180                 185                 190

Gly Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ala Lys Tyr Phe Pro Tyr Thr Phe Gly Gln Gly Thr Lys
225                 230                 235                 240

Leu Glu Ile Lys

<210> SEQ ID NO 133
<211> LENGTH: 1476
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133

```
atgttgctgc tcgtgacctc gctccttctg tgcgagctgc cccatccggc ttttctgctc      60
atccctcaag tgcagctgca gcagtccggt cctggactgg tcaagccgtc ccagactctg     120
agcctgactt gcgatattag cggggactca gtctcgtcca attcggcggc ctggaactgg     180
atccggcagt caccatcaag gggcctggaa tggctcgggc gcacttacta ccggtccaaa     240
tggtataacg actacgccgt gtccgtgaag tcccggatca ccattaaccc cgacacctcg     300
aagaaccagt tctcactcca actgaacagc gtgaccccg  aggataccgc ggtgtactac     360
tgcgcacaag aaatcgaacc gcacgacgcc ttcgacattt gggaccaggg aacgatggtc     420
acagtgtcgt ccggtggagg aggttccgga ggcggtggat ctggaggcgg aggttcggtg     480
atccagatga cccagagccc ctcctcggtg tccgcatccg tgggcgataa ggtcaccatt     540
acctgtagag cgtcccagga cgtgtccgga tggctggcct ggtaccagca gaagccaggc     600
ttggctcctc aactgctgat ctccggcgcc agctcacttc agggggggt  gccatcacgc     660 ttctccggat ccggttccgg caccgacttc accctgacca tcagcagcct ccagcctgag     720
gacttcgcca cttactactg ccaacaggcc aagtacttcc cctataccct cggacaaggc     780
actaagctgg aaatcaaggc ggccgcaact accaccccctg cccctcggcc gcgactccg     840 gccccaacca tcgcaagcca acccctctcc ttgcgccccg aagcttgccg cccggccgcg     900 ggtgagccg  tgcataccg  ggggctggac tttgcctgcg atatctacat ttgggccccg     960
ctggccggca cttgcggcgt gctcctgctg tcgctggtca tcaccctta  ctgcaagagg    1020 ggccggaaga agctgctta  catcttcaag cagccgttca tgcggcccgt gcagacgact    1080
caggaagaga cgggatgctc gtgcagattc cctgaggagg aagaggggg  atgcgaactg    1140 cgcgtcaagt tctcacggtc cgccgacgcc cccgcatatc aacagggcca gaatcagctc    1200
tacaacgagc tgaacctggg aaggagagag gagtacgacg tgctggacaa gcgacgcgga    1260
cgcgaccccg agatgggggg gaaaccacgc cggaaaaacc ctcaggaagg actgtacaac    1320
gaactccaga agacaagat  ggcggaagcc tactcagaaa tcgggatgaa gggagagcgg    1380
``` aggagggggaa agggtcacga cgggctgtac cagggactga gcaccgccac taaggatacc    1440
tacgatgcct tgcatatgca agcactccca ccccgg    1476

<210> SEQ ID NO 134
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Asp Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Ile Glu Pro His
        115                 120                 125

Asp Ala Phe Asp Ile Trp Asp Gln Gly Thr Met Val Thr Val Ser Ser
    130                 135                 140

Gly Gly Gly Gly Ser Gly Gly Gly Ser Gly Gly Gly Gly Ser Val
145                 150                 155                 160

Ile Gln Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Ser Leu Gln Gly Gly Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

-continued

```
Tyr Cys Lys Arg Gly Arg Lys Lys Leu Leu Tyr Ile Phe Lys Gln Pro
                340                 345                 350
Phe Met Arg Pro Val Gln Thr Thr Gln Glu Glu Asp Gly Cys Ser Cys
            355                 360                 365
Arg Phe Pro Glu Glu Glu Glu Gly Cys Glu Leu Arg Val Lys Phe
        370                 375                 380
Ser Arg Ser Ala Asp Ala Pro Ala Tyr Gln Gln Gly Gln Asn Gln Leu
385                 390                 395                 400
Tyr Asn Glu Leu Asn Leu Gly Arg Arg Glu Glu Tyr Asp Val Leu Asp
                405                 410                 415
Lys Arg Arg Gly Arg Asp Pro Glu Met Gly Gly Lys Pro Arg Arg Lys
            420                 425                 430
Asn Pro Gln Glu Gly Leu Tyr Asn Glu Leu Gln Lys Asp Lys Met Ala
        435                 440                 445
Glu Ala Tyr Ser Glu Ile Gly Met Lys Gly Glu Arg Arg Arg Gly Lys
    450                 455                 460
Gly His Asp Gly Leu Tyr Gln Gly Leu Ser Thr Ala Thr Lys Asp Thr
465                 470                 475                 480
Tyr Asp Ala Leu His Met Gln Ala Leu Pro Pro Arg
                485                 490

<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Asp Val Ser Gly Trp
1               5

<210> SEQ ID NO 136
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Ala Ser
1

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gln Gln Ala Lys Tyr Phe Pro Tyr Thr
1               5

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 138

Gly Asp Ser Val Ser Ser Asn Ser Ala Ala
1               5                   10

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Thr Tyr Tyr Arg Ser Lys Trp Tyr Asn
1               5

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Gln Glu Ile Glu Pro His Asp Ala Phe Asp Ile
1               5                   10

<210> SEQ ID NO 141
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
caagtgcagc tgcagcagtc cggtcctgga ctggtcaagc actcccagac tctgagcctg      60
gcctgcgcga ttagcgggga ctcagtctcg tccaattcgg cggcctggaa ctggatccgg     120
cagtcaccat caaggggcct ggaatggctc gggcgcactt actaccggtc caaatggtat     180
aacgactacg ccgtgtccgt gaagtcccgg atcaccatta cccccgacac ctcgaagaac     240
cagttctcac tccaactgaa cagcgtgacc cccgaggata ccgcggtgta ctactgcgca     300
caagaagtgc agccgcagga cgccctggac atttggggc agggaacgat ggtcacagtg     360
tcgtccggtg gaggaggttc cggaggcggt ggatctggag gcggaggttc ggatatccag     420
atgacccaga gcccctcctt cgtgtccgca tccgtgggcg ataaggtcat tattacctgt     480
agagcgtccc aggacgtgtc cggatggctg gcctggtacc agcagaagcc aggcttggct     540
cctcaactgc tgatctccgg cgccagcact cttcaggggg aagtgccatc acgcttctcc     600
ggatccggtt ccggcaccga cttcaccctg accatcagca gcctccagcc tgaggacttc     660
gccacttact actgccaaca ggccaagtac ttccctata ccttcggaca aggcactaag     720
ctggaaatca ag                                                         732

<210> SEQ ID NO 142
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 142

Gln Val Gln Leu Gln Gln Ser Gly Pro Gly Leu Val Lys His Ser Gln
1               5                   10                  15

Thr Leu Ser Leu Ala Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Gln Glu Val Gln Pro Gln Asp Ala Leu Asp Ile Trp
            100                 105                 110

Gly Gln Gly Thr Met Val Thr Val Ser Ser Gly Gly Gly Ser Gly
        115                 120                 125

Gly Gly Gly Ser Gly Gly Gly Ser Asp Ile Gln Met Thr Gln Ser
    130                 135                 140

Pro Ser Phe Val Ser Ala Ser Val Gly Asp Lys Val Ile Ile Thr Cys
145                 150                 155                 160

Arg Ala Ser Gln Asp Val Ser Gly Trp Leu Ala Trp Tyr Gln Gln Lys
                165                 170                 175

Pro Gly Leu Ala Pro Gln Leu Leu Ile Ser Gly Ala Ser Thr Leu Gln
            180                 185                 190

Gly Glu Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ala Lys Tyr Phe Pro Tyr Thr Phe Gly Gln Gly Thr Lys
225                 230                 235                 240

Leu Glu Ile Lys

<210> SEQ ID NO 143
<211> LENGTH: 1476
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
atgttgctgc tcgtgaccct cgctccttct gtgcgagctg cccatccggc ttttctgctc      60
atccctcaag tgcagctgca gcagtccggt cctggactgg tcaagcactc ccagactctg     120
agcctggcct gcgcgattag cggggactca gtctcgtcca attcggcggc ctggaactgg     180
atccggcagt caccatcaag gggcctggaa tggctcgggc gcacttacta ccggtccaaa     240
tggtataacg actacgccgt gtccgtgaag tccggatca ccattaaccc cgacacctcg      300
aagaaccagt tctcactcca actgaacagc gtgaccccg aggataccgc ggtgtactac      360
tgcgcacaag aagtgcagcc gcaggacgcc ctggacattt gggggcaggg aacgatggtc     420
acagtgtcgt ccggtggagg aggttccgga ggcggtggat ctggaggcgg aggttcggat     480
atccagatga cccagagccc ctccttcgtg tccgcatccg tgggcgataa ggtcattatt     540

```
acctgtagag cgtcccagga cgtgtccgga tggctggcct ggtaccagca gaagccaggc    600
ttggctcctc aactgctgat ctccggcgcc agcactcttc aggggaagt gccatcacgc     660 ttctccggat ccggttccgg caccgacttc accctgacca tcagcagcct ccagcctgag    720
gacttcgcca cttactactg ccaacaggcc aagtacttcc cctataccct cggacaaggc    780
actaagctgg aaatcaaggc ggccgcaact accacccctg cccctcggcc gccgactccg    840
gccccaacca tcgcaagcca accctctcc ttgcgccccg aagcttgccg ccggccgcg     900 ggtggagccg tgcataccg ggggctggac tttgcctgcg atatctacat ttgggccccg     960
ctggccggca cttgcggcgt gctcctgctg tcgctggtca tcacccttta ctgcaagagg    1020
ggccggaaga agctgcttta catcttcaag cagccgttca tgcggcccgt gcagacgact    1080
caggaagagg acggatgctc gtgcagattc cctgaggagg aagaggggg atgcgaactg    1140 cgcgtcaagt tctcacggtc cgccgacgcc cccgcatatc aacagggcca gaatcagctc    1200
tacaacgagc tgaacctggg aaggagagag gagtacgacg tgctggacaa gcgacgcgga    1260
cgcgacccgg agatgggggg gaaaccacgg cggaaaaacc ctcaggaagg actgtacaac    1320
gaactccaga agacaagat ggcggaagcc tactcagaaa tcgggatgaa gggagagcgg     1380
aggaggggaa agggtcacga cgggctgtac cagggactga gcaccgccac taaggatacc    1440
tacgatgcct tgcatatgca agcactccca ccccgg                              1476
```

<210> SEQ ID NO 144  
<211> LENGTH: 492  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 144

```
Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
                20                  25                  30

Leu Val Lys His Ser Gln Thr Leu Ser Leu Ala Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Gln Pro Gln
        115                 120                 125

Asp Ala Leu Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Phe Val Ser Ala Ser Val Gly Asp
                165                 170                 175

Lys Val Ile Ile Thr Cys Arg Ala Ser Gln Asp Val Ser Gly Trp Leu
            180                 185                 190
```

```
Ala Trp Tyr Gln Gln Lys Pro Gly Leu Ala Pro Gln Leu Leu Ile Ser
            195                 200                 205

Gly Ala Ser Thr Leu Gln Gly Glu Val Pro Ser Arg Phe Ser Gly Ser
        210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Ala Ala Ala Thr Thr Thr
                260                 265                 270

Pro Ala Pro Arg Pro Pro Thr Pro Ala Pro Thr Ile Ala Ser Gln Pro
                275                 280                 285

Leu Ser Leu Arg Pro Glu Ala Cys Arg Pro Ala Ala Gly Gly Ala Val
            290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
            355                 360                 365

Arg Phe Pro Glu Glu Glu Glu Gly Gly Cys Glu Leu Arg Val Lys Phe
        370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
        450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Asp Val Ser Gly Trp
1               5

<210> SEQ ID NO 146
<211> LENGTH: 3
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 146

Gly Ala Ser
1

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gln Gln Ala Lys Tyr Phe Pro Tyr Thr
1               5

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Asp Ser Val Ser Ser Asn Ser Ala Ala
1               5                   10

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Thr Tyr Tyr Arg Ser Lys Trp Tyr Asn
1               5

<210> SEQ ID NO 150
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ala Gln Glu Val Gln Pro Gln Asp Ala Leu Asp Ile
1               5                   10

<210> SEQ ID NO 151
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180

```
actgattatg cagtatctgt gaaaaatcga ataaccatca acccagacac atccaagaat    240
cagttctccc tgcagctgaa ctctgtgact cccgaggaca cggctgtgta ttactgtgcc    300
caagaggtag aacctcagga tgcttttgat atctggggcc aagggacaat ggtcaccgtc    360
tcttcaggag gtggcgggtc tggcggtgga ggtagcggtg gtggcggatc cgacatccag    420
atgacccagt ctccatcttc cgtgtctgca tctgtaggag acaaagtcac catcacttgt    480
cgggcgagtc aggatgttag cggctggtta gcctggtatc agcagaaacc agggctagcc    540
cctcagctcc tgatctttgg tgcatccact ttgcaaggtg aagtcccatc aaggttcagc    600
ggcagtggat ctgggacaga tttttactctc accatcagta gcctgcagcc tgaagatttt    660
gccacttatt attgtcaaca ggctaaatat ttcccttaca cttttggccg ggggaccaag    720
ctggaaatca aa                                                        732
```

<210> SEQ ID NO 152
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Thr Asp Tyr Ala
    50                  55                  60

Val Ser Val Lys Asn Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Gln Glu Val Glu Pro Gln Asp Ala Phe Asp Ile Trp
            100                 105                 110

Gly Gln Gly Thr Met Val Thr Val Ser Ser Gly Gly Gly Ser Gly
            115                 120                 125

Gly Gly Gly Ser Gly Gly Gly Ser Asp Ile Gln Met Thr Gln Ser
        130                 135                 140

Pro Ser Ser Val Ser Ala Ser Val Gly Asp Lys Val Thr Ile Thr Cys
145                 150                 155                 160

Arg Ala Ser Gln Asp Val Ser Gly Trp Leu Ala Trp Tyr Gln Gln Lys
                165                 170                 175

Pro Gly Leu Ala Pro Gln Leu Leu Ile Phe Gly Ala Ser Thr Leu Gln
            180                 185                 190

Gly Glu Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ala Lys Tyr Phe Pro Tyr Thr Phe Gly Arg Gly Thr Lys
225                 230                 235                 240

Leu Glu Ile Lys

<210> SEQ ID NO 153
<211> LENGTH: 1476
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 153

```
atgttgctgc tcgtgacctc gctccttctg tgcgagctgc cccatccggc ttttctgctc      60
atccctcaag tgcagctgca gcagtccggt cctggactgg tcaagccgtc ccagactctg     120
agcctgactt gcgcaattag cggggactca gtctcgtcca attcggcggc ctggaactgg     180
atccggcagt caccatcaag gggcctggaa tggctcgggc gcacttacta ccggtccaaa     240
tggtataccg actacgccgt gtccgtgaag aatcggatca ccattaaccc cgacacctcg     300
aagaaccagt tctcactcca actgaacagc gtgaccccg aggataccgc ggtgtactac      360
tgcgcacaag aagtggaacc gcaggacgcc ttcgacattt ggggacaggg aacgatggtc     420
acagtgtcgt ccggtggagg aggttccgga ggcggtggat ctggaggcgg aggttcggat     480
atccagatga cccagagccc ctcctcggtg tccgcatccg tgggcgataa ggtcaccatt     540
acctgtagag cgtcccagga cgtgtccgga tggctggcct ggtaccagca gaagccaggc     600
ttggctcctc aactgctgat cttcggcgcc agcactcttc aggggaagt gccatcacgc      660
ttctccggat ccggttccgg caccgacttc accctgacca tcagcagcct ccagcctgag     720
gacttcgcca cttactactg ccaacaggcc aagtacttcc cctatacctt cggaagaggc     780
actaagctgg aaatcaaggc ggccgcaact accaccctg cccctcggcc gccgactccg      840
gccccaacca tcgcaagcca accctctcc ttgcgccccg aagcttgccg cccggccgcg      900
ggtggagccg tgcatacccg ggggctggac tttgcctgcg atatctacat ttgggccccg     960
ctggccggca cttgcggcgt gctcctgctg tcgctggtca tcacccttta ctgcaagagg    1020
ggccggaaga agctgcttta catcttcaag cagccgttca tgcggcccgt gcagacgact    1080
caggaagagg acggatgctc gtgcagattc cctgaggagg aagaggggg atgcgaactg     1140
cgcgtcaagt tctcacggtc cgccgacgcc cccgcatatc aacagggcca gaatcagctc    1200
tacaacgagc tgaacctggg aaggagagag gagtacgacg tgctggacaa gcgacgcgga    1260
cgcgaccccg agatgggggg gaaaccacgc cggaaaaacc ctcaggaagg actgtacaac    1320
gaactccaga agacaagat ggcggaagcc tactcagaaa tcgggatgaa gggagagcgg    1380
aggaggggaa agggtcacga cgggctgtac cagggactga gcaccgccac taaggatacc    1440
tacgatgcct tgcatatgca agcactccca ccccgg                              1476
```

<210> SEQ ID NO 154
<211> LENGTH: 492
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 154

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly

-continued

```
            35                  40                  45
Asp Ser Val Ser Ser Asn Ser Ala Ala Trp Asn Trp Ile Arg Gln Ser
 50                  55                  60
Pro Ser Arg Gly Leu Glu Trp Leu Gly Arg Thr Tyr Tyr Arg Ser Lys
 65                  70                  75                  80
Trp Tyr Thr Asp Tyr Ala Val Ser Val Lys Asn Arg Ile Thr Ile Asn
                 85                  90                  95
Pro Asp Thr Ser Lys Asn Gln Phe Ser Leu Gln Leu Asn Ser Val Thr
                100                 105                 110
Pro Glu Asp Thr Ala Val Tyr Tyr Cys Ala Gln Glu Val Glu Pro Gln
                115                 120                 125
Asp Ala Phe Asp Ile Trp Gly Gln Gly Thr Met Val Thr Val Ser Ser
130                 135                 140
Gly Gly Gly Gly Ser Gly Gly Gly Ser Gly Gly Gly Gly Ser Asp
145                 150                 155                 160
Ile Gln Met Thr Gln Ser Pro Ser Ser Val Ser Ala Ser Val Gly Asp
                165                 170                 175
Lys Val Thr Ile Thr Cys Arg Ala Ser Gln Asp Val Ser Gly Trp Leu
                180                 185                 190
Ala Trp Tyr Gln Gln Lys Pro Gly Leu Ala Pro Gln Leu Leu Ile Phe
                195                 200                 205
Gly Ala Ser Thr Leu Gln Gly Glu Val Pro Ser Arg Phe Ser Gly Ser
210                 215                 220
Gly Ser Gly Thr Asp Phe Thr Leu Thr Ile Ser Ser Leu Gln Pro Glu
225                 230                 235                 240
Asp Phe Ala Thr Tyr Tyr Cys Gln Gln Ala Lys Tyr Phe Pro Tyr Thr
                245                 250                 255
Phe Gly Arg Gly Thr Lys Leu Glu Ile Lys Ala Ala Thr Thr Thr
                260                 265                 270
Pro Ala Pro Arg Pro Pro Thr Pro Ala Pro Thr Ile Ala Ser Gln Pro
                275                 280                 285
Leu Ser Leu Arg Pro Glu Ala Cys Arg Pro Ala Ala Gly Gly Ala Val
                290                 295                 300
His Thr Arg Gly Leu Asp Phe Ala Cys Asp Ile Tyr Ile Trp Ala Pro
305                 310                 315                 320
Leu Ala Gly Thr Cys Gly Val Leu Leu Leu Ser Leu Val Ile Thr Leu
                325                 330                 335
Tyr Cys Lys Arg Gly Arg Lys Lys Leu Leu Tyr Ile Phe Lys Gln Pro
                340                 345                 350
Phe Met Arg Pro Val Gln Thr Thr Gln Glu Glu Asp Gly Cys Ser Cys
                355                 360                 365
Arg Phe Pro Glu Glu Glu Gly Gly Cys Glu Leu Arg Val Lys Phe
                370                 375                 380
Ser Arg Ser Ala Asp Ala Pro Ala Tyr Gln Gln Gly Gln Asn Gln Leu
385                 390                 395                 400
Tyr Asn Glu Leu Asn Leu Gly Arg Arg Glu Glu Tyr Asp Val Leu Asp
                405                 410                 415
Lys Arg Arg Gly Arg Asp Pro Glu Met Gly Gly Lys Pro Arg Arg Lys
                420                 425                 430
Asn Pro Gln Glu Gly Leu Tyr Asn Glu Leu Gln Lys Asp Lys Met Ala
                435                 440                 445
Glu Ala Tyr Ser Glu Ile Gly Met Lys Gly Glu Arg Arg Gly Lys
                450                 455                 460
```

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gln Asp Val Ser Gly Trp
1               5

<210> SEQ ID NO 156
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Ala Ser
1

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gln Gln Ala Lys Tyr Phe Pro Tyr Thr
1               5

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Asp Ser Val Ser Ser Asn Ser Ala Ala
1               5                   10

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Thr Tyr Tyr Arg Ser Lys Trp Tyr Thr
1               5

<210> SEQ ID NO 160

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Gln Glu Val Glu Pro Gln Asp Ala Phe Asp Ile
1               5                   10

<210> SEQ ID NO 161
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161
caggtacagc tgcagcagtc aggtccagga ctggtgaagc cctcgcagac cctctcactc      60
acctgtgcca tctcagggaa cagtgtctct agcaacagtg ctgcttggaa ctggatcagg     120
cagtccccat cgagaggcct tgagtggctg gaaggacat actacaggtc caagtggtat      180
aatgattatg cagtatctgt gaaaagtcga ataaccatca cccagacac atccaagaac      240 cagttctccc tgcagctgaa ctctgtgact cccgaggaca cggctgtgta ttactgtgcc     300
caagaggtag aacctcaaga tgcttttgat atctggggcc aagggacaat ggtcaccgtc     360
tcttcaggag gtggcgggtc tggcggtgga ggtagcggtg gtggcggatc cgacatccag     420
atgacccagt ctccatcttc cgtgtctgca tctgtaggag acaaagtcac catcacttgt     480
cgggcgagtc aggatgttag cggctggtta gcctggtatc agcagaaacc agggctagcc     540
cctcagctcc tgatctttgg tgcatccact ttgcaaggtg aagtcccatc aagattcagc     600
ggcggtggat ctgggacaga ttttactctc accatcagca gcctgcagcc tgaagatttt     660
gccacttatt attgtcaaca ggctaaatat ttcccttaca cttttggcca ggggaccaag     720
ctggaaatca aa                                                          732

<210> SEQ ID NO 162
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asn Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Gln Glu Val Glu Pro Gln Asp Ala Phe Asp Ile Trp
```

```
                   100                 105                 110
Gly Gln Gly Thr Met Val Thr Val Ser Ser Gly Gly Gly Ser Gly
            115                 120                 125
Gly Gly Gly Ser Gly Gly Gly Ser Asp Ile Gln Met Thr Gln Ser
        130                 135                 140
Pro Ser Ser Val Ser Ala Ser Val Gly Asp Lys Val Thr Ile Thr Cys
145                 150                 155                 160
Arg Ala Ser Gln Asp Val Ser Gly Trp Leu Ala Trp Tyr Gln Gln Lys
                165                 170                 175
Pro Gly Leu Ala Pro Gln Leu Leu Ile Phe Gly Ala Ser Thr Leu Gln
            180                 185                 190
Gly Glu Val Pro Ser Arg Phe Ser Gly Gly Ser Gly Thr Asp Phe
        195                 200                 205
Thr Leu Thr Ile Ser Ser Leu Gln Pro Glu Asp Phe Ala Thr Tyr Tyr
        210                 215                 220
Cys Gln Gln Ala Lys Tyr Phe Pro Tyr Thr Phe Gly Gln Gly Thr Lys
225                 230                 235                 240
Leu Glu Ile Lys

<210> SEQ ID NO 163
<211> LENGTH: 1476
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163
atgttgctgc tcgtgacctc gctccttctg tgcgagctgc cccatccggc ttttctgctc      60
atccctcaag tgcagctgca gcagtccggt cctggactgg tcaagccgtc ccagactctg     120
agcctgactt gcgccattag cgggaactca gtctcgtcca attcggcggc ctggaactgg     180
atccggcagt caccatcaag gggcctggaa tggctcgggc gcacttacta ccggtccaaa     240
tggtataacg actacgccgt gtccgtgaag tcccggatca ccattaaccc cgacacctcg     300
aagaaccagt tctcactcca actgaacagc gtgaccccg aggataccgc ggtgtactac     360
tgcgcacaag aagtggaacc gcaggacgcc ttcgacattt ggggacaggg aacgatggtc     420
acagtgtcgt ccggtggagg aggttccgga ggcggtggat ctggaggcgg aggttcggat     480
atccagatga cccagagccc ctcctcggtg tccgcatccg tgggcgataa ggtcaccatt     540
acctgtagag cgtcccagga cgtgtccgga tggctggcct ggtaccagca gaagccaggc     600
ttggctcctc aactgctgat ctttggcgcc agcactcttc aggggaggt gccatcacgc     660
ttctccggag gtggttccgg caccgacttc accctgacca tcagcagcct ccagcctgag     720
gacttcgcca cttactactg ccaacaggcc aagtacttcc cctataccct cggacaaggc     780
actaagctgg aaatcaaggc ggccgcaact accaccctg cccctcggcc gcgactccg     840
gccccaacca tcgcaagcca cccctctcc ttgcgcccg aagcttgccg cccggccgcg     900
ggtggagccg tgcatacccg ggggctggac tttgcctgcg atatctacat ttgggccccg     960
ctggccggca cttgcggcgt gctcctgctg tcgctggtca tcacccttta ctgcaagagg    1020
ggccggaaga agctgcttta catcttcaag cagccgttca tgcggcccgt gcagacgact    1080
caggaagagg acggatgctc gtgcagattc cctgaggagg aagagggggg atgcgaactg    1140
cgcgtcaagt tctcacggtc cgccgacgcc ccgcatatc aacagggcca gaatcagctc    1200
```

```
tacaacgagc tgaacctggg aaggagagag gagtacgacg tgctggacaa gcgacgcgga    1260
cgcgacccgg agatggggggg gaaaccacgg cggaaaaacc ctcaggaagg actgtacaac    1320
gaactccaga agacaagat ggcggaagcc tactcagaaa tcgggatgaa gggagagcgg    1380
aggaggggaa aggtcacga cgggctgtac cagggactga gcaccgccac taaggatacc    1440
tacgatgcct tgcatatgca agcactccca ccccgg                              1476
```

<210> SEQ ID NO 164
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asn Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro Gln
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Phe
        195                 200                 205

Gly Ala Ser Thr Leu Gln Gly Glu Val Pro Ser Arg Phe Ser Gly Gly
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Ala Ala Ala Thr Thr Thr
            260                 265                 270

Pro Ala Pro Arg Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
```

```
                305                 310                 315                 320
Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
                355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
                450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 165
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gln Asp Val Ser Gly Trp
1               5

<210> SEQ ID NO 166
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Ala Ser
1

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gln Gln Ala Lys Tyr Phe Pro Tyr Thr
1               5

<210> SEQ ID NO 168
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Asn Ser Val Ser Ser Asn Ser Ala Ala
1               5                   10

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Thr Tyr Tyr Arg Ser Lys Trp Tyr Asn
1               5

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Gln Glu Val Glu Pro Gln Asp Ala Phe Asp Ile
1               5                   10

<210> SEQ ID NO 171
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 171
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca acccagacac atccaagaac     240
cagttctccc tgcagctgaa ctctgtgact cccgaggaca cggctgtgta ttactgtgcc     300
caagaggtag aacctcatga tgctcttgat atctggggcc aagggacaat ggtcaccgtc     360
tcttcaggag gtggcgggtc tggcggtgga ggtagcggtg gtgcggatc gacatccag      420 atgacgcagt ctccatcatc cgtgtctgca tctgtaggag acaaagtcac catcacttgt     480
cgggcgagtc aggatgttag cggctggtta gcctggtatc aacagaaacc agggctagcc     540
cctcagctcc tgatctttgg tgcatccact ttgcaaggtg aagtcccatc aaggttcagc     600
ggcagtggat ctgggacaga ttttactctc accatcagca gcctgcagcc tgaagatttt     660
gccacttatt attgtcaaca ggctaaatat ttcccttaca cttttggcca ggggaccaag     720
ctggagatca aa                                                         732

<210> SEQ ID NO 172
```

<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

Gln Val Gln Leu Gln Gln Ser Gly Pro Gly Leu Val Lys Pro Ser Gln
1               5                   10                  15
Thr Leu Ser Leu Thr Cys Ala Ile Ser Gly Asp Ser Val Ser Ser Asn
            20                  25                  30
Ser Ala Ala Trp Asn Trp Ile Arg Gln Ser Pro Ser Arg Gly Leu Glu
        35                  40                  45
Trp Leu Gly Arg Thr Tyr Tyr Arg Ser Lys Trp Tyr Asn Asp Tyr Ala
    50                  55                  60
Val Ser Val Lys Ser Arg Ile Thr Ile Asn Pro Asp Thr Ser Lys Asn
65                  70                  75                  80
Gln Phe Ser Leu Gln Leu Asn Ser Val Thr Pro Glu Asp Thr Ala Val
                85                  90                  95
Tyr Tyr Cys Ala Gln Glu Val Glu Pro His Asp Ala Leu Asp Ile Trp
            100                 105                 110
Gly Gln Gly Thr Met Val Thr Val Ser Ser Gly Gly Gly Gly Ser Gly
        115                 120                 125
Gly Gly Gly Ser Gly Gly Gly Ser Asp Ile Gln Met Thr Gln Ser
    130                 135                 140
Pro Ser Ser Val Ser Ala Ser Val Gly Asp Lys Val Thr Ile Thr Cys
145                 150                 155                 160
Arg Ala Ser Gln Asp Val Ser Gly Trp Leu Ala Trp Tyr Gln Gln Lys
                165                 170                 175
Pro Gly Leu Ala Pro Gln Leu Leu Ile Phe Gly Ala Ser Thr Leu Gln
            180                 185                 190
Gly Glu Val Pro Ser Arg Phe Ser Gly Ser Gly Ser Gly Thr Asp Phe
        195                 200                 205
Thr Leu Thr Ile Ser Ser Leu Gln Pro Glu Asp Phe Ala Thr Tyr Tyr
    210                 215                 220
Cys Gln Gln Ala Lys Tyr Phe Pro Tyr Thr Phe Gly Gln Gly Thr Lys
225                 230                 235                 240
Leu Glu Ile Lys

<210> SEQ ID NO 173
<211> LENGTH: 1476
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 173
atgttgctgc tcgtgaccct cgctccttct gtgcgagctg cccatccggc ttttctgctc    60
atccctcaag tgcagctgca gcagtccggt cctggactgg tcaagccgtc ccagactctg    120
agcctgactt gcgcgattag cggggactca gtctcgtcca attcggcggc ctggaactgg    180
atccggcagt caccatcaag gggcctggaa tggctcgggc gcacttacta ccggtccaaa    240
tggtataacg actacgccgt gtccgtgaag tcccggatca ccattaaccc cgacaccctc    300
gaagaaccag tctcactcca actgaacagc gtgaccccga aggataccgc ggtgtactac    360

```
tgcgcacaag aagtggaacc gcacgacgcc ctggacattt ggggtcaggg aacgatggtc    420
acagtgtcgt ccggtggagg aggttccgga ggcggtggat ctggaggcgg aggttcggat    480
atccagatga cccagagccc ctcctcggtg tccgcatccg tgggcgataa ggtcaccatt    540
acctgtagag cgtcccagga cgtgtccgga tggctggcct ggtaccagca gaagccaggc    600
ttggctcctc aactgctgat cttcggcgcc agcacacttc aggggaggt gccatcacgc     660 ttctccggat ccggttccgg caccgacttc accctgacca tcagcagcct ccagcctgag    720
gacttcgcca cttactactg ccaacaggcc aagtacttcc cctatacctt cggacaaggc    780
actaagctgg aaatcaaggc ggccgcaact accaccctg cccctcggcc gccgactccg     840 gcccaacca tcgcaagcca acccctctcc ttgcgcccg aagcttgccg cccggccgcg      900
ggtggagccg tgcataccg ggggctggac tttgcctgcg atatctacat ttgggccccg     960
ctggccggca cttgcggcgt gctcctgctg tcgctggtca tcaccccttta ctgcaagagg    1020 ggccggaaga agctgcttta catcttcaag cagccgttca tgcggcccgt gcagacgact    1080
caggaagagg acggatgctc gtgcagattc cctgaggagg aagaggggg atgcgaactg     1140 cgcgtcaagt tctcacggtc cgccgacgcc cccgcatatc aacagggcca gaatcagctc    1200
tacaacgagc tgaacctggg aaggagagag gagtacgacg tgctggacaa gcgacgcgga    1260
cgcgacccgg agatgggggg gaaaccacgg cggaaaaacc ctcaggaagg actgtacaac    1320
gaactccaga aagacaagat ggcggaagcc tactcagaaa tcgggatgaa gggagagcgg    1380 aggagggaa agggtcacga cgggctgtac cagggactga gcaccgccac taaggatacc    1440
tacgatgcct tgcatatgca agcactccca ccccgg                              1476
```

<210> SEQ ID NO 174
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Leu Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

```
Ile Gln Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Phe
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 175
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gln Asp Val Ser Gly Trp
1               5

<210> SEQ ID NO 176
```

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Ala Ser
1

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gln Gln Ala Lys Tyr Phe Pro Tyr Thr
1               5

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Asp Ser Val Ser Ser Asn Ser Ala Ala
1               5                   10

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Thr Tyr Tyr Arg Ser Lys Trp Tyr Asn
1               5

<210> SEQ ID NO 180
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ala Gln Glu Val Glu Pro His Asp Ala Leu Asp Ile
1               5                   10

<210> SEQ ID NO 181
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
```

```
atttgggccc cgctggccgg cacttgcggc gtgctcctgc tgtcgctggt catcacccct    60
tactgc                                                               66
```

<210> SEQ ID NO 182
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ile Trp Ala Pro Leu Ala Gly Thr Cys Gly Val Leu Leu Ser Leu
1               5                   10                  15

Val Ile Thr Leu Tyr Cys
            20

<210> SEQ ID NO 183
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183

```
actaccaccc ctgcccctcg gccgccgact ccggccccaa ccatcgcaag ccaacccctc    60
tccttgcgcc ccgaagcttg ccgcccggcc gcgggtggag ccgtgcatac ccgggggctg   120
gactttgcct gcgatatcta c                                             141
```

<210> SEQ ID NO 184
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 185
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Ser Leu Val

Ile Thr Leu Tyr Cys
65

<210> SEQ ID NO 186
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 186
aagaggggcc ggaagaagct gctttacatc ttcaagcagc cgttcatgcg gcccgtgcag     60
acgactcagg aagaggacgg atgctcgtgc agattccctg aggaggaaga gggggatgc    120 gaactg                                                              126

<210> SEQ ID NO 187
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 188
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188
cgcgtcaagt tctcacggtc cgccgacgcc cccgcatatc aacagggcca gaatcagctc     60
tacaacgagc tgaacctggg aaggagagag gagtacgacg tgctggacaa gcgacgcgga   120
cgcgaccccg agatggggggg gaaaccacgg cggaaaaacc ctcaggaagg actgtacaac   180
gaactccaga agacaagat ggcggaagcc tactcagaaa tcgggatgaa gggagagcgg    240 aggagggggaa aggtcacga cgggctgtac cagggactga gcaccgccac taaggatacc   300
tacgatgcct tgcatatgca agcactccca ccccgg                              336

<210> SEQ ID NO 189
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Arg Val Lys Phe Ser Arg Ser Ala Asp Ala Pro Ala Tyr Gln Gln Gly
1               5                   10                  15

```
Gln Asn Gln Leu Tyr Asn Glu Leu Asn Leu Gly Arg Arg Glu Tyr
            20                  25                  30

Asp Val Leu Asp Lys Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 190
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
atgctgctgc tggtgaccag cctgctgctg tgcgaactgc cgcatccggc gtttctgctg      60
attccg                                                                66

<210> SEQ ID NO 191
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 192
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192
gacattcaga tgactcagac cacctcttcc ttgtccgcgt cactgggaga cagagtgacc      60
atctcgtgtc gcgcaagcca ggatatctcc aagtacctga actggtacca acagaagccc    120
gacgggactg tgaagctgct gatctaccac acctcacgcc tgcacagcgg agtgccaagc    180
agattctccg gctccggctc gggaaccgat tactcgctta ccattagcaa cctcgagcag    240
gaggacatcg ctacctactt ctgccagcaa ggaaatacc ctgccctacac cttcggcgga    300 ggaaccaaat tggaaatcac cggcggagga ggctccgggg aggaggttc cggggcggg     360 ggttccgaag tgaagctcca ggagtccggc cccggcctgg tggcgccgtc gcaatcactc    420
tctgtgacct gtaccgtgtc gggagtgtcc ctgcctgatt acggcgtgag ctggattcgg    480
cagccgccgc ggaagggcct ggaatggctg ggtgtcatct ggggatccga gactacctac    540
```

```
tacaactcgg ccctgaagtc ccgcctgact atcatcaaag acaactcgaa gtcccaggtc    600
tttctgaaga tgaactccct gcaaactgac gacaccgcca tctattactg tgctaagcac    660
tactactacg gtggaagcta tgctatggac tactgggggc aaggcacttc ggtgactgtg    720
tcaagc                                                               726
```

<210> SEQ ID NO 193
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser
```

<210> SEQ ID NO 194
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194

```
atgcttctcc tggtcacctc cctgctcctc tgcgaactgc ctcaccctgc cttccttctg    60
```
attcctgaca ttcagatgac tcagaccacc tcttccttgt ccgcgtcact gggagacaga    120
gtgaccatct cgtgtcgcgc aagccaggat atctccaagt acctgaactg gtaccaacag    180
aagcccgacg ggactgtgaa gctgctgatc taccacacct cacgcctgca cagcggagtg    240
ccaagcagat tctccggctc cggctcggga accgattact cgcttaccat tagcaacctc    300
gagcaggagg acatcgctac ctacttctgc cagcaaggaa ataccctgcc ctacaccttc    360 ggcgaggaa ccaaattgga aataccggc ggaggaggct ccggggag aggttccggg    420 ggcggggtt ccgaagtgaa gctccaggag tccggccccg gcctggtggc gccgtcgcaa    480
tcactctctg tgacctgtac cgtgtcggga gtgtccctgc ctgattacgg cgtgagctgg    540
attcggcagc cgccgcggaa gggcctggaa tggctgggtg tcatctgggg atccgagact    600
acctactaca actcggccct gaagtcccgc ctgactatca tcaaagacaa ctcgaagtcc    660
caggtctttc tgaagatgaa ctccctgcaa actgacgaca ccgccatcta ttactgtgct    720
aagcactact actacggtgg aagctatgct atggactact gggggcaagg cacttcggtg    780
actgtgtcaa gcgcggccgc aactaccacc cctgccctc ggccgccgac tccggcccca    840
accatcgcaa gccaacccct ctccttgcgc cccgaagctt gccgcccggc cgcgggtgga    900
gccgtgcata cccgggggct ggactttgcc tgcgatatct catttgggc cccgctggcc    960 ggcacttgcg gcgtgctcct gctgtcgctg gtcatcaccc tttactgcaa gaggggccgg   1020
aagaagctgc tttacatctt caagcagccg ttcatgcggc ccgtgcagac gactcaggaa   1080
gaggacggat gctcgtgcag attccctgag gaggaagagg ggggatgcga actgcgcgtc   1140
aagttctcac ggtccgccga cgcccccgca tatcaacagg gccagaatca gctctacaac   1200
gagctgaacc tgggaaggag agaggagtac gacgtgctgg acaagcgacg cggacgcgac   1260
ccggagatgg gggggaaacc acggcggaaa aaccctcagg aaggactgta caacgaactc   1320
cagaaagaca gatggcgga agcctactca gaaatcggga tgaagggaga gcggaggagg   1380
ggaaagggtc acgacgggct gtaccaggga ctgagcaccg ccactaagga tacctacgat   1440
gccttgcata tgcaagcact cccacccgg                                      1470

<210> SEQ ID NO 195
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
            115                 120                 125

Thr Gly Gly Gly Ser Gly Gly Gly Ser Gly Gly Gly Ser
130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
                180                 185                 190

Gly Val Ile Trp Gly Ser Glu Thr Thr Tyr Tyr Asn Ser Ala Leu Lys
                195                 200                 205

Ser Arg Leu Thr Ile Ile Lys Asp Asn Ser Lys Ser Gln Val Phe Leu
210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Ala Thr Thr Thr Pro Ala
                260                 265                 270

Pro Arg Pro Pro Thr Pro Ala Pro Thr Ile Ala Ser Gln Pro Leu Ser
                275                 280                 285

Leu Arg Pro Glu Ala Cys Arg Pro Ala Ala Gly Gly Ala Val His Thr
290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
                340                 345                 350

Arg Pro Val Gln Thr Thr Gln Glu Glu Asp Gly Cys Ser Cys Arg Phe
                355                 360                 365

Pro Glu Glu Glu Glu Gly Gly Cys Glu Leu Arg Val Lys Phe Ser Arg
                370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
                435                 440                 445

Tyr Ser Glu Ile Gly Met Lys Gly Glu Arg Arg Arg Gly Lys Gly His
450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 196
<211> LENGTH: 1482
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 196

```
atgcttcttt tggtgacttc ccttttgctg tgcgagttgc cacaccccgc cttcctgctt      60
attcccagg tacagctcca gcagagtggc ccagggctcg tgaagccaag ccagacgctg     120
tccctgactt gtgcaatttc aggggattca gtttcatcaa atagcgcggc gtggaattgg    180
attcgacaat ctccttcccg agggttgaa tggcttggac gaacatatta cagatccaaa     240
tggtataacg actatgcggt atcagtaaag tcaagaataa ccattaaccc cgacacaagc    300
aagaaccaat tctctttgca gcttaactct gtcacgccag aagacacggc agtctattat    360
tgcgctcgcg aggtaacggg tgacctggaa gacgcttttg acatttgggg gcagggtacg    420
atggtgacag tcagttcagg gggcggtggg agtggggggag ggggtagcgg gggggagggg    480
tcagacattc agatgaccca gtccccttca tccttgtctg cctccgtcgg tgacagggtg    540
acaataacat gcagagcaag ccaaacaatc tggagctatc tcaactggta ccagcagcga    600
ccaggaaaag cgccaaacct gctgatttac gctgcttcct ccctccaatc aggcgtgcct    660
agtagattta gcggtagggg ctccggcacc gattttacgc tcactataag ctctcttcaa    720
gcagaagatt ttgcgactta ttactgccag cagtcctata gtatacctca gactttcgga    780
cagggtacca gttggagat taaggcggcc gcaactacca cccctgcccc tcggccgccg    840
actccggccc caaccatcgc aagccaaccc ctctccttgc gccccgaagc ttgccgcccg    900
gccgcgggtg gagccgtgca tacccggggg ctggactttg cctgcgatat ctacatttgg    960
gccccgctgg ccggcacttg cggcgtgctc ctgctgtcgc tggtcatcac cctttactgc   1020
aagagggggcc ggaagaagct gctttacatc ttcaagcagc cgttcatgcg gcccgtgcag   1080
acgactcagg aagaggacgg atgctcgtgc agattccctg aggaggaaga ggggggatgc   1140
gaactgcgcg tcaagttctc acggtccgcc gacgcccccg catatcaaca gggccagaat   1200
cagctctaca acgagctgaa cctgggaagg agagaggagt acgacgtgct ggacaagcga   1260
cgcggacgcg accccgagat ggggggaaaa ccacggcgga aaaaccctca ggaaggactg   1320
tacaacgaac tccagaaaga caagatggcg gaagcctact cagaaatcgg gatgaaggga   1380
gagcggagga ggggaaaggg tcacgacggg ctgtaccagg gactgagcac cgccactaag   1440
gatacctacg atgccttgca tatgcaagca ctcccacccc gg                       1482
```

<210> SEQ ID NO 197
<211> LENGTH: 494
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 197

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys

```
                65                  70                  75                  80
        Trp Tyr Asn Asp Tyr Ala Val Ser Val Lys Ser Arg Ile Thr Ile Asn
                            85                  90                  95
        Pro Asp Thr Ser Lys Asn Gln Phe Ser Leu Gln Leu Asn Ser Val Thr
                            100                 105                 110
        Pro Glu Asp Thr Ala Val Tyr Tyr Cys Ala Arg Glu Val Thr Gly Asp
                            115                 120                 125
        Leu Glu Asp Ala Phe Asp Ile Trp Gly Gln Gly Thr Met Val Thr Val
                            130                 135                 140
        Ser Ser Gly Gly Gly Gly Ser Gly Gly Gly Gly Ser Gly Gly Gly Gly
        145                 150                 155                 160
        Ser Asp Ile Gln Met Thr Gln Ser Pro Ser Ser Leu Ser Ala Ser Val
                            165                 170                 175
        Gly Asp Arg Val Thr Ile Thr Cys Arg Ala Ser Gln Thr Ile Trp Ser
                            180                 185                 190
        Tyr Leu Asn Trp Tyr Gln Gln Arg Pro Gly Lys Ala Pro Asn Leu Leu
                            195                 200                 205
        Ile Tyr Ala Ala Ser Ser Leu Gln Ser Gly Val Pro Ser Arg Phe Ser
                            210                 215                 220
        Gly Arg Gly Ser Gly Thr Asp Phe Thr Leu Thr Ile Ser Ser Leu Gln
        225                 230                 235                 240
        Ala Glu Asp Phe Ala Thr Tyr Tyr Cys Gln Gln Ser Tyr Ser Ile Pro
                            245                 250                 255
        Gln Thr Phe Gly Gln Gly Thr Lys Leu Glu Ile Lys Ala Ala Ala Thr
                            260                 265                 270
        Thr Thr Pro Ala Pro Arg Pro Pro Thr Pro Ala Pro Thr Ile Ala Ser
                            275                 280                 285
        Gln Pro Leu Ser Leu Arg Pro Glu Ala Cys Arg Pro Ala Ala Gly Gly
                            290                 295                 300
        Ala Val His Thr Arg Gly Leu Asp Phe Ala Cys Asp Ile Tyr Ile Trp
        305                 310                 315                 320
        Ala Pro Leu Ala Gly Thr Cys Gly Val Leu Leu Leu Ser Leu Val Ile
                            325                 330                 335
        Thr Leu Tyr Cys Lys Arg Gly Arg Lys Lys Leu Leu Tyr Ile Phe Lys
                            340                 345                 350
        Gln Pro Phe Met Arg Pro Val Gln Thr Thr Gln Glu Glu Asp Gly Cys
                            355                 360                 365
        Ser Cys Arg Phe Pro Glu Glu Glu Gly Gly Cys Glu Leu Arg Val
        370                 375                 380
        Lys Phe Ser Arg Ser Ala Asp Ala Pro Ala Tyr Gln Gln Gly Gln Asn
        385                 390                 395                 400
        Gln Leu Tyr Asn Glu Leu Asn Leu Gly Arg Arg Glu Glu Tyr Asp Val
                            405                 410                 415
        Leu Asp Lys Arg Arg Gly Arg Asp Pro Glu Met Gly Gly Lys Pro Arg
                            420                 425                 430
        Arg Lys Asn Pro Gln Glu Gly Leu Tyr Asn Glu Leu Gln Lys Asp Lys
                            435                 440                 445
        Met Ala Glu Ala Tyr Ser Glu Ile Gly Met Lys Gly Glu Arg Arg Arg
                            450                 455                 460
        Gly Lys Gly His Asp Gly Leu Tyr Gln Gly Leu Ser Thr Ala Thr Lys
        465                 470                 475                 480
        Asp Thr Tyr Asp Ala Leu His Met Gln Ala Leu Pro Pro Arg
                            485                 490
```

<210> SEQ ID NO 198
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198

```
gaggtccagc tggtacagtc tgggggaggc ttggtacagc ctggggggtc cctgagactc      60
tcctgtgcag cctctggatt cacctttgat gattatgcca tgcactgggt ccggcaagct     120
ccagggaagg gcctggagtg ggtctcaggt attagttgga atagtggtag cataggctat     180
gcggactctg tgaagggccg attcaccatc tccagagaca cgccaagaa ctccctgtat      240 ctgcaaatga acagtctgag agctgaggac acggccttgt attactgtgc aaaagattta     300
tcgtcagtgg ctggacccct taactactgg ggccagggca ccctggtcac cgtctcctca     360
ggaggtggcg gtctggtgg aggcggtagc ggcggtggcg gatcctcttc tgagctgact     420
caggaccctg ctgtgtctgt ggccttggga cagacagtca ggatcacatg ccaaggagac     480
agcctcagaa gctattatgc aagctggtac cagcagaagc caggacaggc ccctgtactt     540
gtcatctatg gtaaaaacaa ccggccctca gggatcccag accgattctc tggctccagc     600
tcaggaaaca cagcttcctt gaccatcact ggggctcagg cggaggatga ggctgactat     660
tactgtaact cccgggacag cagtggtaac catctggtat tcggcggagg cacccagctg     720
accgtcctcg gt                                                          732
```

<210> SEQ ID NO 199
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Leu Ser Ser Val Ala Gly Pro Phe Asn Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160
```

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Ser Gly Asn Thr Ala Ser Leu Thr
        195                 200                 205

Ile Thr Gly Ala Gln Ala Glu Asp Glu Ala Asp Tyr Tyr Cys Asn Ser
    210                 215                 220

Arg Asp Ser Ser Gly Asn His Leu Val Phe Gly Gly Gly Thr Gln Leu
225                 230                 235                 240

Thr Val Leu Gly

<210> SEQ ID NO 200
<211> LENGTH: 1476
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200

| | |
|---|---:|
| atgctgctgc tggtgaccag cctgctgctg tgcgaactgc cgcatccggc gtttctgctg | 60 |
| attccggagg tccagctggt acagtctggg ggaggcttgg tacagcctgg ggggtccctg | 120 |
| agactctcct gtgcagcctc tggattcacc tttgatgatt atgccatgca ctgggtccgg | 180 |
| caagctccag ggaagggcct ggagtgggtc tcaggtatta gttggaatag tggtagcata | 240 |
| ggctatgcgg actctgtgaa gggccgattc accatctcca gagacaacgc caagaactcc | 300 |
| ctgtatctgc aaatgaacag tctgagagct gaggacacgg ccttgtatta ctgtgcaaaa | 360 |
| gatttatcgt cagtggctgg acccttttaac tactggggcc agggcaccct ggtcaccgtc | 420 |
| tcctcaggag gtggcgggtc tggtggaggc ggtagcggcg gtggcggatc ctcttctgag | 480 |
| ctgactcagg accctgctgt gtctgtggcc ttgggacaga cagtcaggat cacatgccaa | 540 |
| ggagacagcc tcagaagcta ttatgcaagc tggtaccagc agaagccagg acaggcccct | 600 |
| gtacttgtca tctatggtaa aaacaaccgg ccctcaggga tcccagaccg attctctggc | 660 |
| tccagctcag gaaacacagc ttccttgacc atcactgggg ctcaggcgga ggatgaggct | 720 |
| gactattact gtaactcccg ggacagcagt ggtaaccatc tggtattcgg cggaggcacc | 780 |
| cagctgaccg tcctcggtgc ggccgcaact accacccctg ccctcggcc gccgactccg | 840 |
| gccccaacca tcgcaagcca ccctctcc ttgcgcccg aagcttgccg ccggccgcg | 900 |
| ggtggagccg tgcatacccg ggggctggac tttgcctgcg atatctacat ttgggcccg | 960 |
| ctggccggca cttgcggcgt gctcctgctg tcgctggtca tcacccttta ctgcaagagg | 1020 |
| ggccggaaga gctgcttta catcttcaag cagccgttca tgcggcccgt gcagacgact | 1080 |
| caggaagagg acggatgctc gtgcagattc cctgaggagg aagaggggg atgcgaactg | 1140 |
| cgcgtcaagt tctcacggtc cgccgacgcc ccgcatatc aacagggcca gaatcagctc | 1200 |
| tacaacgagc tgaacctggg aaggagagag gagtacgacg tgctggacaa gcgacgcgga | 1260 |
| cgcgaccgg gagatggggg gaaaccacg cggaaaaacc ctcaggaagg actgtacaac | 1320 |
| gaactccaga aagacaagat ggcggaagcc tactcagaaa tcgggatgaa gggagagcgg | 1380 |
| aggagggaa aggtcacga cgggctgtac cagggactga gcaccgccac taaggatacc | 1440 |
| tacgatgcct tgcatatgca agcactccca ccccgg | 1476 |

```
<210> SEQ ID NO 201
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Gly Gly
            20                  25                  30

Leu Val Gln Pro Gly Gly Ser Leu Arg Leu Ser Cys Ala Ala Ser Gly
        35                  40                  45

Phe Thr Phe Asp Asp Tyr Ala Met His Trp Val Arg Gln Ala Pro Gly
    50                  55                  60

Lys Gly Leu Glu Trp Val Ser Gly Ile Ser Trp Asn Ser Gly Ser Ile
65                  70                  75                  80

Gly Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Leu Tyr Tyr Cys Ala Lys Asp Leu Ser Ser Val Ala Gly Pro
        115                 120                 125

Phe Asn Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Ser Ser Glu
145                 150                 155                 160

Leu Thr Gln Asp Pro Ala Val Ser Val Ala Leu Gly Gln Thr Val Arg
                165                 170                 175

Ile Thr Cys Gln Gly Asp Ser Leu Arg Ser Tyr Tyr Ala Ser Trp Tyr
            180                 185                 190

Gln Gln Lys Pro Gly Gln Ala Pro Val Leu Val Ile Tyr Gly Lys Asn
        195                 200                 205

Asn Arg Pro Ser Gly Ile Pro Asp Arg Phe Ser Gly Ser Ser Ser Gly
    210                 215                 220

Asn Thr Ala Ser Leu Thr Ile Thr Gly Ala Gln Ala Glu Asp Glu Ala
225                 230                 235                 240

Asp Tyr Tyr Cys Asn Ser Arg Asp Ser Ser Gly Asn His Leu Val Phe
                245                 250                 255

Gly Gly Gly Thr Gln Leu Thr Val Leu Gly Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365
```

```
Arg Phe Pro Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 202
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202
gaggtgcagc tggtggagtc tgggggaggc ttggtacagc ctggagggtc cctgagactc      60
tcctgtgcag cctctggatt caccttcagt agctatggca tgagctgggt ccgccaggct     120
ccaagacaag ggcttgagtg ggtggccaac ataaagcaag atggaagtga aaaatactat     180
gcggactcag tgaagggccg attcaccatc tccagagaca attccaagaa cacgctgtat     240
ctgcaaatga acagcctgag agccgaggac acagccacgt attactgtgc gaaagaaaat     300
gtggactggg gccagggcac cctggtcacc gtctcctca                            339

<210> SEQ ID NO 203
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Arg Gln Gly Leu Glu Trp Val
        35                  40                  45

Ala Asn Ile Lys Gln Asp Gly Ser Glu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Lys Glu Asn Val Asp Trp Gly Gln Gly Thr Leu Val Thr Val Ser
            100                 105                 110
```

Ser

<210> SEQ ID NO 204
<211> LENGTH: 1083
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 204

```
atgctgctgc tggtgaccag cctgctgctg tgcgaactgc cgcatccggc gtttctgctg    60
attccggagg tgcagctggt ggagtctggg ggaggcttgg tacagcctgg agggtccctg   120
agactctcct gtgcagcctc tggattcacc ttcagtagct atggcatgag ctgggtccgc   180
caggctccaa gacaagggct tgagtgggtg gccaacataa agcaagatgg aagtgagaaa   240
tactatgcgg actcagtgaa gggccgattc accatctcca gagacaattc caagaacacg   300
ctgtatctgc aaatgaacag cctgagagcc gaggacacag ccacgtatta ctgtgcgaaa   360
gaaaatgtgg actggggcca gggcaccctg gtcaccgtct cctcagcggc cgcaactacc   420
accctgccc tcggccgcc gactccggcc caaccatcg caagccaacc cctctccttg      480
cgccccgaag cttgccgccc ggccgcgggt ggagccgtgc atacccgggg gctggacttt   540
gcctgcgata tctacatttg gcccccgctg gccggcactt cggcgtgct cctgctgtcg    600
ctggtcatca cccttactg caagagggc cggaagaagc tgctttacat cttcaagcag    660
ccgttcatgc ggcccgtgca gacgactcag gaagaggacg gatgctcgtg cagattccct   720
gaggaggaag aggggggatg cgaactgcgc gtcaagttct cacggtccgc cgacgccccc   780
gcatatcaac agggccagaa tcagctctac aacgagctga acctgggaag agagagggag   840
tacgacgtgc tggacaagcg acgcggacgc gacccggaga tgggggggaa accacggcgg   900
aaaaaccctc aggaaggact gtacaacgaa ctccagaaag acaagatggc ggaagcctac   960
tcagaaatcg ggatgaaggg agagcggagg aggggaaagg gtcacgacgg gctgtaccag  1020
ggactgagca ccgccactaa ggatacctac gatgccttgc atatgcaagc actcccaccc  1080
cgg                                                                1083
```

<210> SEQ ID NO 205
<211> LENGTH: 361
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 205

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Gly Met Ser Trp Val Arg Gln Ala Pro Arg
    50                  55                  60

Gln Gly Leu Glu Trp Val Ala Asn Ile Lys Gln Asp Gly Ser Glu Lys
65                  70                  75                  80

Tyr Tyr Ala Asp Ser Val Lys Gly Arg Phe Thr Ile Ser Arg Asp Asn
                85                  90                  95
```

```
Ser Lys Asn Thr Leu Tyr Leu Gln Met Asn Ser Leu Arg Ala Glu Asp
            100                 105                 110
Thr Ala Thr Tyr Tyr Cys Ala Lys Glu Asn Val Asp Trp Gly Gln Gly
        115                 120                 125
Thr Leu Val Thr Val Ser Ser Ala Ala Ala Thr Thr Thr Pro Ala Pro
    130                 135                 140
Arg Pro Pro Thr Pro Ala Pro Thr Ile Ala Ser Gln Pro Leu Ser Leu
145                 150                 155                 160
Arg Pro Glu Ala Cys Arg Pro Ala Ala Gly Gly Ala Val His Thr Arg
                165                 170                 175
Gly Leu Asp Phe Ala Cys Asp Ile Tyr Ile Trp Ala Pro Leu Ala Gly
            180                 185                 190
Thr Cys Gly Val Leu Leu Leu Ser Leu Val Ile Thr Leu Tyr Cys Lys
        195                 200                 205
Arg Gly Arg Lys Lys Leu Leu Tyr Ile Phe Lys Gln Pro Phe Met Arg
    210                 215                 220
Pro Val Gln Thr Thr Gln Glu Glu Asp Gly Cys Ser Cys Arg Phe Pro
225                 230                 235                 240
Glu Glu Glu Glu Gly Gly Cys Glu Leu Arg Val Lys Phe Ser Arg Ser
                245                 250                 255
Ala Asp Ala Pro Ala Tyr Gln Gln Gly Gln Asn Gln Leu Tyr Asn Glu
            260                 265                 270
Leu Asn Leu Gly Arg Arg Glu Glu Tyr Asp Val Leu Asp Lys Arg Arg
        275                 280                 285
Gly Arg Asp Pro Glu Met Gly Gly Lys Pro Arg Arg Lys Asn Pro Gln
    290                 295                 300
Glu Gly Leu Tyr Asn Glu Leu Gln Lys Asp Lys Met Ala Glu Ala Tyr
305                 310                 315                 320
Ser Glu Ile Gly Met Lys Gly Glu Arg Arg Arg Gly Lys Gly His Asp
                325                 330                 335
Gly Leu Tyr Gln Gly Leu Ser Thr Ala Thr Lys Asp Thr Tyr Asp Ala
            340                 345                 350
Leu His Met Gln Ala Leu Pro Pro Arg
        355                 360

<210> SEQ ID NO 206
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Phe Leu Gly
1
```

COMPOSITIONS AND METHODS FOR TREATING CANCER WITH ANTI-CD22 IMMUNOTHERAPY

CROSS-REFERENCE TO RELATED APPLICATIONS

This application claims the benefit of priority under 35 U.S.C. Section 119(e) to U.S. Provisional Patent Application No. 62/572,926 filed on Oct. 16, 2017, the entire contents of which are incorporated herein by reference.

STATEMENT REGARDING FEDERALLY SPONSORED RESEARCH OR DEVELOPMENT

This invention was created in the performance of a Cooperative Research and Development Agreement with the National Institutes of Health, an Agency of the Department of Health and Human Services. The Government of the United States has certain rights in this invention.

SEQUENCE LISTING

The instant application contains a Sequence Listing which has been submitted electronically in ASCII format and is hereby incorporated by reference in its entirety. The ASCII copy, created on Oct. 12, 2018, is named Sequence Listing.txt and is 234 kilobytes in size.

FIELD OF THE DISCLOSURE

This application relates to the field of cancer, particularly to CD22 antigen binding domains and chimeric antigen receptors (CARs) containing such CD22 antigen binding domains and methods of use thereof.

BACKGROUND

Cancer is one of the most deadly threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult.

The present standard of care for B-lineage leukemias may consists of remission induction treatment by high dose of chemotherapy or radiation, followed by consolidation, and may feature stem cell transplantation and additional courses of chemotherapy as needed (see the world wide web at cancer.gov). High toxicity associated with these treatments, as well as the risk of complications, such as relapse, secondary malignancy, or graft versus host disease (GVHD), motivate the search for better therapeutic alternatives. CD22, also known as SIGLEC-2 (sialic acid-binding immunoglobulin-like lectin-2), is 95 kDa transmembrane surface glycoprotein and contains 6 Ig-like C2-type domains and one Ig-like V-type domain (uniprot.org/uniprot/P20273#structure, accessed Jul. 12, 2017). During B-cell ontogeny, CD22 is expressed on the B-cell surface starting at the pre-B cell stage, persists on mature B cells and is lost on plasma cells (Nitschke L, 2009, Immunological Reviews, 230:128-143). CD22 contains intracellular ITIM (immunoreceptor tyrosine-based inhibition motifs) domains which following the engagement of the B cell receptor for antigen serve to down-modulate cellular activation. Antibody binding of CD22 induces co-localization with SHP-1, and intracellular phosphatase that also serves to down-modulate phosorylation-based signal transduction (Lumb S, Fleishcer S J, Wiedemann A, Daridon C, Maloney A, Shock A, Dorner T, 2016, Journal of Cell Communication and Signaling, 10:143-151). The key point of relevance for treatment of B cell malignancies is that CD22 is expressed in a tightly regulated manner on normal B cells, but not expressed on hematopoietic stem cells, or mature plasma cells, making it a suitable target antigen for B cell leukemias. The expression of CD22 on both adult and pediatric (pre-B-ALL) B cell malignancies has led to exploiting this target for both antibody and chimeric antigen receptor (CAR)-T cell-based therapy (Haso W, Lee D W, Shah N N, Stetler-Stevenson M, Yuan C M, Pastan I H, Dimitrov D S, Morgan R A, FitzGerlad D J, Barrett D M, Wayne A S, Mackall C L, Orentas R J, 2013, Blood, 121:1165-1174) (Wayne A S, Kreitman R J, Findley H W, Lew G, Delbrook C, Steinberg S M, Stetler-Stevenson M, FitzGerald D J, Pastan I, 2010, Clinical Cancer Research, 16:1894-1903).

A number of novel approaches to treat B cell leukemia and lymphoma have been developed, including anti-CD22 antibodies linked to bacterial toxins or chemotherapeutic agents (Wayne A S, FitzGerald D J, Kreitman R J, Pastan I, 2014, Immunotoxins for leukemia, Blood, 123:2470-2477). Inotuzumab Ozogamicin (CMC-544, a humanized version of the murine monoclonal antibody G5/44) is an antibody drug conjugate and is currently being evaluated in clinical trials, either as a single agent or given in combination with chemotherapy (NCT01664910, sponsor: M.D. Anderson Cancer Center) (DiJoseph J F, et al., 2004, Blood, 103:1807-1814). As a single agent, outcomes exceeded those seen with standard therapy, although significant liver toxicity was noted (Kantarjian H, et al., 2016, Inotuzumb ozogamicin versus standard therapy for acute lymphoblastic leukemia (ALL), New England Journal of Medicine, 375:740-753). Unmodified CD22 therapeutic antibody, Epratuzumab, is also being tested in combination with chemotherapy (NCT01219816, sponsor: Nantes University Hospital). Epratuzumab is a chimeric protein composed of murine CDRs grafted onto a human antibody framework. Although effective in some leukemias, Moxetumomab pasudotox in not in broad clinical development due to problems with both immunogenicity of the bacterial toxin to which the antibody is fused and modest or comparable levels of activity with other agents (see NCT01829711, sponsor: MedImmune, LLC). To date, many of the binding moieties for CD22 employed in CAR constructs utilize a domain derived from these murine antibodies and do not effectively activate T cells that target this CD22 domain (such as the HA22 anti-CD22 binder used as the basis for Moxetumomab pasudotox, see James S E, Greenberg P D, Jensen M C, Lin Y, Wang J, Till B G, Raubitschek A A, Forman S J, Press O W, 2008, Journal of Immunology 180:7028-7038). One anti-CD22 binder that is effective as an anti-CD22 CAR is currently in clinical trial at the National Institutes of Health (NIH), although results have not been published (ClinicalTrials.gov Identifier: NCT02315612, Anti-CD22 Chimeric Receptor T Cells in Pediatric and Young Adults with Recurrent or Refractory CD22-expressing B Cell Malignancies, sponsor: NCI). This binder is based on the m971 fully human antibody developed in the laboratory of one of the inventors in this application, Dr. Dimiter Dimitrov (Xiao X, Ho M, Zhu Z, Pastan I, Dimitrov D, 2009, Identification and characterization of fully human anti-CD22 monoclonal antibodies, MABS, 1:297-303). The m971 domain was proven effective as a CAR in work supervised by another of the inventors in this application, Dr. Rimas Orentas (Haso W, et al., 2013, Anti-CD22-CARs targeting B-cell precursor ALL, Blood, 121:1165-1174).

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific CAR. Oncoimmunology. 2013; 2 (4): e23621). The antigen-binding motif of a CAR is commonly fashioned after a single chain Fragment variable (ScFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered into CARS. Alternate cell targets for CAR expression (such as NK or gamma-delta T cells) are also under development (Brown C E et al Clin Cancer Res. 2012; 18(8):2199-209; Lehner M et al. PLoS One. 2012; 7 (2):e31210). There remains significant work to be done with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the ScFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al J Immunol. 2009; 183 (9): 5563-74). With the advent of new technology, the activation of T cells with beads linked to anti-CD3 and anti-CD28 antibody, and the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-CARs targeting B cell precursor ALL, Blood. 2013; 121 (7):1165-74; Kochenderfer J N et al. Blood. 2012; 119 (12):2709-20). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured, for example the inclusion of the cytokines IL-2, IL-7, and/or IL-15 (Kaiser A D et al. Cancer Gene Ther. 2015; 22(2):72-78.

Current challenges in the more widespread and effective adaptation of CAR therapy for cancer relate to a paucity of compelling targets. Creating binders to cell surface antigens is now readily achievable, but discovering a cell surface antigen that is specific for tumor while sparing normal tissues remains a formidable challenge. One potential way to imbue greater target cell specificity to CAR-expressing T cells is to use combinatorial CAR approaches. In one system, the CD3-ζ and CD28 signal units are split between two different CAR constructs expressed in the same cell; in another, two CARs are expressed in the same T cell, but one has a lower affinity and thus requires the alternate CAR to be engaged first for full activity of the second (Lanitis E et al. Cancer Immunol Res. 2013; 1(1):43-53; Kloss C C et al. Nat Biotechnol. 2013; 31(1):71-5). A second challenge for the generation of a single ScFv-based CAR as an immunotherapeutic agent is tumor cell heterogeneity. At least one group has developed a CAR strategy for glioblastoma whereby the effector cell population targets multiple antigens (HER2, IL-13Ra, EphA2) at the same time in the hope of avoiding the outgrowth of target antigen-negative populations. (Hegde M et al. Mol Ther. 2013; 21(11):2087-101).

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with chemical-based dimerizers, such as AP1903, demonstrates one way in which a powerful switch that can control T-cell populations can be initiated pharmacologically (Di Stasi A et al. N Engl J Med. 2011; 365(18):1673-83). The creation of effector T-cell populations that are immune to the negative regulatory effects of transforming growth factor-β by the expression of a decoy receptor further demonstrates the degree to which effector T cells can be engineered for optimal antitumor activity (Foster A E et al. J Immunother. 2008; 31(5):500-5). Thus, while it appears that CARs can trigger T-cell activation in a manner similar to an endogenous T-cell receptor, a major impediment to the clinical application of this technology to date has been limited in vivo expansion of CAR+ T cells, rapid disappearance of the cells after infusion, and disappointing clinical activity. This may be due in part to the murine origin of some of the CAR sequences employed, an obstacle directly addressed by our inventions disclosed herein.

Accordingly, there is an urgent and long felt need in the art for discovering novel compositions and methods for treatment of B-ALL, DLBCL, FL, and other CD22-expressing B cell malignancies using an approach that can exhibit specific and efficacious anti-tumor effect without the aforementioned short comings.

The present invention addresses these needs by providing CAR compositions and therapeutic methods that can be used to treat cancers and other diseases and/or conditions. In particular, the present invention as disclosed and described herein provides CARs that may be used for the treatment of diseases, disorders or conditions associated with dysregulated expression of CD22 and which CARs contain CD22 antigen binding domains that exhibit a high surface expression on transduced T cells, exhibit a high degree of cytolysis of CD22-expressing cells, and in which the transduced T cells demonstrate in vivo expansion and persistence.

SUMMARY

Novel anti-CD22 antibodies or antigen binding domains thereof and chimeric antigen receptors (CARs) that contain such CD22 antigen binding domains are provided herein, as well as host cells (e.g., T cells) expressing the receptors, and nucleic acid molecules encoding the receptors. The CARs exhibit a high surface expression on transduced T cells, with a high degree of cytolysis, and with transduced T cell expansion and persistence in vivo. Methods of using the disclosed CARs, host cells, and nucleic acid molecules are also provided, for example, to treat a cancer in a subject.

Thus, in one aspect, an isolated polynucleotide encoding a human anti-CD22 antibody or a fragment thereof is provided comprising a nucleic acid sequence selected from the group consisting of SEQ ID NOs: 1, 11, 21, 31, 41, 51, 61, 71, 81, 91, 101, 111, 121, 131, 141, 151, 161, and 171.

In one embodiment, an isolated polynucleotide encoding a fully human anti-CD22 antibody or a fragment thereof is provided, wherein the antibody or a fragment thereof comprises a fragment selected from the group consisting of an Fab fragment, an F(ab')$_2$ fragment, an Fv fragment, and a single chain Fv (ScFv).

In one embodiment, an isolated polynucleotide encoding a fully human anti-CD22 antibody or a fragment thereof is provided, wherein the antibody or a fragment thereof comprises an amino acid sequence selected from the group consisting of SEQ ID NOs: 2, 12, 22, 32, 42, 52, 62, 72, 82, 92, 102, 112, 122, 132, 142, 152, 162, and 172.

In one aspect, an isolated nucleic acid molecule encoding a CAR is provided comprising, from N-terminus to C-terminus, at least one CD22 antigen binding domain encoded by a nucleotide sequence comprising a nucleic acid sequence selected from the group consisting of SEQ ID NOs: 1, 11, 21, 31, 41, 51, 61, 71, 81, 91, 101, 111, 121, 131, 141, 151, 161 and 171, at least one transmembrane domain, and at least one intracellular signaling domain.

In one embodiment, an isolated nucleic acid molecule encoding the CAR is provided wherein the encoded extracellular CD22 antigen binding domain comprises at least one single chain variable fragment of an antibody that binds to CD22.

In another embodiment, an isolated nucleic acid molecule encoding the CAR is provided wherein the encoded extracellular CD22 antigen binding domain comprises at least one heavy chain variable region of an antibody that binds to CD22.

In yet another embodiment, an isolated nucleic acid molecule encoding the CAR is provided wherein the encoded CAR extracellular CD22 antigen binding domain further comprises at least one lipocalin-based antigen binding antigen (anticalins) that binds to CD22.

In one embodiment, an isolated nucleic acid molecule is provided wherein the encoded extracellular CD22 antigen binding domain is connected to the transmembrane domain by a linker domain.

In another embodiment, an isolated nucleic acid molecule encoding the CAR is provided wherein the encoded CD22 extracellular antigen binding domain is preceded by a sequence encoding a leader or signal peptide.

In yet another embodiment, an isolated nucleic acid molecule encoding the CAR is provided comprising at least one CD22 antigen binding domain encoded by a nucleotide sequence comprising a nucleic acid sequence selected from the group consisting of SEQ ID NOs: 1, 11, 21, 31, 41, 51, 61, 71, 81, 91, 101, 111, 121, 131, 141, 151, 161, and 171 and wherein the CAR additionally encodes an extracellular antigen binding domain targets an antigen that includes, but is not limited to, CD20, CD22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, TSLPR, NY-ESO-1 TCR, MAGE A3 TCR, or any combination thereof.

In certain embodiments, an isolated nucleic acid molecule encoding the CAR is provided wherein the additionally encoded extracellular antigen binding domain comprises an anti-CD19 ScFv antigen binding domain, an anti-CD20 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-TSLPR ScFv antigen binding domain an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESO-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In one aspect, the CARs provided herein further comprise a linker or spacer domain.

In one embodiment, an isolated nucleic acid molecule encoding the CAR is provided wherein the extracellular CD22 antigen binding domain, the intracellular signaling domain, or both are connected to the transmembrane domain by a linker or spacer domain.

In one embodiment, an isolated nucleic acid molecule encoding the CAR is provided wherein the encoded linker domain is derived from the extracellular domain of CD8 or CD28, and is linked to a transmembrane domain.

In another embodiment, an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD83, CD86, CD134, CD137, CD154, TNFRSF19, or a combination thereof.

In yet another embodiment, an isolated nucleic acid molecule encoding the CAR is provided wherein the encoded intracellular signaling domain further comprises a CD3 zeta intracellular domain.

In another embodiment, an isolated nucleic acid molecule encoding the CAR is provided wherein the encoded at least one intracellular signaling domain comprises a costimulatory domain, a primary signaling domain, or a combination thereof.

In further embodiments, an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1 BB (CD137), or a combination thereof.

In one embodiment, an isolated nucleic acid molecule encoding the CAR is provided that further contains a leader sequence or signal peptide wherein the leader or signal peptide nucleotide sequence comprises the nucleotide sequence of SEQ ID NO: 190.

In yet another embodiment, an isolated nucleic acid molecule encoding the CAR is provided wherein the encoded leader sequence comprises the amino acid sequence of SEQ ID NO: 191.

In one aspect, a CAR is provided herein comprising, from N-terminus to C-terminus, at least one CD22 antigen binding domain, at least one transmembrane domain, and at least one intracellular signaling domain.

In one embodiment, a CAR is provided wherein the extracellular CD22 antigen binding domain comprises at least one single chain variable fragment of an antibody that binds to the antigen, or at least one heavy chain variable region of an antibody that binds to the antigen, or a combination thereof.

In another embodiment, a CAR is provided wherein the at least one transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, TNFRSF19, or a combination thereof.

In some embodiments, the CAR is provided wherein CAR additionally encodes an extracellular antigen binding domain comprising CD19, CD20, ROR1, mesothelin, CD33, CD38, CD123 (IL3RA), CD138, BCMA (CD269), GPC2, GPC3, FGFR4, TSLPR, c-Met, PSMA, Glycolipid F77, EGFRvIII, GD-2, TSLPR, NY-ESO-1 TCR, MAGE A3 TCR, or an amino acid sequence with 85%, 90%, 95%, 96%, 97%, 98% or 99% identity thereof, or any combination thereof.

In one embodiment, the CAR is provided wherein the extracellular antigen binding domain comprises an anti-CD19 ScFv antigen binding domain, an anti-CD20 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, anti-TSLPR ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESO-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In another embodiment, a CAR is provided wherein the at least one intracellular signaling domain comprises a costimulatory domain and a primary signaling domain.

In yet another embodiment, a CAR is provided wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, the nucleic acid sequence encoding a CAR comprises the nucleic acid sequence of SEQ ID NO: 3 (LTG 2202 LP-16P-CD8 TM-41BB-CD3zeta CAR nucleic acid sequence (FIG. 2A)). In one embodiment, the nucleic acid sequence encodes a CAR comprising the amino acid sequence of SEQ ID NO: 4 (LTG 2202 LP-16P-CD8 TM-41BB-CD3zeta CAR amino acid sequence (FIG. 2A)).

In another embodiment, the nucleic acid sequence encoding a CAR comprises the nucleic acid sequence of SEQ ID NO: 13 (LTG 2246 LP-24P-CD8 TM-41BB-CD3zeta CAR nucleic acid sequence (FIG. 2B)). In one embodiment, the nucleic acid sequence encodes a CAR comprising the amino acid sequence of SEQ ID NO: 14 (LTG 2246 LP-24P-CD8 TM-41BB-CD3zeta CAR amino acid sequence (FIG. 2B)).

In another embodiment, the nucleic acid sequence encoding a CAR comprises the nucleic acid sequence of SEQ ID NO: 23 (LTG 2247 LP-25P-CD8 TM-41BB-CD3zeta CAR nucleotide sequence (FIG. 2C)). In one embodiment, the nucleic acid sequence encodes a CAR comprising the amino acid sequence of SEQ ID NO: 24 (LTG 2247 LP-25P-CD8 TM-41BB-CD3zeta CAR amino acid sequence (FIG. 2C)).

In another embodiment, the nucleic acid sequence encoding a CAR comprises the nucleic acid sequence of SEQ ID NO: 33 (LTG 2248 LP-11S-CD8 TM-41BB-CD3zeta CAR nucleic acid sequence (FIG. 2D)). In one embodiment, the nucleic acid sequence encodes a CAR comprising the amino acid sequence of SEQ ID NO: 34 (LTG 2248 LP-11S-CD8 TM-41BB-CD3zeta CAR amino acid sequence (FIG. 2D)).

In another embodiment, the nucleic acid sequence encoding a CAR comprises the nucleic acid sequence of SEQ ID NO: 43 (LTG 2249 LP-12S-CD8 TM-41BB-CD3zeta CAR nucleic acid sequence (FIG. 2E)). In one embodiment, the nucleic acid sequence encodes a CAR comprising the amino acid sequence of SEQ ID NO: 28 LTG 2208 LP-12S-CD8 TM-41BB-CD3zeta CAR amino acid sequence (FIG. 2E)).

In another embodiment, the nucleic acid sequence encoding a CAR comprises the nucleic acid sequence of SEQ ID NO: 53 (LTG 2203 LP-16P3-CD8 TM-41BB-CD3zeta CAR nucleic acid sequence (FIG. 2F)). In one embodiment, the nucleic acid sequence encodes a CAR comprising the amino acid sequence of SEQ ID NO: 54 (LTG 2203 LP-16P3-CD8 TM-41BB-CD3zeta CAR amino acid sequence (FIG. 2F)).

In another embodiment, the nucleic acid sequence encoding a CAR comprises the nucleic acid sequence of SEQ ID NO: 63 (LTG 2204 LP-16P16-CD8 TM-41BB-CD3zeta CAR nucleic acid sequence (FIG. 2G)). In one embodiment, the nucleic acid sequence encodes a CAR comprising the amino acid sequence of SEQ ID NO: 34 (LTG 2204 LP-16P16-CD8 TM-41BB-CD3zeta CAR amino acid sequence (FIG. 2G)).

In another embodiment, the nucleic acid sequence encoding a CAR comprises the nucleic acid sequence of SEQ ID NO: 73 (LTG 2205 LP-16P20-CD8 TM-41BB-CD3zeta CAR nucleic acid sequence (FIG. 2H)). In one embodiment, the nucleic acid sequence encodes a CAR comprising the amino acid sequence of SEQ ID NO: 74 (LTG 2205 LP-16P20-CD8 TM-41BB-CD3zeta CAR amino acid sequence (FIG. 2H)).

In another embodiment, the nucleic acid sequence encoding a CAR comprises the nucleic acid sequence of SEQ ID NO: 83 (LTG 2206 LP-16P2-CD8 TM-41BB-CD3zeta CAR nucleic acid sequence (FIG. 2I)). In one embodiment, the nucleic acid sequence encodes a CAR comprising the amino acid sequence of SEQ ID NO: 84 (LTG 2206 LP-16P2-CD8 TM-41BB-CD3zeta CAR amino acid sequence (FIG. 2I)).

In another embodiment, the nucleic acid sequence encoding a CAR comprises the nucleic acid sequence of SEQ ID NO: 93 (LTG 2207 LP-16P6-CD8 TM-41BB-CD3zeta CAR nucleic acid sequence (FIG. 2J)). In one embodiment, the nucleic acid sequence encodes a CAR comprising the amino acid sequence of SEQ ID NO: 94 (LTG 2205 LP-16P20-CD8 TM-41BB-CD3zeta CAR amino acid sequence (FIG. 2J)).

In another embodiment, the nucleic acid sequence encoding a CAR comprises the nucleic acid sequence of SEQ ID NO: 103 (LTG 2208 LP-16P10-CD8 TM-41BB-CD3zeta CAR nucleic acid sequence (FIG. 2K)). In one embodiment, the nucleic acid sequence encodes a CAR comprising the amino acid sequence of SEQ ID NO: 104 (LTG 2208 LP-16P10-CD8 TM-41BB-CD3zeta CAR amino acid sequence (FIG. 2K)).

In another embodiment, the nucleic acid sequence encoding a CAR comprises the nucleic acid sequence of SEQ ID NO: 113 (LTG 2209 LP-16P17-CD8 TM-41BB-CD3zeta CAR nucleic acid sequence (FIG. 2L)). In one embodiment, the nucleic acid sequence encodes a CAR comprising the amino acid sequence of SEQ ID NO: 114 (LTG 2209 LP-16P17-CD8 TM-41BB-CD3zeta CAR amino acid sequence (FIG. 2L)).

In another embodiment, the nucleic acid sequence encoding a CAR comprises the nucleic acid sequence of SEQ ID NO: 123 (LTG 2210 LP-16P20v2-CD8 TM-41BB-CD3zeta CAR nucleic acid sequence (FIG. 2M)). In one embodiment, the nucleic acid sequence encodes a CAR comprising the amino acid sequence of SEQ ID NO: 124 (LTG 2210 LP-16P20v2-CD8 TM-41BB-CD3zeta CAR amino acid sequence (FIG. 2M)).

In another embodiment, the nucleic acid sequence encoding a CAR comprises the nucleic acid sequence of SEQ ID NO: 133 (LTG 2216 LP-16P1-CD8 TM-41BB-CD3zeta CAR nucleic acid sequence (FIG. 2N)). In one embodiment, the nucleic acid sequence encodes a CAR comprising the amino acid sequence of SEQ ID NO: 134 (LTG 2216 LP-16P1-CD8 TM-41BB-CD3zeta CAR amino acid sequence (FIG. 2H)).

In another embodiment, the nucleic acid sequence encoding a CAR comprises the nucleic acid sequence of SEQ ID NO: 143 (LTG 2217 LP-16P3v2-CD8 TM-41BB-CD3zeta CAR nucleic acid sequence (FIG. 2O)). In one embodiment, the nucleic acid sequence encodes a CAR comprising the amino acid sequence of SEQ ID NO: 144 (LTG 2217 LP-16P3v2-CD8 TM-41BB-CD3zeta CAR amino acid sequence (FIG. 2O)).

In another embodiment, the nucleic acid sequence encoding a CAR comprises the nucleic acid sequence of SEQ ID NO: 153 (LTG 2218 LP-16P8-CD8 TM-41BB-CD3zeta CAR nucleic acid sequence (FIG. 2P)). In one embodiment, the nucleic acid sequence encodes a CAR comprising the amino acid sequence of SEQ ID NO: 154 (LTG 2218 LP-16P8-CD8 TM-41BB-CD3zeta CAR amino acid sequence (FIG. 2P)).

In another embodiment, the nucleic acid sequence encoding a CAR comprises the nucleic acid sequence of SEQ ID NO: 163 (LTG 2219 LP-16P13-CD8 TM-41BB-CD3zeta CAR nucleic acid sequence (FIG. 2Q)). In one embodiment, the nucleic acid sequence encodes a CAR comprising the amino acid sequence of SEQ ID NO: 164 (LTG 2219 LP-16P13-CD8 TM-41BB-CD3zeta CAR amino acid sequence (FIG. 2Q)).

In another embodiment, the nucleic acid sequence encoding a CAR comprises the nucleic acid sequence of SEQ ID NO: 173 (LTG 2220 LP-16P15-CD8 TM-41BB-CD3zeta CAR nucleic acid sequence (FIG. 2R)). In one embodiment, the nucleic acid sequence encodes a CAR comprising the amino acid sequence of SEQ ID NO: 174 (LTG 2220 LP-16P15-CD8 TM-41BB-CD3zeta CAR amino acid sequence (FIG. 2R)).

In one aspect, the CARs disclosed herein are modified to express or contain a detectable marker for use in diagnosis, monitoring, and/or predicting the treatment outcome such as progression free survival of cancer patients or for monitoring the progress of such treatment.

In one embodiment, the nucleic acid molecule encoding the disclosed CARS can be contained in a vector, such as a viral vector. The vector is a DNA vector, an RNA vector, a plasmid vector, a cosmid vector, a herpes virus vector, a measles virus vector, a lentivirus vector, adenoviral vector, or a retrovirus vector, or a combination thereof.

In certain embodiments, the vector further comprises a promoter wherein the promoter is an inducible promoter, a tissue specific promoter, a constitutive promoter, a suicide promoter or any combination thereof.

In yet another embodiment, the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect, host cells including the nucleic acid molecule encoding the CAR are also provided. In some embodiments, the host cell is a T cell, such as a primary T cell obtained from a subject. In one embodiment, the host cell is a CD8+ T cell.

In yet another aspect, a pharmaceutical composition is provided comprising an anti-tumor effective amount of a population of human T cells, wherein the T cells comprise a nucleic acid sequence that encodes a CAR, wherein the CAR comprises at least one extracellular antigen binding domain comprising a CD22 antigen binding domain comprising the amino acid sequence of SEQ ID NO. 2, 12, 22, 32, 42, 52, 62, 72, 82, 92, 102, 112, 122, 132, 142, 152, 162, or 172, at least one linker domain, at least one transmembrane domain, and at least one intracellular signaling domain, wherein the T cells are T cells of a human having a cancer. The cancer includes, inter alia, a hematological cancer such as leukemia (e.g., (CLL, ALL, AML or CML, lymphoma (e.g., mantle cell lymphoma, non-Hodgkin's lymphoma (NHL) or Hodgkin's lymphoma) or multiple myeloma, or a combination thereof.

In one embodiment, a pharmaceutical composition is provided wherein the at least one transmembrane domain of the CAR contains a transmembrane domain of a protein selected from the group consisting of the alpha, beta or zeta chain of the T-cell receptor, CD28, CD3 epsilon, CD45, CD4, CD5, CD8, CD9, CD16, CD22, Mesothelin, CD33, CD37, CD64, CD80, CD83, CD86, CD134, CD137, CD154, TNFRSF19, or a combination thereof.

In another embodiment, a pharmaceutical composition is provided wherein the human cancer includes an adult carcinoma comprising coral and pharynx cancer (tongue, mouth, pharynx, head and neck), digestive system cancers (esophagus, stomach, small intestine, colon, rectum, anus, liver, interhepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-tumor effective amount of a population of human T cells of a human having a cancer wherein the cancer is a refractory cancer non-responsive to one or more chemotherapeutic agents. The cancer includes hematopoietic cancer, myelodysplastic syndrome pancreatic cancer, head and neck cancer, cutaneous tumors, minimal residual disease (MRD) in ALL, AML, adult B cell malignancies including, CLL, CML, NHL, pediatric B cell malignancies (including B lineage ALL), multiple myeloma lung cancer, breast cancer, ovarian cancer, prostate cancer, colon cancer, melanoma or other hematological cancer and solid tumors, or any combination thereof.

In another aspect, methods of making CAR-containing T cells (hereinafter "CAR-T cells") are provided. The methods include transducing a T cell with a vector or nucleic acid molecule encoding a disclosed CAR that specifically binds CD22, thereby making the CAR-T cell.

In yet another aspect, a method of generating a population of RNA-engineered cells is provided that comprises introducing an in vitro transcribed RNA or synthetic RNA of a nucleic acid molecule encoding a disclosed CAR into a cell of a subject, thereby generating a CAR cell.

In yet another aspect, a method for diagnosing a disease, disorder or condition associated with the expression of CD22 on a cell, is provided comprising a) contacting the cell with a human anti-CD19 antibody or fragment thereof, wherein the antibody or a fragment thereof comprises an amino acid sequence selected from the group consisting of SEQ ID NOs: 2, 12, 22, 32, 42, 52, 62, 72, 82, 92, 102, 112, 122, 132, 142, 152, 162, 172; and b) detecting the presence of CD22 wherein the presence of CD19 diagnoses for the disease, disorder or condition associated with the expression of CD22.

In one embodiment, the disease, disorder or condition associated with the expression of CD22 is cancer including hematopoietic cancer, myelodysplastic syndrome pancreatic cancer, head and neck cancer, cutaneous tumors, minimal residual disease (MRD) in ALL, AML, adult B cell malignancies including, CLL, CML, NHL, pediatric B cell malignancies (including B lineage ALL), multiple myeloma lung cancer, breast cancer, ovarian cancer, prostate cancer, colon cancer, melanoma or other hematological cancer and solid tumors, or any combination thereof.

In another embodiment, a method of diagnosing, prognosing, or determining risk of a CD19-related disease in a mammal, is provided comprising detecting the expression of CD22 in a sample derived from the mammal comprising: a) contacting the sample with a human anti-CD22 antibody or fragment thereof, wherein the antibody or a fragment thereof comprises an amino acid sequence selected from the group consisting of SEQ ID NOs: 2, 12, 22, 32, 42, 52, 62, 72, 82, 92, 102, 112, 122, 132, 142, 152, 162, or 172; and b) detecting the presence of CD22 wherein the presence of CD22 diagnoses for a CD22-related disease in the mammal.

In another embodiment, a method of inhibiting CD22-dependent T cell inhibition, is provided comprising contacting a cell with a human anti-CD22 antibody or fragment thereof, wherein the antibody or a fragment thereof comprises an amino acid sequence selected from the group consisting of SEQ ID NOs: 2, 12, 22, 32, 42, 52, 62, 72, 82, 92, 102, 112, 122, 132, 142, 152, 162, or 172. In one embodiment, the cell is selected from the group consisting of a CD22-expressing tumor cell, a tumor-associated macrophage, and any combination thereof.

In another embodiment, a method of blocking T-cell inhibition mediated by a CD22-expressing cell and altering the tumor microenvironment to inhibit tumor growth in a mammal, is provided comprising administering to the mammal an effective amount of a composition comprising an isolated anti-CD22 antibody or fragment thereof, wherein the antibody or a fragment thereof comprises an amino acid sequence selected from the group consisting of SEQ ID NOs: 2, 12, 22, 32, 42, 52, 62, 72, 82, 92, 102, 112, 122, 132, 142, 152, 162, and 172. In one embodiment, the cell is selected from the group consisting of a CD19-expressing tumor cell, a tumor-associated macrophage, and any combination thereof.

In another embodiment, a method of inhibiting, suppressing or preventing immunosuppression of an anti-tumor or anti-cancer immune response in a mammal, is provided comprising administering to the mammal an effective amount of a composition comprising an isolated anti-CD22 antibody or fragment thereof, wherein the antibody or a fragment thereof comprises an amino acid sequence selected from the group consisting of SEQ ID NOs: 2, 12, 22, 32, 42, 52, 62, 72, 82, 92, 102, 112, 122, 132, 142, 152, 162 and 172. In one embodiment, the antibody or fragment thereof inhibits the interaction between a first cell with a T cell, wherein the first cell is selected from the group consisting of a CD22-expressing tumor cell, a tumor-associated macrophage, and any combination thereof.

In another aspect, a method is provided for inducing an anti-tumor immunity in a mammal comprising administering to the mammal a therapeutically effective amount of a T cell transduced with vector or nucleic acid molecule encoding a disclosed CAR.

In another embodiment, a method of treating or preventing cancer in a mammal is provided comprising administering to the mammal one or more of the disclosed CARs, in an amount effective to treat or prevent cancer in the mammal. The method includes administering to the subject a therapeutically effective amount of host cells expressing a disclosed CAR that specifically binds CD22 and/or one or more of the aforementioned antigens, under conditions sufficient to form an immune complex of the antigen binding domain on the CAR and the extracellular domain of CD22 and/or one or more of the aforementioned antigens in the subject.

In yet another embodiment, a method is provided for treating a mammal having a disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a CAR, wherein the CAR includes at least one extracellular CD22 antigen binding domain comprising the amino acid sequence of SEQ ID NOs. 2, 12, 22, 32, 42, 52, 62, 72, 82, 92, 102, 112, 122, 132, 142, 152, 162, or 172, or any combination thereof, at least one linker or spacer domain, at least one transmembrane domain, at least one intracellular signaling domain, and wherein the T cells are T cells of the subject having cancer.

In yet another embodiment, a method is provided for treating cancer in a subject in need thereof comprising administering to the subject a pharmaceutical composition comprising an anti-tumor effective amount of a population of T cells, wherein the T cells comprise a nucleic acid sequence that encodes a CAR, wherein the CAR comprises at least one CD22 antigen binding domain comprising the amino acid sequence of SEQ ID NOs. 2, 12, 22, 32, 42, 52, 62, 72, 82, 92, 102, 112, 122, 132, 142, 152, 162, or 172, or any combination thereof, at least one linker or spacer domain, at least one transmembrane domain, at least one intracellular signaling domain, wherein the T cells are T cells of the subject having cancer. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD19, CD22, Mesothelin, CD33, CD37, CD64, CD80, CD83, CD86, CD134, CD137, CD154, TNFRSF16, TNFRSF19, or a combination thereof.

In yet another embodiment, a method is provided for generating a persisting population of genetically engineered T cells in a human diagnosed with cancer. In one embodiment, the method comprises administering to a human a T cell genetically engineered to express a CAR wherein the CAR comprises at least one CD22 antigen binding domain comprising the amino acid sequence of SEQ ID NOs. 2, 12, 22, 32, 42, 52, 62, 72, 82, 92, 102, 112, 122, 132, 142, 152, 162, or 172, or any combination thereof, at least one transmembrane domain, and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using one or more of the CARs disclosed herein, In yet another aspect, a kit is provided for making a CAR T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

It will be understood that the CARs, host cells, nucleic acids, and methods are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE FIGURES

FIGS. 2A-R depict several CARs containing novel extracellular CD22 antigen binding domain sequences. The general scheme for the CARs includes, from the N terminus to the C terminus, a Signal peptide, anti-CD22 binder variable heavy chain fragment or a linked single chain fragment variable (ScFv), extracellular linker, transmembrane, 4-1BB, CD3 zeta.

FIG. 2A depicts a lentiviral vector expressing the CAR containing the LTG 2202 16P CD22ScFv-CD8 TM-41BB-CD3zeta nucleic acid sequence (SEQ ID NO: 3) and the encoded amino acid sequence (SEQ ID NO: 4).

FIG. 2B depicts a lentiviral vector expressing the CAR containing the LTG 2246 24P CD22ScFv-CD8 TM-41BB-CD3zeta nucleic acid sequence (SEQ ID NO: 13) and the encoded amino acid sequence (SEQ ID NO: 14).

FIG. 2C depicts a lentiviral vector expressing the CAR containing the LTG 2247 25P CD22ScFv-CD8 TM-41BB-CD3zeta nucleotide sequence (SEQ ID NO: 23) and the encoded amino acid sequence (SEQ ID NO: 24).

FIG. 2D depicts a lentiviral vector expressing the CAR containing the LTG 2248 11s CD22ScFv-CD8 TM-41BB-CD3zeta nucleic acid sequence (SEQ ID NO: 33) and the encoded amino acid sequence.

FIG. 2E depicts a lentiviral vector expressing the CAR containing the LTG 2249 12s CD22ScFv-CD8 TM-41BB-CD3zeta nucleic acid sequence (SEQ ID NO: 43) and the encoded amino acid sequence (SEQ ID NO: 44).

FIG. 2F depicts a lentiviral vector expressing the CAR containing the LTG 2203 16P3 CD22ScFv-CD8 TM-41BB-CD3zeta nucleic acid sequence (SEQ ID NO: 53) and the encoded amino acid sequence (SEQ ID NO: 54).

FIG. 2G depicts a lentiviral vector expressing the CAR containing the LTG 2204 16P16 CD22ScFv-CD8 TM-41BB-CD3zeta nucleic acid sequence (SEQ ID NO: 63) and the encoded amino acid sequence (SEQ ID NO: 64).

FIG. 2H depicts a lentiviral vector expressing the CAR containing the LTG 2205 16P20 CD22ScFv-CD8 TM-41BB-CD3zeta nucleic acid sequence (SEQ ID NO: 73) and the encoded amino acid sequence (SEQ ID NO: 74).

FIG. 2I depicts a lentiviral vector expressing the CAR containing the LTG 2206 16P2 CD22ScFv-CD8 TM-41BB-CD3zeta nucleic acid sequence (SEQ ID NO: 83) and the encoded amino acid sequence (SEQ ID NO: 84).

FIG. 2J depicts a lentiviral vector expressing the CAR containing the LTG 2207 16P6 CD22ScFv-CD8 TM-41BB-CD3zeta nucleic acid sequence (SEQ ID NO: 93) and the encoded amino acid sequence (SEQ ID NO: 94).

FIG. 2K depicts a lentiviral vector expressing the CAR containing the LTG 2208 16P10 CD22ScFv-CD8 TM-41BB-CD3zeta nucleic acid sequence (SEQ ID NO: 103) and the encoded amino acid sequence (SEQ ID NO: 104).

FIG. 2L depicts a lentiviral vector expressing the CAR containing the LTG 2209 16P17 CD22ScFv-CD8 TM-41BB-CD3zeta nucleic acid sequence (SEQ ID NO: 113) and the encoded amino acid sequence (SEQ ID NO: 114).

FIG. 2M depicts a lentiviral vector expressing the CAR containing the LTG 2210 16P20v2 CD22ScFv-CD8 TM-41BB-CD3zeta nucleic acid sequence (SEQ ID NO: 123) and the encoded amino acid sequence (SEQ ID NO: 124).

FIG. 2N depicts a lentiviral vector expressing the CAR containing the LTG 2216 16P1 CD22ScFv-CD8 TM-41BB-CD3zeta nucleic acid sequence (SEQ ID NO: 133) and the encoded amino acid sequence (SEQ ID NO: 134).

FIG. 2O depicts a lentiviral vector expressing the CAR containing the LTG 2217 16P3v2 CD22ScFv-CD8 TM-41BB-CD3zeta nucleic acid sequence (SEQ ID NO: 143) and the encoded amino acid sequence (SEQ ID NO: 144).

FIG. 2P depicts a lentiviral vector expressing the CAR containing the LTG 2218 16P8 CD22ScFv-CD8 TM-41BB-CD3zeta nucleic acid sequence (SEQ ID NO: 153) and the encoded amino acid sequence (SEQ ID NO: 154).

FIG. 2Q depicts a lentiviral vector expressing the CAR containing the LTG 2219 16P13 CD22ScFv-CD8 TM-41BB-CD3zeta nucleic acid sequence (SEQ ID NO: 163) and the encoded amino acid sequence (SEQ ID NO: 164).

FIG. 2R depicts a lentiviral vector expressing the CAR containing the LTG 2220 16P15 CD22ScFv-CD8 TM-41BB-CD3zeta nucleic acid sequence (SEQ ID NO: 173) and the encoded amino acid sequence (SEQ ID NO: 174).

FIGS. 7A-B show cytolytic activity (CTL activity) as percent lysis of target cell lines that each express luciferase.

FIG. 7A shows the CD22 positive cell lines Raji and Reh and the CD22 non-expressing line K562.

FIG. 7B shows K562-CD19 and K562-CD22 cell lines, which were specifically transfected to express the target antigens. Three effector to target ratios were tested (E:T 10:1, 5:1, 2.5:1) for each LV-transduced T cell population, as listed on the x-axis: utd (untransduced, GFP-LV, LTG1538 (anti-CD19), m971 (LTG2200, control anti-CD22), 16p (LTG2202), 16p1 (LTG2216), 16p2 (LTG2206), 16p3v2 (LTG2217), 16p6 (LTG2207), 16p8 (LTG2218), 16p10 (LTG2208), 16p13 (LTG2219), 16p15 (LTG2220), 16p17 (TG2209), 16p20 (LTG2205).

DETAILED DESCRIPTION

Definitions

Figure 1:
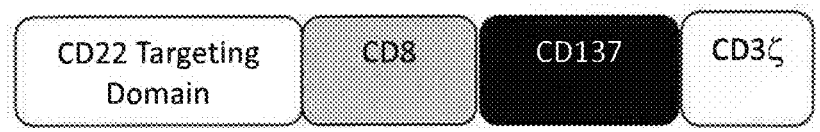
FIG. 1 depicts a schematic of the general domain structure of CARs with novel extracellular CD22 antigen binding domain sequences. A CAR is composed of an extracellular CD22-binding ScFv domain, a CD8 spacer and transmembrane domain, an intracellular signaling CD137 costimulatory domain and CD3 zeta signaling domain.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or"

means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term "about" when referring to a measurable value such as an amount, a temporal duration, and the like, is meant to encompass variations of .+−.20% or in some instances .+−.10%, or in some instances .+−.5%, or in some instances .+−.1%, or in some instances .+−.0.1% from the specified value, as such variations are appropriate to perform the disclosed methods.

Unless otherwise noted, the technical terms herein are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

The present disclosure provides for CD22 antibodies or fragments thereof as well as CARs having such CD22 antigen binding domains. The enhancement of the functional activity of the CAR directly relates to the enhancement of functional activity of the CAR-expressing T cell. As a result of one or more of these modifications, the CARs exhibit both a high degree of cytokine-induced cytolysis and cell surface expression on transduced T cells, along with an increased level of in vivo T cell expansion and persistence of the transduced CAR-expressing T cell.

The unique ability to combine functional moieties derived from different protein domains has been a key innovative feature of CARs. The choice of each of these protein domains is a key design feature, as is the way in which they are specifically combined. Each design domain is an essential component that can be used across different CAR platforms to engineer the function of lymphocytes. For example, the choice of the extracellular binding domain can make an otherwise ineffective CAR be effective.

The invariable framework components of the immunoglobulin-derived protein sequences used to create the extracellular antigen binding domain of a CAR can either be entirely neutral, or they can self-associate and drive the T cell to a state of metabolic exhaustion, thus making the therapeutic T cell expressing that CAR far less effective. This occurs independently of the antigen binding function of this CAR domain. Furthermore, the choice of the intracellular signaling domain(s) also can govern the activity and the durability of the therapeutic lymphocyte population used for immunotherapy. While the ability to bind target antigen and the ability to transmit an activation signal to the T cell through these extracellular and intracellular domains, respectively, are important CAR design aspects, what has also become apparent is that the choice of the source of the extracellular antigen binding fragments can have a significant effect on the efficacy of the CAR and thereby have a defining role for the function and clinical utility of the CAR.

Surprisingly and unexpectedly it has now been discovered that use of an entirely human antigen binding domain in a CAR, rather than using mouse-derived antigen binding fragments which are prone to induce anti-mouse immune response and CAR T elimination in a host (c.f., the UPenn-sponsored clinical trial using mouse derived SS1 ScFv sequence, NCT02159716), may also determine the functional activity of a CAR-expressing T cell.

The CARs disclosed herein are expressed at a high level in a cell. A cell expressing the CAR has a high in vivo proliferation rate, produces large amounts of cytokines, and has a high cytotoxic activity against a cell having, on its surface, a CD22 antigen to which a CAR binds. The use of a human extracellular CD22 antigen binding domain results in generation of a CAR that functions better in vivo, while avoiding the induction of anti-CAR immunity in the host immune response and the killing of the CAR T cell population. The CARs expressing the entirely human extracellular CD22 ScFv antigen binding domain exhibit superior activities/properties including i) prevention of poor CAR T persistence and function as seen with mouse-derived binding sequences; ii) lack of regional (i.e. intrapleural) delivery of the CAR to be efficacious; and iii) ability to generate CAR T cell designs based both on binders with high and low affinity to CD19. This latter property allows investigators to better tune efficacy vs toxicity, and/or tissue specificity of the CAR T product, since lower-affinity binders may have higher specificity to tumors vs normal tissues due to higher expression of CD22 on tumors than normal tissue, which may prevent on-target off tumor toxicity and bystander cell killing.

What follows is a detailed description of the inventive CARs including a description of their extracellular CD22 antigen binding domain, the transmembrane domain and the intracellular domain, along with additional description of the CARs, antibodies and antigen binding fragments thereof, conjugates, nucleotides, expression, vectors, and host cells, methods of treatment, compositions, and kits employing the disclosed CARs.

A. Chimeric Antigen Receptors (CARs)

The CARs disclosed herein comprise at least one CD22 antigen binding domain capable of binding to CD22, at least one transmembrane domain, and at least one intracellular domain.

A chimeric antigen receptor (CAR) is an artificially constructed hybrid protein or polypeptide containing the antigen binding domains of an antibody (e.g., single chain variable fragment (ScFv)) linked to T-cell signaling domains via the transmembrane domain. Characteristics of CARs include their ability to redirect T-cell specificity and reactivity toward a selected target in a non-Major Histocompatibiliy Complex (MHC)-restricted manner, and exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

As disclosed herein, the intracellular T cell signaling domains of the CARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Domain

In one embodiment, the CAR comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens include, for example, a glioma-associated antigen, carcinoembryonic antigen (CEA), .beta.-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD19, insulin growth factor (IGF)-I, IGF-II, IGF-I receptor and CD22. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20, CD22, BCMA, ROR1, and CD37 are other candidates for target antigens in B-cell lymphoma. Some of these antigens (CEA, HER-2, CD19, CD20, CD22, idiotype) have been used as targets for passive immunotherapy with monoclonal antibodies with limited success.

In one preferred embodiment, the tumor antigen is CD22 and the tumors associated with expression of CD22 comprise lung mesothelioma, ovarian, and pancreatic cancers that express high levels of the extracellular protein CD22, or any combination thereof.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In one embodiment, the antigen binding domain portion of the CAR targets an antigen that includes but is not limited to CD19, CD20, CD22, ROR1, CD33, CD38, CD123, CD138, BCMA, c-Met, PSMA, Glycolipid F77, EGFRvIII, GD-2, FGFR4, TSLPR, NY-ESO-1 TCR, MAGE A3 TCR, and the like.

In a preferred embodiment, the antigen binding domain portion of the CAR targets the extracellular CD22 antigen.

In one preferred embodiment, the isolated nucleic acid molecule encoding the extracellular CD22 scFv1 antigen binding domain comprises a nucleotide sequence of SEQ ID NO: 1, or a sequence with 85%, 90%, 95%, 96%, 97%, 98% or 99% identity thereof. In one embodiment, an isolated nucleic acid molecule is provided wherein the encoded extracellular CD22 antigen binding domain comprises an amino acid sequence of SEQ ID NO: 2, or an amino acid sequence with 85%, 90%, 95%, 96%, 97%, 98% or 99% identity to an amino acid sequence of SEQ ID NO: 2.

In one preferred embodiment, the isolated nucleic acid molecule encoding the extracellular CD22 scFv2 antigen binding domain comprises a nucleotide sequence of SEQ ID NO: 11, or a sequence with 85%, 90%, 95%, 96%, 97%, 98% or 99% identity thereof. In one embodiment, an isolated nucleic acid molecule is provided wherein the encoded extracellular CD22 antigen binding domain comprises an amino acid sequence of SEQ ID NO: 12, or an amino acid sequence with 85%, 90%, 95%, 96%, 97%, 98% or 99% identity to an amino acid sequence of SEQ ID NO: 12.

In one preferred embodiment, the isolated nucleic acid molecule encoding the extracellular CD22 ScFv3 antigen binding domain comprises a nucleotide sequence of SEQ ID NO: 21, or a sequence with 85%, 90%, 95%, 96%, 97%, 98% or 99% identity thereof. In one embodiment, an isolated nucleic acid molecule is provided wherein the encoded extracellular CD22 ScFv3 antigen binding domain comprises an amino acid sequence of SEQ ID NO: 22, or an amino acid sequence with 85%, 90%, 95%, 96%, 97%, 98% or 99% identity to an amino acid sequence of SEQ ID NO: 22.

In one preferred embodiment, the isolated nucleic acid molecule encoding the extracellular CD22 ScFv4 antigen binding domain comprises a nucleotide sequence of SEQ ID NO: 31, or a sequence with 85%, 90%, 95%, 96%, 97%, 98% or 99% identity thereof. In one embodiment, an isolated nucleic acid molecule is provided wherein the encoded extracellular CD22 ScFv4 antigen binding domain comprises an amino acid sequence of SEQ ID NO: 32, or an amino acid sequence with 85%, 90%, 95%, 96%, 97%, 98% or 99% identity to an amino acid sequence of SEQ ID NO: 32.

In one preferred embodiment, the isolated nucleic acid molecule encoding the extracellular CD22 ScFv5 antigen binding domain comprises a nucleotide sequence of SEQ ID NO: 41, or a sequence with 85%, 90%, 95%, 96%, 97%, 98% or 99% identity thereof. In one embodiment, an isolated nucleic acid molecule is provided wherein the encoded extracellular CD22 ScFv5 antigen binding domain comprises an amino acid sequence of SEQ ID NO: 42, or an amino acid sequence with 85%, 90%, 95%, 96%, 97%, 98% or 99% identity to an amino acid sequence of SEQ ID NO: 42.

In one preferred embodiment, the isolated nucleic acid molecule encoding the extracellular CD22 ScFv6 antigen binding domain comprises a nucleotide sequence of SEQ ID NO: 51, or a sequence with 85%, 90%, 95%, 96%, 97%, 98% or 99% identity thereof. In one embodiment, an isolated nucleic acid molecule is provided wherein the encoded extracellular CD22 ScFv6 antigen binding domain comprises an amino acid sequence of SEQ ID NO: 52, or an amino acid sequence with 85%, 90%, 95%, 96%, 97%, 98% or 99% identity to an amino acid sequence of SEQ ID NO: 52.

In one preferred embodiment, the isolated nucleic acid molecule encoding the extracellular CD22 ScFv7 antigen binding domain comprises a nucleotide sequence of SEQ ID NO: 61, or a sequence with 85%, 90%, 95%, 96%, 97%, 98% or 99% identity thereof. In one embodiment, an isolated nucleic acid molecule is provided wherein the encoded extracellular CD22 ScFv7 antigen binding domain comprises an amino acid sequence of SEQ ID NO: 62, or an amino acid sequence with 85%, 90%, 95%, 96%, 97%, 98% or 99% identity to an amino acid sequence of SEQ ID NO: 62.

In one preferred embodiment, the isolated nucleic acid molecule encoding the extracellular CD22 ScFv8 antigen binding domain comprises a nucleotide sequence of SEQ ID NO: 71, or a sequence with 85%, 90%, 95%, 96%, 97%, 98% or 99% identity thereof. In one embodiment, an isolated nucleic acid molecule is provided wherein the encoded extracellular CD22 ScFv8 antigen binding domain comprises an amino acid sequence of SEQ ID NO: 72, or an amino acid sequence with 85%, 90%, 95%, 96%, 97%, 98% or 99% identity to an amino acid sequence of SEQ ID NO: 72.

In one preferred embodiment, the isolated nucleic acid molecule encoding the extracellular CD22 ScFv9 antigen binding domain comprises a nucleotide sequence of SEQ ID NO: 81, or a sequence with 85%, 90%, 95%, 96%, 97%, 98% or 99% identity thereof. In one embodiment, an isolated nucleic acid molecule is provided wherein the encoded extracellular CD22 ScFv9 antigen binding domain comprises an amino acid sequence of SEQ ID NO: 82, or an amino acid sequence with 85%, 90%, 95%, 96%, 97%, 98% or 99% identity to an amino acid sequence of SEQ ID NO: 82.

In one preferred embodiment, the isolated nucleic acid molecule encoding the extracellular CD22 ScFv10 antigen binding domain comprises a nucleotide sequence of SEQ ID NO: 91, or a sequence with 85%, 90%, 95%, 96%, 97%, 98% or 99% identity thereof. In one embodiment, an isolated nucleic acid molecule is provided wherein the encoded extracellular CD22 ScFv10 antigen binding domain comprises an amino acid sequence of SEQ ID NO: 92, or an amino acid sequence with 85%, 90%, 95%, 96%, 97%, 98% or 99% identity to an amino acid sequence of SEQ ID NO: 92.

In one preferred embodiment, the isolated nucleic acid molecule encoding the extracellular CD22 ScFv11 antigen binding domain comprises a nucleotide sequence of SEQ ID NO: 101, or a sequence with 85%, 90%, 95%, 96%, 97%, 98% or 99% identity thereof. In one embodiment, an isolated nucleic acid molecule is provided wherein the encoded extracellular CD22 ScFv102 antigen binding domain comprises an amino acid sequence of SEQ ID NO: 92, or an amino acid sequence with 85%, 90%, 95%, 96%, 97%, 98% or 99% identity to an amino acid sequence of SEQ ID NO: 102.

In one preferred embodiment, the isolated nucleic acid molecule encoding the extracellular CD22 ScFv12 antigen binding domain comprises a nucleotide sequence of SEQ ID NO: 111, or a sequence with 85%, 90%, 95%, 96%, 97%, 98% or 99% identity thereof. In one embodiment, an isolated nucleic acid molecule is provided wherein the encoded extracellular CD22 ScFv112 antigen binding domain comprises an amino acid sequence of SEQ ID NO: 92, or an amino acid sequence with 85%, 90%, 95%, 96%, 97%, 98% or 99% identity to an amino acid sequence of SEQ ID NO: 112.

In one preferred embodiment, the isolated nucleic acid molecule encoding the extracellular CD22 ScFv13 antigen binding domain comprises a nucleotide sequence of SEQ ID NO: 121, or a sequence with 85%, 90%, 95%, 96%, 97%, 98% or 99% identity thereof. In one embodiment, an isolated nucleic acid molecule is provided wherein the encoded extracellular CD22 ScFv13 antigen binding domain comprises an amino acid sequence of SEQ ID NO: 122, or an amino acid sequence with 85%, 90%, 95%, 96%, 97%, 98% or 99% identity to an amino acid sequence of SEQ ID NO: 122.

In one preferred embodiment, the isolated nucleic acid molecule encoding the extracellular CD22 ScFv14 antigen binding domain comprises a nucleotide sequence of SEQ ID NO: 131, or a sequence with 85%, 90%, 95%, 96%, 97%, 98% or 99% identity thereof. In one embodiment, an isolated nucleic acid molecule is provided wherein the encoded extracellular CD22 ScFv14 antigen binding domain comprises an amino acid sequence of SEQ ID NO: 132, or an amino acid sequence with 85%, 90%, 95%, 96%, 97%, 98% or 99% identity to an amino acid sequence of SEQ ID NO: 132.

In one preferred embodiment, the isolated nucleic acid molecule encoding the extracellular CD22 ScFv15 antigen binding domain comprises a nucleotide sequence of SEQ ID NO: 141, or a sequence with 85%, 90%, 95%, 96%, 97%, 98% or 99% identity thereof. In one embodiment, an isolated nucleic acid molecule is provided wherein the encoded extracellular CD22 ScFv15 antigen binding domain comprises an amino acid sequence of SEQ ID NO: 142, or an amino acid sequence with 85%, 90%, 95%, 96%, 97%, 98% or 99% identity to an amino acid sequence of SEQ ID NO: 142.

In one preferred embodiment, the isolated nucleic acid molecule encoding the extracellular CD22 ScFv16 antigen binding domain comprises a nucleotide sequence of SEQ ID NO: 151, or a sequence with 85%, 90%, 95%, 96%, 97%, 98% or 99% identity thereof. In one embodiment, an isolated nucleic acid molecule is provided wherein the encoded extracellular CD22 ScFv16 antigen binding domain comprises an amino acid sequence of SEQ ID NO: 152, or an amino acid sequence with 85%, 90%, 95%, 96%, 97%, 98% or 99% identity to an amino acid sequence of SEQ ID NO: 152.

In one preferred embodiment, the isolated nucleic acid molecule encoding the extracellular CD22 ScFv17 antigen binding domain comprises a nucleotide sequence of SEQ ID NO: 161, or a sequence with 85%, 90%, 95%, 96%, 97%, 98% or 99% identity thereof. In one embodiment, an isolated nucleic acid molecule is provided wherein the encoded extracellular CD22 ScFv17 antigen binding domain comprises an amino acid sequence of SEQ ID NO: 162, or an amino acid sequence with 85%, 90%, 95%, 96%, 97%, 98% or 99% identity to an amino acid sequence of SEQ ID NO: 162.

In one preferred embodiment, the isolated nucleic acid molecule encoding the extracellular CD22 ScFv18 antigen binding domain comprises a nucleotide sequence of SEQ ID NO: 171, or a sequence with 85%, 90%, 95%, 96%, 97%, 98% or 99% identity thereof. In one embodiment, an isolated nucleic acid molecule is provided wherein the encoded extracellular CD22 ScFv18 antigen binding domain comprises an amino acid sequence of SEQ ID NO: 172, or an amino acid sequence with 85%, 90%, 95%, 96%, 97%, 98% or 99% identity to an amino acid sequence of SEQ ID NO: 172.

In one preferred embodiment, the isolated light chain complementarity determining region amino acid sequences (LCDR1, LCDR2, LCDR2, identified as SEQ ID NO: 5, SEQ ID NO: 6, and SEQ ID NO: 7, respectively) and the heavy chain complementarity determining region amino acid sequences (HCDR1, HCDR2, HCDR3, identified as SEQ ID NO: 8, SEQ ID NO: 9, and SEQ ID NO: 10, respectively) that each individually contribute to create the binding characteristics of the CD22 specific scFv1, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv1 by co-expression of SEQ ID NO: 5, SEQ ID NO: 6, SEQ ID NO: 7, SEQ ID NO: 8, SEQ ID NO: 9, and SEQ ID NO: 10, in a single ScFv amino acid sequence.

In one preferred embodiment, the isolated light chain complementarity determining region amino acid sequences (LCDR1, LCDR2, LCDR2, identified as SEQ ID NO: 15, SEQ ID NO: 16, and SEQ ID NO: 17, respectively) and the heavy chain complementarity determining region amino acid sequences (HCDR1, HCDR2, HCDR3, identified as SEQ ID NO: 18, SEQ ID NO: 19, and SEQ ID NO: 20, respectively) that each individually contribute to create the binding characteristics of the CD22 specific scFv2, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv2 by co-expression of SEQ ID NO: 15, SEQ ID NO: 16, SEQ ID NO: 17, SEQ ID NO: 18, SEQ ID NO:19, and SEQ ID NO: 20, in a single amino acid sequence.

In one preferred embodiment, the isolated light chain complementarity determining region amino acid sequences (LCDR1, LCDR2, LCDR2, identified as SEQ ID NO: 25, SEQ ID NO: 26, and SEQ ID NO: 27, respectively) and the heavy chain complementarity determining region amino acid sequences (HCDR1, HCDR2, HCDR3, identified as SEQ ID NO: 28, SEQ ID NO: 29, and SEQ ID NO: 30, respectively) that each individually contribute to create the binding characteristics of the CD22 specific scFv3, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv3 by co-expression of SEQ ID NO: 25, SEQ ID NO: 26, SEQ ID NO: 27, SEQ ID NO: 28, SEQ ID NO: 29, and SEQ ID NO: 30, in a single amino acid sequence.

In one preferred embodiment, the isolated light chain complementarity determining region amino acid sequences (LCDR1, LCDR2, LCDR2, identified as SEQ ID NO: 35, SEQ ID NO: 36, and SEQ ID NO: 37, respectively) and the heavy chain complementarity determining region amino acid sequences (HCDR1, HCDR2, HCDR3, identified as SEQ ID NO: 38, SEQ ID NO: 39, and SEQ ID NO: 40, respectively) that each individually contribute to create the binding characteristics of the CD22 specific scFv4, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv4 by co-expression of SEQ ID NO: 35, SEQ ID NO: 36, SEQ ID NO: 37, SEQ ID NO: 38, SEQ ID NO: 39, and SEQ ID NO: 40, in a single amino acid sequence.

In one preferred embodiment, the isolated light chain complementarity determining region amino acid sequences (LCDR1, LCDR2, LCDR2, identified as SEQ ID NO: 45, SEQ ID NO: 46, and SEQ ID NO: 47, respectively) and the heavy chain complementarity determining region amino acid sequences (HCDR1, HCDR2, HCDR3, identified as SEQ ID NO: 48, SEQ ID NO: 49, and SEQ ID NO: 50, respectively) that each individually contribute to create the binding characteristics of the CD22 specific scFv5, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv5 by co-expression of SEQ ID NO: 45, SEQ ID NO: 46, SEQ ID NO: 47, SEQ ID NO: 48, SEQ ID NO: 49, and SEQ ID NO: 50, in a single amino acid sequence.

In one preferred embodiment, the isolated light chain complementarity determining region amino acid sequences (LCDR1, LCDR2, LCDR2, identified as SEQ ID NO: 55, SEQ ID NO: 56, and SEQ ID NO: 57, respectively) and the heavy chain complementarity determining region amino acid sequences (HCDR1, HCDR2, HCDR3, identified as SEQ ID NO: 58, SEQ ID NO: 59, and SEQ ID NO: 60, respectively) that each individually contribute to create the binding characteristics of the CD22 specific scFv6, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv6 by co-expression of SEQ ID NO: 55, SEQ ID NO: 56, SEQ ID NO: 57, SEQ ID NO: 58, SEQ ID NO: 59, and SEQ ID NO: 60, in a single amino acid sequence.

In one preferred embodiment, the isolated light chain complementarity determining region amino acid sequences (LCDR1, LCDR2, LCDR2, identified as SEQ ID NO: 65, SEQ ID NO: 66, and SEQ ID NO: 67, respectively) and the heavy chain complementarity determining region amino acid sequences (HCDR1, HCDR2, HCDR3, identified as SEQ ID NO: 68, SEQ ID NO: 69, and SEQ ID NO: 70, respectively) that each individually contribute to create the binding characteristics of the CD22 specific scFv7, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv7 by co-expression of SEQ ID NO: 65, SEQ ID NO: 66, SEQ ID NO: 67, SEQ ID NO: 68, SEQ ID NO: 69, and SEQ ID NO: 70, in a single amino acid sequence.

In one preferred embodiment, the isolated light chain complementarity determining region amino acid sequences (LCDR1, LCDR2, LCDR2, identified as SEQ ID NO: 75, SEQ ID NO: 76, and SEQ ID NO: 77, respectively) and the heavy chain complementarity determining region amino acid sequences (HCDR1, HCDR2, HCDR3, identified as SEQ ID NO: 78, SEQ ID NO: 79, and SEQ ID NO: 80, respectively) that each individually contribute to create the binding characteristics of the CD22 specific scFv8, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv8 by co-expression of SEQ ID NO: 75, SEQ ID NO: 76, SEQ ID NO: 77, SEQ ID NO: 78, SEQ ID NO: 79, and SEQ ID NO: 80, in a single amino acid sequence.

In one preferred embodiment, the isolated light chain complementarity determining region amino acid sequences (LCDR1, LCDR2, LCDR2, identified as SEQ ID NO: 85, SEQ ID NO: 86, and SEQ ID NO: 87, respectively) and the heavy chain complementarity determining region amino acid sequences (HCDR1, HCDR2, HCDR3, identified as SEQ ID NO: 88, SEQ ID NO: 89, and SEQ ID NO: 90, respectively) that each individually contribute to create the binding characteristics of the CD22 specific scFv9, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv9 by co-expression of SEQ ID NO: 85, SEQ ID NO: 86, SEQ ID NO: 87, SEQ ID NO: 88, SEQ ID NO: 89, and SEQ ID NO: 90, in a single amino acid sequence.

In one preferred embodiment, the isolated light chain complementarity determining region amino acid sequences (LCDR1, LCDR2, LCDR2, identified as SEQ ID NO: 95, SEQ ID NO: 96, and SEQ ID NO: 97, respectively) and the heavy chain complementarity determining region amino acid sequences (HCDR1, HCDR2, HCDR3, identified as SEQ ID NO: 98, SEQ ID NO: 99, and SEQ ID NO: 100, respectively) that each individually contribute to create the binding characteristics of the CD22 specific scFv10, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv10 by co-expression of SEQ ID NO: 95, SEQ ID NO: 96, SEQ ID NO: 97, SEQ ID NO: 98, SEQ ID NO: 99, and SEQ ID NO: 100, in a single amino acid sequence.

In one preferred embodiment, the isolated light chain complementarity determining region amino acid sequences (LCDR1, LCDR2, LCDR2, identified as SEQ ID NO: 105, SEQ ID NO: 106, and SEQ ID NO: 107, respectively) and the heavy chain complementarity determining region amino acid sequences (HCDR1, HCDR2, HCDR3, identified as SEQ ID NO: 108, SEQ ID NO: 109, and SEQ ID NO: 110, respectively) that each individually contribute to create the binding characteristics of the CD22 specific scFv11, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv11 by co-expression of SEQ ID NO: 105, SEQ ID NO: 106, SEQ ID NO: 107, SEQ ID NO: 108, SEQ ID NO: 109, and SEQ ID NO: 110, in a single amino acid sequence.

In one preferred embodiment, the isolated light chain complementarity determining region amino acid sequences (LCDR1, LCDR2, LCDR2, identified as SEQ ID NO: 115, SEQ ID NO: 116, and SEQ ID NO: 117, respectively) and the heavy chain complementarity determining region amino acid sequences (HCDR1, HCDR2, HCDR3, identified as SEQ ID NO: 118, SEQ ID NO: 119, and SEQ ID NO: 120, respectively) that each individually contribute to create the binding characteristics of the CD22 specific scFv12, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv12 by co-expression of SEQ ID NO: 115, SEQ ID NO: 116, SEQ ID NO: 117, SEQ ID NO: 118, SEQ ID NO: 119, and SEQ ID NO: 120, in a single amino acid sequence.

In one preferred embodiment, the isolated light chain complementarity determining region amino acid sequences (LCDR1, LCDR2, LCDR2, identified as SEQ ID NO: 125, SEQ ID NO: 126, and SEQ ID NO: 127, respectively) and the heavy chain complementarity determining region amino acid sequences (HCDR1, HCDR2, HCDR3, identified as SEQ ID NO: 128, SEQ ID NO: 129, and SEQ ID NO: 130, respectively) that each individually contribute to create the binding characteristics of the CD22 specific scFv13, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv13 by co-expression of SEQ ID NO: 125, SEQ ID NO: 126, SEQ ID NO:

127, SEQ ID NO: 128, SEQ ID NO: 129, and SEQ ID NO: 130, in a single amino acid sequence.

In one preferred embodiment, the isolated light chain complementarity determining region amino acid sequences (LCDR1, LCDR2, LCDR2, identified as SEQ ID NO: 135, SEQ ID NO: 136, and SEQ ID NO: 137, respectively) and the heavy chain complementarity determining region amino acid sequences (HCDR1, HCDR2, HCDR3, identified as SEQ ID NO: 138, SEQ ID NO: 139, and SEQ ID NO: 140, respectively) that each individually contribute to create the binding characteristics of the CD22 specific scFv14, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv14 by co-expression of SEQ ID NO: 135, SEQ ID NO: 136, SEQ ID NO:137, SEQ ID NO: 138, SEQ ID NO: 139, and SEQ ID NO: 140, in a single amino acid sequence.

In one preferred embodiment, the isolated light chain complementarity determining region amino acid sequences (LCDR1, LCDR2, LCDR2, identified as SEQ ID NO: 145, SEQ ID NO: 146, and SEQ ID NO: 147, respectively) and the heavy chain complementarity determining region amino acid sequences (HCDR1, HCDR2, HCDR3, identified as SEQ ID NO: 148, SEQ ID NO: 149, and SEQ ID NO: 150, respectively) that each individually contribute to create the binding characteristics of the CD22 specific scFv15, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv15 by co-expression of SEQ ID NO: 145, SEQ ID NO: 146, SEQ ID NO: 147, SEQ ID NO: 148, SEQ ID NO: 149, and SEQ ID NO: 150, in a single amino acid sequence.

In one preferred embodiment, the isolated light chain complementarity determining region amino acid sequences (LCDR1, LCDR2, LCDR2, identified as SEQ ID NO: 155, SEQ ID NO: 156, and SEQ ID NO: 157, respectively) and the heavy chain complementarity determining region amino acid sequences (HCDR1, HCDR2, HCDR3, identified as SEQ ID NO: 158, SEQ ID NO: 159, and SEQ ID NO: 160, respectively) that each individually contribute to create the binding characteristics of the CD22 specific scFv16, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv16 by co-expression of SEQ ID NO: 155, SEQ ID NO: 156, SEQ ID NO: 157, SEQ ID NO: 158, SEQ ID NO: 159, and SEQ ID NO: 160, in a single amino acid sequence.

In one preferred embodiment, the isolated light chain complementarity determining region amino acid sequences (LCDR1, LCDR2, LCDR2, identified as SEQ ID NO: 165, SEQ ID NO: 166, and SEQ ID NO: 167, respectively) and the heavy chain complementarity determining region amino acid sequences (HCDR1, HCDR2, HCDR3, identified as SEQ ID NO: 168, SEQ ID NO: 169, and SEQ ID NO: 170, respectively) that each individually contribute to create the binding characteristics of the CD22 specific scFv17, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv17 by co-expression of SEQ ID NO: 165, SEQ ID NO: 166, SEQ ID NO: 167, SEQ ID NO: 168, SEQ ID NO: 169, and SEQ ID NO: 170, in a single amino acid sequence.

In one preferred embodiment, the isolated light chain complementarity determining region amino acid sequences (LCDR1, LCDR2, LCDR2, identified as SEQ ID NO: 175, SEQ ID NO: 176, and SEQ ID NO: 177, respectively) and the heavy chain complementarity determining region amino acid sequences (HCDR1, HCDR2, HCDR3, identified as SEQ ID NO: 178, SEQ ID NO: 179, and SEQ ID NO: 180, respectively) that each individually contribute to create the binding characteristics of the CD22 specific scFv18, as a grouping to create the light chain binding characteristic of the scFv (LCDR1 plus LCDR2 plus LCDR3), as a grouping to create the heavy chain binding characteristics of the scFv (HCDR1 plus HCDR2 plus HCDR3), and as a grouping of six SEQ IDs that together as a group create the binding characteristics of the CD22 specific scFv18 by co-expression of SEQ ID NO: 175, SEQ ID NO: 176, SEQ ID NO: 177, SEQ ID NO: 178, SEQ ID NO: 179, and SEQ ID NO: 180, in a single amino acid sequence.

In the various embodiments of the CD22-specific CARs disclosed herein, the general scheme is set forth in FIG. 1 and includes, from the N-terminus to the C-terminus, a signal or leader peptide, anti-CD22 ScFv, extracellular linker, CD8 transmembrane, 4-1BB, CD3zeta, wherein the bolded text represents the cloning sites for linking domains.

In one embodiment, the nucleic acid sequence encoding a CAR comprises the nucleic acid sequence of SEQ ID NO: 3, and encodes the CAR comprising the amino acid sequence as set forth in SEQ ID NO: 4 [LTG 2202 LP-16P-CD8 TM-41BB-CD3zeta amino acid sequence (as depicted in FIG. 2A)].

In one embodiment, the nucleic acid sequence encoding a CAR comprises the nucleic acid sequence of SEQ ID NO: 3, or a sequence with 85%, 90%, 95%, 96%, 97%, 98% or 99% identity thereof, and encodes the CAR comprising the amino acid sequence as set forth in SEQ ID NO: 4 or a sequence with 85%, 90%, 95%, 96%, 97%, 98% or 99% identity thereof, LTG 2202 LP-16P-CD8 TM-41BB-CD3zeta amino acid sequence (as depicted in FIG. 2A)].

In another embodiment, the nucleic acid sequence encoding a CAR comprises the nucleic acid sequence of SEQ ID NO: 13, and encodes the CAR comprising the amino acid sequence as set forth in SEQ ID NO: 14 [LTG 2246 LP-24P-CD8 TM-41BB-CD3zeta amino acid sequence (as depicted in FIG. 2B)].

In another embodiment, the nucleic acid sequence encoding a CAR comprises the nucleic acid sequence of SEQ ID NO: 13 or a sequence with 85%, 90%, 95%, 96%, 97%, 98% or 99% identity thereof, and encodes the CAR comprising the amino acid sequence as set forth in SEQ ID NO: 14 or a sequence with 85%, 90%, 95%, 96%, 97%, 98% or 99% identity thereof [LTG 2246 LP-24P-CD8 TM-41BB-CD3zeta amino acid sequence (as depicted in FIG. 2B)].

In another embodiment, the nucleic acid sequence encoding a CAR comprises the nucleic acid sequence of SEQ ID NO: 23, and encodes the CAR comprising the amino acid sequence as set forth in SEQ ID NO: 24 [LTG 2247 LP-25P-CD8 TM-41BB-CD3zeta CAR amino acid sequence (as depicted in FIG. 2C)].

In another embodiment, the nucleic acid sequence encoding a CAR comprises the nucleic acid sequence of SEQ ID NO: 23 or a sequence with 85%, 90%, 95%, 96%, 97%, 98% or 99% identity thereof, and encodes the CAR comprising the amino acid sequence as set forth in SEQ ID NO: 24 or a sequence with 85%, 90%, 95%, 96%, 97%, 98% or 99% identity thereof [LTG 2247 LP-25P-CD8 TM-41BB-CD3zeta CAR amino acid sequence (as depicted in FIG. 2C)].

In yet another embodiment, the nucleic acid sequence encoding a CAR comprises the nucleic acid sequence of SEQ ID NO: 33, and encodes the CAR comprising the amino acid sequence as set forth in SEQ ID NO: 34 [LTG2248 LP-11S-CD8 TM-41BB-CD3zeta amino acid sequence (as depicted in FIG. 2D)].

In yet another embodiment, the nucleic acid sequence encoding a CAR comprises the nucleic acid sequence of SEQ ID NO: 33 or a sequence with 85%, 90%, 95%, 96%, 97%, 98% or 99% identity thereof, and encodes the CAR comprising the amino acid sequence as set forth in SEQ ID NO: 34 or a sequence with 85%, 90%, 95%, 96%, 97%, 98% or 99% identity thereof [LTG2248 LP-11S-CD8 TM-41BB-CD3zeta amino acid sequence (as depicted in FIG. 2D)].

In yet another embodiment, the nucleic acid sequence encoding a CAR comprises the nucleic acid sequence of SEQ ID NO: 43, and encodes the CAR comprising the amino acid sequence as set forth in SEQ ID NO: 44 [LTG2249 LP-12S-CD8 TM-41BB-CD3zeta amino acid sequence (as depicted in FIG. 2E)].

In yet another embodiment, the nucleic acid sequence encoding a CAR comprises the nucleic acid sequence of SEQ ID NO: 43 or a sequence with 85%, 90%, 95%, 96%, 97%, 98% or 99% identity thereof, and encodes the CAR comprising the amino acid sequence as set forth in SEQ ID NO: 44 or a sequence with 85%, 90%, 95%, 96%, 97%, 98% or 99% identity thereof [LTG2249 LP-12S-CD8 TM-41BB-CD3zeta amino acid sequence (as depicted in FIG. 2E)].

In yet another embodiment, the nucleic acid sequence encoding a CAR comprises the nucleic acid sequence of SEQ ID NO: 53, and encodes the CAR comprising the amino acid sequence as set forth in SEQ ID NO: 54 [(LTG2203 LP-16P3-CD8 TM-41BB-CD3zeta amino acid sequence (as depicted in FIG. 2F)].

In yet another embodiment, the nucleic acid sequence encoding a CAR comprises the nucleic acid sequence of SEQ ID NO: 53 or a sequence with 85%, 90%, 95%, 96%, 97%, 98% or 99% identity thereof, and encodes the CAR comprising the amino acid sequence as set forth in SEQ ID NO: 54 or a sequence with 85%, 90%, 95%, 96%, 97%, 98% or 99% identity thereof [LTG2203 LP-16P3-CD8 TM-41BB-CD3zeta amino acid sequence (as depicted in FIG. 2F)].

In yet another embodiment, the nucleic acid sequence encoding a CAR comprises the nucleic acid sequence of SEQ ID NO: 63, and encodes the CAR comprising the amino acid sequence as set forth in SEQ ID NO: 64 [(LTG2204 LP-16P16-CD8 TM-41BB-CD3zeta amino acid sequence (as depicted in FIG. 2G)].

In yet another embodiment, the nucleic acid sequence encoding a CAR comprises the nucleic acid sequence of SEQ ID NO: 63 or a sequence with 85%, 90%, 95%, 96%, 97%, 98% or 99% identity thereof, and encodes the CAR comprising the amino acid sequence as set forth in SEQ ID NO: 64 or a sequence with 85%, 90%, 95%, 96%, 97%, 98% or 99% identity thereof [(LTG2204 LP-16P16-CD8 TM-41BB-CD3zeta amino acid sequence (as depicted in FIG. 2G)].

In yet another embodiment, the nucleic acid sequence encoding a CAR comprises the nucleic acid sequence of SEQ ID NO: 73, and encodes the CAR comprising the amino acid sequence as set forth in SEQ ID NO: 74 [(LTG2205 LP-16P20-CD8 TM-41BB-CD3zeta amino acid sequence (as depicted in FIG. 2H)].

In yet another embodiment, the nucleic acid sequence encoding a CAR comprises the nucleic acid sequence of SEQ ID NO: 73 or a sequence with 85%, 90%, 95%, 96%, 97%, 98% or 99% identity thereof, and encodes the CAR comprising the amino acid sequence as set forth in SEQ ID NO: 74 or a sequence with 85%, 90%, 95%, 96%, 97%, 98% or 99% identity thereof [(LTG2205 LP-16P20-CD8 TM-41BB-CD3zeta amino acid sequence (as depicted in FIG. 2H)].

In yet another embodiment, the nucleic acid sequence encoding a CAR comprises the nucleic acid sequence of SEQ ID NO: 83, and encodes the CAR comprising the amino acid sequence as set forth in SEQ ID NO: 84 [(LTG2206 LP-16P2-CD8 TM-41BB-CD3zeta amino acid sequence (as depicted in FIG. 2I)].

In yet another embodiment, the nucleic acid sequence encoding a CAR comprises the nucleic acid sequence of SEQ ID NO: 83 or a sequence with 85%, 90%, 95%, 96%, 97%, 98% or 99% identity thereof, and encodes the CAR comprising the amino acid sequence as set forth in SEQ ID NO: 84 or a sequence with 85%, 90%, 95%, 96%, 97%, 98% or 99% identity thereof [(LTG2206 LP-16P2-CD8 TM-41BB-CD3zeta amino acid sequence (as depicted in FIG. 2I)].

In yet another embodiment, the nucleic acid sequence encoding a CAR comprises the nucleic acid sequence of SEQ ID NO: 93, and encodes the CAR comprising the amino acid sequence as set forth in SEQ ID NO: 94 [(LTG2207 LP-16P6-CD8 TM-41BB-CD3zeta amino acid sequence (as depicted in FIG. 2J)].

In yet another embodiment, the nucleic acid sequence encoding a CAR comprises the nucleic acid sequence of SEQ ID NO: 93 or a sequence with 85%, 90%, 95%, 96%, 97%, 98% or 99% identity thereof, and encodes the CAR comprising the amino acid sequence as set forth in SEQ ID NO: 94 or a sequence with 85%, 90%, 95%, 96%, 97%, 98% or 99% identity thereof [(LTG2207 LP-16P6-CD8 TM-41BB-CD3zeta amino acid sequence (as depicted in FIG. 2J)].

In yet another embodiment, the nucleic acid sequence encoding a CAR comprises the nucleic acid sequence of SEQ ID NO: 103, and encodes the CAR comprising the amino acid sequence as set forth in SEQ ID NO: 104 [(LTG2208 LP-16P10-CD8 TM-41BB-CD3zeta amino acid sequence (as depicted in FIG. 2K)].

In yet another embodiment, the nucleic acid sequence encoding a CAR comprises the nucleic acid sequence of SEQ ID NO: 103 or a sequence with 85%, 90%, 95%, 96%, 97%, 98% or 99% identity thereof, and encodes the CAR comprising the amino acid sequence as set forth in SEQ ID NO: 104 or a sequence with 85%, 90%, 95%, 96%, 97%, 98% or 99% identity thereof [(LTG2208 LP-16P10-CD8 TM-41BB-CD3zeta amino acid sequence (as depicted in FIG. 2K)].

In yet another embodiment, the nucleic acid sequence encoding a CAR comprises the nucleic acid sequence of SEQ ID NO: 113, and encodes the CAR comprising the amino acid sequence as set forth in SEQ ID NO: 114 [(LTG2209 LP-16P17-CD8 TM-41BB-CD3zeta amino acid sequence (as depicted in FIG. 2L)].

In yet another embodiment, the nucleic acid sequence encoding a CAR comprises the nucleic acid sequence of SEQ ID NO: 113 or a sequence with 85%, 90%, 95%, 96%, 97%, 98% or 99% identity thereof, and encodes the CAR comprising the amino acid sequence as set forth in SEQ ID NO: 114 or a sequence with 85%, 90%, 95%, 96%, 97%, 98% or 99% identity thereof [(LTG2209 LP-16P17-CD8 TM-41BB-CD3zeta amino acid sequence (as depicted in FIG. 2L)].

In yet another embodiment, the nucleic acid sequence encoding a CAR comprises the nucleic acid sequence of SEQ ID NO: 123, and encodes the CAR comprising the amino acid sequence as set forth in SEQ ID NO: 124 [(LTG2210 LP-16P20v2-CD8 TM-41BB-CD3zeta amino acid sequence (as depicted in FIG. 2M)].

In yet another embodiment, the nucleic acid sequence encoding a CAR comprises the nucleic acid sequence of SEQ ID NO: 123 or a sequence with 85%, 90%, 95%, 96%, 97%, 98% or 99% identity thereof, and encodes the CAR comprising the amino acid sequence as set forth in SEQ ID NO: 124 or a sequence with 85%, 90%, 95%, 96%, 97%, 98% or 99% identity thereof [(LTG2210 LP-16P20v2-CD8 TM-41BB-CD3zeta amino acid sequence (as depicted in FIG. 2M)].

In yet another embodiment, the nucleic acid sequence encoding a CAR comprises the nucleic acid sequence of SEQ ID NO: 133, and encodes the CAR comprising the amino acid sequence as set forth in SEQ ID NO: 134 [(LTG2216 LP-16P1-CD8 TM-41BB-CD3zeta amino acid sequence (as depicted in FIG. 2N)].

In yet another embodiment, the nucleic acid sequence encoding a CAR comprises the nucleic acid sequence of SEQ ID NO: 133 or a sequence with 85%, 90%, 95%, 96%, 97%, 98% or 99% identity thereof, and encodes the CAR comprising the amino acid sequence as set forth in SEQ ID NO: 134 or a sequence with 85%, 90%, 95%, 96%, 97%, 98% or 99% identity thereof [(LTG2216 LP-16P1-CD8 TM-41BB-CD3zeta amino acid sequence (as depicted in FIG. 2N)].

In yet another embodiment, the nucleic acid sequence encoding a CAR comprises the nucleic acid sequence of SEQ ID NO: 143, and encodes the CAR comprising the amino acid sequence as set forth in SEQ ID NO: 144 [(LTG2217 LP-16P3v2-CD8 TM-41BB-CD3zeta amino acid sequence (as depicted in FIG. 2O)].

In yet another embodiment, the nucleic acid sequence encoding a CAR comprises the nucleic acid sequence of SEQ ID NO: 143 or a sequence with 85%, 90%, 95%, 96%, 97%, 98% or 99% identity thereof, and encodes the CAR comprising the amino acid sequence as set forth in SEQ ID NO: 144 or a sequence with 85%, 90%, 95%, 96%, 97%, 98% or 99% identity thereof [(LTG2217 LP-16P17-CD8 TM-41BB-CD3zeta amino acid sequence (as depicted in FIG. 2O)].

In yet another embodiment, the nucleic acid sequence encoding a CAR comprises the nucleic acid sequence of SEQ ID NO: 153, and encodes the CAR comprising the amino acid sequence as set forth in SEQ ID NO: 154 [(LTG2218 LP-16P8-CD8 TM-41BB-CD3zeta amino acid sequence (as depicted in FIG. 2P)].

In yet another embodiment, the nucleic acid sequence encoding a CAR comprises the nucleic acid sequence of SEQ ID NO: 153 or a sequence with 85%, 90%, 95%, 96%, 97%, 98% or 99% identity thereof, and encodes the CAR comprising the amino acid sequence as set forth in SEQ ID NO: 154 or a sequence with 85%, 90%, 95%, 96%, 97%, 98% or 99% identity thereof [(LTG2218 LP-16P8-CD8 TM-41BB-CD3zeta amino acid sequence (as depicted in FIG. 2P)].

In yet another embodiment, the nucleic acid sequence encoding a CAR comprises the nucleic acid sequence of SEQ ID NO: 163, and encodes the CAR comprising the amino acid sequence as set forth in SEQ ID NO: 164 [(LTG2219 LP-16P13-CD8 TM-41BB-CD3zeta amino acid sequence (as depicted in FIG. 2Q)].

In yet another embodiment, the nucleic acid sequence encoding a CAR comprises the nucleic acid sequence of SEQ ID NO: 163 or a sequence with 85%, 90%, 95%, 96%, 97%, 98% or 99% identity thereof, and encodes the CAR comprising the amino acid sequence as set forth in SEQ ID NO: 164 or a sequence with 85%, 90%, 95%, 96%, 97%, 98% or 99% identity thereof [(LTG2219 LP-16P13-CD8 TM-41BB-CD3zeta amino acid sequence (as depicted in FIG. 2Q)].

In yet another embodiment, the nucleic acid sequence encoding a CAR comprises the nucleic acid sequence of SEQ ID NO: 173, and encodes the CAR comprising the amino acid sequence as set forth in SEQ ID NO: 174 [(LTG2220 LP-16P15-CD8 TM-41BB-CD3zeta amino acid sequence (as depicted in FIG. 2R)].

In yet another embodiment, the nucleic acid sequence encoding a CAR comprises the nucleic acid sequence of SEQ ID NO: 173 or a sequence with 85%, 90%, 95%, 96%, 97%, 98% or 99% identity thereof, and encodes the CAR comprising the amino acid sequence as set forth in SEQ ID NO: 174 or a sequence with 85%, 90%, 95%, 96%, 97%, 98% or 99% identity thereof [(LTG2220 LP-16P15-CD8 TM-41BB-CD3zeta amino acid sequence (as depicted in FIG. 2R)].

Figure 6:
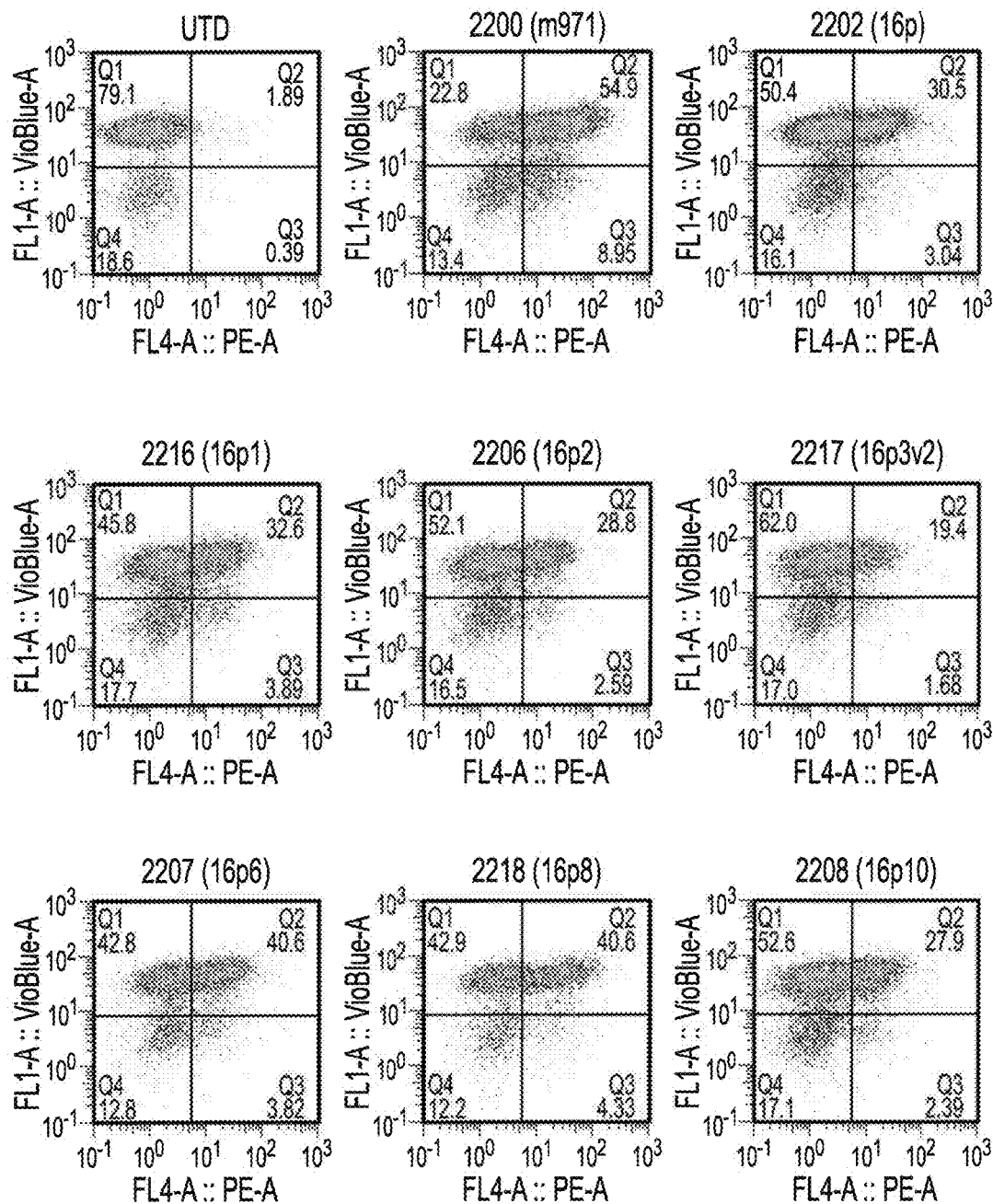
FIG. 6 shows two-dimensional flow cytometric analysis of CAR expression on the surface of T cells transduced with LV to express: no CAR (UTD), or LTG2200, 2202, 2216, 2206, 2217, 2207, 2218, 2208, 2219, 2220, 2209, 2205, control GFP-expressing vector, or control CAR-19 (LTG1538), as shown reading down the rows, left to right, and listed above each plot. The y-axis dimension shows staining for CD4 and the x-axis dimension shows CAR expression by virtue of staining with target antigen (CD22-Fc recombinant protein (R&D Biosystems), secondarily stained with anti-Fc PE antibody).
Figure 6:
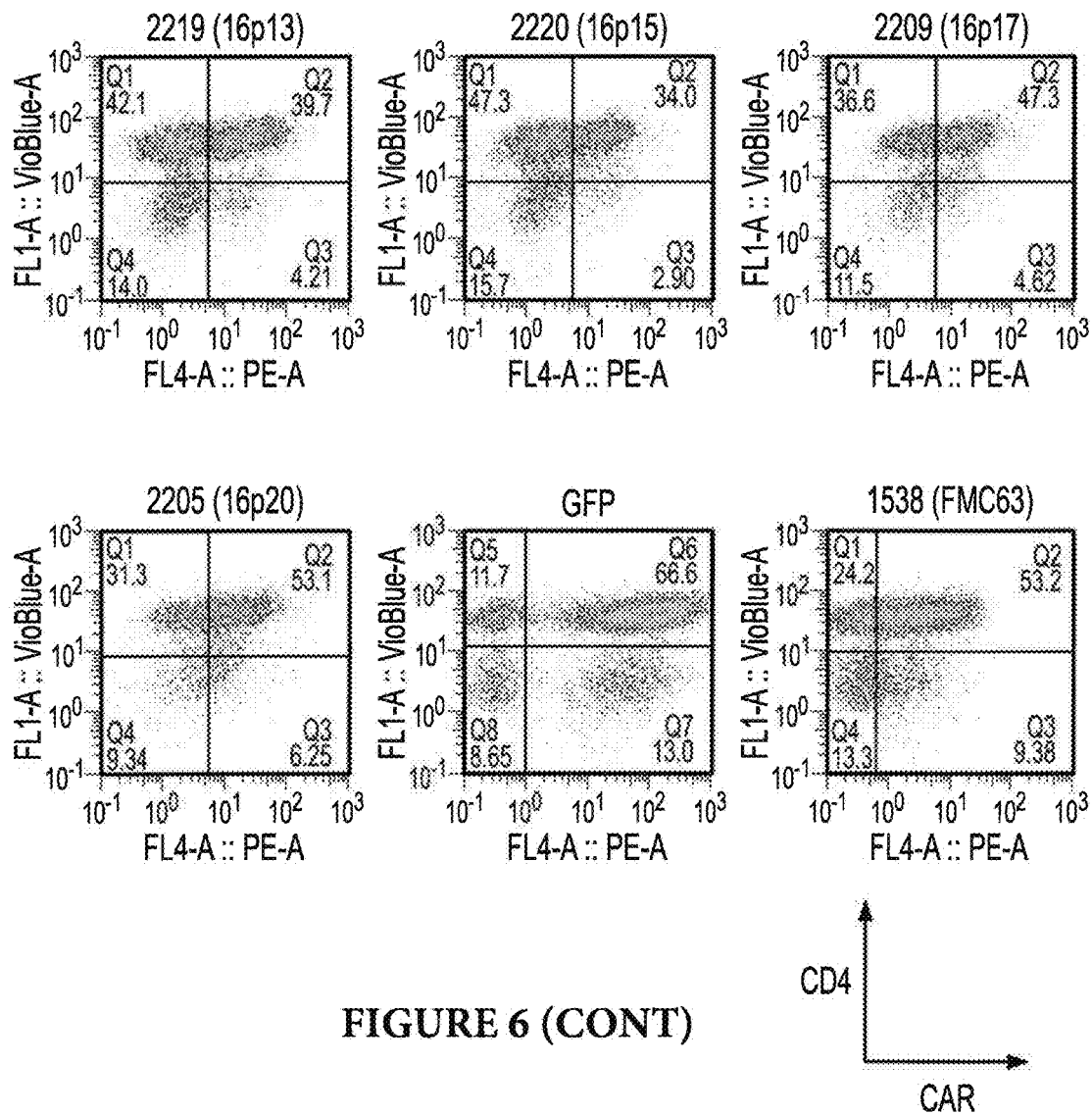

The surface expression of anti-CD22 CARs incorporating single chain fragment variable (ScFv) sequences reactive with CD22 antigen, is shown in Example 2 infra and summarized in Table 2, Table 3, and FIG. 6. The expression level for each ScFv-containing CAR was determined by flow cytometric analysis of LV-transduced T cells from healthy donors using a recombinant CD22-Fc peptide, followed by anti-human Fc F(ab')2 fragment conjugated to PE, and detected by flow cytometry, (c.f., FIG. 6). The ScFv-based anti-CD22 CAR constructs LTG2202, LTG2216, LTG2217, LTG2218, LTG2208, LTG2219, LTG2220, and LTG2209 were highly expressed in human primary T cells (as indicated by the gated population) as compared to non-transduced T cell controls (non-gated cell population, UTD). Representative results from one donor are shown.

Figure 4:
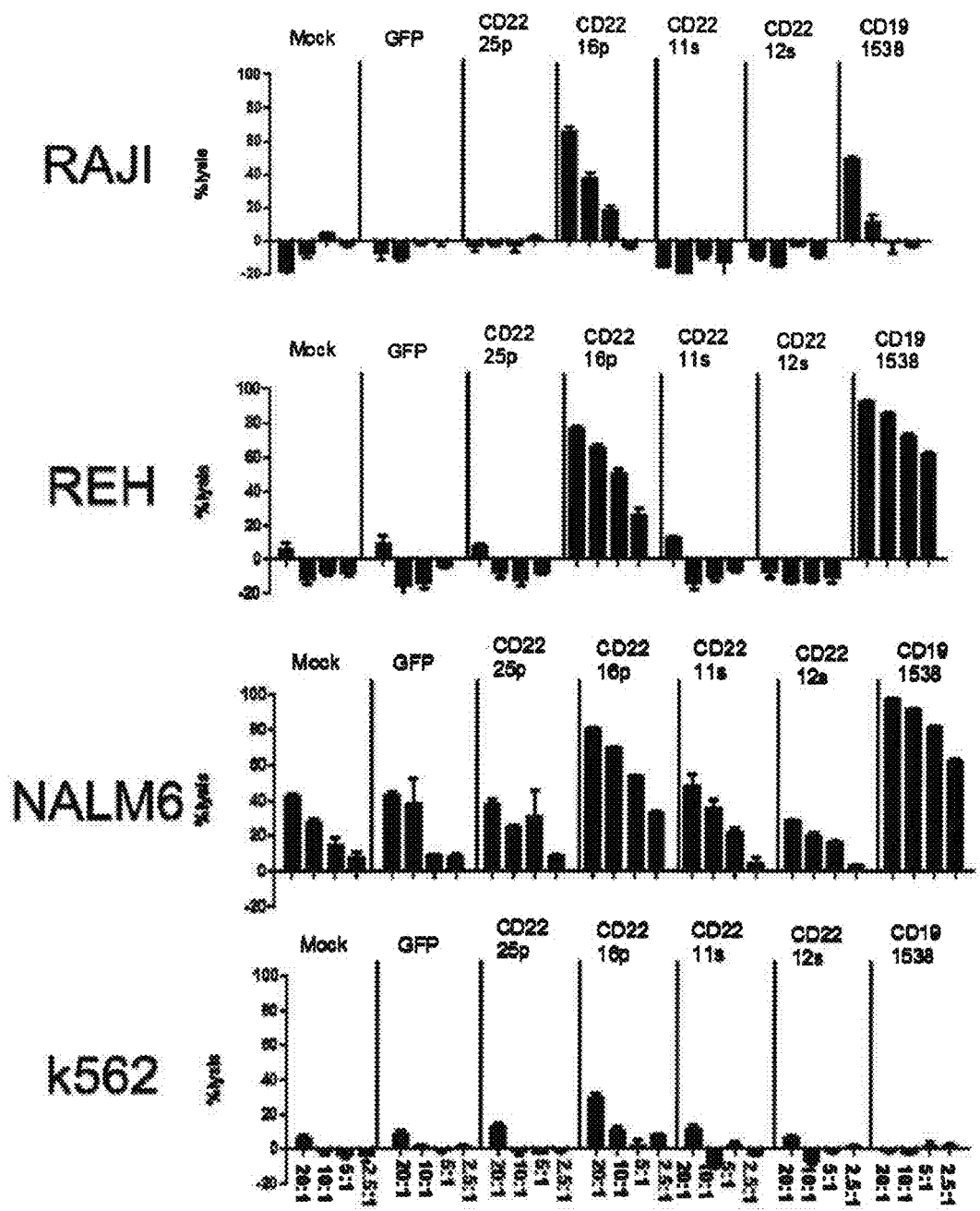
FIG. 4 depicts anti CD22 CAR T cells incorporating ScFv binders (16P, 16P1, 16P3v2, 16P8, 16P10, 16P13, 16P15, 16P17), utd=untransduced negative control, m971=previously published anti-CD22 CAR positive control) mediating cytolysis of CD22-positive tumors in vitro. CAR T cells expressing anti-CD22 constructs were incubated with CD22-positive cell lines (Raji and Reh), or CD19-negative lines (K562 and 293T) that were stably transduced with firefly luciferase, at effector to target ratio of 1.25, 2.5, 5, 10, 20, and 40 (x-axis) overnight. Then, CART cytotoxic activity was assessed by luciferase activity measurement as described in the Materials and Methods. Each bar is the mean of 3 technical replicates and error bars represent SD. Representative of at least three separate experiments.
Figure 7B:
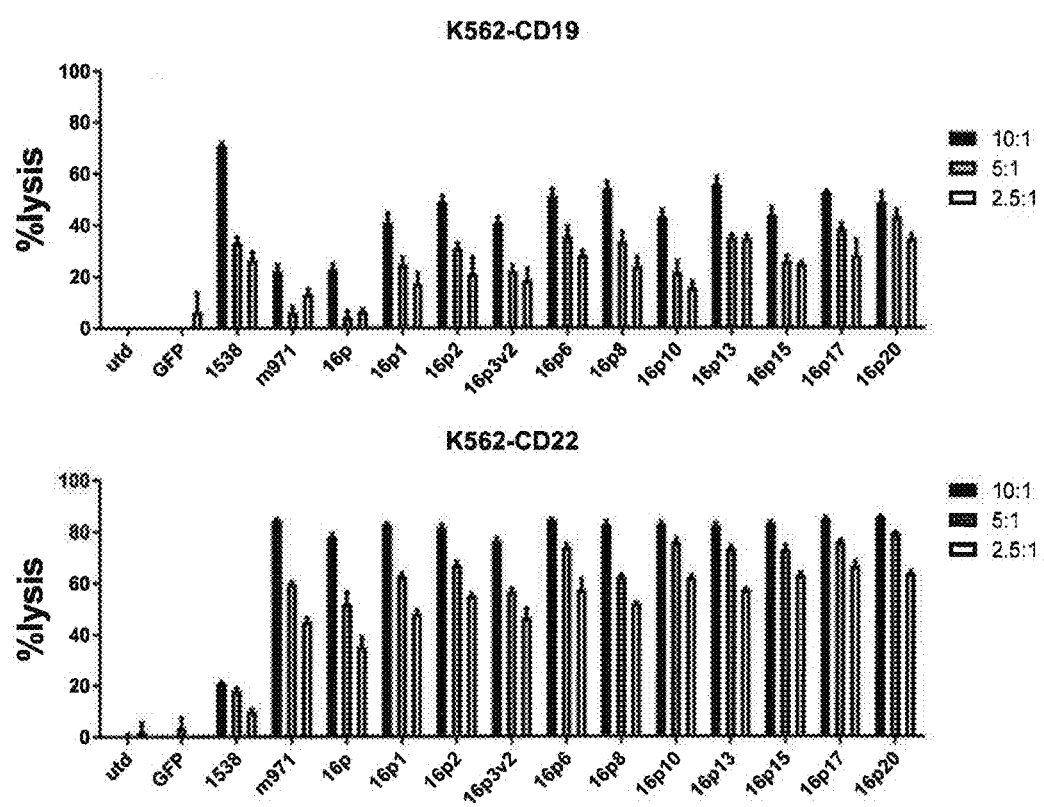

As shown in Example 2 and FIGS. 4, 7A, and 7B, high cytolytic activity of the CD22 CARs was demonstrated when lentiviral vectors (LV) expressing the following CARs were created and tested for anti-leukemia activity. Each experimental CAR contains the 4-1BB/CD3-zeta chain signaling motif and the specific anti-CD22 binding motif/domain noted therein. Leukemia target lines with varying CD22 surface expression were used: Raji and Reh; and CD19 negative K562 and 293T. ScFv-based anti-CD22 CAR constructs LTG2202, LTG2216, LTG2217, LTG2218, LTG2208, LTG2219, LTG220, and LTG2209, expressing scFv1 (16P), ScFv2 (16P1), scFv3 (16P3v2), scFv3 (16P3v2), scFv4 (16P8), scFv5 (16P10), scFv6 (16P13), scFv7 (16P15), scFv8 (16P17), respectively, were able to efficiently lyse CD22-high tumor lines Raji and Reh, whereas they had little or no specific lytic activity against K562 or 293T, (c.f., FIG. 4, 7A, 7B). These results demonstrate the efficiency and specificity of the generated CAR constructs.

Figure 8:
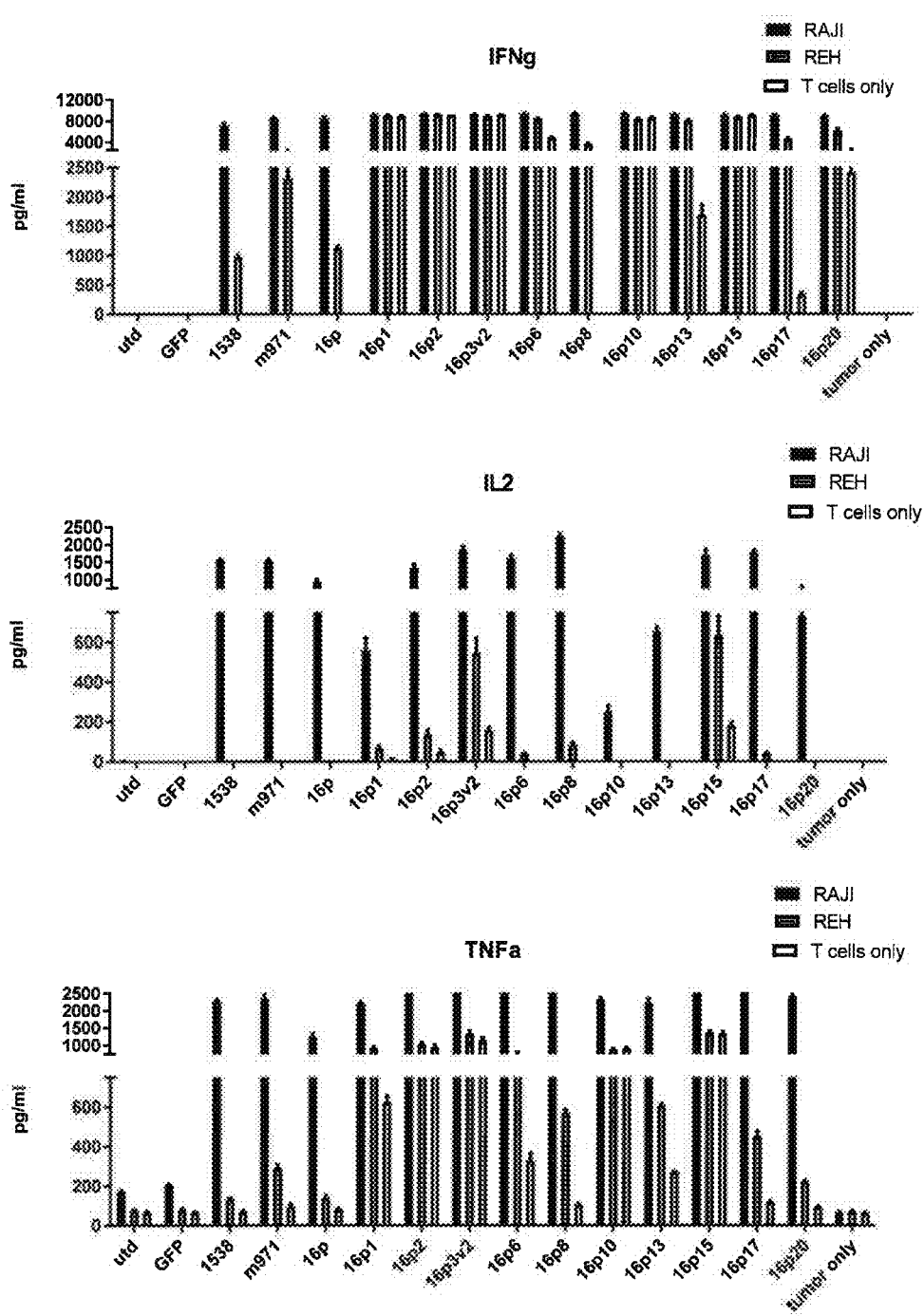
FIG. 8 shows the production of IFN-gamma (top), IL-2 (middle), and TNF-alpha (lower panel) by anti-CD22 CART cells upon co-incubated with CD22-positive Raji and Reh leukemia cell lines (black or gray bars, respectively), or without target tumor cells (T cells only), overnight at E:T ratio of 10:1, then supernatants analyzed for cytokine concentration by ELISA. CAR only negative control groups were used to assess spontaneous cytokine secretion by CAR T cells. Representative of at least three separate experiments. CAR-T activity is illustrated, as listed on the x-axis, for untransduced T cells (utd), T cells transduced with GFP-LV (GFP), CD19-CAR (LTG1538), CD22 control CAR (LTG2220, m971), 16p (LTF2202), 16p1 (LTG2216), 16p2 (LTG2206), 16p3v2 (LTG2217), 16p6 (LTG2207), 16p8 (LTG2218), 16p10 (LTG2208), 16p13 (LTG2219), 16p15 (LTG2220), 16p17 (LTG2209), 16p20 (LTG2205), or leukemia targets incubated without CAR T cells (tumor only).

The capacity of anti-CD22 CAR T cells for cytokine secretion was then evaluated. Tumor cells were co-incubated with CAR T cells or control T cells at effector to target ratio of 10:1 overnight, and culture supernatants were analyzed by ELISA for IFN gamma, TNF alpha and IL-2 (c.f., FIG. 8). Of note, CAR T-cells transduced with LTG2202, LTG2216, LTG2217, LTG2218, LTG2208, LTG2219, LTG2220, and LTG2209, expressing scFv1 (16P), ScFv2 (16P1), scFv3 (16P3v2), scFv3 (16P3v2), scFv4 (16P8), scFv5 (16P10), scFv6 (16P13), scFv7 (16P15), scFv8 (16P17), respectively, elaborated high levels of IFN gamma, whereas the negative control (untransduced, utd) yielded no appreciable cytokine induction. However, clear differences in, TNF-alpha and IL-2 production were seen. Surprisingly, CD22 CAR LTG2202, yielded significantly lower levels of TNF-alpha and IL-2, against the Reh tumor line, and each vector had a differential ability to produce IL-2 and TNF-alpha to the tumor line targets tested. These differences will result in different anti-tumor and toxicity profiles, and will be individually implemented according to the disease burden, in specific disease settings. The CAR used as a positive control, m971, was used to benchmark results, as it is currently in clinical trials and, thus far, is safe for use in advanced disease settings.

Without being intended to limit to any particular mechanism of action, it is believed that possible reasons for the enhanced therapeutic function associated with the exemplary CARs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or any combination thereof.

While the disclosure has been illustrated with an exemplary extracellular CD22 variable heavy chain only and ScFv antigen binding domains, other nucleotide and/or amino acid variants within the CD22 variable heavy chain only and ScFv antigen binding domains may be used to derive the CD22 antigen binding domains for use in the CARs described herein.

Depending on the desired antigen to be targeted, the CAR can be additionally engineered to include the appropriate antigen binding domain that is specific to the desired antigen target. For example, if CD22 is the desired antigen that is to be targeted, an antibody for CD22 can be used as the antigen bind domain incorporation into the CAR.

In one exemplary embodiment, the antigen binding domain portion of the CAR additionally targets CD33. Preferably, the antigen binding domain in the CAR is anti-CD33 heavy chain only binder VH-4, wherein the nucleic acid sequence of the anti-CD33 heavy chain-only binder comprises the sequence set forth in SEQ ID NO: 202. In one embodiment, the anti-CD33 heavy chain-only binder comprises the nucleic acid sequence that encodes the amino acid sequence of SEQ ID NO: 202. In another embodiment, the anti-CD33 heavy chain only portion of the CAR comprises the amino acid sequence set forth in SEQ ID NO: 203. In another exemplary embodiment, the nucleic acid sequence of the CAR expressing anti-CD33 heavy chain only binder, LTG1906 is comprised of SEQ ID: 204. In another embodiment, the amino acid sequence of anti-CD33 heavy chain only binder expressing CAR LTG1906 is comprised of SEQ ID NO: 205.

In one exemplary embodiment, the antigen binding domain portion of the CAR additionally targets mesothelin. Preferably, the antigen binding domain in the CAR is anti-mesothelin ScFv, wherein the nucleic acid sequence of the anti-mesothelin ScFv comprises the sequence set forth in SEQ ID NO: 198. In one embodiment, the anti-mesothelin ScFv comprises the nucleic acid sequence that encodes the amino acid sequence of SEQ ID NO: 199. In another embodiment, the anti-mesothelin ScFv portion of the CAR comprises the amino acid sequence set forth in SEQ ID NO: 199. In another exemplary embodiment, the nucleic acid sequence of the CAR expressing the anti-mesothelin scFv is comprised of SEQ ID: 200. In another embodiment, the amino acid sequence of the anti-mesothelin CAR LTG1904 is set forth in SEQ ID NO: 201

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of Staphylococci, *Streptococcus, Escherichia coli, Pseudomonas*, or *Salmonella*. Particularly, there is provided a CAR capable of binding to an antigen derived from an infectious bacterium, for example, *Helicobacter pyloris, Legionella pneumophilia*, a bacterial strain of *Mycobacteria* sps. (e.g. *M. tuberculosis, M. avium, M. intracellulare, M. kansaii,* or *M. gordonea*), *Staphylococcus aureus, Neisseria gonorrhoeae, Neisseria meningitides, Listeria monocytogenes, Streptococcus pyogenes*, Group A *Streptococcus*, Group B *Streptococcus* (*Streptococcus agalactiae*), *Streptococcus pneumoniae*, or *Clostridium tetani*, or a combination thereof.

2. Transmembrane Domain

With respect to the transmembrane domain, the CAR comprises one or more transmembrane domains fused to the extracellular CD22 antigen binding domain of the CAR.

The transmembrane domain may be derived either from a natural or from a synthetic source. Where the source is natural, the domain may be derived from any membrane-bound or transmembrane protein.

Transmembrane regions of particular use in the CARs described herein may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, mesothelin, CD33, CD37, CD64, CD80, CD83, CD86, CD134, CD137, CD154, TNFRSF16, or TNFRSF19. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain that naturally is associated with one of the domains in the CAR is used in addition to the transmembrane domains described supra.

In some instances, the transmembrane domain can be selected or by amino acid substitution to avoid binding of such domains to the transmembrane domains of the same or different surface membrane proteins to minimize interactions with other members of the receptor complex.

In one embodiment, the transmembrane domain in the CAR of the invention is the CD8 transmembrane domain. In one embodiment, the CD8 transmembrane domain comprises the nucleic acid sequence of SEQ ID NO: 181. In one embodiment, the CD8 transmembrane domain comprises the nucleic acid sequence that encodes the amino acid sequence of SEQ ID NO: 182. In another embodiment, the CD8 transmembrane domain comprises the amino acid sequence of SEQ ID NO: 182.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO: 182, or a sequence with 95-99% identity to an amino acid sequence of SEQ ID NO: 182.

In some instances, the transmembrane domain of the CAR comprises the CD8.alpha.hinge domain. In one embodiment, the CD8 hinge domain comprises the nucleic acid sequence of SEQ ID NO: 183. In one embodiment, the CD8 hinge domain comprises the nucleic acid sequence that encodes the amino acid sequence of SEQ ID NO: 184. In another embodiment, the CD8 hinge domain comprises the amino acid sequence of SEQ ID NO: 184, or a sequence with 95-99% identify thereof.

In one embodiment, an isolated nucleic acid molecule is provided wherein the encoded linker domain is derived from the extracellular domain of CD8, and is linked to the transmembrane CD8 domain, the transmembrane CD28 domain, or a combination thereof.

3. Spacer Domain

In the CAR, a spacer domain can be arranged between the extracellular domain and the transmembrane domain, or between the intracellular domain and the transmembrane domain. The spacer domain means any oligopeptide or polypeptide that serves to link the transmembrane domain with the extracellular domain and/or the transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 137-206 (SEQ ID NO: 39) which is a hinge region of CD8.alpha. (NCBI RefSeq: NP.sub.--001759.3), amino acid numbers 135 to 195 of CD8.beta. (GenBank: AAA35664.1), amino acid numbers 315 to 396 of CD4 (NCBI RefSeq: NP.sub.--000607.1), or amino acid numbers 137 to 152 of CD28 (NCBI RefSeq: NP.sub.--006130.1) can be used. Also, as the spacer domain, a part of a constant region of an antibody H chain or L chain can be used. Further, the spacer domain may be an artificially synthesized sequence.

Further, in the CAR, a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the amino acid sequence shown in SEQ ID NO: 191.

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARS disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.--932170.1), amino acid numbers 45 to 86 of Fc.epsilon.RI.gamma. (NCBI RefSeq: NP.sub.--004097.1), amino acid numbers 201 to 244 of Fc.epsilon.RI.beta. (NCBI RefSeq: NP.sub.--000130.1), amino acid numbers 139 to 182 of CD3.gamma. (NCBI RefSeq: NP.sub.--000064.1), amino acid numbers 128 to 171 of CD3.delta. (NCBI RefSeq: NP.sub.--000723.1), amino acid numbers 153 to 207 of CD3.epsilon. (NCBI RefSeq: NP.sub.--000724.1), amino acid numbers 402 to 495 of CD5 (NCBI RefSeq: NP.sub.--055022.2), amino acid numbers 707 to 847 of 0022 (NCBI RefSeq: NP.sub.--001762.2), amino acid numbers 166 to 226 of CD79a (NCBI RefSeq: NP.sub.--001774.1), amino acid numbers 182 to 229 of CD79b (NCBI RefSeq: NP.sub.--000617.1), and amino acid numbers 177 to 252 of CD66d (NCBI RefSeq: NP.sub.--001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.--001758.2), amino acid numbers 421 to 458 of CD4 (NCBI RefSeq: NP.sub.--000607.1), amino acid numbers 402 to 495 of CD5 (NCBI RefSeq: NP.sub.--055022.2), amino acid numbers 207 to 235 of CD8.alpha. (NCBI RefSeq: NP.sub.--001759.3), amino acid numbers 196 to 210 of CD83 (GenBank: AAA35664.1), amino acid numbers 181 to 220 of CD28 (NCBI RefSeq: NP.sub.--006130.1), amino acid numbers 214 to 255 of CD137 (4-1BB, NCBI RefSeq: NP.sub.--001552.2), amino acid numbers 241 to 277 of CD134 (OX40, NCBI RefSeq: NP.sub.--003318.1), and amino acid numbers 166 to 199 of ICOS (NCBI RefSeq: NP.sub.--036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 186 and the signaling domain of CD3-zeta comprises the nucleic acid sequence set forth in SEQ ID NO: 188.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 187 and the signaling domain of CD3-zeta comprises the nucleic acid sequence that encodes the amino acid sequence of SEQ ID NO: 189.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 187 and the signaling domain of CD3-zeta comprises the amino acid sequence set forth in SEQ ID NO: 189.

5. Additional Description of CARs

Also expressly included within the scope of the invention are functional portions of the CARs disclosed herein. The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, -aminocyclopentane carboxylic acid, a-aminocyclohexane carboxylic acid, a-aminocycloheptane carboxylic acid, a-(2-amino-2-norbornane)-carboxylic acid, γ-diaminobutyric acid, β-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994. Further, some of the CARS (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the CARS can be synthetic, recombinant, isolated, and/or purified.

B. Antibodies and Antigen Binding Fragments

One embodiment further provides a CAR, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, $6^{th}$ ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, ScFv, dsFv or Fab. References to "VL" or "VL" refer to the variable domain of an antibody light chain, including that of an Fv, ScFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," $5^{th}$ Ed. Public Health Service, National Institutes of Health, Bethesda, Md., 1991; "Kabat" numbering scheme), Al-Lazikani et al., (JMB 273, 927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as HCDR1, HCDR2, and HCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. ScFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (ScFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a ScFv, is typically not decisive for ScFvs. Thus, ScFvs with both possible arrangements (VH-domain-linker domain-VL-domain; VL-domain-linker domain-VH-domain) may be used.

In a dsFv, the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338,929).

Also, a CAR, a T cell expressing a CAR, an antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

A CAR, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}$I, $^{32}$P, $^{14}$C, $^{3}$H and $^{35}$S and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated RCA60 and RCA120 according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

A CAR, a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the CARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, Iowa, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.).

Bacteriophage vectors, such as λgt10, λgt11, λZapII (Stratagene), EMBL4, and λNM1149, also can be used. Examples of plant expression vectors include pBI01, pBI101.2, pBHO10.3, pBI121 and pBIN19 (Clontech). Examples of animal expression vectors include pEUK-C1, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2µ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4+/CD8+ double positive T cells, CD4+ helper T cells, e.g., Th1 and Th2 cells, CD8+ T cells (e.g., cytotoxic T cells), tumor infiltrating cells, memory T cells, memory stem cells, i.e. Tscm, naive T cells, and the like. The T cell may be a CD8+ T cell or a CD4+ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the CARs disclosed herein can be used in methods of treating or preventing a disease in a mammal. In this regard, an embodiment provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions in an amount effective to treat or prevent cancer in the mammal.

An embodiment further comprises lymphodepleting the mammal prior to administering the CARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of ALL, AML, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia (CLL), chronic myeloid cancer (CML), colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, NHL, B-chronic lymphocytic leukemia, hairy cell leukemia, Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor a (TNF-a) or interleukin 2 (IL-2)). In addition, CAR function can be evaluated by measurement of cellular cytotoxicity, as described in Zhao et al, J. Immunol, 174: 4415-4423 (2005).

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masopro col, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Biopharmaceutical Compositions

Biopharmaceutical or biologics compositions (hereinafter, "compositions") are provided herein for use in gene therapy, immunotherapy and/or cell therapy that include one or more of the disclosed CARs, or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington's Pharmaceutical Science*, 19th ed., Mack Publishing Company, Easton, Pa. (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the CARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, poloxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

G. Kits

In one aspect, kits employing the CARs disclosed herein are also provided. For example, kits for treating a tumor in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Isolation of CD22-Specific Antibodies from a Fully Human Phage and Yeast-Displayed ScFv Library Materials and Methods:

a) Production of Human ScFv and CD22-Specific Antibodies

A naïve human ScFv (recombinant single chain fragment variable of immunoglobulin) phage display library (approximate diversity, $10^{10}$ unique specificities), constructed from peripheral blood B cells of 50 healthy donors (Z. Y. Zhu and D. S. Dimitrov, unpublished data), were used for selection of ScFvs for recombinant human CD19 protein (Miltenyi Biotec, unpublished). Amplified libraries of $10^{12}$ phage-displayed ScFv were incubated with 5, 3, and 1, µg of coated CD22 in a 5×100-µl volume, distributed equally in 5 wells of a 96-well plate for 2 h at room temperature during the first, second and third rounds of biopanning, respectively. After each round of incubation the wells were washed 5 times for the first round and 10 times for the later rounds with phosphate-buffered saline containing 0.05% Tween 20 (PBST) to remove nonspecifically bound phage, the bound phage were mixed with TG1 competent cells for 1 hour at 37° C., and the phage was amplified from the infected cells and used in the next round of biopanning. After the third round of biopanning, 380 clones were randomly picked from the infected TG1 cells and each inoculated into 150 µl 2YT medium containing 100 µg/ml carbenicillin and 0.2% glucose in 96-well plates by using the automated BioRobotics BioPick colony picking system (Genomic Solutions, Ann Arbor, Mich.). After the bacterial cultures reached an optical density at 600 nm (OD600) of 0.5, helper phage M13K07 at a multiplicity of infection (MOI) of 10 and kanamycin at 50 µg/ml (final concentration) were added to the medium, and the plates were further incubated at 30° C. overnight in a shaker at 250 rpm. The phage supernatants were mixed with 3% nonfat milk in PBS at a 4:1 volume ratio and used for enzyme-linked immunosorbent assay (ELISA) to identify clones of phage displaying ScFvs or VHs with high CD22 binding affinity. The supernatants were incubated for 2 h at room temperature with recombinant human CD22 coated at 50 ng per well in 96-well plates and washed five times with PBST, (after overnight incubation at 4° C. it was blocked with 3% nonfat milk in PBS and washed three times with PBS containing 0.05% Tween 20.) CD22-bound phage were detected using horseradish peroxidase-conjugated goat anti-M13 antibody. After incubation with the antibody, the non-specifically bound antibody was removed by washing wells, and the 3,3',5,5'-tetramethylbenzidine (TMB) substrate was added, and solution absorbance at 450 nm (A450) measured. Clones that bound to CD22 with A450 of >1.0 were selected for further characterization.

b) Expression and Purification of Selected Soluble ScFvs

The VH and VL of the selected clones were DNA sequenced, and the ScFvs encoded by clones with unique sequences were expressed and purified as described below. Plasmids extracted from these clones were used for transformation of HB2151 cells. A single colony was picked from the plate containing freshly transformed cells, inoculated into 200 ml 2YT medium containing 100 µg/ml ampicillin and 0.2% glucose, and incubated at 37° C. with shaking at 250 rpm. When the culture OD at 600 nm reached 0.90, isopropyl-β-d-thiogalactopyranoside at a 0.5 mM final concentration was added, and the culture was further incubated overnight at 30° C. The bacterial pellet was collected after centrifugation at 8,000×g for 20 min and resuspended in PBS buffer containing 0.5 mU polymixin B (Sigma-Aldrich, St. Louis, Mo.). After 30 min incubation with rotation at 50 rpm at room temperature, the resuspended pellet was centrifuged at 25,000×g for 25 min at 4° C., and the supernatant was used for ScFv purification using the Ni-NTA resin following vendor protocol (Qiagen).

c) ELISA Binding Assay

For ELISA analysis 50 µl of the diluted recombinant human CD22 in PBS at 2 ug/ml was coated in a 96-well plate at 4° C. overnight. Purified ScFv with His and Flag tags were serially diluted and added into the target protein coated wells. After washing, a 1:3000 diluted HRP conjugated anti-Flag antibody was added for 1 hr at RT. After washing, 3, 3, 5, 5'-Tetramethylbenzidine (TMB) substrate was added, 1N $H_2SO_4$ was added to stop the reaction after incubation at room temperature for 10 minutes, and the O.D. was read at 450 nm to quantify the relative ability of ScFv to bind CD22.

d) Yeast Display of scFv Library

The same ScFv starting material as for phage display was also incorporated into a yeast ScFv display system. To supplement phage-based scFv analysis, yeast libraries expressing the human scFv library were also screened. To enrich the yeast expressing scFvs that bind to both the recombinant CD22-Fc and the CD19 expressed on the cell surface of the CHOK1 cells, cell panning on CHOK1 transfected with CD22 cells was performed. For the first round of panning on the cell surface, two days prior to panning, the CHOK1-CD22 cells were seeded into 6-well plates and grown to 50% confluency in F12 K medium. $5×10^7$ yeast cells were then washed 2× with PBSA buffer and resuspended into 3 mL F12 K medium, and then gently added dropwise to the CHOK1-CD22 cells. After rocking gently on ice for 2 hours, the CHOK1-CD22 cells were then washed 3 times with ice-cold PBSA to remove the yeast cells that did not bind to the CHOK1-CD22, and 0.05% Trypsin-EDTA (Gibco) was then used to dissociate the CHOK1-CD22 cells and bound yeast cells from the plate. The cell mix containing both the yeast and CHOK1 cells were then inoculated into 10 mL SDCAA medium and amplified overnight at 30° C. and then induced in SGCAA medium at 30° C. for 16 hours. For the second round of cell panning, a similar protocol as above was performed, but more stringent wash conditions were used. This method of panning yielded the 16P, 24P, 25P, 11S and 12S binders. Binder sequences were incorporated into CART constructs as described in Example 2, infra, in a series of in vitro CART functional assays. Characterization of these binders from phage display in CART format revealed that only 16P binder had specific tumor-lytic activity in vitro, but it was low as compared to CAR positive control. Further, when 16P-based CART cells were tested in in vivo xenograft model, its antitumor function was very weak (Example 2, infra). Taken together, these results indicated that affinity maturation of anti-CD22 ScFv binders was required, as the biological characteristics of the CAR created from this binder set were still not optimal.

To increase the affinity of 16P, a yeast-display mutant scFv library was created by using error-prone PCR to create random point mutations in scFv gene sequences. After electroporation, the resulting mutant library was then grown overnight at 30° C. for 16 hours in SDCAA medium and then switched into SGCAA medium at 30° C. for another 16 hours. The mutant library was then sorted through MACS (immunomagentic column, Miltenyi Biotec) with CD22-Fc as the capture antigen to downsize the library and to increase the population of mutants that could bind to CD22-Fc. The strongest binders were then selected by double staining the pools with Anti-c-Myc-Alexa 488 and CD19-Fc/Anti-Hu-Fc and selecting for the binders that had the highest binding affinities as well as c-Myc expression levels. This process was then repeated two more times, until flow cytometry of yeast particles with fluorescently tagged antigen yielded average binding affinities of the mutant pools that were increased over the starting construct. Binding affinities were estimated by flow cytometry of yeast pools using decreasing amounts of labeled CD22. This process resulted in an increase of EC50 (Effective concentration for 50% binding of labeled CD19 on yeast displaying ScFv) for 16P of 0.5 ug/ml to an affinity of <0.01 ug/ml for the affinity matured binders (16P1, 16P2, 16P3, 16P3v2, 16P6, 16P8, 16P10, 16P13, 16P15, 16P16, 16P17, 16P20, 16P20v2).

Results:

Due to the unique challenges of CD22 structure, phage display candidates did not yield sufficient functional CAR constructs with high biological activity and specificity. Thus, ScFv for biologically active and highly specific binders were generated by yeast display. Based upon flow cytometry analysis of yeast-displayed ScFv, thirteen ScFv clones specific for recombinant human CD22 were identified and labeled as human anti-CD22 ScFv binders 16P (LTG2202, founder clone, EC50 of 0.5 ug/ml), and the following affinity matured binders (EC50<0.01 ug/ml): 16P1, 16P2, 16P3, 16P3v2, 16P6, 16P8, 16P10, 16P13, 16P15, 16P17, 16P20, and 16P20v2 respectively. The generation of CARs expressing the LTG2203, LTG2205, LTG2206, LTG2207, LTG2208, LTG2209, LTG2210, LTG2216, LTG2217, LTG2218, LTG2219, and LTG2220 human anti-CD22 binders is outlined in Example 2, infra.

Example 2

CARs Expressing Anti-CD22 Fully Human Binding Sequences.

*Homo sapiens* CD22 (SIGLEC-2, Leu14) is a well-investigated cell surface glycoprotein expressed on B cell leukemias and lymphomas. At least two anti-CD22 antibody drug (Inotuzumab Ozogamicin) or immunotoxin conjugates (Moxetumomab Pasudotox) have been the subject of clinical trials (NCT02981628, NCT00659425). These approaches have had some success, and are still being investigated, for example in combination with other chemotherapeutic agents (Muller F, Stookey S, Cunningham T, Pastan I, 2017, Paclitaxel synergizes with exposure tume adjusted CD22-targeted immunotoxins against B-cell malignancies, Oncotarget 8:30644-30655). However, given the current advances with T-cell based therapy with CD19 CARs, the best approach to targeting CD22-expressing malignancies may be cell-based immunotherapy. Therapy featuring the m971-based anti-CD22 CAR is currently undergoing clinical trial at the National Cancer Institute (NCT02315612, P.I.: Terry Fry, M.D.), although results have not yet been published. The CAR constructs presented here are an innovative new approach to creating and implementing new CD22 binding moieties derived from human sequences and given the range of cytotoxicity and cytokine-producing capabilities of each construct, very different activity profiles may be seen in vivo.

The novel anti-CD22 CAR-T constructs described here have high levels of cell surface expression in primary human T cells and specific and potent cytotoxic and cytokine functions against CD22-positive tumor cells. CD22 CARs were designed using CD22 binding sequences derived from ScFv candidates initially identified by phage display, as in Example 1, and for characterization were cloned into lentiviral expression vectors that contained selected structural and signaling domains under the control of the EF1a promoter and tested in vitro for transduction efficiency, killing function and cytokine production in both model cell lines and primary human T cells. Table 1 summarizes the nomenclature used. CAR Construct LTG1538, an anti-CD19 CAR, serves as a positive control and a comparator. The m971 CAR LTG2200, is used as an anti-CD22 CAR positive control.

TABLE 1

Construct LTG numbers and corresponding ScFv binder designations used in the design of fully human CD22 CARs

| CAR Construct LTG# | ScFv Binder Designation | CAR Construct Description |
|---|---|---|
| 2200 | m971 | CAR22 positive control |
| 2202 | 16P | New construct |
| 2246 | 24P | New construct |
| 2247 | 25P | New construct |
| 2248 | 11S | New construct |
| 2249 | 12S | New construct |
| 2203 | 16P3 | New construct |
| 2204 | 16P16 | New construct |
| 2205 | 16P20 | New construct |
| 2206 | 16P2 | New construct |
| 2207 | 16P6 | New construct |
| 2208 | 16P10 | New construct |
| 2209 | 16P17 | New construct |
| 2210 | 16P20v2 | New construct |
| 2216 | 16P1 | New construct |
| 2217 | 16P3v2 | New construct |
| 2218 | 16P8 | New construct |
| 2219 | 16P13 | New construct |
| 2220 | 16P15 | New construct |
| 1538 | FMC63 | CD19-specific CAR |
| UTD | N/A | Untransduced T cells |

Materials and Methods:

(a) Cell Lines

The Burkitt lymphoma cell line Raji, and the chronic myelogenous leukemia line K562 were purchased from American Tissue Culture Collection (ATCC, Manassass, Va.). The REH and NALM-6 leukemia lines were purchased from DSMZ (Leibniz Institute DSMZ, Braunschwieg, Germany). Cells were cultured in RPMI-1640 medium supplemented with 10% heat-inactivated fetal bovine serum (FBS, Hyclone, Logan, Utah) and 2 mM L-Glutamax (Thermo Fisher Scientific, Grand Island, N.Y.). Human Embryonic kidney line 293T was purchased from ATCC (Gibco/Thermo Fisher Scientific, Grand Island, N.Y.). Single-cell clones of luciferase-expressing cell lines were generated by stably transducing wild-type tumor lines with lentiviral vector encoding firefly luciferase (Lentigen Technology, Inc., Gaithersburg, Md.), followed by cloning and selection of luciferase-positive clones. Whole blood or buffy coats were collected from healthy volunteers at Oklahoma Blood Institute (OBI, Oklahoma City, Okla.) with donors' written consent. CD4-positive and CD8-positive human T cells were purified from buffy coats via positive selection using a 1:1 mixture of CD4– and CD8– MicroBeads (Miltenyi Biotec, Bergisch Gladbach, Germany) according to manufacturer's protocol.

(b) Creation of Chimeric Antigen Receptor (CAR)—Expression Vectors

CAR antigen-binding domains, ScFv, sequences were derived from human anti-CD22 ScFv or heavy chain variable fragments. CAR T constructs were generated by linking the binder sequence in frame to CD8a linking and transmembrane domains (aa 123-191, Ref sequence ID NP_001759.3), and then to 4-1BB (CD137, aa 214-255, UniProt sequence ID Q07011) signaling domain and CD3 zeta signaling domain (CD247, aa 52-163, Ref sequence ID: NP_000725.1). CAR constructs sequences were cloned into a third generation lentiviral plasmid backbone (Lentigen Technology Inc., Gaithersburg, Md.). Lentiviral vector (LV) containing supernatants were generated by transient transfection of HEK 293T cells and LV pelleted by centrifugation of LV-containing supernatants, and stored at −80° C.

(c) Primary T Cell Purification and Transduction

Human primary T cells from healthy volunteers were purified from whole blood or buffy coats using immunomagnetic bead selection of CD4+ and CD8+ cells according to manufacturer's protocol (Miltenyi Biotec, Bergisch-Gladbach, Germany). T cells were cultivated in TexMACS medium supplemented with 200 IU/ml IL-2 at a density of 0.3 to $2 \times 10^6$ cells/ml, activated with CD3/CD28 MACS® GMP T Cell TransAct reagent (Miltenyi Biotec) and transduced on day 2 with lentiviral vectors encoding CAR constructs in the presence of 10 ug/ml protamine sulfate (Sigma-Aldrich, St. Louis, Mo.) overnight, and media exchanged on day 3. Cultures were propagated in TexMACS medium supplemented with 200 IU/ml IL-2 until harvest on day 8-13.

(d) Immune Effector Assays (CTL and Cytokine)

To determine cell-mediated cytotoxicity (CTL assay), 5,000 target cells stably transduced with firefly luciferase were combined with CAR T cells at various effector to target ratios and incubated overnight. SteadyGlo reagent (Promega, Madison Wis.) was added to each well and the resulting luminescence quantified as counts per second (sample CPS). Target only wells (max CPS) and target only wells plus 1% Tween-20 (min CPS) were used to determine assay range. Percent specific lysis was calculated as: (1− (sample CPS−min CPS)/(max CPS−min CPS)). Supernatants from co-cultures at E:T ratio of 10:1 were removed and analyzed by ELISA (eBioscience, San Diego, Calif.) for IFNγ, TNFα and IL-2 concentration.

(e) Flow Cytometric Analysis

For cell staining, half a million CAR T transduced cells were harvested from culture, washed two times in cold AutoMACS buffer supplemented with 0.5% bovine serum albumin (Miltenyi Biotec), and CAR surface expression detected by staining with CD22-Fc peptide followed by anti Fc-PE conjugate (Jackson ImmunoResearch, West Grove, Pa.). Anti-CD4 antibody conjugated to VioBlue fluorophore (Miltenyi Biotec) was used where indicated, as per vendors' protocol. Non-transduced cells were used as negative controls. Dead cells in all studies were excluded by 7AAD staining (BD Biosciences, San Jose, Calif.). Cells were washed twice and resuspended in 200 ul Staining Buffer before quantitative analysis by flow cytometry. Flow cytometric analysis was performed on a MACSQuant®10 Analyzer (Miltenyi Biotec), and data plots were generated using FlowJo software (Ashland, Oreg.).

(f) In Vivo Analysis of CAR Function

All animal studies were approved by MI Bioresearch Animal Care and Use ommittee (Ann Arbor, Mich.). A half million mouse-adapted Raji-luc cells were injected into the tail vein of NSG (NOD.Cg-Prkdc$^{scid}$ Il2rg$^{tm1Wjl}$/SzJ) mice. On day 6 following Raji-luc injection, tumor engraftment was measured by i.p. injection of 150 mg/kg luciferin and imaging on a Xenogen IVIS-200 instrument (Caliper Biosciences, now Perkin Elmer, Shelton, Conn.). Images were analyzed using Living Image, version 4.1, software (Perkin Elmer) and the bioluminescent signal flux for each mouse was expressed as average radiance (photons per second per cm$^2$ per steradian). CAR T cells were administered to mice via tail vein injection on Day 7. Imaging was performed on indicated days following CAR T injection to establish the kinetics of tumor growth and eradication by CAR T cells.

Results:

In order to evaluate the novel anti-CD22 fully human ScFv binding sequences, CAR constructs in Set 1 were designed incorporating constructs 2246-2249: ScFv sequences derived from phage display library, Table 1, ScFv1 (16P), ScFv2 (24P), ScFv3 (25P), ScFv4 (11S), ScFv5 (12S), and CAR construct 2202 (m971-positive control), as a tumor antigen binding domain. In each CAR design, the tumor targeting domain was followed by a linker and transmembrane domains derived from the human CD8 protein, a 4-1BB costimulatory domain and a CD3 zeta signaling domain (Table 2 infra).

TABLE 2

List of CD22 - Targeting CAR Constructs incorporating ScFv sequences

| | CAR construct LTG# | Composition |
|---|---|---|
| Set 1 | 2202 | ScFv1-CD8 TM-41BB-CD3 zeta |
| | 2246 | ScFv2-CD8 TM-41BB-CD3 zeta |
| | 2247 | ScFv3-CD8 TM-41BB-CD3 zeta |
| | 2248 | ScFv4-CD8 TM-41BB-CD3 zeta |
| | 2249 | ScFv5-CD8 TM-41BB-CD3 zeta |
| Set 2 | 2203 | ScFv6-CD8 TM-41BB-CD3 zeta |
| | 2204 | ScFv7-CD8 TM-41BB-CD3 zeta |

| | CAR LTG# | Composition | Binder ScFv | CTL | Cytokine Response | Ligand-independent CTL (K562, K562-19) | CAR only IL-2 | CAR only TNFa | CAR only IFNg |
|---|---|---|---|---|---|---|---|---|---|
| | | 2205 | ScFv8-CD8 TM-41BB-CD3 zeta | | | | | | |
| | | 2206 | ScFv9-CD8 TM-41BB-CD3 zeta | | | | | | |
| | | 2207 | ScFv10-CD8 TM-41BB-CD3 zeta | | | | | | |
| | | 2208 | ScFv11-CD8 TM-41BB-CD3 zeta | | | | | | |
| | | 2209 | ScFv12-CD8 TM-41BB-CD3 zeta | | | | | | |
| | | 2210 | ScFv13-CD8 TM-41BB-CD3 zeta | | | | | | |
| | | 2216 | ScFv14-CD8 TM-41BB-CD3 zeta | | | | | | |
| | | 2217 | ScFv15-CD8 TM-41BB-CD3 zeta | | | | | | |
| | | 2218 | ScFv16-CD8 TM-41BB-CD3 zeta | | | | | | |
| | | 2219 | ScFv17-CD8 TM-41BB-CD3 zeta | | | | | | |
| | | 2220 | ScFv18-CD8 TM-41BB-CD3 zeta | | | | | | |
| Controls | | 1538 | FMC63-CD8 TM-41BB-CD3 zeta | | | | | | |
| | | 2200 | m971-CD8 TM-41BB-CD3 zeta | | | | | | |

T Cells Transduced with Anti-CD22 Chimeric Antigen Receptors Demonstrate Surface Expression and Cytolytic Activity.

a) Surface Expression of Anti-CD22 CARs

To evaluate the novel anti-CD22 CARs, lentiviral vectors (LV) encoding CAR constructs under the control of human EF1a promoter were generated as described in Materials and Methods. Human primary T cells derived from healthy donors were transduced lentiviral vectors encoding CARs. Non-transduced cells from same donor (termed UTD or Mock) or GFP-transduced cells from same donor served as negative controls. Data is representative of results from at least 3 assays from different donors.

TABLE 3

Summary of in vitro function of CARs targeting CD22

| | | | | | | | | | |
|---|---|---|---|---|---|---|---|---|---|
| Set 1 | 2202 | ScFv1-CD8 TM-41BB-CD3 zeta | 16P | med | med | low | low | low | low |
| | 2246 | ScFv2-CD8 TM-41BB-CD3 zeta | 24P | low | NA | NA | NA | NA | NA |
| | 2247 | ScFv3-CD8 TM-41BB-CD3 zeta | 25P | non | NA | NA | NA | NA | NA |
| | 2248 | ScFv4-CD8 TM-41BB-CD3 zeta | 11s | non | NA | NA | NA | NA | NA |
| | 2249 | ScFv5-CD8 TM-41BB-CD3 zeta | 12s | non | NA | NA | NA | NA | NA |
| Set 2 | 2203 | ScFv6-CD8 TM-41BB-CD3 zeta | 16P3 | high | high | high | low | med | high |
| | 2204 | ScFv7-CD8 TM-41BB-CD3 zeta | 16P16 | high | high | high | low | med | high |
| | 2205 | ScFv8-CD8 TM-41BB-CD3 zeta | 16P20 | high | high | high | low | med | high |
| | 2206 | ScFv9-CD8 TM-41BB-CD3 zeta | 16P2 | high | high | high | low | med | high |
| | 2207 | ScFv10-CD8 TM-41BB-CD3 zeta | 16P6 | high | high | high | low | med | high |
| | 2208 | ScFv11-CD8 TM-41BB-CD3 zeta | 16P10 | high | high | high | low | med | high |
| | 2209 | ScFv12-CD8 TM-41BB-CD3 zeta | 16P17 | high | high | high | low | low | low |
| | 2210 | ScFv13-CD8 TM-41BB-CD3 zeta | 16P20v1 | high | high | high | low | med | high |
| | 2216 | ScFv14-CD8 TM-41BB-CD3 zeta | 16P1 | high | high | high | low | med | high |
| | 2217 | ScFv15-CD8 TM-41BB-CD3 zeta | 16P3v2 | high | high | high | low | med | high |
| | 2218 | ScFv16-CD8 TM-41BB-CD3 zeta | 16P8 | high | high | high | low | low | low |
| | 2219 | ScFv17-CD8 TM-41BB-CD3 zeta | 16P13 | high | high | high | low | med | med |
| | 2220 | ScFv18-CD8 TM-41BB-CD3 zeta | 16P15 | high | high | high | low | med | high |
| Controls | 2200 | m971-CD8 TM-41BB-CD3 zeta | m971 | high | high | low | low | low | low |
| | 1538 | FMC63-CD8 TM-41BB-CD3 zeta | FMC63 | high | high | low | low | low | low |

Figure 3:
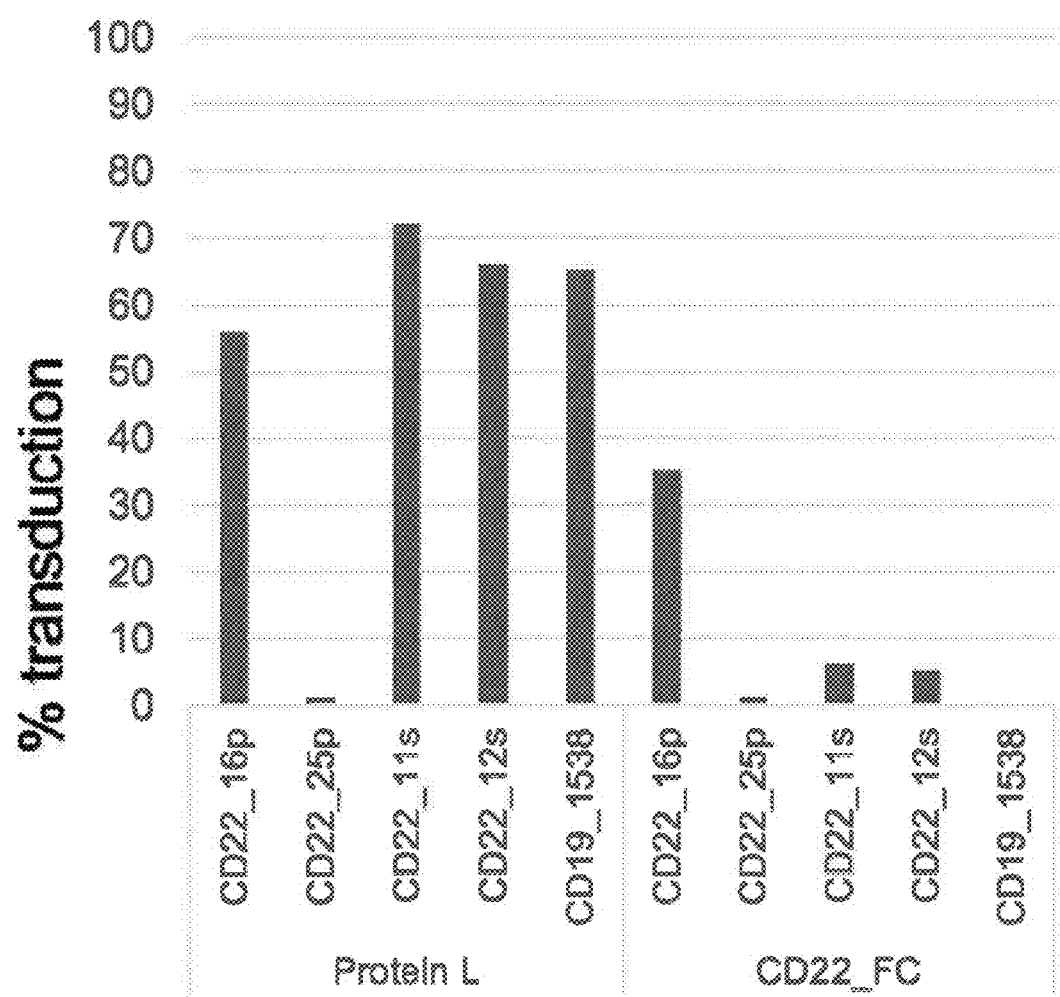
FIG. 3 depicts Anti-CD22 CART surface expression in primary human T cells. CAR T cells redirected to CD22 tumor antigen via the use of ScFv domains (as listed in each row of the figure) were generated by lentiviral transduction with CAR expression constructs. CART detection was performed by flow cytometry. T cells were washed twice in cold PBS-EDTA buffer and stained with CD22-Fc peptide followed by anti Fc-PE reagent. At least 20,000 cells were acquired for each analysis. Cells were gated based on forward scatter and side scatter, singlet discrimination, and 7AAD negativity so that only viable cells were analyzed. Data were acquired on MACSQuant 10 flow cytometer (Miltenyi Biotec, Inc.). The vertical dotted line running through the panel identifies the CAR-expressing population (those falling to the right of this gate). At the top of the panel untransduced cells (UTD) are shown as a negative control and immediately below, in the second row, cells transduced with the m971 positive control are shown. Subsequent rows show CAR expression for each vector construct listed on the left axis of the figure. Results are representative of T cell transductions in three donors.

Med: medium,
CTL: cytotoxic T lymphocytes response (target cell lysis),
NA: data not available,
non: no lysis T cells were activated on culture Day 0 with TransAct T cell reagent (Miltenyi Biotec, Inc.) in the presence of IL-2 as described in Materials and Methods. On culture day 8-10, expression of anti-CD22 CARs on the surface of transduced T cells was detected by protein L conjugated to biotin, followed by staining with streptavidin-PE reagent. Alternatively, CD22-Fc peptide (R&D Systems, Inc.) followed by staining with anti-Fc-PE antibody was used for CAR T staining, and data acquired by flow cytometry (FIG. 3). Except for CAR 2247, which is comprised of lambda light chain (and thereby non-reactive with protein L), all CAR constructs demonstrated surface CAR expression above 50-70% as detected by protein L staining. By contrast, only CAR16P demonstrated CAR expression (~30%) when using the CD22-Fc peptide staining, which specifically associates with the anti-CD22 ScFv—antigen binding site (CAR 24P is not shown). These data indicate that whereas most CARs constructs were expressed on T cell surface, only the CAR16P construct had assumed a ScFv configuration that maintained CD22 protein binding.

b) Cytolytic Assay and Cytokine Assay of Anti-CD22 CARs

To demonstrate the cytolytic function of the generated CAR T cells, a luciferase-based killing assay was performed by combining CAR-T with CD22-positive Raji-luc cells, CD22-positive Reh-luc cells, CD22-negative K562-luc cells at E:T ratios of 20:1, 10:1, 5:1, or 2.5:1 in overnight cell killing assays as described in Materials and Methods (FIG. 4). Anti CD19 CAR construct 1538, previously shown to react with Raji and Reh (CD19+) but not K562 (CD19−) lines, was utilized as a positive control. Only CAR2202 (binder 16P) showed dose-dependent, CD22-specific tumor killing, whereas CARs 2247 (25P), 2248 (11S), and 2249 (12S) had no tumor specific activity.

Figure 5:
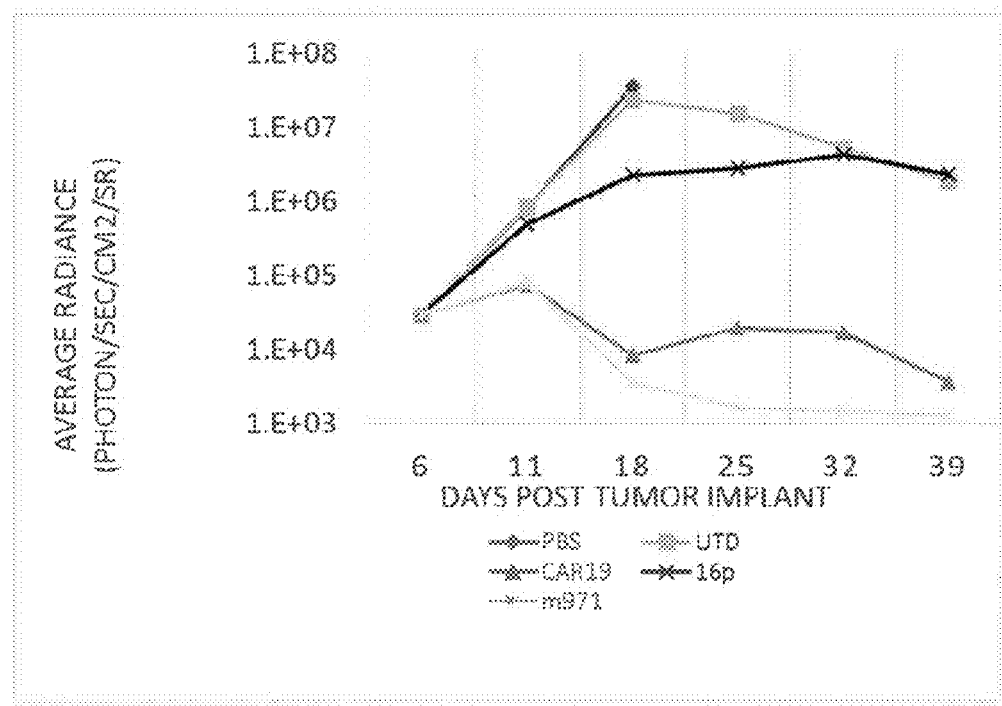
FIG. 5 depicts CD22-specific CART cell production of three cytokines (interferon-gamma, TNF-alpha, and IL-2) when co-cultured alone (medium gray, CAR only), with CD22-positive leukemia lines (Raji, black bars, Reh, light gray), or a CD22-negative line (293T, pale gray). The assay was carried out overnight at E:T ratio of 10:1, then supernatants were analyzed for cytokine concentrations by ELISA. N=3+SEM. Negative control: untransduced T cells (utd), positive control: transduced m971 CD22 CAR-T cells. LTG numbers of each LV used to transduce human T cells are listed on the x-axis.

After determining that the novel human construct CAR2202 (16P) is functional in vitro, its anti-tumor activity was tested in vivo, in an established NSG mouse xenograft model of Raji Burkitts' lymphoma, as described in Material and Methods. Tumors were implanted via tail vein on day 0, staging was performed on day 6, and mice were treated with $4\times10^6$ CART cells i.v. on day 7. Treatment groups were CAR16P (2202), CAR19 (1538) positive control, CAR22 (2200 m971) positive control, and UTD (non-transduced T cells) negative control. As shown in FIG. 5, positive control CART preparations CAR22 (2200 m971), and CAR19 (1538) effectively inhibited tumor growth from study day 18 and onwards, whereas the test construct CAR 2202 (16P) only mildly slowed down tumor progression, and its effect was no longer discernable from the negative control treatment (UTD) after study day 32. Therefore, ScFv binder 2202 (16P) had only weak anti-tumor activity in vitro and in vivo, and there was a need for generating additional CAR constructs incorporating improved ScFv binder sequences.

A set 2 of CAR constructs (LTG numbers 2203-2220) incorporating ScFv binder sequences with improved affinity for CD22 (Table 1 infra, Set 2) were constructed as described in the Materials and Methods. Derivation of the improved affinity ScFv binders is described in Example 1. LV encoding Set 2 CAR constructs under the control of human EF1a promoter were generated and tested in vitro for expression and function as described above. Briefly, T cells were activated on culture Day 0 with TransAct T cell reagent (active engagement of CD3 and CD28 antigens, Miltenyi Biotec, Inc.) in the presence of IL-2 as described in Materials and Methods. On culture Day 8-10 CAR T cells were harvested and assessed for CAR surface expression by flow cytometry. CTL activity was assessed by co-incubation assay, and secretion of inflammatory cytokines was assessed by ELISA. A comparative summary of functional outcomes for all CAR22 constructs is provided in Table 3. Positive control CAR constructs, as well as novel CAR22 candidates with most favorable functional profile are noted in bold.

The set of 2 CAR constructs (LTG numbers 2203-2220) were tested by transducing LV-encoded CAR sequences into cells from independent donors in at least three separate experiments. Transduction of CART constructs from Set 2 into donor cells typically yielded CAR expression ranging from 20% to 80%, as detected by CD22-Fc staining method and consisted mostly of CD4+ T cells (FIG. 6, select constructs).

CAR CTL activity was determined in an overnight assay by co-incubating CART cells with luciferase-expressing tumor cells at E:T ratios ranging from 10:1 to 2.5:1 (FIG. 7). Residual luciferase activity originating in the surviving portion of tumor cell population at the end of culture period was determined and % lysis was calculated as described in Materials and Methods. The novel CD22-targeting CAR cells demonstrated strong killing activity in CD22+ Raji lymphoma and in Reh leukemia lines, whereas negative control groups GFP and UTD caused no lysis (FIG. 7A). The exception to this rule was construct 2202 (16P), which yielded relatively modest killing of tumor lines. CAR19-targeting control 1538 and CD22-targeting control 2200 (m971) killed Raji and Reh tumors, as expected. K562 line, which is CD22− and CD19−, showed background killing activity for the positive control constructs 2202 and 1538, which was 40% and 60% lysed tumor cells at E:T ratio of 10:1, respectively. This activity may be due to indirect effect of inflammatory cytokines secreted by CART cells, or contaminating NK/NKT activity. The killing activity of the test CAR22 constructs vs K56 was comparable in magnitude to control 2200 (m971), or slightly higher. To further delineate the specificity of the novel CAR22 constructs, we employed K562 cells engineered to stably express CD22, or CD19 (FIG. 7B).

In K562-CD19 line, the positive control CAR19 (1538) yielded ~70% lysis for E:T 10:1, whereas the background killing activity of control CAR22 2200 (m971) was at only ~20% for E:T ratio of 10:1. By contrast, the % lysis produced by the majority of test CAR22 constructs under same E:T ratio was between 20% and 60%.

By comparison, in K562-CD22 line, the specific CTL activity of the CD22 CAR control CAR22 2200 (m971) and the majority of novel CAR22 constructs was at 80%, whereas the non-specific killing activity of CAR19 control 1538 was only 20%. Therefore, despite the sensitivity of K562 line to CAR constructs, the novel CD22 CARs tested all demonstrated specific lytic activity against CD22-expressing targets.

Then, the concentration of inflammatory cytokines IFN-gamma, TNF-alpha and IL-2 secreted by CAR T cells transduced with CAR22 constructs, when challenged by CD22-positive cell lines Raji and REH (FIG. 8) were then measured. CAR T cells alone controls were included for each construct, in order to test for basal levels of cytokine production. Levels of TNF-alpha, IFN-gamma and IL-2 were strongly induced by T cells exposed to CD22+ Raji cells, however, for most CAR22 constructs, Reh tumors mediated induction of IFNg and TNFa only, but not IL-2. For a subset of constructs, T cells only control groups also showed induction of cytokines, raising the possibility that these constructs are activated in the absence of specific ligands. Therefore, CAR design and binder choice are not trivial, as some binders active in a soluble IgG or ScFv format and amenable to expression on T cell surface in a CAR T format, are nevertheless inefficient in killing or producing cytokines when co-incubated with CD22-positive tumors. In case of LTG2217 (16P3v2 binder) and LTG 2220 (16P15), for example, IL-2 and TNF-alpha were tonically produced by the construct indicating self-activation of the T cell in the absence of tumor target. This would likely prove toxic for clinical use and LTG2217 and LTG2220 are therefore disqualified as a therapeutic candidates.

To avoid the possibility of non-specific activation of CAR22 cells, we have identified constructs with no/minimal secretion of inflammatory cytokines in the absence of specific tumors: LTG2209 (16P17), LTG2218 (16P8) and LTG2219 (16P13).

Figure 9:
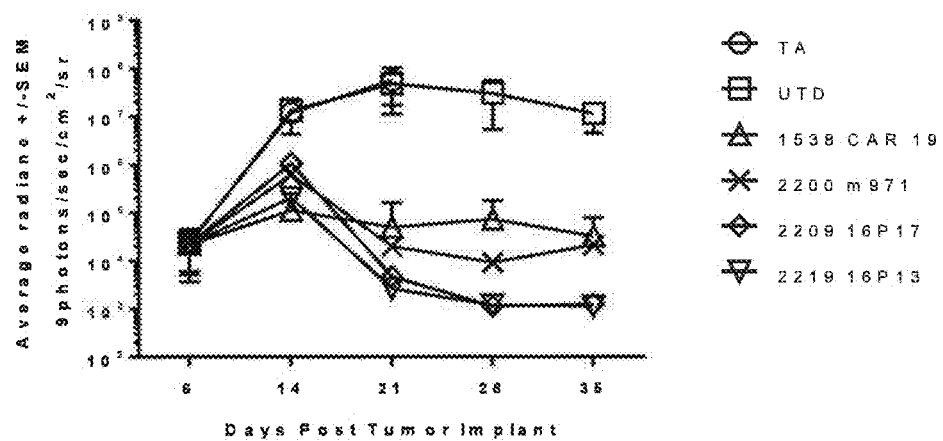
FIG. 9 shows the ability of CAR T specific for CD22 to control disease in an animal model. Immunodeficient mice (NSG) were injected i.v. with Raji leukemia cells that stably express firefly luciferase on study day 0. The disease burden is measured on the x-axis, reported as average radiance for each group, following injection with the luciferase substrate luciferin and imaged in an IVIS instrument that images each animal. Animals were assigned to equivalent disease burden groups of 6 mice each on day 6 and injected with CAR T cells on day 7 and disease progression was followed over time. Animals infused with Raji cells and not treated with T cells (TA, open circle) progressed rapidly and had to be sacrificed by day 21. Other groups received untransduced T cells (UTD, open square), CAR-19 transduced T cells (1538 CAR 19, open triangle), control anti-CD22 CAR (2200 m971, -x-), new CAR LTG2209 (2209 16P17, open diamond), new CAR LTG2219 (2219 16P13, open inverted triangle)

Next, novel CAR22 constructs 2219 and 2209 were tested in the NSG Raji xenograft tumor model. Constructs 2200 (m971) and 1538 (FMC63) served as positive controls, and tumor alone (TA) and non-transduced T cells (UTD) served as negative controls. Experimental procedures were performed as detailed in Materials and Methods. Raji-luciferase expressing tumor cells were implanted in mice on day 0, followed by CART treatment of day 7. Tumor progression and CART activity were determined by weekly bioluminescence measurements starting on study day 6 (FIG. 9). In comparison to negative control groups, TA and UTD, in which tumor growth proceeded unabated from day 6 and on, CAR test constructs 2209 and 2209 inhibited tumor progression, and by day 21 have reduced tumor bioluminescence to baseline at treatment initiation (day 6). The antitumor effect of the test constructs 2209 and 2209 was equal to, or greater than that produced by the positive control CD22 CAR construct 2200 (m971).

In summary, high functionality of novel fully human, improved-affinity anti-CD22 CAR constructs derived from the yeast screening library, LTG numbers 2203 through 2220 (Table 2 infra), was demonstrated. Notably CAR constructs, 2209, 2219, 2218, were superior or showed a different activity profile to the positive control, LTG2220 (m971), and thus are expected to have potent therapeutic activity.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

SEQUENCES OF THE DISCLOSURE

The nucleic and amino acid sequences listed below are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

```
SEQ ID NO: 1 is the nucleic acid sequence of the CD22-specific binder
(scFv1) 16P:
CAAGTACAACTCCAGCAAAGCGGGCCTGGTCTGGTGAAGCCGTCACAGAC
GCTTTCACTTACGTGTGCGATCTCCGGTGACTCCGTGAGTTCTAATAGCGC
GGCTTGGAACTGGATTAGGCAGTCTCCATCCCGAGGATTGGAATGGCTCG
GCAGGACTTATTATAGAAGTAAGTGGTACAACGATTATGCAGTCTCTGTG
AAATCTCGCATCACCATTAACCCAGACACGTCTAAGAATCAGTTCAGTCTT
CAACTCAACTCTGTAACCCCCGAAGATACAGCGGTCTACTACTGTGCTCA
GGAGGTGCAACCCCACGATGCTTTTGATATCTGGGGCCAGGGTACCATGG
TTACGGTGTCTTCTGGGGGAGGGGGGTCCGGTGGGGAGGATCAGGGGGT
GGGGGCAGCGACATACAAATGACGCAATCCCCGTCTTCTGTTTCTGCGTCT
GTCGGAGATAAAGTAACAATAACCTGTCGAGCGTCACAGGACGTTAGTGG
CTGGCTTGCGTGGTATCAGCAAAAACCGGGGCTCGCCCCGCAATTGCTTA
TATTTGGAGCGAGTACTCTTCAGGGCGAGGTACCTAGCAGATTTTCTGGGT
CCGGCTCAGGTACGGACTTCACCCTGACCATATCTAGCTTGCAGCCTGAA
GATTTCGCCACCTACTATTGTCAACAGGCGAAGAACTTTCCATATACGTTC
GGGCAGGGTACGAAATTGGAGATAAAA SEQ ID NO: 2 is the amino acid sequence of the CD22-specific binder
(scFv1) 16P:
QVQLQQSGPGLVKPSQTLSLTCAISGDSVSSNSAAWNWIRQSPSRGLEWLGR
TYYRSKWYNDYAVSVKSRITINPDTSKNQFSLQLNSVTPEDTAVYYCAQEVQ
PHDAFDIWGQGTMVTVSSGGGGSGGGGSGGGGSDIQMTQSPSSVSASVGDK
VTITCRASQDVSGWLAWYQQKPGLAPQLLIFGASTLQGEVPSRFSGSGSGTDF
TLTISSLQPEDFATYYCQQAKNFPYTFGQGTKLEIKR SEQ ID NO: 3 is the nucleic acid sequence of the CD22 CAR LTG2202 (LP-scFv1-
CD8TM-41BB-CD3zeta):
ATGCTTCTCCTGGTGACAAGCCTTCTGCTCTGTGAGTTACCACACCCAGCA
TTCCTCCTGATCCCACAAGTACAACTCCAGCAAAGCGGGCCTGGTCTGGT
GAAGCCGTCACAGACGCTTTCACTTACGTGTGCGATCTCCGGTGACTCCGT
GAGTTCTAATAGCGCGGCTTGGAACTGGATTAGGCAGTCTCCATCCCGAG
GATTGGAATGGCTCGGCAGGACTTATTATAGAAGTAAGTGGTACAACGAT
TATGCAGTCTCTGTGAAATCTCGCATCACCATTAACCCAGACACGTCTAAG
AATCAGTTCAGTCTTCAACTCAACTCTGTAACCCCCGAAGATACAGCGGT
CTACTACTGTGCTCAGGAGGTGCAACCCCACGATGCTTTTGATATCTGGGG
CCAGGGTACCATGGTTACGGTGTCTTCTGGGGGAGGGGGGTCCGGTGGGG
GAGGATCAGGGGGTGGGGGCAGCGACATACAAATGACGCAATCCCCGTC
TTCTGTTTCTGCGTCTGTCGGAGATAAAGTAACAATAACCTGTCGAGCGTC
ACAGGACGTTAGTGGCTGGCTTGCGTGGTATCAGCAAAAACCGGGGCTCG
CCCCGCAATTGCTTATATTTGGAGCGAGTACTCTTCAGGGCGAGGTACCTA
GCAGATTTTCTGGGTCCGGCTCAGGTACGGACTTCACCCTGACCATATCTA
GCTTGCAGCCTGAAGATTTCGCCACCTACTATTGTCAACAGGCGAAGAAC
TTTCCATATACGTTCGGGCAGGGTACGAAATTGGAGATAAAAGCGGCCGC
AACTACCACCCCTGCCCCTCGGCCGCCGACTCCGGCCCCAACCATCGCAA
GCCAACCCCTCTCCTTGCGCCCCGAAGCTTGCCGCCCGGCCGCGGGTGGA
GCCGTGCATACCCGGGGGCTGGACTTTGCCTGCGATATCTACATTTGGGCC
CCGCTGGCCGGCACTTGCGGCGTGCTCCTGCTGTCGCTGGTCATCACCCTT
TACTGCAAGAGGGGCCGGAAGAAGCTGCTTTACATCTTCAAGCAGCCGTT
CATGCGGCCCGTGCAGACGACTCAGGAAGAGGACGGATGCTCGTGCAGA
TTCCCTGAGGAGGAAGAGGGGGGATGCGAACTGCGCGTCAAGTTCTCACG
GTCCGCCGACGCCCCCGCATATCAACAGGGCCAGAATCAGCTCTACAACG
AGCTGAACCTGGGAAGGAGAGAGGAGTACGACGTGCTGGACAAGCGACG
CGGACGCGACCCGGAGATGGGGGGGAAACCACGGCGGAAAAACCCTCAG
GAAGGACTGTACAACGAACTCCAGAAAGACAAGATGGCGGAAGCCTACT
CAGAAATCGGGATGAAGGGAGAGCGGAGGAGGGGAAAGGGTCACGACG
GGCTGTACCAGGGACTGAGCACCGCCACTAAGGATACCTACGATGCCTTG
CATATGCAAGCACTCCCACCCCGG SEQ ID NO: 4 is the amino acid sequence of the CD22 CAR LTG2202 (LP-scFv1-
CD8TM-41BB-CD3zeta):
MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAQEVQPHDAFDIWGQGTMVTVSSGGGGSGGGGSGG
GGSDIQMTQSPSSVSASVGDKVTITCRASQDVSGWLAWYQQKPGLAPQLLIF
GASTLQGEVPSRFSGSGSGTDFTLTISSLQPEDFATYYCQQAKNFPYTFGQGT
KLEIKAAATTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSC
RFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGL
YQGLSTATKDTYDALHMQALPPR
```

SEQ ID NO: 5 is the amino acid sequence of the scFv1 (16P) LCDR1:
QDVSGW

SEQ ID NO: 6 is the amino acid sequence of the scFv1 (16P) LCDR2:
GAS

SEQ ID NO: 7 is the amino acid sequence of the scFv1 (16P) LCDR3:
QQAKNFPYT

SEQ ID NO: 8 is the amino acid sequence of the scFv1 (16P) HCDR1:
GDSVSSNSAA

SEQ ID NO: 9 is the amino acid sequence of the scFv1 (16P) HCDR2:
TYYRSKWYN

SEQ ID NO: 10 is the amino acid sequence of the scFv1 (16P) HCDR3:
AQEVQPHDAFDI

SEQ ID NO: 11 is the nucleic acid sequence of the CD22-specific binder (scFv2) 24P:
CAAGTACAGCTGCAACAATCTGGCCCTGGGCTTGTGAAACCCTCTCAGAC
TTTGTCCTTGACGTGCGCGATAAGTGGCGATTCAGTTAGTTCTAACAGCGC
CGCTTGGAACTGGATTAGACAGAGCCCCAGTCGGGGACTCGAATGGCTTG
GCCGGACTTATTATCGCAGTAAATGGTATAATGATTATGCTGTGAGTGTGA
AAAGTAGGATCACAATCAACCCCGATACGAGCAAGAATCAATTCTCATTG
CAACTGAACAGCGTCACTCCCGAGGATACAGCTGTATATTATTGTGCAAG
AGAAGGTGGGTGGTATGGCGAGATGGATGTATGGGGGAAAGGAACTACG
GTAACTGTGTCCAGTGGCGGAGGCGGTTCAGGTGGTGGAGGCTCTGGAGG
AGGAGGGTCCGAAATCGTGCTTACCCAGTCTCCGGCTACTCTGAGCGTTA
GTCCGGGTGAAAGGGCCTCACTCTCTTGTCGAGCTTCACAGTCAGTCTCTT
CCTACTTGGCTTGGTATCAGCAGAAGCCAGGTCAGGCGCCCCGCTTGCTC
ATTTACGACGCAAGCACACGAGCGACAGGCATTCCAGACAGATTTTCTGG
TTCTGGTTCTGGCACGGACTTTACTCTTACTATAAACTCACTTGAGGCAGA
GGATGCTGCGACTTACTATTGTCACCAATCAAGCTCTCTGCCTTACACCTT
TGGGCAAGGCACCAAACTCGAAATCAAG SEQ ID NO: 12 is the amino acid sequence of the CD22-specific binder (scFv2) 24P:
QVQLQQSGPGLVKPSQTLSLTCAISGDSVSSNSAAWNWIRQSPSRGLEWLGR
TYYRSKWYNDYAVSVKSRITINPDTSKNQFSLQLNSVTPEDTAVYYCAREGG
WYGEMDVWGKGTTVTVSSGGGGSGGGGSGGGGSEIVLTQSPATLSVSPGER
ASLSCRASQSVSSYLAWYQQKPGQAPRLLIYDASTRATGIPDRFSGSGSGTDF
TLTINSLEAEDAATYYCHQSSSLPYTFGQGTKLEIKR SEQ ID NO: 13 is the nucleic acid sequence of the CD22 CAR LTG2246 (LP-scFv2-CD8TM-41BB-CD3zeta):
ATGCTGCTGTTGGTGACATCACTTCTGCTCTGTGAACTCCCCCATCCAGCC
TTTCTGCTTATACCGCAAGTACAGCTGCAACAATCTGGCCCTGGGCTTGTG
AAACCCTCTCAGACTTTGTCCTTGACGTGCGCGATAAGTGGCGATTCAGTT
AGTTCTAACAGCGCCGCTTGGAACTGGATTAGACAGAGCCCCAGTCGGGG
ACTCGAATGGCTTGGCCGGACTTATTATCGCAGTAAATGGTATAATGATTA
TGCTGTGAGTGTGAAAAGTAGGATCACAATCAACCCCGATACGAGCAAGA
ATCAATTCTCATTGCAACTGAACAGCGTCACTCCCGAGGATACAGCTGTA
TATTATTGTGCAAGAGAAGGTGGGTGGTATGGCGAGATGGATGTATGGGG
GAAAGGAACTACGGTAACTGTGTCCAGTGGCGGAGGCGGTTCAGGTGGTG
GAGGCTCTGGAGGAGGAGGGTCCGAAATCGTGCTTACCCAGTCTCCGGCT
ACTCTGAGCGTTAGTCCGGGTGAAAGGGCCTCACTCTCTTGTCGAGCTTCA
CAGTCAGTCTCTTCCTACTTGGCTTGGTATCAGCAGAAGCCAGGTCAGGC
GCCCCGCTTGCTCATTTACGACGCAAGCACACGAGCGACAGGCATTCCAG
ACAGATTTTCTGGTTCTGGTTCTGGCACGGACTTTACTCTTACTATAAACT
CACTTGAGGCAGAGGATGCTGCGACTTACTATTGTCACCAATCAAGCTCT
CTGCCTTACACCTTTGGGCAAGGCACCAAACTCGAAATCAAGGTTACGGT
ATCATCTGCGGCCGCAACTACCACCCCTGCCCCTCGGCCGCCGACTCCGG
CCCCAACCATCGCAAGCCAACCCCTCTCCTTGCGCCCCGAAGCTTGCCGCC
CGGCCGCGGGTGGAGCCGTGCATACCCGGGGCTGGACTTTGCCTGCGAT
ATCTACATTTGGGCCCCGCTGGCCGGCACTTGCGGCGTGCTCCTGCTGTCG
CTGGTCATCACCCTTTACTGCAAGAGGGGCCGGAAGAAGCTGCTTTACAT
CTTCAAGCAGCCGTTCATGCGGCCCGTGCAGACGACTCAGGAAGAGGACG
GATGCTCGTGCAGATTCCCTGAGGAGGAAGAGGGGGGATGCGAACTGCG
CGTCAAGTTCTCACGGTCCGCCGACGCCCCCGCATATCAACAGGGCCAGA
ATCAGCTCTACAACGAGCTGAACCTGGGAAGGAGAGAGGAGTACGACGT
GCTGGACAAGCGACGCGGACGCGACCCGGAGATGGGGGGAAACCACGG
CGGAAAAACCCTCAGGAAGGACTGTACAACGAACTCCAGAAAGACAAGA
TGGCGGAAGCCTACTCAGAAATCGGGATGAAGGGAGAGCGGAGGAGGGG
AAAGGGTCACGACGGGCTGTACCAGGGACTGAGCACCGCCACTAAGGAT
ACCTACGATGCCTTGCATATGCAAGCACTCCCACCCCGG SEQ ID NO: 14 is the amino acid sequence of the CD22 CAR LTG2246 (LP-scFv2-CD8TM-41BB-CD3zeta):
MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAREGGWYGEMDVWGKGTTVTVSSGGGGSGGGGSG
GGGSEIVLTQSPATLSVSPGERASLSCRASQSVSSYLAWYQQKPGQAPRLLIY
DASTRATGIPDRFSGSGSGTDFTLTINSLEAEDAATYYCHQSSSLPYTFGQGTK
LEIKVTVSSAAATTTPAPRPPTPAPTIASQPLSLRPEACRPAAGGAVHTRGLDF
ACDIYIWAPLAGTCGVLLLSLVITLYCKRGRKKLLYIFKQPFMRPVQTTQEED
GCSCRFPEEEEGGCELRVKFSRSADAPAYQQGQNQLYNELNLGRREEYDVLD
KRRGRDPEMGGKPRRKNPQEGLYNELQKDKMAEAYSEIGMKGERRRGKGH
DGLYQGLSTATKDTYDALHMQALPPR SEQ ID NO: 15 is the amino acid sequence of the scFv2 (24P) LCDR1:
QSVSSY SEQ ID NO: 16 is the amino acid sequence of the scFv2 (24P) LCDR2:
DAS SEQ ID NO: 17 is the amino acid sequence of the scFv2 (24P) LCDR3:
HQSSSLPYT SEQ ID NO: 18 is the amino acid sequence of the scFv2 (24P) HCDR1:
GDSVSSNSAA SEQ ID NO: 19 is the amino acid sequence of the scFv2 (24P) HCDR2:
TYYRSKWYN SEQ ID NO: 20 is the amino acid sequence of the scFv2 (24P) HCDR3:
AREGGWYGEMDV SEQ ID NO: 21 is the nucleic acid sequence of the CD22-specific binder (scFv3) 25P:
CAAGTACAGCTCCAACAGAGTGGACCTGGTCTCGTTAAGCCGTCCCAAAC
ACTGTCTTTGACGTGCGCTATTAGTGGCGACAGCGTATCATCCAATTCTGC
TGCTTGGAACTGGATTAGACAGTCACCGTCCAGAGGCTTGGAATGGCTGG
GCAGGACGTACTACCGCTCAAAATGGTATAACGATTACGCGGTTAGTGTC
AAATCCAGGATTACCATTAACCCTGACACAAGTAAGAATCAGTTTTCTCTT
CAGCTGAATTCCCTGACTCCTGAGGATACGGCCGTTTACTACTGTGCCCGA
GAACACCAGAATGAGGCGGCTTTTGATATTTGGGGGCAAGGAACAATGGT
CACAGTTAGCAGTGGGGGGGTGGCTCCGGGGAGGTGGTTCCGGCGGC
GGTGGTTCTCAATCCGTCCTGACACAACCTCCCTCAGCGAGCGGGACTCC
CGGTCAAAGGGTGACCATCTCTTGTTCTGGGGGAGGTAGTAACATCGGGA
CAAATACTGCGTCCTGGTATCAGCAACTCCCTGGGACCGCTCCCAAGTTGT
TGATATATCGCAATACGCAACGACCTAGTGGGATACCTGATAGATTCAGC
GGAAGCAAAAGTGGTACGAGTGCGTCTTTGGCAATATCTGGCCTCCAGTC
CGAGGACGAAGCGGATTACTATTGTGCGGCCTGGGATGACTCACTGAATG
GTTATGTGTTCGGTGCAGGTACTCAACTCACCGTACTTGGT SEQ ID NO: 22 is the amino acid sequence of the CD22-specific binder (scFv3) 25P:
QVQLQQSGPGLVKPSQTLSLTCAISGDSVSSNSAAWNWIRQSPSRGLEWLGR
TYYRSKWYNDYAVSVKSRITINPDTSKNQFSLQLNSLTPEDTAVYYCAREHQ
NEAAFDIWGQGTMVTVSSGGGGSGGGGSGGGGSQSVLTQPPSASGTPGQRV
TISCSGGGSNIGTNTASWYQQLPGTAPKLLIYRNTQRPSGIPDRFSGSKSGTSA
SLAISGLQSEDEADYYCAAWDDSLNGYVFGAGTQLTVLG SEQ ID NO: 23 is the nucleic acid sequence of the CD22 CAR LTG2247 (LP-scFv3-CD8TM-41BB-CD3zeta):
ATGCTTCTCCTGGTGACAAGCTTCTGCTCTGTGAGTTACCACACCCAGCA
TTCCTCCTGATCCCACAAGTACAGCTCCAACAGAGTGGACCTGGTCTCGTT
AAGCCGTCCCAAACACTGTCTTTGACGTGCGCTATTAGTGGCGACAGCGT
ATCATCCAATTCTGCTGCTTGGAACTGGATTAGACAGTCACCGTCCAGAG
GCTTGGAATGGCTGGGCAGGACGTACTACCGCTCAAAATGGTATAACGAT
TACGCGGTTAGTGTCAAATCCAGGATTACCATTAACCCTGACACAAGTAA
GAATCAGTTTTCTCTTCAGCTGAATTCCCTGACTCCTGAGGATACGGCCGT
TTACTACTGTGCCCGAGAACACCAGAATGAGGCGGCTTTTGATATTTGGG
GGCAAGGAACAATGGTCACAGTTAGCAGTGGGGGGGTGGCTCCGGGGG
AGGTGGTTCCGGCGGCGGTGGTTCTCAATCCGTCCTGACACAACCTCCCTC
AGCGAGCGGGACTCCCGGTCAAAGGGTGACCATCTCTTGTTCTGGGGGAG
GTAGTAACATCGGGACAAATACTGCGTCCTGGTATCAGCAACTCCCTGGG
ACCGCTCCCAAGTTGTTGATATATCGCAATACGCAACGACCTAGTGGGAT
ACCTGATAGATTCAGCGGAAGCAAAAGTGGTACGAGTGCGTCTTTGGCAA
TATCTGGCCTCCAGTCCGAGGACGAAGCGGATTACTATTGTGCGGCCTGG
GATGACTCACTGAATGGTTATGTGTTCGGTGCAGGTACTCAACTCACCGTA
CTTGGTGCGGCCGCAACTACCACCCCTGCCCCTCGGCCGCCGACTCCGGC
CCCAACCATCGCAAGCCAACCCCTCTCCTTGCGCCCCGAAGCTTGCCGCCC
GGCCGCGGGTGGAGCCGTGCATACCCGGGGGCTGGACTTTGCCTGCGATA
TCTACATTTGGGCCCCGCTGGCCGGCACTTGCGGCGTGCTCCTGCTGTCGC

```
TGGTCATCACCCTTTACTGCAAGAGGGGCCGGAAGAAGCTGCTTTACATC
TTCAAGCAGCCGTTCATGCGGCCCGTGCAGACGACTCAGGAAGAGGACGG
ATGCTCGTGCAGATTCCCTGAGGAGGAAGAGGGGGGATGCGAACTGCGC
GTCAAGTTCTCACGGTCCGCCGACGCCCCCGCATATCAACAGGGCCAGAA
TCAGCTCTACAACGAGCTGAACCTGGAAGGAGAGAGGAGTACGACGTG
CTGGACAAGCGACGCGGACGCGACCCGGAGATGGGGGGGAAACCACGGC
GGAAAAACCCTCAGGAAGGACTGTACAACGAACTCCAGAAAGACAAGAT
GGCGGAAGCCTACTCAGAAATCGGGATGAAGGGAGAGCGGAGGAGGGA
AAGGGTCACGACGGGCTGTACCAGGGACTGAGCACCGCCACTAAGGATA
CCTACGATGCCTTGCATATGCAAGCACTCCCACCCCGG

SEQ ID NO: 24 is the amino acid sequence of the CD22 CAR LTG2247 (LP-scFv3-
CD8TM-41BB-CD3zeta):
MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSLTPEDTAVYYCAREHQNEAAFDIWGQGTMVTVSSGGGGSGGGGSGGG
GSQSVLTQPPSASGTPGQRVTISCSGGGSNIGTNTASWYQQLPGTAPKLLIYR
NTQRPSGIPDRFSGSKSGTSASLAISGLQSEDEADYYCAAWDDSLNGYVFGA
GTQLTVLGAAATTTPAPRPPTPAPTIASQPLSLRPEACRPAAGGAVHTRGLDF
ACDIYIWAPLAGTCGVLLLSLVITLYCKRGRKKLLYIFKQPFMRPVQTTQEED
GCSCRFPEEEEGGCELRVKFSRSADAPAYQQGQNQLYNELNLGRREEYDVLD
KRRGRDPEMGGKPRRKNPQEGLYNELQKDKMAEAYSEIGMKGERRRGKGH
DGLYQGLSTATKDTYDALHMQALPPR SEQ ID NO: 25 is the amino acid sequence of the scFv3 (25P) LCDR1:
GSNIGTNT SEQ ID NO: 26 is the amino acid sequence of the scFv3 (25P) LCDR2:
RNT SEQ ID NO: 27 is the amino acid sequence of the scFv3 (25P) LCDR3:
AAWDDSLNGYV SEQ ID NO: 28 is the amino acid sequence of the scFv3 (25P) HCDR1:
GDSVSSNSAA SEQ ID NO: 29 is the amino acid sequence of the scFv3 (25P) HCDR2:
TYYRSKWYN SEQ ID NO: 30 is the amino acid sequence of the scFv3 (25P) HCDR3:
AREHQNEAAFDI SEQ ID NO: 31 is the nucleic acid sequence of the CD22-specific binder (scFv4)
11s:
CAAGTCCAGTTGCAACAGTCCGGGCCAGGTCTGGTTAAGCCATCCCAAAC
TCTGAGTTTGACGTGCGCTATTAGCGGAGATTCCGTGTCCAGCAATTCTGC
AACCTGGAATTGGATCCGGCAGAGTCCGAGTGGCGGTTTGGAATGGCTCG
GACGCACTTACTACAGGAGCAAATGGTACGATGATTATGCTGTTTCTGTG
CGCTCTCGAATCACCATGAATCCTGATACTTCTAAGAACCAATTTTCTTTG
CAGTTGAACTCCGTCACGCCTGAAGATACTGCGGTCTACTATTGCGCACG
CGAAGGCGTAGCCGGCGATTTTGATTACTGGGGGCAAGGAACATTGGTCA
CGGTCTCCTCTGGTGGAGGAGGATCAGGAGGCGGGGGTTCAGGTGGAGGT
GGGAGCGATATTCAACTTACGCAGTCTCCGAGCAGTCTTTCTGCTTCCGTG
GGAGACCGAGTGACGATTACTTGTAGGGCATCTCAGTCAATAAGTTCCTA
TCTTAACTGGTATCAGCAGAAGCCTGGAAAGGCTCCAAAACTTCTTATTTA
TGCCGCATCCTCATTGCAATCCGGCGTGCCTTCCCGATTTTCCGGATCTGG
CTCAGGCACTGACTTTACCTTGACTATTAGTTCCCTTCAACCAGAAGATTT
TGCTACCTATTACTGCCAACAATCATACAGTACCCCATATACATTCGGCCA
AGGCACGAAATTGGAGATTAAA SEQ ID NO: 32 is the amino acid sequence of the CD22-specific binder
(scFv4) 11s:
QVQLQQSGPGLVKPSQTLSLTCAISGDSVSSNSATWNWIRQSPSGGLEWLGR
TYYRSKWYDDYAVSVRSRITMNPDTSKNQFSLQLNSVTPEDTAVYYCAREG
VAGDFDYWGQGTLVTVSSGGGGSGGGGSGGGGSDIQLTQSPSSLSASVGDR
VTITCRASQSISSYLNWYQQKPGKAPKLLIYAASSLQSGVPSRFSGSGSGTDFT
LTISSLQPEDFATYYCQQSYSTPYTFGQGTKLEIKR SEQ ID NO: 33 is the nucleic acid sequence of the CD22 CAR LTG2248 (LP-scFv4-
CD8TM-41BB-CD3zeta):
ATGCTTCTCCTGGTGACAAGCCTTCTGCTCTGTGAGTTACCACACCCAGCA
TTCCTCCTGATCCCACAAGTCCAGTTGCAACAGTCCGGGCCAGGTCTGGTT
AAGCCATCCCAAACTCTGAGTTTGACGTGCGCTATTAGCGGAGATTCCGT
GTCCAGCAATTCTGCAACCTGGAATTGGATCCGGCAGAGTCCGAGTGGCG
GTTTGGAATGGCTCGGACGCACTTACTACAGGAGCAAATGGTACGATGAT
TATGCTGTTTCTGTGCGCTCTCGAATCACCATGAATCCTGATACTTCTAAG
AACCAATTTTCTTTGCAGTTGAACTCCGTCACGCCTGAAGATACTGCGGTC
TACTATTGCGCACGCGAAGGCGTAGCCGGCGATTTTGATTACTGGGGGCA
AGGAACATTGGTCACGGTCTCCTCTGGTGGAGGAGGATCAGGAGGCGGG
```

```
GGTTCAGGTGGAGGTGGGAGCGATATTCAACTTACGCAGTCTCCGAGCAG
TCTTTCTGCTTCCGTGGGAGACCGAGTGACGATTACTTGTAGGGCATCTCA
GTCAATAAGTTCCTATCTTAACTGGTATCAGCAGAAGCCTGGAAAGGCTC
CAAAACTTCTTATTTATGCCGCATCCTCATTGCAATCCGGCGTGCCTTCCC
GATTTTCCGGATCTGGCTCAGGCACTGACTTTACCTTGACTATTAGTTCCC
TTCAACCAGAAGATTTTGCTACCTATTACTGCCAACAATCATACAGTACCC
CATATACATTCGGCCAAGGCACGAAATTGGAGATTAAAGCGGCCGCAACT
ACCACCCCTGCCCCTCGGCCGCCGACTCCGGCCCCAACCATCGCAAGCCA
ACCCCTCTCCTTGCGCCCCGAAGCTTGCCGCCCGGCCGCGGGTGGAGCCG
TGCATACCCGGGGGCTGGACTTTGCCTGCGATATCTACATTTGGGCCCCGC
TGGCCGGCACTTGCGGCGTGCTCCTGCTGTCGCTGGTCATCACCCTTTACT
GCAAGAGGGGCCGGAAGAAGCTGCTTTACATCTTCAAGCAGCCGTTCATG
CGGCCCGTGCAGACGACTCAGGAAGAGGACGGATGCTCGTGCAGATTCCC
TGAGGAGGAAGAGGGGGGATGCGAACTGCGCGTCAAGTTCTCACGGTCC
GCCGACGCCCCCGCATATCAACAGGGCCAGAATCAGCTCTACAACGAGCT
GAACCTGGGAAGGAGAGAGGAGTACGACGTGCTGGACAAGCGACGCGGA
CGCGACCCGGAGATGGGGGGGAAACCACGGCGGAAAAACCCTCAGGAAG
GACTGTACAACGAACTCCAGAAAGACAAGATGGCGGAAGCCTACTCAGA
AATCGGGATGAAGGGAGAGCGGAGGAGGGGAAAGGGTCACGACGGGCT
GTACCAGGGACTGAGCACCGCCACTAAGGATACCTACGATGCCTTGCATA
TGCAAGCACTCCCACCCCGG

SEQ ID NO: 34 is the amino acid sequence of the CD22 CAR LTG2248 (LP-scFv4-
CD8TM-41BB-CD3zeta):
MLLLVTSLLLCELPHPAFLLIPVQLQQSGPGLVKPSQTLSLTCAISGDSVSSN
SATWNWIRQSPSGGLEWLGRTYYRSKWYDDYAVSVRSRITMNPDTSKNQFS
LQLNSVTPEDTAVYYCAREGVAGDFDYWGQGTLVTVSSGGGGSGGGGSGG
GGSDIQLTQSPSSLSASVGDRVTITCRASQSISSYLNWYQQKPGKAPKLLIYAA
SSLQSGVPSRFSGSGSGTDFTLTISSLQPEDFATYYCQQSYSTPYTFGQGTKLEI
KAAATTTPAPRPPTPAPTIASQPLSLRPEACRPAAGGAVHTRGLDFACDIYIW
APLAGTCGVLLLSLVITLYCKRGRKKLLYIFKQPFMRPVQTTQEEDGCSCRFP
EEEEGGCELRVKFSRSADAPAYQQGQNQLYNELNLGRREEYDVLDKRRGRD
PEMGGKPRRKNPQEGLYNELQKDKMAEAYSEIGMKGERRRGKGHDGLYQG
LSTATKDTYDALHMQALPPR SEQ ID NO: 35 is the amino acid sequence of the scFv4 (11s) LCDR1:
QSISSY SEQ ID NO: 36 is the amino acid sequence of the scFv4 (11s) LCDR2:
AAS SEQ ID NO: 37 is the amino acid sequence of the scFv4 (11s) LCDR3:
QQSYSTPYT SEQ ID NO: 38 is the amino acid sequence of the scFv4 (11s) HCDR1:
GDSVSSNSAT SEQ ID NO: 39 is the amino acid sequence of the scFv4 (11s) HCDR2:
TYYRSKWYD SEQ ID NO: 40 is the amino acid sequence of the scFv4 (11s) HCDR3:
AREGVAGDFDY SEQ ID NO: 41 is the nucleic acid sequence of the CD22-specific binder (scFv5)
12s:
CAAGTTCAGTTGCAGCAGAGTGGCCCTGGGCTTGTTAAACCATCACAGAC
GCTCTCACTGACCTGTGCCATCTCTGGAGACAGTGTAAGTTCTAACTCAGC
CGCGTGGAATTGGATTAGACAATCACCAAGCCGGGGACTTGAATGGCTTG
GTCGGACGTACTATAGATCTAAGTGGTATAATGACTACGCAGTGTCAGTG
AAATCACGGATAACCATAAACCCTGACACCAGCAAAAACCAATTTTCTCT
TCAGCTTAATTCCGTCACGCCAGAAGATACGGCCGTTTACTACTGTGCGA
GGGAAGGTGATGACGCATTGGACATCTGGGGTCAGGGGACCATGGTGACT
GTCTCTTCCGGCGGGGGGGGTAGTGGAGGGGGTGGCTCAGGTGGTGGCGG
GTCAGATATACAAATGACACAGAGCCCTAGTAGTCTGAGTGCTTCAGTGG
GCGACCGCGTAACTATAACCTGTAGAGCATCCCAAAGCATTTCCCACTTC
CTTAATTGGTACCAGCAGAAGCCGGGCACAGCGCCCAAACTCCTGATCAC
CACTGCGAGCGGACTTGGTTCAGGTGTTCCTAGCCGGTTTAGTGGGTCAG
GTAGCGGTACAGATTTCACTCTCACGATAAACTCCCTTCAGCCTGAGGAC
CTGGCGACATATTACTGTCAACAATCCTATACCACCCCACTGACATTCGGA
GGGGGCACAAAACTGGAGATCAAA SEQ ID NO: 42 is the amino acid sequence of the CD22-specific binder (scFv5)
12s:
QVQLQQSGPGLVKPSQTLSLTCAISGDSVSSNSAAWNWIRQSPSRGLEWLGR
TYYRSKWYNDYAVSVKSRITINPDTSKNQFSLQLNSVTPEDTAVYYCAREGD
DALDIWGQGTMVTVSSGGGGSGGGGSGGGGSDIQMTQSPSSLSASVGDRVTI
TCRASQSISHFLNWYQQKPGTAPKLLITTASGLGSGVPSRFSGSGSGTDFTLTI
NSLQPEDLATYYCQQSYTTPLTFGGGTKLEIKR
```

SEQ ID NO: 43 is the nucleic acid sequence of the CD22 CAR LTG2249 (LP-scFv5-CD8TM-41BB-CD3zeta):
ATGCTTCTCCTGGTGACAAGCCTTCTGCTCTGTGAGTTACCACACCCAGCA
TTCCTCCTGATCCCACAAGTTCAGTTGCAGCAGAGTGGCCCTGGGCTTGTT
AAACCATCACAGACGCTCTCACTGACCTGTGCCATCTCTGGAGACAGTGT
AAGTTCTAACTCAGCCGCGTGGAATTGGATTAGACAATCACCAAGCCGGG
GACTTGAATGGCTTGGTCGGACGTACTATAGATCTAAGTGGTATAATGAC
TACGCAGTGTCAGTGAAATCACGGATAACCATAAACCCTGACACCAGCAA
AAACCAATTTTCTCTTCAGCTTAATTCCGTCACGCCAGAAGATACGGCCGT
TTACTACTGTGCGAGGGAAGGTGATGACGCATTGGACATCTGGGGTCAGG
GGACCATGGTGACTGTCTCTTCCGGCGGGGGGGGTAGTGGAGGGGGTGGC
TCAGGTGGTGGCGGGTCAGATATACAAATGACACAGAGCCCTAGTAGTCT
GAGTGCTTCAGTGGGCGACCGCGTAACTATAACCTGTAGAGCATCCCAAA
GCATTTCCCACTTCCTTAATTGGTACCAGCAGAAGCCGGGCACAGCGCCC
AAACTCCTGATCACCACTGCGAGCGGACTTGGTTCAGGTGTTCCTAGCCG
GTTTAGTGGGTCAGGTAGCGGTACAGATTTCACTCTCACGATAAACTCCCT
TCAGCCTGAGGACCTGGCGACATATTACTGTCAACATCCTATACCACCC
CACTGACATTCGGAGGGGGCACAAAACTGGAGATCAAAGCGGCCGCAAC
TACCACCCCTGCCCCTCGGCCGCCGACTCCGGCCCCAACCATCGCAAGCC
AACCCCTCTCCTTGCGCCCCGAAGCTTGCCGCCCGGCCGCGGGTGGAGCC
GTGCATACCCGGGGCTGGACTTTGCCTGCGATATCTACATTTGGGCCCCG
CTGGCCGGCACTTGCGGCGTGCTCCTGCTGTCGCTGGTCATCACCCTTTAC
TGCAAGAGGGGCCGGAAGAAGCTGCTTTACATCTTCAAGCAGCCGTTCAT
GCGGCCCGTGCAGACGACTCAGGAAGAGGACGGATGCTCGTGCAGATTCC
CTGAGGAGGAAGAGGGGGGATGCGAACTGCGCGTCAAGTTCTCACGGTC
CGCCGACGCCCCCGCATATCAACAGGGCCAGAATCAGCTCTACAACGAGC
TGAACCTGGGAAGGAGAGAGGAGTACGACGTGCTGGACAAGCGACGCGG
ACGCGACCCGGAGATGGGGGGGAAACCACGGCGGAAAAACCCTCAGGAA
GGACTGTACAACGAACTCCAGAAAGACAAGATGGCGGAAGCCTACTCAG
AAATCGGGATGAAGGGGAGAGCGGAGGAGGGGAAAGGGTCACGACGGGC
TGTACCAGGGACTGAGCACCGCCACTAAGGATACCTACGATGCCTTGCAT
ATGCAAGCACTCCCACCCCGG SEQ ID NO: 44 is the amino acid sequence of the CD22 CAR LTG2249 (LP-scFv5-CD8TM-41BB-CD3zeta):
MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAREGDDALDIWGQGTMVTVSSGGGGSGGGGSGGG
SDIQMTQSPSSLSASVGDRVTITCRASQSISHFLNWYQQKPGTAPKLLITTASG
LGSGVPSRFSGSGSGTDFTLTINSLQPEDLATYYCQQSYTTPLTFGGGTKLEIK
AAATTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEE
EEGGCELRVKFSRSADAPAYQQGQNQLYNELNLGRREEYDVLDKRRGRDPE
MGGKPRRKNPQEGLYNELQKDKMAEAYSEIGMKGERRRGKGHDGLYQGLS
TATKDTYDALHMQALPPR SEQ ID NO: 45 is the amino acid sequence of the scFv5 (12s) LCDR1:
QSISHF SEQ ID NO: 46 is the amino acid sequence of the scFv5 (12s) LCDR2:
TAS SEQ ID NO: 47 is the amino acid sequence of the scFv5 (12s) LCDR3:
QQSYTTPLT SEQ ID NO: 48 is the amino acid sequence of the scFv5 (12s) HCDR1:
GDSVSSNSAA SEQ ID NO: 49 is the amino acid sequence of the scFv5 (12s) HCDR2:
TYYRSKWYN SEQ ID NO: 50 is the amino acid sequence of the scFv5 (12s) HCDR3:
AREGDDALDI SEQ ID NO: 51 is the nucleic acid sequence of the CD22-specific binder (scFv6) 16P3:
CAGATACAGTTGCAGCAGTCAGGTCCAGGACTAGTGAAGCCCTCGCAGAC
CCTCTCACTCACCTGTGCCATCTCCGGGGACAGTGTCTCTAGCAACAGTGC
TGCTTGGAACTGGATCAGGCAGTCCCCATCGAGAGGCCTTGAGTGGCTGG
GAAGGACATACTACAGGTCCAAGTGGTATAATGATTATGCAGTATCTGTG
AAAAGTCGAATAACCATCAACCCAGACACATCCAAGAACCAGTTCTCCCT
GCAGCTGAACTCTGTGACTCCCGAGGACACGGCTGTGTATTACTGTGCCC
AAGAGGTACAACCTGATGATGCTTTAGATATCTGGGGCCAAGGGACAATG
GTCACCGTCTCTTCAGGAGGTGGCGGGTCTGGCGGTGGAGGTAGCGGTGG
TGGCGGATCCGACATCCAGATGACCCAGTCTCCATCTTCCGTGTCTGCATC
TGTAGGAGACAAAGTCACCATCACTTGTCGGGCGAGTCAGGATGTTAGCG
GCTGGTTAGCCTGGTATCAGCAGAAACCAGGGCTAGCCCCTCAGCTCCTG
ATCTCTGGTGCATCCACTTTGCAAGGTGAAGTCCCATCAAGGTTCAGCGG
CAGTGGATCTGGGACAGATTTTACTCTCACCATCAGCAGCCTGCAGCCTG AAGATTTTGCCACTTATTATTGTCAACAGGCTAAAAATTTCCCTTACACTT
TTGGCCAGGGGACCAAGCTGGAAATCAAA SEQ ID NO: 52 is the amino acid sequence of the CD22-specific binder (scFv6)
16P3:
QIQLQQSGPGLVKPSQTLSLTCAISGDSVSSNSAAWNWIRQSPSRGLEWLGRT
YYRSKWYNDYAVSVKSRITINPDTSKNQFSLQLNSVTPEDTAVYYCAQEVQP
DDALDIWGQGTMVTVSSGGGGSGGGGSGGGGSDIQMTQSPSSVSASVGDKV
TITCRASQDVSGWLAWYQQKPGLAPQLLISGASTLQGEVPSRFSGSGSGTDFT
LTISSLQPEDFATYYCQQAKNFPYTFGQGTKLEIK SEQ ID NO: 53 is the nucleic acid sequence of the CD22 CAR LTG2203 (LP-scFv6-
CD8TM-41BB-CD3zeta):
ATGTTGTTGCTTGTCACAAGCCTTCTTCTCTGTGAGCTTCCGCACCCGGCTTTCCT
GCTGATCCCGCAGATACAGCTTCAGCAGTCCGGCCCCGGTCTGGTAAAGCCGTCC
CAAACGCTTTCACTCACATGCGCGATCTCTGGTGATTCTGTGTCATCCAACAGCG
CAGCATGGAATTGGATCCGCCAATCACCCAGTAGAGGCTTGGAGTGGTTGGGCC
GGACTTATTATCGAAGTAAGTGGTACAATGATTATGCAGTCTCAGTTAAATCCAG
GATCACTATTAACCCAGATACAAGTAAAAACCAGTTCTCATTGCAACTTAATTCC
GTAACTCCGGAGGACACTGCAGTATATTACTGCGCTCAGGAGGTGCAGCCTGAT
GATGCTCTGGACATTTGGGGACAAGGCACGATGGTCACGGTTAGTTCCGGGGGG
GGAGGTTCTGGCGGAGGTGGTAGTGGGGGGGCGGCAGTGACATCCAGATGACA
CAGAGTCCCAGCAGCGTGTCTGCGTCAGTCGGGGATAAGGTAACAATTACGTGT
AGAGCGAGCCAGGACGTTTCCGGGTGGCTGGCGTGGTACCAACAAAAACCCGGT
CTCGCTCCGCAGTTGCTCATCTCTGGAGCGTCCACCCTTCAGGGAGAGGTGCCTA
GCAGATTTTCTGGGTCTGGATCCGGCACGGATTTTACACTTAGTATTTCCTCTCTT
CAACCCGAAGATTTTGCTACTTACTATTGCCAGCAGGCCAAAAACTTCCCGTACA
CGTTTGGACAGGGCACAAAGTTGGAAATTAAGGCGGCCGCAACTACCACCCCTG
CCCCTCGGCCGCCGACTCCGGCCCCAACCATCGCAAGCCAACCCCTCTCCTTGCG
CCCCGAAGCTTGCCGCCCGGCCGCGGGTGGAGCCGTGCATACCCGGGGGCTGGA
CTTTGCCTGCGATATCTACATTTGGGCCCCGCTGGCCGGCACTTGCGGCGTGCTC
CTGCTGTCGCTGGTCATCACCCTTTACTGCAAGAGGGGCCGGAAGAAGCTGCTTT
ACATCTTCAAGCAGCCGTTCATGCGGCCCGTGCAGACGACTCAGGAAGAGGACG
GATGCTCGTGCAGATTCCCTGAGGAGGAAGAGGGGGGATGCGAACTGCGCGTCA
AGTTCTCACGGTCCGCCGACGCCCCCGCATATCAACAGGGCCAGAATCAGCTCTA
CAACGAGCTGAACCTGGGAAGGAGAGAGGAGTACGACGTGCTGGACAAGCGAC
GCGGACGCGACCCGGAGATGGGGGGGAAACCACGGCGGAAAAACCCTCAGGAA
GGACTGTACAACGAACTCCAGAAAGACAAGATGGCGGAAGCCTACTCAGAAATC
GGGATGAAGGGAGAGCGGAGGAGGGGAAAGGGTCACGACGGGCTGTACCAGGG
ACTGAGCACCGCCACTAAGGATACCTACGATGCCTTGCATATGCAAGCACTCCCA
CCCCGG SEQ ID NO: 54 is the amino acid sequence of the CD22 CAR LTG2203 (LP-scFv6-
CD8TM-41BB-CD3zeta):
MLLLVTSLLLCELPHPAFLLIPQIQLQQSGPGLVKPSQTLSLTCAISGDSVSSNS
AAWNWIRQSPSRGLEWLGRTYYRSKWYNDYAVSVKSRITINPDTSKNQFSLQ
LNSVTPEDTAVYYCAQEVQPDDALDIWGQGTMVTVSSGGGGSGGGGSGGGG
GSDIQMTQSPSSVSASVGDKVTITCRASQDVSGWLAWYQQKPGLAPQLLISG
ASTLQGEVPSRFSGSGSGTDFTLTISSLQPEDFATYYCQQAKNFPYTFGQGTKL
EIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGER
RRGKGHDGLYQGLSTATKDTYDALHMQALPPR SEQ ID NO: 55 is the amino acid sequence of the scFv6 (16P3) LCDR1:
QDVSGW SEQ ID NO: 56 is the amino acid sequence of the scFv6 (16P3) LCDR2:
GAS SEQ ID NO: 57 is the amino acid sequence of the scFv6 (16P3) LCDR3:
QQAKNFPYT SEQ ID NO: 58 is the amino acid sequence of the scFv6 (16P3) HCDR1:
GDSVSSNSAA SEQ ID NO: 59 is the amino acid sequence of the scFv6 (16P3) HCDR2:
TYYRSKWYN SEQ ID NO: 60 is the amino acid sequence of the scFv6 (16P3) HCDR3:
AQEVQPDDALDI SEQ ID NO: 61 is the nucleic acid sequence of the CD22-specific binder (scFv7)
16P16:
CAAGTACAGTTGCAGCAGTCAGGACCTGGCCTTGTGAAACCATCCCAAAC
TCTCAGCCTCACGTGTGCTATTTCTGGTGACTCAGTAAGTAGCAATAGCGC
TGCTTGGAACTGGATCAGACAATCTCCCTCCAGGGGTCTCGAATGGCTGG
GGCGAACCTATTACCGATCTAAATGGTATAACGATTATGCAGTATCCGTG

```
AAATCCAGGATTACAATCAACCCAGATACGTTCAAGAATCAATTCTCTCTT
CAGCTCAACTCCGTAACTCCAGAGGACACTGCGGTATATTATTGCGCCCA
AGAAGTCGAGCCACACGATGCCCTCGATATCTGGGGTCAAGGTACCATGG
TTACAGTTAGTAGTGGGGGTGGGGAAGCGGGGCGGTGGGTCCGGTGG
CGGGGGTTCAGACATCAAGATGACCCAATCCCCAAGCTCTGTTTCAGCAT
CCGTGGGCGATAAGGTAACCATTACATGCAGAGCGAGTCAGGACGTTTCA
GGGTGGCTGGCTTGGTACCAGCAAAAACCGGGACTCGCACCGCAGCTGTT
GATTTTCGGCGCCAGTACGCTTCAGGGCGAAGTACCGTCCAGGTTCAGTG
GGTCAGGTTCTGGCACCGATTTTACGCTCACGATATCCAGTCTCCAACCGG
AGGATTTTGCTACTTATTACTGCCAGCAGGCTAAGTATTTTCCATACACAT
TTGGCCAGGGGACAAAGTTGGAGATCAAA

SEQ ID NO: 62 is the amino acid sequence of the CD22-specific binder (scFv7)
16P16:
QVQLQQSGPGLVKPSQTLSLTCATSGDSVSSNSAAWNWIRQSPSRGLEWLGR
TYYRSKWYNDYAVSVKSRITINPDTFKNQFSLQLNSVTPEDTAVYYCAQEVE
PHDALDIWGQGTMVTVSSGGGGSGGGGSGGGGSDIKMTQSPSSVSASVGDK
VTITCRASQDVSGWLAWYQQKPGLAPQLLIFGASTLQGEVPSRFSGSGSTDF
TLTISSLQPEDFATYYCQQAKYFPYTFGQGTKLEIK SEQ ID NO: 63 is the nucleic acid sequence of the CD22 CAR LTG2204 (LP-scFv7-
CD8TM-41BB-CD3zeta):
ATGCTGCTTTTGGTAACTTCCCTCCTTTTGTGCGAGCTGCCCCATCCAGCG
TTCCTCCTCATCCCTCAAGTACAGTTGCAGCAGTCAGGACCTGGCCTTGTG
AAACCATCCCAAACTCTCAGCCTCACGTGTGCATTTCTGGTGACTCAGTA
AGTAGCAATAGCGCTGCTTGGAACTGGATCAGACAATCTCCCTCCAGGGG
TCTCGAATGGCTGGGGCGAACCTATTACCGATCTAAATGGTATAACGATT
ATGCAGTATCCGTGAAATCCAGGATTACAATCAACCCAGATACGTTCAAG
AATCAATTCTCTCTTCAGCTCAACTCCGTAACTCCAGAGGACACTGCGGTA
TATTATTGCGCCCAAGAAGTCGAGCCACACGATGCCCTCGATATCTGGGG
TCAAGGTACCATGGTTACAGTTAGTAGTGGGGGTGGGGAAGCGGGGGC
GGTGGGTCCGGTGGCGGGGGTTCAGACATCAAGATGACCCAATCCCCAAG
CTCTGTTTCAGCATCCGTGGGCGATAAGGTAACCATTACATGCAGAGCGA
GTCAGGACGTTTCAGGGTGGCTGGCTTGGTACCAGCAAAAACCGGGACTC
GCACCGCAGCTGTTGATTTTCGGCGCCAGTACGCTTCAGGGCGAAGTACC
GTCCAGGTTCAGTGGGTCAGGTTCTGGCACCGATTTTACGCTCACGATATC
CAGTCTCCAACCGGAGGATTTTGCTACTTATTACTGCCAGCAGGCTAAGTA
TTTTCCATACACATTTGGCCAGGGGACAAAGTTGGAGATCAAAGCGGCCG
CAACTACCACCCCTGCCCCTCGGCCGCCGACTCCGGCCCCAACCATCGCA
AGCCAACCCCTCTCCTTGCGCCCCGAAGCTTGCCGCCCGGCCGCGGGTGG
AGCCGTGCATACCCGGGGCTGGACTTTGCCTGCGATATCTACATTTGGG
CCCCGCTGGCCGGCACTTGCGGCGTGCTCCTGCTGTCGCTGGTCATCACCC
TTTACTGCAAGAGGGGCCGGAAGAAGCTGCTTTACATCTTCAAGCAGCCG
TTCATGCGGCCCGTGCAGACGACTCAGGAAGAGGACGGATGCTCGTGCAG
ATTCCCTGAGGAGGAAGAGGGGGGATGCGAACTGCGCGTCAAGTTCTCAC
GGTCCGCCGACGCCCCCGCATATCAACAGGGCCAGAATCAGCTCTACAAC
GAGCTGAACCTGGGAAGGAGAGAGGAGTACGACGTGCTGGACAAGCGAC
GCGGACGCGACCCGGAGATGGGGGGAAACCACGGCGGAAAAACCCTCA
GGAAGGACTGTACAACGAACTCCAGAAAGACAAGATGGCGGAAGCCTAC
TCAGAAATCGGGATGAAGGGAGAGCGGAGGAGGGGAAAGGGTCACGAC
GGGCTGTACCAGGGACTGAGCACCGCCACTAAGGATACCTACGATGCCTT
GCATATGCAAGCACTCCCACCCCGG SEQ ID NO: 64 is the amino acid sequence of the CD22 CAR LTG2204 (LP-scFv7-
41BB-CD3zeta):
MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTFKNQFSL
QLNSVTPEDTAVYYCAQEVEPHDALDIWGQGTMVTVSSGGGGSGGGGSGG
GGSDIKMTQSPSSVSASVGDKVTITCRASQDVSGWLAWYQQKPGLAPQLLIF
GASTLQGEVPSRFSGSGSTDFTLTISSLQPEDFATYYCQQAKYFPYTFGQGT
KLEIKAAATTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSC
RFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGL
YQGLSTATKDTYDALHMQALPPR SEQ ID NO: 65 is the amino acid sequence of the scFv7 (16P16) LCDR1:
QDVSGW SEQ ID NO: 66 is the amino acid sequence of the scFv7 (16P16) LCDR2:
GAS SEQ ID NO: 67 is the amino acid sequence of the scFv7 (16P16) LCDR3:
QQAKYFPYT SEQ ID NO: 68 is the amino acid sequence of the scFv7 (16P16) HCDR1:
GDSVSSNSAA
```

SEQ ID NO: 69 is the amino acid sequence of the scFv7 (16P16) HCDR2:
TYYRSKWYN

SEQ ID NO: 70 is the amino acid sequence of the scFv7 (16P16) HCDR3:
AQEVEPHDALDI SEQ ID NO: 71 is the nucleic acid sequence of the CD22-specific binder (scFv8)
16P20:
CAGGTACAGCTGCAGCAGTCAGGTCCAGGACTGGTGAAGCCCTCGCAGAC
CCTCTCACTCACCTGTGCCATCTCCGGGGACAGTGTCTCTAGCAACAGTGC
TGCTTGGAACTGGATCAGGCAGTCCCCATCGAGAGGCCTTGAGTGGCTGG
GAAGGACATACTACAGGTCCAAGTGGTATAATGATTATGCAGTATCTGTG
AAAAGTCGAATAACCATCAACCCAGACACATCCAAGAACCAGTTCTCCCT
GCAGCTGAACTCTGTGACTCCCGAGGACACGGCTGTGTATTACTGTGCCC
AAGAGGTAGAACCTCATGATGCTCTTGATATCTGGGGCCAAGGGACAATG
GTCACCGTCTCTTCAGGAGGTGGCGGGTCTGGCGGAGGCGGTAGCGGTGG
TGGCGGATCCGACATCCAGATGACGCAGTCTCCATCATCCGTGTCTGCATC
TGTAGGAGACAAAGTCACCATCACTTGTCGGGCGAGTCAGGATGTTAGCG
GCTGGTTAGCCTGGTATCAACAGAAACCAGGGCTAGCCCCTCAGCTCCTG
ATCTTTGGTGCATCCACTTTGCAAGGTGAAGTCCCATCAAGGTTCAGCGGC
AGTGGATCTGGGACAGATTTTACTCTCACCATCAGCAGCCTGCAGCCTGA
AGATTTTGCCACTTATTATTGTCAACAGGCTAAATATTTCCCTTACACTTTT
GGCCAGGGGACCAAGCTGGAGATCAAA SEQ ID NO: 72 is the amino acid sequence of the CD22-specific binder (scFv8)
16P20:
QVQLQQSGPGLVKPSQTLSLTCATSGDSVSSNSAAWNWIRQSPSRGLEWLGR
TYYRSKWYNDYAVSVKSRITINPDTSKNQFSLQLNSVTPEDTAVYYCAQEVE
PHDALDIWGQGTMVTVSSGGGGSGGGGSGGGGSDIQMTQSPSSVSASVGDK
VTITCRASQDVSGWLAWYQQKPGLAPQLLIFGASTLQGEVPSRFSGSGSGTDF
TLTISSLQPEDFATYYCQQAKYFPYTFGQGTKLEIK SEQ ID NO: 73 is the nucleic acid sequence of the CD22 CAR LTG2205 (LP-scFv8-
CD8TM-41BB-CD3zeta):
ATGCTGCTCCTCGTAACCTCTCTTCTTCTTTGTGAGTTGCCACATCCAGCAT
TTCTTCTGATACCTCAAGTTCAACTCCAGCAGAGTGGTCCAGGTTTGGTAA
AACCCAGCCAGACTCTCTCATTGACGTGTGCCATATCAGGTGATTCAGTTT
CCTCTAATAGCGCGGCATGGAATTGGATCAGGCAAAGCCCTAGTCGCGGG
CTGGAGTGGCTCGGCCGGACATACTACCGCTCAAAGTGGTACAACGACTA
CGCCGTCAGCGTAAAATCTCGGATTACCATTAACCCGGATACTTCCAAAA
ACCAATTCTCCCTGCAGCTTAACAGTGTCACGCCGGAAGATACGGCCGTT
TATTACTGCGCACAAGAGGTGGAACCGCACGACGCCCTCGATATCTGGGG
CCAAGGCACTATGGTGACCGTCAGTAGCGGAGGGGGTGGTTCCGGAGGA
GGCGGCTCTGGTGGCGGAGGATCTGATATCCAAATGACCCAATCACCGTC
TTCAGTATCAGCTTCTGTTGGTGACAAAGTTACGATTACCTGTCGAGCGTC
ACAGGACGTTTCTGGTTGGTTGGCTTGGTATCAGCAAAAACCAGGGCTTG
CGCCTCAGTTGCTTATTTTTGGGGCATCTACTTTGCAGGGAGAGGTGCCCT
CCCGGTTCTCCGGCAGTGGGAGCGGCACCGATTTTACACTTACCATCTCTT
CCTTGCAACCCGAAGACTTTGCGACGTACTATTGCCAGCAGGCAAAGTAT
TTTCCCTACACTTTTGGACAAGGGACTAAACTTGAAATCAAGGCGGCCGC
AACTACCACCCCTGCCCCTCGGCCGCCGACTCCGGCCCCAACCATCGCAA
GCCAACCCCTCTCCTTGCGCCCCGAAGCTTGCCGCCCGGCCGCGGGTGGA
GCCGTGCATACCCGGGGCTGGACTTTGCCTGCGATATCTACATTTGGGCC
CCGCTGGCCGGCACTTGCGGCGTGCTCCTGCTGTCGCTGGTCATCACCCTT
TACTGCAAGAGGGGCCGGAAGAAGCTGCTTTACATCTTCAAGCAGCCGTT
CATGCGGCCCGTGCAGACGACTCAGGAAGAGGACGGATGCTCGTGCAGA
TTCCCTGAGGAGGAAGAGGGGGATGCGAACTGCGCGTCAAGTTCTCACG
GTCCGCCGACGCCCCCGCATATCAACAGGGCCAGAATCAGCTCTACAACG
AGCTGAACCTGGGAAGGAGAGAGGAGTACGACGTGCTGGACAAGCGACG
CGGACGCGACCCGGAGATGGGGGGAAACCACGGCGGAAAAACCCTCAG
GAAGGACTGTACAACGAACTCCAGAAAGACAAGATGGCGAAGCCTACT
CAGAAATCGGGATGAAGGGAGAGCGGAGGAGGGGAAAGGGTCACGACG
GGCTGTACCAGGGACTGAGCACCGCCACTAAGGATACCTACGATGCCTTG
CATATGCAAGCACTCCCACCCCGG SEQ ID NO: 74 is the amino acid sequence of the CD22 CAR LTG2205 (LP-scFv8-
CD8TM-41BB-CD3zeta):
MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAQEVEPHDALDIWGQGTMVTVSSGGGGSGGGGSGG
GGSDIQMTQSPSSVSASVGDKVTITCRASQDVSGWLAWYQQKPGLAPQLLIF
GASTLQGEVPSRFSGSGSGTDFTLTISSLQPEDFATYYCQQAKYFPYTFGQGT
KLEIKAAATTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSC
RFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGL
YQGLSTATKDTYDALHMQALPPR SEQ ID NO: 75 is the amino acid sequence of the scFv8 (16P20) LCDR1:
QDVSGW SEQ ID NO: 76 is the amino acid sequence of the scFv8 (16P20) LCDR2:
GAS SEQ ID NO: 77 is the amino acid sequence of the scFv8 (16P20) LCDR3:
QQAKYFPYT SEQ ID NO: 78 is the amino acid sequence of the scFv8 (16P20) HCDR1:
GDSVSSNSAA SEQ ID NO: 79 is the amino acid sequence of the scFv8 (16P20) HCDR2:
TYYRSKWYN SEQ ID NO: 80 is the amino acid sequence of the scFv8 (16P20) HCDR3:
AQEVEPHDALDI SEQ ID NO: 81 is the nucleic acid sequence of the CD22-specific binder (scFv9) 16P2:
CAGGTACAGCTGCAGCAGTCAGGTCCAGGACTGGTGAAGCCCTCGCAGAC
CCTCTCACTCACCTGTGCCATCTCCGGGGACAGTGTCTCTAGCAACAGTGC
TGCTTGGAACTGGATCAGGCAGTCCCCATCGAGAGGCCTTGAGTGGCTGG
GAAGGACATACTACAGGTCCAAGTGGTATAATGATTATGCAGTATCTGTG
AAAAGTCGAATAACCATCAACCCAGACACATTCAAGAACCAGTTCTCCCT
GCAGCTGAACTCTGTGACTCCCGAGGACACGGCTGTGTATTACTGTGCCC
AAGAGGTAGAACCTCATGATGCTCTTGATATCTGGGGCCAAGGGACAATG
GTCACCGTCTCTTCAGGAGGTGGCGGGTCTGGCGGTGGAGGTAGCGGTGG
TGGCGGATCCGACATCAAGATGACCCAGTCTCCATCTTCCGTGTCTGCATC
TGTAGGAGACAAAGTCACCATCACTTGTCGGGCGAGTCAGGATGTTAGCG
GCTGGTTAGCCTGGTATCAGCAGAAACCAGGGCTAGCCCCTCAGCTCCTG
ATCTTTGGTGCATCCACTTTGCAAGGTGAAGTCCCATCAAGGTTCAGCGGC
AGTGGATCTGGGACAGATTTTACTCTCACCATCAGCAGCCTGCAGCCTGA
AGATTTTGCCACTTATTATTGTCAACAGGCTAAATATTTCCCTTACACTTTT
GGCCAGGGGACCAAGCTGGAAATCAAA SEQ ID NO: 82 is the amino acid sequence of the CD22-specific binder (scFv9) 16P2:
QVQLQQSGPGLVKPSQTLSLTCAISGDSVSSNSAAWNWIRQSPSRGLEWLGR
TYYRSKWYNDYAVSVKSRITINPDTFKNQFSLQLNSVTPEDTAVYYCAQEVE
PHDALDIWGQGTMVTVSSGGGGSGGGGSGGGGSDIKMTQSPSSVSASVGDK
VTITCRASQDVSGWLAWYQQKPGLAPQLLIFGASTLQGEVPSRFSGSGSGTDF
TLTISSLQPEDFATYYCQQAKYFPYTFGQGTKLEIK SEQ ID NO: 83 is the nucleic acid sequence of the CD22 CAR LTG2206 (LP-scFv9-CD8TM-41BB-CD3zeta):
ATGCTTCTTTTGGTGACTTCCCTTTTGCTGTGCGAGTTGCCACACCCCGCCT
TCCTGCTTATTCCCCAAGTCCAGCTCCAACAATCCGGACCCGGACTTGTTA
AGCCGTCTCAGACGTTGTCACTCACATGCGCCATCAGTGGCGATAGCGTG
TCCAGCAACAGTGCCGCATGGAATTGGATACGACAGAGCCCTTCCCGAGG
ATTGGAATGGCTGGGACGAACGTACTATAGGTCCAAGTGGTATAACGACT
ACGCGGTGTCAGTTAAATCTCGGATTACTATAAATCCCGACACTTTTAAGA
ATCAGTTTTCCCTGCAACTCAATTCAGTCACACCGGAAGATACGGCAGTG
TACTATTGCGCTCAAGAAGTTGAGCCACATGATGCGCTGGATATTTGGGG
TCAGGGGACTATGGTGACGGTAAGCAGTGGGGGCGGGGCAGTGGCGGA
GGTGGCAGCGGGGGCGGTGGAAGCGACATTAAGATGACTCAGTCTCCGTC
TTCAGTTTCCGCCTCCGTAGGGGACAAGGTTACAATTACTTGTCGCGCATC
TCAGGATGTCTCAGGTTGGCTGGCTTGGTATCAACAGAAGCCTGGCCTCG
CCCCTCAGCTTCTCATATTCGGGGCTAGTACCCTGCAAGGAGAAGTCCCG
AGCAGGTTTTCCGGTTCAGGGTCCGGGACAGACTTTACCTTGACCATCAG
CTCCCTGCAACCGGAGGACTTCGCGACCTACTATTGTCAACAGGCGAAGT
ACTTCCCCTACACGTTCGGCAAGGGACTAAGCTCGAAATCAAGGCGGCC
GCAACTACCACCCCTGCCCCTCGGCCGCCGACTCCGGCCCCAACCATCGC
AAGCCAACCCCTCTCCTTGCGCCCCGAAGCTTGCCGCCCGGCCGCGGGTG
GAGCCGTGCATACCCGGGGGCTGGACTTTGCCTGCGATATCTACATTTGG
GCCCCGCTGGCCGGCACTTGCGGCGTGCTCCTGCTGTCGCTGGTCATCACC
CTTTACTGCAAGAGGGGCCGGAAGAAGCTGCTTTACATCTTCAAGCAGCC
GTTCATGCGGCCCGTGCAGACGACTCAGGAAGAGGACGGATGCTCGTGCA
GATTCCCTGAGGAGGAAGAGGGGGGATGCGAACTGCGCGTCAAGTTCTCA
CGGTCCGCCGACGCCCCCGCATATCAACAGGGCCAGAATCAGCTCTACAA
CGAGCTGAACCTGGGAAGGAGAGAGGAGTACGACGTGCTGGACAAGCGA
CGCGGACGCGACCCGGAGATGGGGGGGAAACCACGGCGGAAAAACCCTC
AGGAAGGACTGTACAACGAACTCCAGAAAGACAAGATGGCGGAAGCCTA
CTCAGAAATCGGGATGAAGGGAGAGCGGAGGAGGGGAAAGGGTCACGAC
GGGCTGTACCAGGGACTGAGCACCGCCACTAAGGATACCTACGATGCCTT
GCATATGCAAGCACTCCCACCCCGG SEQ ID NO: 84 is the amino acid sequence of the CD22 CAR LTG2206 (LP-scFv9-
CD8TM-41BB-CD3zeta):
MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTFKNQFSL
QLNSVTPEDTAVYYCAQEVEPHDALDIWGQGTMVTVSSGGGGSGGGGSGG
GGSDIKMTQSPSSVSASVGDKVTITCRASQDVSGWLAWYQQKPGLAPQLLIF
GASTLQGEVPSRFSGSGSGTDFTLTISSLQPEDFATYYCQQAKYFPYTFGQGT
KLEIKAAATTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSC
RFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGL
YQGLSTATKDTYDALHMQALPPR SEQ ID NO: 85 is the amino acid sequence of the scFv9 (16P2) LCDR1:
QDVSGW SEQ ID NO: 86 is the amino acid sequence of the scFv9 (16P2) LCDR2:
GAS SEQ ID NO: 87 is the amino acid sequence of the scFv9 (16P2) LCDR3:
QQAKYFPYT SEQ ID NO: 88 is the amino acid sequence of the scFv9 (16P2) HCDR1:
GDSVSSNSAA SEQ ID NO: 89 is the amino acid sequence of the scFv9 (16P2) HCDR2:
TYYRSKWYN SEQ ID NO: 90 is the amino acid sequence of the scFv9 (16P2) HCDR3:
AQEVEPHDALDI SEQ ID NO: 91 is the nucleic acid sequence of the CD22-specific binder (scFv10)
16P6:
CAGGTACAGCTGCAGCAGTCAGGTCCAGGACTGGTGAAGCCCTCGCAGAC
CCTCTCACTCACCTGTGCCATCTCCGGGGACAGTGTCTCTAGCAACAGTGC
TGCTTGGAACTGGATCAGGCAGTCCCCATCGAGAGGCCTTGAGTGGCTGG
GAAGGACATACTACAGGTCCAAGTGGTATAATGATTATGCAGTATCTGTG
AAAAGTCGAATAACCATCAACCCAGACACATCCAAGAACCAGTTCTCCCT
GCAGCTGAACTCTGTGACTCCCGAGGATACGGCTGTGTATTACTGTGCCC
AAGAGGTACAACCTGATGATGCTTTTGATATCTGGGGCCAAGGGACAATG
ATCACCGTCTCTTCAGGAGGTGGCGGGTCTGGCGGTGGAGGTAGCGGTGG
TGGCGGATCCGACATCCAGATGACCCAGTCTCCATCTTCCGTGTCTGCATC
TGTAGGAGACAAAGTCACCATCACTTGTCGGGCGAGTCAGGATGTTAGCG
GCTGGTTAGCCTGGTATCAGCAGAAACCAGGGCTAGCCCCTCAGCTCCTG
ATCTCTGGTGCATCCACTTTGCAAGGTGGAGTCCCATCAAGGTTCAGCGG
CAGTGGATCTGGGACAGATTTTACTCTCACCATCAGCAGCCTGCAGCCTG
AAGATTTTGCCACTTATTATTGTCAACAGGCTAAAAATTTCCCTTACACTT
TTGGTCAGGGGACCAAGCTGGAAATCAAA SEQ ID NO: 92 is the amino acid sequence of the CD22-specific binder (scFv10)
16P6:
QVQLQQSGPGLVKPSQTLSLTCATSGDSVSSNSAAWNWIRQSPSRGLEWLGR
TYYRSKWYNDYAVSVKSRITINPDTSKNQFSLQLNSVTPEDTAVYYCAQEVQ
PDDAFDIWGQGTMITVSSGGGGSGGGGSGGGGSDIQMTQSPSSVSASVGDKV
TITCRASQDVSGWLAWYQQKPGLAPQLLISGASTLQGGVPSRFSGSGSGTDFT
LTISSLQPEDFATYYCQQAKNFPYTFGQGTKLEIK SEQ ID NO: 93 is the nucleic acid sequence of the CD22 CAR LTG2207 (LP-
scFv10-CD8TM-41BB-CD3zeta):
ATGCTTCTTTTGGTGACTTCCCTTTTGCTGTGCGAGTTGCCACACCCCGCCT
TCCTGCTTATTCCCCAAGTACAACTCCAGCAATCAGGGCCTGGCCTTGTCA
AGCCGAGTCAAACCTTGAGTTTGACGTGTGCCATCAGCGGTGACTCTGTC
AGTTCAAACTCCGCAGCTTGGAACTGGATTCGGCAGTCCCCCTCCAGGGG
CCTCGAATGGCTTGGACGGACGTACTACAGATCAAAATGGTACAACGACT
ACGCAGTCAGTGTAAAATCAAGGATTACGATAAACCCTGATACGAGTAAA
AACCAGTTCTCTCTCCAACTGAACAGCGTCACACCGGAAGATACAGCCGT
GTATTACTGTGCTCAGGAAGTGCAACCTGACGACGCATTTGACATCTGGG
GTCAGGGCACGATGATCACCGTGAGTAGTGGAGGAGGAGGCAGTGGGGG
AGGCGGTTCTGGCGGGGGTGGGTCTGATATACAGATGACACAGAGTCCCT
CCTCAGTTTCCGCCTCTGTTGGAGATAAGGTGACAATTACATGCAGGGCG
TCCCAAGATGTTTCTGGATGGCTCGCATGGTACCAACAGAAGCCAGGACT
CGCCCCTCAGCTCCTCATTAGCGGCGCTAGCACTCTCCAAGGGGGAGTAC
CGAGCAGGTTCTCTGGGTCCGGAAGTGGGACGGACTTTACCCTGACAATA
TCCTCCCTTCAGCCAGAAGACTTCGCAACCTACTATTGCCAACAGGCGAA
AAATTTCCCTTACACGTTCGGCCAAGGAACTAAACTTGAAATCAAGGCGG
CCGCAACTACCACCCCTGCCCCTCGGCCGCCGACTCCGGCCCCAACCATC
GCAAGCCAACCCCTCTCCTTGCGCCCCGAAGCTTGCCGCCCGGCCGCGGG
TGGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCAC

```
CCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGC
AGATTCCCTGAGGAGGAAGAGGGGGGATGCGAACTGCGCGTCAAGTTCTC
ACGGTCCGCCGACGCCCCCGCATATCAACAGGGCCAGAATCAGCTCTACA
ACGAGCTGAACCTGGGAAGGAGAGAGGAGTACGACGTGCTGGACAAGCG
ACGCGGACGCGACCCGGAGATGGGGGGGAAACCACGGCGGAAAAACCCT
CAGGAAGGACTGTACAACGAACTCCAGAAAGACAAGATGGCGGAAGCCT
ACTCAGAAATCGGGATGAAGGGAGAGCGGAGGAGGGGAAAGGGTCACG
ACGGGCTGTACCAGGGACTGAGCACCGCCACTAAGGATACCTACGATGCC
TTGCATATGCAAGCACTCCCACCCCGG

SEQ ID NO: 94 is the amino acid sequence of the CD22 CAR LTG2207 (LP-
scFv10-CD8TM-41BB-CD3zeta):
MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAQEVQPDDAFDIWGQGTMITVSSGGGGSGGGGSGGG
GSDIQMTQSPSSVSASVGDKVTITCRASQDVSGWLAWYQQKPGLAPQLLISG
ASTLQGGVPSRFSGSGSGTDFTLTISSLQPEDFATYYCQQAKNFPYTFGQGTK
LEIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGFIDGLYQ
GLSTATKDTYDALHMQALPPR SEQ ID NO: 95 is the amino acid sequence of the scFv10 (16P6) LCDR1:
QDVSGW SEQ ID NO: 96 is the amino acid sequence of the scFv10 (16P6) LCDR2:
GAS SEQ ID NO: 97 is the amino acid sequence of the scFv10 (16P6) LCDR3:
QQAKNFPYT SEQ ID NO: 98 is the amino acid sequence of the scFv10 (16P6) HCDR1:
GDSVSSNSAA SEQ ID NO: 99 is the amino acid sequence of the scFv10 (16P6) HCDR2:
TYYRSKWYN SEQ ID NO: 100 is the amino acid sequence of the scFv10 (16P6) HCDR3:
AQEVQPDDAFDI SEQ ID NO: 101 is the nucleic acid sequence of the CD22-specific binder (scFv11)
16P10:
CAGGTACAGCTGCAGCAGTCAGGTCCAGGACTGGTGAAGCCCTCGCAGAC
CCTCTCACTCACCTGTGCCATCTCCGGGGACAGTGTCTCTAGCAACAGTGC
TGCTTGGAACTGGATCAGGCAGTCCCCATCGAGAGGCCTTGGTGGCTGG
GAAGGACATACTACAGGTCCAAGTGGTATAATGATTATGCAGTATCTGTG
AAAAGTCGAATAACCATCAACCCAGACACATCCAAGAACCAGTTCTCCCT
GCAGCTGAACTCTGTGACTCCCGAGGACACGGCTGTGTATTACTGTGCCC
AAGAGGTAGAACCTCAGGATGCTTTTGATATCTGGGGCCAAGGGACAATG
GTCACCGTCTCTTCAGGAGGTGGCGGGTCTGGTGGTGGCGGTAGCGGTGG
TGGCGGATCCGACATCCAGATGACCCAGTCTCCATCTTCCGTGTCTGCATC
TGTAGGAGACAAAGTCACCATCACTTGTCGGGCGAGTCAGGATGTTAGCG
GCTGGTTAGCCTGGTATCAGCAGAAACCAGGGCTAGCCCCTCAGCTCCTG
ATCTTTGGTGCATCCACTCTGCAAGGTGAAGTCCCATCAAGGTTCAGTGGC
AGTGGATCTGGGACAGATTTTACTCTCACCATCAGCAGCCTGCAGCCTGA
AGATTTTGCCACTTATTATTGTCAACAGGCTAAATATTTCCCTTACACTTTT
GGCCCGGGGACCAAGCTGGAAATCAAA SEQ ID NO: 102 is the amino acid sequence of the CD22-specific binder (scFv11)
16P10:
QVQLQQSGPGLVKPSQTLSLTCAISGDSVSSNSAAWNWIRQSPSRGLEWLGR
TYYRSKWYNDYAVSVKSRITINPDTSKNQFSLQLNSVTPEDTAVYYCAQEVE
PQDAFDIWGQGTMVTVSSGGGGSGGGGSGGGGSDIQMTQSPSSVSASVGDK
VTITCRASQDVSGWLAWYQQKPGLAPQLLIFGASTLQGEVPSRFSGSGSGTDF
TLTISSLQPEDFATYYCQQAKYFPYTFGPGTKLEIK SEQ ID NO: 103 is the nucleic acid sequence of the CD22 CAR LTG2208 (LP-
scFv11-CD8TM-41BB-CD3zeta):
ATGCTTCTTTTGGTGACTTCCCTTTTGCTGTGCGAGTTGCCACACCCCGCCT
TCCTGCTTATTCCCCAAGTGCAGTTGCAACAGTCTGGACCAGGCCTCGTAA
AACCTTCTCAAACTTTGTCACTCACTTGTGCCATCTCAGGGGACAGTGTCA
GTTCCAACAGTGCGGCATGGAATTGGATTAGGCAATCCCCCTCTCGAGGT
CTGGAATGGCTTGGCGGACTTACTACCGAAGTAAGTGGTACAACGATTA
TGCAGTTTCTGTAAAATCACGAATCACTATAAATCCGGACACTTCTAAGA
ATCAGTTCTCTTTGCAGCTTAACTCTGTTACTCCTGAAGACACAGCCGTAT
ATTACTGTGCTCAAGAGGTAGAGCCGCAAGATGCCTTCGACATCTGGGGC
CAAGGGACTATGGTGACAGTAAGCTCCGGAGGTGGGGGATCAGGGGGAG
```

```
GTGGGTCCGGTGGTGGTGGCTCTGACATACAGATGACACAGTCCCCTAGC
TCTGTGTCAGCAAGTGTCGGTGACAAGGTTACGATAACGTGCAGGGCCAG
TCAAGATGTGTCAGGATGGTTGGCGTGGTACCAACAGAAACCCGGCTTGG
CACCGCAGCTTTTGATATTCGGCGCGTCCACACTCCAAGGCGAAGTGCCTT
CTCGGTTTTCTGGAAGCGGCAGCGGGACGGACTTTACTTTGACAATATCCT
CCCTCCAACCCGAGGATTTCGCGACGTATTATTGCCAGCAAGCAAAATAC
TTCCCATACACCTTCGGGCCTGGGACCAAACTGGAGATCAAAGCGGCCGC
AACTACCACCCCTGCCCCTCGGCCGCCGACTCCGGCCCCAACCATCGCAA
GCCAACCCCTCTCCTTGCGCCCCGAAGCTTGCCGCCCGGCCGCGGGTGGA
GCCGTGCATACCCGGGGGCTGGACTTTGCCTGCGATATCTACATTTGGGCC
CCGCTGGCCGGCACTTGCGGCGTGCTCCTGCTGTCGCTGGTCATCACCCTT
TACTGCAAGAGGGGCCGGAAGAAGCTGCTTTACATCTTCAAGCAGCCGTT
CATGCGGCCCGTGCAGACGACTCAGGAAGAGGACGGATGCTCGTGCAGA
TTCCCTGAGGAGGAAGAGGGGGATGCGAACTGCGCGTCAAGTTCTCACG
GTCCGCCGACGCCCCCGCATATCAACAGGGCCAGAATCAGCTCTACAACG
AGCTGAACCTGGGAAGGAGAGAGGAGTACGACGTGCTGGACAAGCGACG
CGGACGCGACCCGGAGATGGGGGGGAAACCACGGCGGAAAAACCCTCAG
GAAGGACTGTACAACGAACTCCAGAAAGACAAGATGGCGGAAGCCTACT
CAGAAATCGGGATGAAGGGAGAGCGGAGGAGGGGAAAGGGTCACGACG
GGCTGTACCAGGGACTGAGCACCGCCACTAAGGATACCTACGATGCCTTG
CATATGCAAGCACTCCCACCCCGG

SEQ ID NO: 104 is the amino acid sequence of the CD22 CAR LTG2208 (LP-
scFv11-CD8TM-41BB-CD3zeta):
MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAQEVEPQDAFDIWGQGTMVTVSSGGGGSGGGGSGGG
GSDIQMTQSPSSVSASVGDKVTITCRASQDVSGWLAWYQQKPGLAPQLLIFG
ASTLQGEVPSRFSGSGSGTDFTLTISSLQPEDFATYYCQQAKYFPYTFGPGTKL
EIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGFIDGLYQ
GLSTATKDTYDALHMQALPPR SEQ ID NO: 105 is the amino acid sequence of the scFv11 (16P10) LCDR1:
QDVSGW SEQ ID NO: 106 is the amino acid sequence of the scFv11 (16P10) LCDR2:
GAS SEQ ID NO: 107 is the amino acid sequence of the scFv11 (16P10) LCDR3:
QQAKYFPYT SEQ ID NO: 108 is the amino acid sequence of the scFv11 (16P10) HCDR1:
GDSVSSNSAA SEQ ID NO: 109 is the amino acid sequence of the scFv11 (16P10) HCDR2:
TYYRSKWYN SEQ ID NO: 110 is the amino acid sequence of the scFv11 (16P10) HCDR3:
AQEVEPQDAFDI SEQ ID NO: 111 is the nucleic acid sequence of the CD22-specific binder (scFv12)
16P17:
CAGGTACAGCTGCAGCAGTCAGGTCCAGGACTGGTGAAGCACTCGCAGAC
CCTCTCACTCACCTGTGCCATCTCCGGGGACAGTGTCTCTAGCAACAGTGC
TGCTTGGAACTGGATCAGGCAGTCCCCATCGAGAGGCCTTGAGTGGCTGG
GAAGGACATACTACAGGTCCAAGTGGTATAATGATTATGCAGTATCTGTG
AAAAGTCGAATAACCATCAACCCAGACACATCCAAGAACCAGTTCTCCCT
GCAGTTGAACTCTGTGACTCCCGAGGACACGGCTGTGTATTACTGTGCCC
AAGAGGTAGAACCTCATGATGCTTTTGATATCTGGGGCCAAGGGACAATG
GTCACCGTCTCTTCAGGAGGTGGCGGGTCTGGCGGTGGAGGTAGCGGTGG
TGGCGGATCCGACATCCAGATGACCCAGTCTCCATCTTCCGTGTATGCATC
TGTAGGAGACAAAGTCACCATCACTTGTCGGGCGAGTCAGGATGTTAGCG
GCTGGTTAGCCTGGTATCAGCAGAAACCAGGGCTAGCCCCTCAGCTCCTG
ATCTCTGGTGCATCCACTTTGCAAGGTGAAGTCCCATCAAGGTTCAGCGG
CAGTGGATCTGGGACAGATTTTACTCTCACCATCAGCAGCCTGCAGCCTG
AAGATTTTGCCACTTATTATTGTCAACAGGCTAAATATTTCCCTTACACTTT
TGGCCAGGGGACCAAGCTGGAAATCAAA SEQ ID NO: 112 is the amino acid sequence of the CD22-specific binder (scFv12)
16P17:
QVQLQQSGPGLVKHSQTLSLTCAISGDSVSSNSAAWNWIRQSPSRGLEWLGR
TYYRSKWYNDYAVSVKSRITINPDTSKNQFSLQLNSVTPEDTAVYYCAQEVE
PHDAFDIWGQGTMVTVSSGGGGSGGGGSGGGGSDIQMTQSPSSVYASVGDK
VTITCRASQDVSGWLAWYQQKPGLAPQLLISGASTLQGEVPSRFSGSGSGTDF
TLTISSLQPEDFATYYCQQAKYFPYTFGQGTKLEIK
```

SEQ ID NO: 113 is the nucleic acid sequence of the CD22 CAR LTG2209 (LP-scFv12-CD8TM-41BB-CD3zeta):
ATGCTTCTTTTGGTGACTTCCCTTTTGCTGTGCGAGTTGCCACACCCCGCCT
TCCTGCTTATTCCCCAGGTACAGCTTCAACAGAGTGGGCCGGGACTGGTG
AAACACTCCCAAACACTTTCTCTGACGTGCGCTATATCAGGTGACTCTGTT
TCATCTAATTCTGCTGCGTGGAACTGGATTCGACAATCTCCCAGTCGCGGG
TTGGAATGGCTGGGACGAACATATTATCGGTCTAAGTGGTATAACGATTA
TGCTGTATCTGTTAAATCTCGAATTACGATTAATCCTGACACCTCCAAGAA
CCAGTTCTCCCTCCAGTTGAACTCAGTCACACCGAAGACACTGCCGTCT
ACTATTGCGCTCAAGAAGTCGAGCCACATGATGCATTCGACATCTGGGGC
CAGGGAACGATGGTCACCGTCAGCAGTGGCGGCGGCGGATCTGGGGGTG
GCGGTTCTGGCGGTGGAGGATCAGACATACAAATGACGCAGAGTCCCTCA
AGTGTGTACGCGAGTGTGGGGGATAAGGTAACTATTACGTGCAGAGCGTC
ACAGGATGTTAGTGGATGGCTTGCCTGGTATCAGCAGAAGCCAGGCCTTG
CTCCACAGCTCCTTATCAGTGGTGCTTCTACACTTCAGGGCGAGGTTCCGA
GTAGATTCTCTGGTTCTGGATCTGGTACTGACTTCACTCTTACAATTTCTTC
TTTGCAACCAGAAGACTTTGCGACTTATTACTGCCAACAGGCCAAATACTT
CCCTTATACATTTGGCCAAGGTACCAAGTTGGAGATAAAGGCGGCCGCAA
CTACCACCCCTGCCCCTCGGCCGCCGACTCCGGCCCCAACCATCGCAAGC
CAACCCCTCTCCTTGCGCCCCGAAGCTTGCCGCCCGGCCGCGGGTGGAGC
CGTGCATACCCGGGGGCTGGACTTTGCCTGCGATATCTACATTTGGGCCCC
GCTGGCCGGCACTTGCGGCGTGCTCCTGCTGTCGCTGGTCATCACCCTTTA
CTGCAAGAGGGGCCGGAAGAAGCTGCTTTACATCTTCAAGCAGCCGTTCA
TGCGGCCCGTGCAGACGACTCAGGAAGAGGACGGATGCTCGTGCAGATTC
CCTGAGGAGGAAGAGGGGGATGCGAACTGCGCGTCAAGTTCTCACGGT
CCGCCGACGCCCCCGCATATCAACAGGGCCAGAATCAGCTCTACAACGAG
CTGAACCTGGGAAGGAGAGAGGAGTACGACGTGCTGGACAAGCGACGCG
GACGCGACCCGGAGATGGGGGGGAAACCACGGCGGAAAAACCCTCAGGA
AGGACTGTACAACGAACTCCAGAAAGACAAGATGGCGGAAGCCTACTCA
GAAATCGGGATGAAGGGAGAGCGGAGGAGGGGAAAGGGTCACGACGGG
CTGTACCAGGGACTGAGCACCGCCACTAAGGATACCTACGATGCCTTGCA
TATGCAAGCACTCCCACCCCGG SEQ ID NO: 114 is the amino acid sequence of the CD22 CAR LTG2209 (LP-scFv12-CD8TM-41BB-CD3zeta):
MLLLVTSLLLCELPHPAFLLIPQVQLQQSGPGLVKHSQTLSLTCAISGDSVSSN
SAAWNWIRQSPSRGLEWLGRTYYRSKWYNDYAVSVKSRITINPDTSKNQFSL
QLNSVTPEDTAVYYCAQEVEPHDAFDIWGQGTMVTVSSGGGGSGGGGSGGG
GSDIQMTQSPSSVYASVGDKVTITCRASQDVSGWLAWYQQKPGLAPQLLISG
ASTLQGEVPSRFSGSGSGTDFTLTISSLQPEDFATYYCQQAKYFPYTFGQGTKL
EIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGFIDGLYQ
GLSTATKDTYDALHMQALPPR SEQ ID NO: 115 is the amino acid sequence of the scFv12 (16P17) LCDR1:
QDVSGW SEQ ID NO: 116 is the amino acid sequence of the scFv12 (16P17) LCDR2:
GAS SEQ ID NO: 117 is the amino acid sequence of the scFv12 (16P17) LCDR3:
QQAKYFPYT SEQ ID NO: 118 is the amino acid sequence of the scFv12 (16P17) HCDR1:
GDSVSSNSAA SEQ ID NO: 119 is the amino acid sequence of the scFv12 (16P17) HCDR2:
TYYRSKWYN SEQ ID NO: 120 is the amino acid sequence of the scFv12 (16P17) HCDR3:
AQEVEPHDAFDI SEQ ID NO: 121 is the nucleic acid sequence of the CD22-specific binder (scFv13) 16P20v2:
CAAGTACAACTTCAACAGTCTGGGCCTGGGCTTGTAAAACCTAGCCAAAC
TCTGTCCCTCACGTGCGCGATTTCAGGGGACAGTGTAAGTTCCAACTCAGC
CGCATGGAACTGGATCAGGCAGTCACCTTCAAGGGGCTCGAATGGCTTG
GCCGAACGTACTACAGGAGTAAGTGGTACAACGATTATGCAGTGTCTGTG
AAATCACGGATTACTATCAATCCCGACACGTCCAAGAACCAGTTCTCTCT
GCAACTCAACTCAGTGACACCAGAGGATACGGCCGTTTACTATTGTGCAC
AGGAAGTGCAACCTGATGATGCCTTTGACATTTGGGGTCAGGGCACGATG
GTTACGGTAAGCTCTGGGGGAGGCGGCAGTGGAGGGGGAGGTAGTGGG
GAGGGGGATCTGATATACAGATGACACAAAGCCCGTCATCCGTCAGTGCT
TCAGTTGGTGATAAAGTAACCATTACGTGCCGCGCTTCCCAAGACGTTAG
CGGATGGTTGGCTTGGTATCAACAAAAACCGGGGTTGGCTCCGCAACTCC
TCATATCCGGTGCGAGTACGCTCCAAGGCGAAGTCCCTAGCAGATTTTCC
GGGAGCGGTTCCGGTACAGATTTCACGTTGACCATTAGCTCTCTCCAGCCC

```
GAAGATTTTGCAACCTACTATTGCCAACAGGCCAAAAATTTTCCATATAC
ATTTGGTCAAGGCACTAAGCTCGAAATCAAA
```

SEQ ID NO: 122 is the amino acid sequence of the CD22-specific binder (scFv13) 16P20v2:
```
QVQLQQSGPGLVKPSQTLSLTCAISGDSVSSNSAAWNWIRQSPSRGLEWLGR
TYYRSKWYNDYAVSVKSRITINPDTSKNQFSLQLNSVTPEDTAVYYCAQEVQ
PDDAFDIWGQGTMVTVSSGGGGSGGGGSGGGGSDIQMTQSPSSVSASVGDK
VTITCRASQDVSGWLAWYQQKPGLAPQLLISGASTLQGEVPSRFSGSGSGTDF
TLTISSLQPEDFATYYCQQAKNFPYTFGQGTKLEIK
```

SEQ ID NO: 123 is the nucleic acid sequence of the CD22 CAR LTG2210 (LP-scFv13-CD8TM-41BB-CD3zeta):
```
ATGCTTCTTTTGGTGACTTCCCTTTTGCTGTGCGAGTTGCCACACCCCGCCT
TCCTGCTTATTCCCCAAGTACAACTTCAACAGTCTGGGCCTGGGCTTGTAA
AACCTAGCCAAACTCTGTCCCTCACGTGCGCGATTTCAGGGGACAGTGTA
AGTTCCAACTCAGCCGCATGGAACTGGATCAGGCAGTCACCTTCAAGGGG
GCTCGAATGGCTTGGCCGAACGTACTACAGGAGTAAGTGGTACAACGATT
ATGCAGTGTCTGTGAAATCACGGATTACTATCAATCCCGACACGTCCAAG
AACCAGTTCTCTCTGCAACTCAACTCAGTGACACCAGAGGATACGGCCGT
TTACTATTGTGCACAGGAAGTGCAACCTGATGATGCCTTTGACATTTGGGG
TCAGGGCACGATGGTTACGGTAAGCTCTGGGGGAGGCGGCAGTGGAGGG
GGAGGTAGTGGGGGAGGGGGATCTGATATACAGATGACACAAAGCCCGT
CATCCGTCAGTGCTTCAGTTGGTGATAAAGTAACCATTACGTGCCGCGCTT
CCCAAGACGTTAGCGGATGGTTGGCTTGGTATCAACAAAAACCGGGGTTG
GCTCCGCAACTCCTCATATCCGGTGCGAGTACGCTCCAAGGCGAAGTCCC
TAGCAGATTTTCCGGGAGCGGTTCCGGTACAGATTTCACGTTGACCATTAG
CTCTCTCCAGCCCGAAGATTTTGCAACCTACTATTGCCAACAGGCCAAAA
ATTTTCCATATACATTTGGTCAAGGCACTAAGCTCGAAATCAAAGCGGCC
GCAACTACCACCCCTGCCCCTCGGCCGCCGACTCCGGCCCCAACCATCGC
AAGCCAACCCCTCTCCTTGCGCCCCGAAGCTTGCCGCCCGGCCGCGGGTG
GAGCCGTGCATACCCGGGGGCTGGACTTTGCCTGCGATATCTACATTTGG
GCCCCGCTGGCCGGCACTTGCGGCGTGCTCCTGCTGTCGCTGGTCATCACC
CTTTACTGCAAGAGGGGCCGGAAGAAGCTGCTTTACATCTTCAAGCAGCC
GTTCATGCGGCCCGTGCAGACGACTCAGGAAGAGGACGGATGCTCGTGCA
GATTCCCTGAGGAGGAAGAGGGGGATGCGAACTGCGCGTCAAGTTCTCA
CGGTCCGCCGACGCCCCCGCATATCAACAGGGCCAGAATCAGCTCTACAA
CGAGCTGAACCTGGGAAGGAGAGAGGAGTACGACGTGCTGGACAAGCGA
CGCGGACGCGACCCGGAGATGGGGGGGAAACCACGGCGGAAAAACCCTC
AGGAAGGACTGTACAACGAACTCCAGAAAGACAAGATGGCGGAAGCCTA
CTCAGAAATCGGGATGAAGGGAGAGCGGAGGAGGGGAAAGGGTCACGAC
GGGCTGTACCAGGGACTGAGCACCGCCACTAAGGATACCTACGATGCCTT
GCATATGCAAGCACTCCCACCCCGG
```

SEQ ID NO: 124 is the amino acid sequence of the CD22 CAR LTG2210 (LP-scFv13-CD8TM-41BB-CD3zeta):
```
MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAQEVQPDDAFDIWGQGTMVTVSSGGGGSGGGGSGG
GGSDIQMTQSPSSVSASVGDKVTITCRASQDVSGWLAWYQQKPGLAPQLLIS
GASTLQGEVPSRFSGSGSGTDFTLTISSLQPEDFATYYCQQAKNFPYTFGQGT
KLEIKAAATTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSC
RFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGL
YQGLSTATKDTYDALHMQALPPR
```

SEQ ID NO: 125 is the amino acid sequence of the scFv13 (16P20v2) LCDR1:
QDVSGW

SEQ ID NO: 126 is the amino acid sequence of the scFv13 (16P20v2) LCDR2:
GAS

SEQ ID NO: 127 is the amino acid sequence of the scFv13 (16P20v2) LCDR3:
QQAKNFPYT SEQ ID NO: 128 is the amino acid sequence of the scFv13 (16P20v2) HCDR1:
GDSVSSNSAA SEQ ID NO: 129 is the amino acid sequence of the scFv13 (16P20v2) HCDR2:
TYYRSKWYN SEQ ID NO: 130 is the amino acid sequence of the scFv13 (16P20v2) HCDR3:
AQEVQPDDAFDI SEQ ID NO: 131 is the nucleic acid sequence of the CD22-specific binder (scFv14) 16P1:
```
CAGGTACAGCTGCAGCAGTCAGGTCCAGGACTGGTGAAGCCCTCGCAGAC
CCTCTCACTCACCTGTGACATCTCCGGGGACAGTGTCTCTAGCAACAGTGC
```

```
TGCTTGGAACTGGATCAGGCAGTCCCCATCGAGAGGCCTTGAGTGGCTGG
GAAGGACATACTACAGGTCCAAGTGGTATAATGATTATGCAGTATCTGTG
AAAAGTCGAATAACCATCAACCCAGACACATCCAAGAACCAGTTCTCCCT
GCAGCTGAACTCTGTGACTCCCGAGGACACGGCTGTGTATTACTGTGCCC
AAGAGATAGAACCTCATGATGCTTTTGATATCTGGGACCAAGGGACAATG
GTCACCGTCTCTTCAGGAGGTGGCGGGTCTGGCGGTGGAGGTAGCGGTGG
TGGCGGATCCGTCATCCAGATGACCCAGTCTCCATCTTCCGTGTCTGCATC
TGTAGGAGACAAAGTCACCATCACTTGTCGGGCGAGTCAGGATGTTAGCG
GCTGGTTAGCCTGGTATCAGCAGAAACCAGGGCTAGCCCCTCAGCTCCTG
ATCTCTGGTGCATCCTCTTTGCAAGGTGGAGTCCCATCAAGGTTCAGCGGC
AGTGGATCTGGGACAGATTTTACTCTCACCATCAGCAGCCTGCAGCCTGA
AGATTTTGCCACTTATTATTGTCAACAGGCTAAATATTTCCCTTACACTTTT
GGCCAGGGGACCAAGCTGGAAATCAAA
```

SEQ ID NO: 132 is the amino acid sequence of the CD22-specific binder (scFv14) 16P1:
QVQLQQSGPGLVKPSQTLSLTCDISGDSVSSNSAAWNWIRQSPSRGLEWLGR
TYYRSKWYNDYAVSVKSRITINPDTSKNQFSLQLNSVTPEDTAVYYCAQEIEP
FIDAFDIWDQGTMVTVSSGGGGSGGGGSGGGGSVIQMTQSPSSVSASVGDKV
TITCRASQDVSGWLAWYQQKPGLAPQLLISGASSLQGGVPSRFSGSGSTDFT
LTISSLQPEDFATYYCQQAKYFPYTFGQGTKLEIK SEQ ID NO: 133 is the nucleic acid sequence of the CD22 CAR LTG2216 (LP-scFv14-CD8TM-41BB-CD3zeta):
```
ATGTTGCTGCTCGTGACCTCGCTCCTTCTGTGCGAGCTGCCCCATCCGGCT
TTTCTGCTCATCCCTCAAGTGCAGCTGCAGCAGTCCGGTCCTGGACTGGTC
AAGCCGTCCCAGACTCTGAGCCTGACTTGCGATATTAGCGGGGACTCAGT
CTCGTCCAATTCGGCGGCCTGGAACTGGATCCGGCAGTCACCATCAAGGG
GCCTGGAATGGCTCGGGCGCACTTACTACCGGTCCAAATGGTATAACGAC
TACGCCGTGTCCGTGAAGTCCCGGATCACCATTAACCCCGACACCTCGAA
GAACCAGTTCTCACTCCAACTGAACAGCGTGACCCCCGAGGATACCGCGG
TGTACTACTGCGCACAAGAAATCGAACCGCACGACGCCTTCGACATTTGG
GACCAGGGAACGATGGTCACAGTGTCGTCCGGTGGAGGAGGTTCCGGAG
GCGGTGGATCTGGAGGCGGAGGTTCGGTGATCCAGATGACCCAGAGCCCC
TCCTCGGTGTCCGCATCCGTGGGCGATAAGGTCACCATTACCTGTAGAGC
GTCCCAGGACGTGTCCGGATGGCTGGCCTGGTACCAGCAGAAGCCAGGCT
TGGCTCCTCAACTGCTGATCTCCGGCGCCAGCTCACTTCAGGGGGGGGTG
CCATCACGCTTCTCCGGATCCGGTTCCGGCACCGACTTCACCCTGACCATC
AGCAGCCTCCAGCCTGAGGACTTCGCCACTTACTACTGCCAACAGGCCAA
GTACTTCCCCTATACCTTCGGACAAGGCACTAAGCTGGAAATCAAGGCGG
CCGCAACTACCACCCCTGCCCCTCGGCCGCCGACTCCGGCCCCAACCATC
GCAAGCCAACCCCTCTCCTTGCGCCCCGAAGCTTGCCGCCCGGCCGCGGG
TGGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGC
AGATTCCCTGAGGAGGAAGAGGGGGGATGCGAACTGCGCGTCAAGTTCTC
ACGGTCCGCCGACGCCCCCGCATATCAACAGGGCCAGAATCAGCTCTACA
ACGAGCTGAACCTGGGAAGGAGAGAGGAGTACGACGTGCTGGACAAGCG
ACGCGGACGCGACCCGGAGATGGGGGGGAAACCACGGCGGAAAAACCCT
CAGGAAGGACTGTACAACGAACTCCAGAAAGACAAGATGGCGGAAGCCT
ACTCAGAAATCGGGATGAAGGGAGAGCGGAGGAGGGGAAAGGGTCACG
ACGGGCTGTACCAGGGACTGAGCACCGCCACTAAGGATACCTACGATGCC
TTGCATATGCAAGCACTCCCACCCCGG
```

SEQ ID NO: 134 is the amino acid sequence of the CD22 CAR LTG2216 (LP-scFv14-CD8TM-41BB-CD3zeta):
MLLLVTSLLLCELPHPAFLLIPQVQLQQSGPGLVKPSQTLSLTCDISGDSVSSN
SAAWNWIRQSPSRGLEWLGRTYYRSKWYNDYAVSVKSRITINPDTSKNQFSL
QLNSVTPEDTAVYYCAQEIEPHDAFDIWDQGTMVTVSSGGGGSGGGGSGGG
GSVIQMTQSPSSVSASVGDKVTITCRASQDVSGWLAWYQQKPGLAPQLLISG
ASSLQGGVPSRFSGSGSTDFTLTISSLQPEDFATYYCQQAKYFPYTFGQGTK
LEIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGFIDGLYQ
GLSTATKDTYDALHMQALPPR SEQ ID NO: 135 is the amino acid sequence of the scFv14 (16P1) LCDR1:
QDVSGW SEQ ID NO: 136 is the amino acid sequence of the scFv14 (16P1) LCDR2:
GAS SEQ ID NO: 137 is the amino acid sequence of the scFv14 (16P1) LCDR3:
QQAKYFPYT SEQ ID NO: 138 is the amino acid sequence of the scFv14 (16P1) HCDR1:
GDSVSSNSAA SEQ ID NO: 139 is the amino acid sequence of the scFv14 (16P1) HCDR2:
TYYRSKWYN SEQ ID NO: 140 is the amino acid sequence of the scFv14 (16P1) HCDR3:
AQEIEPHDAFDI SEQ ID NO: 141 is the nucleic acid sequence of the CD22-specific binder (scFv15) 16P3v3:
CAAGTGCAGCTGCAGCAGTCCGGTCCTGGACTGGTCAAGCACTCCCAGAC
TCTGAGCCTGGCCTGCGCGATTAGCGGGGACTCAGTCTCGTCCAATTCGG
CGGCCTGGAACTGGATCCGGCAGTCACCATCAAGGGGCCTGGAATGGCTC
GGGCGCACTTACTACCGGTCCAAATGGTATAACGACTACGCCGTGTCCGT
GAAGTCCCGGATCACCATTAACCCCGACACCTCGAAGAACCAGTTCTCAC
TCCAACTGAACAGCGTGACCCCCGAGGATACCGCGGTGTACTACTGCGCA
CAAGAAGTGCAGCCGCAGGACGCCCTGGACATTTGGGGGCAGGGAACGA
TGGTCACAGTGTCGTCCGGTGGAGGAGGTTCCGGAGGCGGTGGATCTGGA
GGCGGAGGTTCGGATATCCAGATGACCCAGAGCCCCTCCTTCGTGTCCGC
ATCCGTGGGCGATAAGGTCATTATTACCTGTAGAGCGTCCCAGGACGTGT
CCGGATGGCTGGCCTGGTACCAGCAGAAGCCAGGCTTGGCTCCTCAACTG
CTGATCTCCGGCGCCAGCACTCTTCAGGGGGAAGTGCCATCACGCTTCTCC
GGATCCGGTTCCGGCACCGACTTCACCCTGACCATCAGCAGCCTCCAGCC
TGAGGACTTCGCCACTTACTACTGCCAACAGGCCAAGTACTTCCCCTATAC
CTTCGGACAAGGCACTAAGCTGGAAATCAAG SEQ ID NO: 142 is the amino acid sequence of the CD22-specific binder (scFv15) 16P3v2:
QVQLQQSGPGLVKHSQTLSLACAISGDSVSSNSAAWNWIRQSPSRGLEWLGR
TYYRSKWYNDYAVSVKSRITINPDTSKNQFSLQLNSVTPEDTAVYYCAQEVQ
PQDALDIWGQGTMVTVSSGGGGSGGGGSGGGGSDIQMTQSPSFVSASVGDK
VIITCRASQDVSGWLAWYQQKPGLAPQLLISGASTLQGEVPSRFSGSGSGTDF
TLTISSLQPEDFATYYCQQAKYFPYTFGQGTKLEIK SEQ ID NO: 143 is the nucleic acid sequence of the CD22 CAR LTG2217 (LP-scFv15-CD8TM-41BB-CD3zeta):
ATGTTGCTGCTCGTGACCTCGCTCCTTCTGTGCGAGCTGCCCCATCCGGCT
TTTCTGCTCATCCCTCAAGTGCAGCTGCAGCAGTCCGGTCCTGGACTGGTC
AAGCACTCCCAGACTCTGAGCCTGGCCTGCGCGATTAGCGGGGACTCAGT
CTCGTCCAATTCGGCGGCCTGGAACTGGATCCGGCAGTCACCATCAAGGG
GCCTGGAATGGCTCGGGCGCACTTACTACCGGTCCAAATGGTATAACGAC
TACGCCGTGTCCGTGAAGTCCCGGATCACCATTAACCCCGACACCTCGAA
GAACCAGTTCTCACTCCAACTGAACAGCGTGACCCCCGAGGATACCGCGG
TGTACTACTGCGCACAAGAAGTGCAGCCGCAGGACGCCCTGGACATTTGG
GGGCAGGGAACGATGGTCACAGTGTCGTCCGGTGGAGGAGGTTCCGGAG
GCGGTGGATCTGGAGGCGGAGGTTCGGATATCCAGATGACCCAGAGCCCC
TCCTTCGTGTCCGCATCCGTGGGCGATAAGGTCATTATTACCTGTAGAGCG
TCCCAGGACGTGTCCGGATGGCTGGCCTGGTACCAGCAGAAGCCAGGCTT
GGCTCCTCAACTGCTGATCTCCGGCGCCAGCACTCTTCAGGGGGAAGTGC
CATCACGCTTCTCCGGATCCGGTTCCGGCACCGACTTCACCCTGACCATCA
GCAGCCTCCAGCCTGAGGACTTCGCCACTTACTACTGCCAACAGGCCAAG
TACTTCCCCTATACCTTCGGACAAGGCACTAAGCTGGAAATCAAGGCGGC
CGCAACTACCACCCCTGCCCCTCGGCCGCCGACTCCGGCCCCAACCATCG
CAAGCCAACCCCTCTCCTTGCGCCCCGAAGCTTGCCGCCCGGCCGCGGGT
GGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGC
AGATTCCCTGAGGAGGAAGAGGGGGGATGCGAACTGCGCGTCAAGTTCTC
ACGGTCCGCCGACGCCCCCGCATATCAACAGGGCCAGAATCAGCTCTACA
ACGAGCTGAACCTGGGAAGGAGAGAGGAGTACGACGTGCTGGACAAGCG
ACGCGGACGCGACCCGGAGATGGGGGGGAAACCACGGCGGAAAAACCCT
CAGGAAGGACTGTACAACGAACTCCAGAAAGACAAGATGGCGGAAGCCT
ACTCAGAAATCGGGATGAAGGGAGAGCGGAGGAGGGGAAAGGGTCACG
ACGGGCTGTACCAGGGACTGAGCACCGCCACTAAGGATACCTACGATGCC
TTGCATATGCAAGCACTCCCACCCCGG SEQ ID NO: 144 is the amino acid sequence of the CD22 CAR LTG2217 (LP-scFv15-CD8TM-41BB-CD3zeta):
MLLLVTSLLLCELPHPAFLLIPQVQLQQSGPGLVKHSQTLSLACAISGDSVSSN
SAAWNWIRQSPSRGLEWLGRTYYRSKWYNDYAVSVKSRITINPDTSKNQFSL
QLNSVTPEDTAVYYCAQEVQPQDALDIWGQGTMVTVSSGGGGSGGGGSGG
GGSDIQMTQSPSFVSASVGDKVIITCRASQDVSGWLAWYQQKPGLAPQLLISG
ASTLQGEVPSRFSGSGSGTDFTLTISSLQPEDFATYYCQQAKYFPYTFGQGTKL
EIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGFIDGLYQ
GLSTATKDTYDALHMQALPPR SEQ ID NO: 145 is the amino acid sequence of the scFv15 (16P3v2) LCDR1:
QDVSGW SEQ ID NO: 146 is the amino acid sequence of the scFv15 (16P3v2) LCDR2:
GAS SEQ ID NO: 147 is the amino acid sequence of the scFv15 (16P3v2) LCDR3:
QQAKYFPYT SEQ ID NO: 148 is the amino acid sequence of the scFv15 (16P3v2) HCDR1:
GDSVSSNSAA SEQ ID NO: 149 is the amino acid sequence of the scFv15 (16P3v2) HCDR2:
TYYRSKWYN SEQ ID NO: 150 is the amino acid sequence of the scFv15 (16P3v2) HCDR3:
AQEVQPQDALDI SEQ ID NO: 151 is the nucleic acid sequence of the CD22-specific binder (scFv16)
16P8:
CAGGTACAGCTGCAGCAGTCAGGTCCAGGACTGGTGAAGCCCTCGCAGAC
CCTCTCACTCACCTGTGCCATCTCCGGGGACAGTGTCTCTAGCAACAGTGC
TGCTTGGAACTGGATCAGGCAGTCCCCATCGAGAGGCCTTGAGTGGCTGG
GAAGGACATACTACAGGTCCAAGTGGTATACTGATTATGCAGTATCTGTG
AAAAATCGAATAACCATCAACCCAGACACATCCAAGAATCAGTTCTCCCT
GCAGCTGAACTCTGTGACTCCCGAGGACACGGCTGTGTATTACTGTGCCC
AAGAGGTAGAACCTCAGGATGCTTTTGATATCTGGGGCCAAGGGACAATG
GTCACCGTCTCTTCAGGAGGTGGCGGGTCTGGCGGTGGAGGTAGCGGTGG
TGGCGGATCCGACATCCAGATGACCCAGTCTCCATCTTCCGTGTCTGCATC
TGTAGGAGACAAAGTCACCATCACTTGTCGGGCGAGTCAGGATGTTAGCG
GCTGGTTAGCCTGGTATCAGCAGAAACCAGGGCTAGCCCCTCAGCTCCTG
ATCTTTGGTGCATCCACTTTGCAAGGTGAAGTCCCATCAAGGTTCAGCGGC
AGTGGATCTGGGACAGATTTTACTCTCACCATCAGTAGCCTGCAGCCTGA
AGATTTTGCCACTTATTATTGTCAACAGGCTAAATATTTCCCTTACACTTTT
GGCCGGGGGACCAAGCTGGAAATCAAA SEQ ID NO: 152 is the amino acid sequence of the CD22-specific binder (scFv16)
16P8:
QVQLQQSGPGLVKPSQTLSLTCAISGDSVSSNSAAWNWIRQSPSRGLEWLGR
TYYRSKWYTDYAVSVKNRITINPDTSKNQFSLQLNSVTPEDTAVYYCAQEVE
PQDAFDIWGQGTMVTVSSGGGGSGGGGSGGGGSDIQMTQSPSSVSASVGDK
VTITCRASQDVSGWLAWYQQKPGLAPQLLIFGASTLQGEVPSRFSGSGSGTDF
TLTISSLQPEDFATYYCQQAKYFPYTFGRGTKLEIK SEQ ID NO: 153 is the nucleic acid sequence of the CD22 CAR LTG2218 (LP-
scFv16-CD8TM-41BB-CD3zeta):
ATGTTGCTGCTCGTGACCTCGCTCCTTCTGTGCGAGCTGCCCCATCCGGCT
TTTCTGCTCATCCCTCAAGTGCAGCTGCAGCAGTCCGGTCCTGGACTGGTC
AAGCCGTCCCAGACTCTGAGCCTGACTTGCGCAATTAGCGGGGACTCAGT
CTCGTCCAATTCGGCGGCCTGGAACTGGATCCGGCAGTCACCATCAAGGG
GCCTGGAATGGCTCGGGCGCACTTACTACCGGTCCAAATGGTATACCGAC
TACGCCGTGTCCGTGAAGAATCGGATCACCATTAACCCCGACACCTCGAA
GAACCAGTTCTCACTCCAACTGAACAGCGTGACCCCCGAGGATACCGCGG
TGTACTACTGCGCACAAGAAGTGGAACCGCAGGACGCCTTCGACATTTGG
GGACAGGGAACGATGGTCACAGTGTCGTCCGGTGGAGGAGGTTCCGGAG
GCGGTGGATCTGGAGGCGGAGGTTCGGATATCCAGATGACCCAGAGCCCC
TCCTCGGTGTCCGCATCCGTGGGCGATAAGGTCACCATTACCTGTAGAGC
GTCCCAGGACGTGTCCGGATGGCTGGCCTGGTACCAGCAGAAGCCAGGCT
TGGCTCCTCAACTGCTGATCTTCGGCGCCAGCACTCTTCAGGGGGAAGTG
CCATCACGCTTCTCCGGATCCGGTTCCGGCACCGACTTCACCCTGACCATC
AGCAGCCTCCAGCTGAGGACTTCGCCACTTACTACTGCCAACAGGCCAA
GTACTTCCCCTATACCTTCGGAAGAGGCACTAAGCTGGAAATCAAGGCGG
CCGCAACTACCACCCCTGCCCCTCGGCCGCCGACTCCGGCCCCAACCATC
GCAAGCCAACCCCTCTCCTTGCGCCCCGAAGCTTGCCGCCCGGCCGCGGG
TGGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGC
AGATTCCCTGAGGAGGAAGAGGGGGGATGCGAACTGCGCGTCAAGTTCTC
ACGGTCCGCCGACGCCCCCGCATATCAACAGGGCCAGAATCAGCTCTACA
ACGAGCTGAACCTGGGAAGGAGAGAGGAGTACGACGTGCTGGACAAGCG
ACGCGGACGCGACCCGGAGATGGGGGGGAAACCACGGCGGAAAAACCCT
CAGGAAGGACTGTACAACGAACTCCAGAAAGACAAGATGGCGGAAGCCT
ACTCAGAAATCGGGATGAAGGGAGAGCGGAGGAGGGGAAAGGGTCACG
ACGGGCTGTACCAGGGACTGAGCACCGCCACTAAGGATACCTACGATGCC
TTGCATATGCAAGCACTCCCACCCCGG SEQ ID NO: 154 is the amino acid sequence of the CD22 CAR LTG2218 (LP-scFv16-CD8TM-41BB-CD3zeta):
MLLLVTSLLLCELPHPAFLLIPQVQLQQSGPGLVKPSQTLSLTCAISGDSVSSN
SAAWNWIRQSPSRGLEWLGRTYYRSKWYTDYAVSVKNRITINPDTSKNQFSL
QLNSVTPEDTAVYYCAQEVEPQDAFDIWGQGTMVTVSSGGGGSGGGGSGGG
GSDIQMTQSPSSVSASVGDKVTITCRASQDVSGWLAWYQQKPGLAPQLLIFG
ASTLQGEVPSRFSGSGSGTDFTLTISSLQPEDFATYYCQQAKYFPYTFGRGTKL
EIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGFIDGLYQ
GLSTATKDTYDALHMQALPPR SEQ ID NO: 155 is the amino acid sequence of the scFv16 (16P8) LCDR1:
QDVSGW SEQ ID NO: 156 is the amino acid sequence of the scFv16 (16P8) LCDR2:
GAS SEQ ID NO: 157 is the amino acid sequence of the scFv16 (16P8) LCDR3:
QQAKYFPYT SEQ ID NO: 158 is the amino acid sequence of the scFv16 (16P8) HCDR1:
GDSVSSNSAA SEQ ID NO: 159 is the amino acid sequence of the scFv16 (16P8) HCDR2:
TYYRSKWYT SEQ ID NO: 160 is the amino acid sequence of the scFv16 (16P8) HCDR3:
AQEVEPQDAFDI SEQ ID NO: 161 is the nucleic acid sequence of the CD22-specific binder (scFv17) 16P13:
CAGGTACAGCTGCAGCAGTCAGGTCCAGGACTGGTGAAGCCCTCGCAGAC
CCTCTCACTCACCTGTGCCATCTCAGGGAACAGTGTCTCTAGCAACAGTGC
TGCTTGGAACTGGATCAGGCAGTCCCCATCGAGAGGCCTTGAGTGGCTGG
GAAGGACATACTACAGGTCCAAGTGGTATAATGATTATGCAGTATCTGTG
AAAAGTCGAATAACCATCAACCCAGACACATCCAAGAACCAGTTCTCCCT
GCAGCTGAACTCTGTGACTCCCGAGGACACGGCTGTGTATTACTGTGCCC
AAGAGGTAGAACCTCAAGATGCTTTTGATATCTGGGGCCAAGGGACAATG
GTCACCGTCTCTTCAGGAGGTGGCGGGTCTGGCGGTGGAGGTAGCGGTGG
TGGCGGATCCGACATCCAGATGACCCAGTCTCCATCTTCCGTGTCTGCATC
TGTAGGAGACAAAGTCACCATCACTTGTCGGGCGAGTCAGGATGTTAGCG
GCTGGTTAGCCTGGTATCAGCAGAAACCAGGGCTAGCCCCTCAGCTCCTG
ATCTTTGGTGCATCCACTTTGCAAGGTGAAGTCCCATCAAGATTCAGCGGC
GGTGGATCTGGGACAGATTTTACTCTCACCATCAGCAGCCTGCAGCCTGA
AGATTTTGCCACTTATTATTGTCAACAGGCTAAATATTTCCCTTACACTTTT
GGCCAGGGGACCAAGCTGGAAATCAAA SEQ ID NO: 162 is the amino acid sequence of the CD22-specific binder (scFv17) 16P13:
QVQLQQSGPGLVKPSQTLSLTCAISGNSVSSNSAAWNWIRQSPSRGLEWLGR
TYYRSKWYNDYAVSVKSRITINPDTSKNQFSLQLNSVTPEDTAVYYCAQEVE
PQDAFDIWGQGTMVTVSSGGGGSGGGGSGGGGSDIQMTQSPSSVSASVGDK
VTITCRASQDVSGWLAWYQQKPGLAPQLLIFGASTLQGEVPSRFSGGGSGTD
FTLTISSLQPEDFATYYCQQAKYFPYTFGQGTKLEIK SEQ ID NO: 163 is the nucleic acid sequence of the CD22 CAR LTG2219 (LP-scFv17-CD8TM-41BB-CD3zeta):
ATGTTGCTGCTCGTGACCTCGCTCCTTCTGTGCGAGCTGCCCCATCCGGCT
TTTCTGCTCATCCCTCAAGTGCAGCTGCAGCAGTCCGGTCCTGGACTGGTC
AAGCCGTCCCAGACTCTGAGCCTGACTTGCGCCATTAGCGGGAACTCAGT
CTCGTCCAATTCGGCGGCCTGGAACTGGATCCGGCAGTCACCATCAAGGG
GCCTGGAATGGCTCGGGCGCACTTACTACCGGTCCAAATGGTATAACGAC
TACGCCGTGTCCGTGAAGTCCCGGATCACCATTAACCCCGACACCTCGAA
GAACCAGTTCTCACTCCAACTGAACAGCGTGACCCCCGAGGATACCGCGG
TGTACTACTGCGCACAAGAAGTGGAACCGCAGGACGCCTTCGACATTTGG
GGACAGGGAACGATGGTCACAGTGTCGTCCGGTGAGGAGGTTCCGGAG
GCGGTGGATCTGGAGGCGGAGGTTCGGATATCCAGATGACCCAGAGCCCC
TCCTCGGTGTCCGCATCCGTGGGCGATAAGGTCACCATTACCTGTAGAGC
GTCCCAGGACGTGTCCGGATGGCTGGCCTGGTACCAGCAGAAGCCAGGCT
TGGCTCCTCAACTGCTGATCTTTGGCGCCAGCACTCTTCAGGGGAGGTGC
CATCACGCTTCTCCGGAGGTGGTTCCGGCACCGACTTCACCCTGACCATCA
GCAGCCTCCAGCCTGAGGACTTCGCCACTTACTACTGCCAACAGGCCAAG
TACTTCCCCTATACCTTCGGACAAGGCACTAAGCTGGAAATCAAGGCGGC
CGCAACTACCACCCCTGCCCCTCGGCCGCCGACTCCGGCCCCAACCATCG
CAAGCCAACCCCTCTCCTTGCGCCCCGAAGCTTGCCGCCCGGCCGCGGGT
GGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCAC

```
CCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGC
AGATTCCCTGAGGAGGAAGAGGGGGGATGCGAACTGCGCGTCAAGTTCTC
ACGGTCCGCCGACGCCCCCGCATATCAACAGGGCCAGAATCAGCTCTACA
ACGAGCTGAACCTGGGAAGGAGAGAGGAGTACGACGTGCTGGACAAGCG
ACGCGGACGCGACCCGGAGATGGGGGGGAAACCACGGCGGAAAAACCCT
CAGGAAGGACTGTACAACGAACTCCAGAAAGACAAGATGGCGGAAGCCT
ACTCAGAAATCGGGATGAAGGGAGAGCGGAGGAGGGGAAAGGGTCACG
ACGGGCTGTACCAGGGACTGAGCACCGCCACTAAGGATACCTACGATGCC
TTGCATATGCAAGCACTCCCACCCCGG

SEQ ID NO: 164 is the amino acid sequence of the CD22 CAR LTG2219 (LP-
scFv17-CD8TM-41BB-CD3zeta):
MLLLVTSLLLCELPHPAFLLIPQVQLQQSGPGLVKPSQTLSLTCAISGNSVSSN
SAAWNWIRQSPSRGLEWLGRTYYRSKWYNDYAVSVKSRITINPDTSKNQFSL
QLNSVTPEDTAVYYCAQEVEPQDAFDIWGQGTMVTVSSGGGGSGGGGSGGG
GSDIQMTQSPSSVSASVGDKVTITCRASQDVSGWLAWYQQKPGLAPQLLIFG
ASTLQGEVPSRFSGGGSGTDFTLTISSLQPEDFATYYCQQAKYFPYTFGQGTK
LEIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGFIDGLYQ
GLSTATKDTYDALHMQALPPR SEQ ID NO: 165 is the amino acid sequence of the scFv17 (16P13) LCDR1:
QDVSGW SEQ ID NO: 166 is the amino acid sequence of the scFv17 (16P13) LCDR2:
GAS SEQ ID NO: 167 is the amino acid sequence of the scFv17 (16P13) LCDR3:
QQAKYFPYT SEQ ID NO: 168 is the amino acid sequence of the scFv17 (16P13) HCDR1:
GNSVSSNSAA SEQ ID NO: 169 is the amino acid sequence of the scFv17 (16P13) HCDR2:
TYYRSKWYN SEQ ID NO: 170 is the amino acid sequence of the scFv17 (16P13) HCDR3:
AQEVEPQDAFDI SEQ ID NO: 171 is the nucleic acid sequence of the CD22-specific binder (scFv18)
16P15:
CAGGTACAGCTGCAGCAGTCAGGTCCAGGACTGGTGAAGCCCTCGCAGAC
CCTCTCACTCACCTGTGCCATCTCCGGGGACAGTGTCTCTAGCAACAGTGC
TGCTTGGAACTGGATCAGGCAGTCCCCATCGAGAGGCCTTGGTGGCTGG
GAAGGACATACTACAGGTCCAAGTGGTATAATGATTATGCAGTATCTGTG
AAAAGTCGAATAACCATCAACCCAGACACATCCAAGAACCAGTTCTCCCT
GCAGCTGAACTCTGTGACTCCCGAGGACACGGCTGTGTATTACTGTGCCC
AAGAGGTAGAACCTCATGATGCTCTTGATATCTGGGGCCAAGGGACAATG
GTCACCGTCTCTTCAGGAGGTGGCGGGTCTGGCGGTGGAGGTAGCGGTGG
TGGCGGATCCGACATCCAGATGACGCAGTCTCCATCATCCGTGTCTGCATC
TGTAGGAGACAAAGTCACCATCACTTGTCGGGCGAGTCAGGATGTTAGCG
GCTGGTTAGCCTGGTATCAACAGAAACCAGGGCTAGCCCCTCAGCTCCTG
ATCTTTGGTGCATCCACTTTGCAAGGTGAAGTCCCATCAAGGTTCAGCGGC
AGTGGATCTGGGACAGATTTTACTCTCACCATCAGCAGCCTGCAGCCTGA
AGATTTTGCCACTTATTATTGTCAACAGGCTAAATATTTCCCTTACACTTTT
GGCCAGGGGACCAAGCTGGAGATCAAA SEQ ID NO: 172 is the amino acid sequence of the CD22-specific binder (scFv18)
16P15:
QVQLQQSGPGLVKPSQTLSLTCAISGDSVSSNSAAWNWIRQSPSRGLEWLGR
TYYRSKWYNDYAVSVKSRITINPDTSKNQFSLQLNSVTPEDTAVYYCAQEVE
PHDALDIWGQGTMVTVSSGGGGSGGGGSGGGGSDIQMTQSPSSVSASVGDK
VTITCRASQDVSGWLAWYQQKPGLAPQLLIFGASTLQGEVPSRFSGSGSGTDF
TLTISSLQPEDFATYYCQQAKYFPYTFGQGTKLEIK SEQ ID NO: 173 is the nucleic acid sequence of the CD22 CAR LTG2220 (LP-
scFv18-CD8TM-41BB-CD3zeta):
ATGTTGCTGCTCGTGACCTCGCTCCTTCTGTGCGAGCTGCCCCATCCGGCT
TTTCTGCTCATCCCTCAAGTGCAGCTGCAGCAGTCCGGTCCTGGACTGGTC
AAGCCGTCCCAGACTCTGAGCCTGACTTGCGCGATTAGCGGGGACTCAGT
CTCGTCCAATTCGGCGGCTGGAACTGGATCCGGCAGTCACCATCAAGGG
GCCTGGAATGGCTCGGGCGCACTTACTACCGGTCCAAATGGTATAACGAC
TACGCCGTGTCCGTGAAGTCCCGGATCACCATTAACCCCGACACCTCGAA
GAACCAGTTCTCACTCCAACTGAACAGCGTGACCCCCGAGGATACCGCGG
TGTACTACTGCGCACAAGAAGTGGAACCGCACGACGCCCTGGACATTTGG
GGTCAGGGAACGATGGTCACAGTGTCGTCCGGTGGAGGAGGTTCCGGAG
```

```
GCGGTGGATCTGGAGGCGGAGGTTCGGATATCCAGATGACCCAGAGCCCC
TCCTCGGTGTCCGCATCCGTGGGCGATAAGGTCACCATTACCTGTAGAGC
GTCCCAGGACGTGTCCGGATGGCTGGCCTGGTACCAGCAGAAGCCAGGCT
TGGCTCCTCAACTGCTGATCTTCGGCGCCAGCACACTTCAGGGGGAGGTG
CCATCACGCTTCTCCGGATCCGGTTCCGGCACCGACTTCACCCTGACCATC
AGCAGCCTCCAGCCTGAGGACTTCGCCACTTACTACTGCCAACAGGCCAA
GTACTTCCCCTATACCTTCGGACAAGGCACTAAGCTGGAAATCAAGGCGG
CCGCAACTACCACCCCTGCCCCTCGGCCGCCGACTCCGGCCCCAACCATC
GCAAGCCAACCCCTCTCCTTGCGCCCCGAAGCTTGCCGCCCGGCCGCGGG
TGGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGC
AGATTCCCTGAGGAGGAAGAGGGGGGATGCGAACTGCGCGTCAAGTTCTC
ACGGTCCGCCGACGCCCCCGCATATCAACAGGGCCAGAATCAGCTCTACA
ACGAGCTGAACCTGGGAAGGAGAGAGGAGTACGACGTGCTGGACAAGCG
ACGCGGACGCGACCCGGAGATGGGGGGGAAACCACGGCGGAAAAACCCT
CAGGAAGGACTGTACAACGAACTCCAGAAAGACAAGATGGCGGAAGCCT
ACTCAGAAATCGGGATGAAGGGAGAGCGGAGGAGGGGAAAGGGTCACG
ACGGGCTGTACCAGGGACTGAGCACCGCCACTAAGGATACCTACGATGCC
TTGCATATGCAAGCACTCCCACCCCGG

SEQ ID NO: 174 is the amino acid sequence of the CD22 CAR LTG2220 (LP-
scFv18-CD8TM-41BB-CD3zeta):
MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAQEVEPHDALDIWGQGTMVTVSSGGGGSGGGGSGG
GGSDIQMTQSPSSVSASVGDKVTITCRASQDVSGWLAWYQQKPGLAPQLLIF
GASTLQGEVPSRFSGSGSGTDFTLTISSLQPEDFATYYCQQAKYFPYTFGQGT
KLEIKAATTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSC
RFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGL
YQGLSTATKDTYDALHMQALPPR SEQ ID NO: 175 is the amino acid sequence of the scFv18 (16P15) LCDR1:
QDVSGW SEQ ID NO: 176 is the amino acid sequence of the scFv18 (16P15) LCDR2:
GAS SEQ ID NO: 177 is the amino acid sequence of the scFv18 (16P15) LCDR3:
QQAKYFPYT SEQ ID NO: 178 is the amino acid sequence of the scFv18 (16P15) HCDR1:
GDSVSSNSAA SEQ ID NO: 179 is the amino acid sequence of the scFv18 (16P15) HCDR2:
TYYRSKWYN SEQ ID NO: 180 is the amino acid sequence of the scFv18 (16P15) HCDR3:
AQEVEPHDALDI SEQ ID NO: 181 nucleotide sequence of DNA CD8 transmembrane domain
ATTTGGGCCCCGCTGGCCGGCACTTGCGGCGTGCTCCTGCTGTCGCTGGTCATCA
CCCTTTACTGC SEQ ID NO: 182 amino acid sequence of CD8 transmembrane domain
IWAPLAGTCGVLLLSLVITLYC SEQ ID NO: 183 nucleotide sequence of DNA CD8 hinge domain
ACTACCACCCCTGCCCCTCGGCCGCCGACTCCGGCCCCAACCATCGCAAG
CCAACCCCTCTCCTTGCGCCCCGAAGCTTGCCGCCCGGCCGCGGGTGGAG
CCGTGCATACCCGGGGGCTGGACTTTGCCTGCGATATCTAC SEQ ID NO: 184 amino acid sequence of CD8 hinge domain
TTTPAPRPPTPAPTIASQPLSLRPEACRPAAGGAVHTRGLDFACDIY SEQ ID NO: 185 amino acid sequence of amino acid numbers 137 to 206 hinge and
transmembrane region of CD8.alpha. (NCBI RefSeq: NP.sub.--001759.3)
TTTPAPRPPTPAPTIASQPLSLRPEACRPAAGGAVHTRGLDFACDIYIWAPLAG
TCGVLLLSLVITLYC SEQ ID NO: 186 nucleotide sequence of DNA signaling domain of 4-1BB
AAGAGGGGCCGGAAGAAGCTGCTTTACATCTTCAAGCAGCCGTTCATGCG
GCCCGTGCAGACGACTCAGGAAGAGGACGGATGCTCGTGCAGATTCCCTG
AGGAGGAAGAGGGGGGATGCGAACTG
```

SEQ ID NO: 187 amino acid sequence of signaling domain of 4-1BB
KRGRKKLLYIFKQPFMRPVQTTQEEDGCSCRFPEEEEGGCEL SEQ ID NO: 188 nucleotide sequence of DNA signaling domain of CD3-zeta
CGCGTCAAGTTCTCACGGTCCGCCGACGCCCCCGCATATCAACAGGGCCA
GAATCAGCTCTACAACGAGCTGAACCTGGGAAGGAGAGAGGAGTACGAC
GTGCTGGACAAGCGACGCGGACGCGACCCGGAGATGGGGGGGAAACCAC
GGCGGAAAAACCCTCAGGAAGGACTGTACAACGAACTCCAGAAAGACAA
GATGGCGGAAGCCTACTCAGAAATCGGGATGAAGGGAGAGCGGAGGAGG
GGAAAGGGTCACGACGGGCTGTACCAGGGACTGAGCACCGCCACTAAGG
ATACCTACGATGCCTTGCATATGCAAGCACTCCCACCCCGG SEQ ID NO: 189 amino acid sequence of CD3zeta
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR SEQ ID NO: 190 nucleotide sequence of leader/signal peptide sequence (LP)
ATGCTGCTGCTGGTGACCAGCCTGCTGCTGTGCGAACTGCCGCATCCGGCGTTTC
TGCTGATTCCG SEQ ID NO: 191 amino acid sequence of leader/signal peptide sequence (LP)
MLLLVTSLLLCELPHPAFLLIP SEQ ID NO: 192 nucleotide sequence of ScFv CD19 (FMC63)
GACATTCAGATGACTCAGACCACCTCTTCCTTGTCCGCGTCACTGGGAGAC
AGAGTGACCATCTCGTGTCGCGCAAGCCAGGATATCTCCAAGTACCTGAA
CTGGTACCAACAGAAGCCCGACGGGACTGTGAAGCTGCTGATCTACCACA
CCTCACGCCTGCACAGCGGAGTGCCAAGCAGATTCTCCGGCTCCGGCTCG
GGAACCGATTACTCGCTTACCATTAGCAACCTCGAGCAGGAGGACATCGC
TACCTACTTCTGCCAGCAAGGAAATACCCTGCCCTACACCTTCGGCGGAG
GAACCAAATTGGAAATCACCGGCGGAGGAGGCTCCGGGGGAGGAGGTTC
CGGGGGCGGGGGTTCCGAAGTGAAGCTCCAGGAGTCCGGCCCCGGCCTG
GTGGCGCCGTCGCAATCACTCTCTGTGACCTGTACCGTGTCGGGAGTGTCC
CTGCCTGATTACGGCGTGAGCTGGATTCGGCAGCCGCCGCGGAAGGGCCT
GGAATGGCTGGGTGTCATCTGGGGATCCGAGACTACCTACTACAACTCGG
CCCTGAAGTCCGCCTGACTATCATCAAAGACAACTCGAAGTCCCAGGTC
TTTCTGAAGATGAACTCCCTGCAAACTGACGACACCGCCATCTATTACTGT
GCTAAGCACTACTACTACGGTGGAAGCTATGCTATGGACTACTGGGGCA
AGGCACTTCGGTGACTGTGTCAAGC SEQ ID NO: 193 amino acid sequence of ScFv CD19 (FMC63)
DIQMTQTTSSLSASLGDRVTISCRASQDISKYLNWYQQKPDGTVKLLIYHTSR
LHSGVPSRFSGSGSGTDYSLTISNLEQEDIATYFCQQGNTLPYTFGGGTKLEIT
GGGGSGGGGSGGGGSEVKLQESGPGLVAPSQSLSVTCTVSGVSLPDYGVSWI
RQPPRKGLEWLGVIWGSETTYYNSALKSRLTIIKDNSKSQVFLKMNSLQTDD
TAIYYCAKHYYYGGSYAMDYWGQGTSVTVSS SEQ ID NO: 194 1538 FMC63 CAR nucleotides (LP-FMC63-CD8TM-41BB-
CD3zeta)
ATGCTTCTCCTGGTCACCTCCCTGCTCCTCTGCGAACTGCCTCACCCTGCCT
TCCTTCTGATTCCGGACATTCAGATGACTCAGACCACCTCTTCCTTGTCCG
CGTCACTGGGAGACAGAGTGACCATCTCGTGTCGCGCAAGCCAGGATATC
TCCAAGTACCTGAACTGGTACCAACAGAAGCCCGACGGGACTGTGAAGCT
GCTGATCTACCACACCTCACGCCTGCACAGCGGAGTGCCAAGCAGATTCT
CCGGCTCCGGCTCGGGAACCGATTACTCGCTTACCATTAGCAACCTCGAG
CAGGAGGACATCGCTACCTACTTCTGCCAGCAAGGAAATACCCTGCCCTA
CACCTTCGGCGGAGGAACCAAATTGGAAATCACCGGCGGAGGAGGCTCC
GGGGGAGGAGGTTCCGGGGGCGGGGGTTCCGAAGTGAAGCTCCAGGAGT
CCGGCCCCGGCCTGGTGGCGCCGTCGCAATCACTCTCTGTGACCTGTACCG
TGTCGGGAGTGTCCCTGCCTGATTACGGCGTGAGCTGGATTCGGCAGCCG
CCGCGGAAGGGCCTGGAATGGCTGGGTGTCATCTGGGGATCCGAGACTAC
CTACTACAACTCGGCCCTGAAGTCCGCCTGACTATCATCAAAGACAACT
CGAAGTCCCAGGTCTTTCTGAAGATGAACTCCCTGCAAACTGACGACACC
GCCATCTATTACTGTGCTAAGCACTACTACTACGGTGGAAGCTATGCTATG
GACTACTGGGGCAAGGCACTTCGGTGACTGTGTCAAGCGCGGCCGCAAC
TACCACCCCTGCCCCTCGGCCGCCGACTCCGCCCCAACCATCGCAAGCC
AACCCCTCTCCTTGCGCCCCGAAGCTTGCCGCCCGGCCGCGGGTGGAGCC
GTGCATACCCGGGGGCTGGACTTTGCCTGCGATATCTACATTTGGGCCCCG
CTGGCCGGCACTTGCGGCGTGCTCCTGCTGTCGCTGGTCATCACCCTTTAC
TGCAAGAGGGGCCGGAAGAAGCTGCTTTACATCTTCAAGCAGCCGTTCAT
GCGGCCCGTGCAGACGACTCAGGAAGAGGACGGATGCTCGTGCAGATTCC
CTGAGGAGGAAGAGGGGGGATGCGAACTGCGCGTCAAGTTCTCACGGTC
CGCCGACGCCCCCGCATATCAACAGGGCCAGAATCAGCTCTACAACGAGC
TGAACCTGGGAAGGAGAGAGGAGTACGACGTGCTGGACAAGCGACGCGG
ACGCGACCCGGAGATGGGGGGGAAACCACGGCGGAAAAACCCTCAGGAA
GGACTGTACAACGAACTCCAGAAAGACAAGATGGCGGAAGCCTACTCAG
AAATCGGGATGAAGGGAGAGCGGAGGAGGGGAAAGGGTCACGACGGGC

TGTACCAGGGACTGAGCACCGCCACTAAGGATACCTACGATGCCTTGCAT
ATGCAAGCACTCCCACCCCGG

SEQ ID NO: 195 is the amino acid sequence of CD19-specific CAR LTG1538 (scFv,
FMC63) protein (LP-FMC63-CD8TM-41BB-CD3zeta)
MLLLVTSLLLCELPHPAFLLIPDIQMTQTTSSLSASLGDRVTISCRASQDISKYL
NVVYQQKPDGTVKLLIYHTSRLHSGVPSRFSGSGSGTDYSLTISNLEQEDIATY
FCQQGNTLPYTFGGGTKLEITGGGSGGGGSGGGGSEVKLQESGPGLVAPSQ
SLSVTCTVSGVSLPDYGVSWIRQPPRKGLEWLGVIWGSETTYYNSALKSRLTI
IKDNSKSQVFLKMNSLQTDDTAIYYCAKHYYYGGSYAMDYWGQGTSVTVSS
AAATTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEE
EEGGCELRVKFSRSADAPAYQQGQNQLYNELNLGRREEYDVLDKRRGRDPE
MGGKPRRKNPQEGLYNELQKDKMAEAYSEIGMKGERRRGKGHDGLYQGLS
TATKDTYDALHMQALPPR SEQ ID NO: 196 is the nucleic acid sequence of CD22-specifc CAR LTG2200
(scFv, m971 CAR nucleotides (LP-m971-CD8TM-41BB-CD3zeta):
ATGCTTCTTTTGGTGACTTCCCTTTTGCTGTGCGAGTTGCCACACCCCGCCT
TCCTGCTTATTCCCCAGGTACAGCTCCAGCAGAGTGGCCCAGGGCTCGTG
AAGCCAAGCCAGACGCTGTCCCTGACTTGTGCAATTTCAGGGGATTCAGT
TTCATCAAATAGCGCGGCGTGGAATTGGATTCGACAATCTCCTTCCCGAG
GGTTGGAATGGCTTGGACGAACATATTACAGATCCAAATGGTATAACGAC
TATGCGGTATCAGTAAAGTCAAGAATAACCATTAACCCCGACACAAGCAA
GAACCAATTCTCTTTGCAGCTTAACTCTGTCACGCCAGAAGACACGGCAG
TCTATTATTGCGCTCGCGAGGTAACGGGTGACCTGGAAGACGCTTTTGAC
ATTTGGGGGCAGGGTACGATGGTGACAGTCAGTTCAGGGGGCGGTGGGA
GTGGGGGAGGGGGTAGCGGGGGGGGAGGGTCAGACATTCAGATGACCCA
GTCCCCTTCATCCTTGTCTGCCTCCGTCGGTGACAGGGTGACAATAACATG
CAGAGCAAGCCAAACAATCTGGAGCTATCTCAACTGGTACCAGCAGCGAC
CAGGAAAAGCGCCAAACCTGCTGATTTACGCTGCTTCCTCCCTCCAATCA
GGCGTGCCTAGTAGATTTAGCGGTAGGGGCTCCGGCACCGATTTTACGCT
CACTATAAGCTCTCTTCAAGCAGAAGATTTTGCGACTTATTACTGCCAGCA
GTCCTATAGTATACCTCAGACTTTCGGACAGGGTACCAAGTTGGAGATTA
AGGCGGCCGCAACTACCACCCCTGCCCCTCGGCCGCCGACTCCGGCCCCA
ACCATCGCAAGCCAACCCCTCTCCTTGCGCCCCGAAGCTTGCCGCCCGGC
CGCGGGTGGAGCCGTGCATACCCGGGGCTGGACTTTGCCTGCGATATCT
ACATTTGGGCCCCGCTGGCCGGCACTTGCGGCGTGCTCCTGCTGTCGCTGG
TCATCACCCTTTACTGCAAGAGGGGCCGGAAGAAGCTGCTTTACATCTTC
AAGCAGCCGTTCATGCGGCCCGTGCAGACGACTCAGGAAGAGGACGGAT
GCTCGTGCAGATTCCCTGAGGAGGAAGAGGGGGGATGCGAACTGCGCGT
CAAGTTCTCACGGTCCGCCGACGCCCCCGCATATCAACAGGGCCAGAATC
AGCTCTACAACGAGCTGAACCTGGGAAGGAGAGAGGAGTACGACGTGCT
GGACAAGCGACGCGGACGCGACCCGGAGATGGGGGGGAAACCACGGCGG
AAAAACCCTCAGGAAGGACTGTACAACGAACTCCAGAAAGACAAGATGG
CGGAAGCCTACTCAGAAATCGGGATGAAGGGAGAGCGGAGGAGGGGAAA
GGGTCACGACGGGCTGTACCAGGGACTGAGCACCGCCACTAAGGATACCT
ACGATGCCTTGCATATGCAAGCACTCCCACCCCGG SEQ ID NO: 197 is the amino acid sequence of LTG2200 CD22-cpecific CAR (LP-
m971 scFv-CDTN-41BB-CD3zeta):
MLLLVTSLLLCELPHPAFLLIPQVQLQQSGPGLVKPSQTLSLTCAISGDSVSSN
SAAWNWIRQSPSRGLEWLGRTYYRSKWYNDYAVSVKSRITINPDTSKNQFSL
QLNSVTPEDTAVYYCAREVTGDLEDAFDIWGQGTMVTVSSGGGGSGGGGSG
GGGSDIQMTQSPSSLSASVGDRVTITCRASQTIWSYLNWYQQRPGKAPNLLIY
AASSLQSGVPSRFSGRGSGTDFTLTISSLQAEDFATYYCQQSYSIPQTFGQGTK
LEIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGFIDGLYQ
GLSTATKDTYDALHMQALPPR SEQ ID NO: 198 is the nucleotide sequence of mesothelin-reactive scFv binding
domain (LTG1904):
GAGGTCCAGCTGGTACAGTCTGGGGGAGGCTTGGTACAGCCTGGGGGGTC
CCTGAGACTCTCCTGTGCAGCCTCTGGATTCACCTTTGATGATTATGCCAT
GCACTGGGTCCGGCAAGCTCCAGGGAAGGGCCTGGAGTGGGTCTCAGGTA
TTAGTTGGAATAGTGGTAGCATAGGCTATGCGGACTCTGTGAAGGGCCGA
TTCACCATCTCCAGAGACAACGCCAAGAACTCCCTGTATCTGCAAATGAA
CAGTCTGAGAGCTGAGGACACGGCCTTGTATTACTGTGCAAAAGATTTAT
CGTCAGTGGCTGGACCCTTTAACTACTGGGGCCAGGGCACCCTGGTCACC
GTCTCCTCAGGAGGTGGCGGGTCTGGTGGAGGCGGTAGCGGCGGTGGCGG
ATCCTCTTCTGAGCTGACTCAGGACCCTGCTGTGTCTGTGGCCTTGGGACA
GACAGTCAGGATCACATGCCAAGGAGACAGCCTCAGAAGCTATTATGCAA
GCTGGTACCAGCAGAAGCCAGGACAGGCCCCTGTACTTGTCATCTATGGT
AAAAACAACCGGCCCTCAGGGATCCCAGACCGATTCTCTGGCTCCAGCTC
AGGAAACACAGCTTCCTTGACCATCACTGGGGCTCAGGCGGAGGATGAGG
CTGACTATTACTGTAACTCCCGGGACAGCAGTGGTAACCATCTGGTATTCG
GCGGAGGCACCCAGCTGACCGTCCTCGGT SEQ ID NO: 199 is the amino acid sequence of mesothelin-reactive scFv binding
domain (LTG1904):
EVQLVQSGGGLVQPGGSLRLSCAASGFTFDDYAMHWVRQAPGKGLEWVSGI
SWNSGSIGYADSVKGRFTISRDNAKNSLYLQMNSLRAEDTALYYCAKDLSSV
AGPFNYWGQGTLVTVSSGGGGSGGGGSGGGGSSSELTQDPAVSVALGQTVR
ITCQGDSLRSYYASWYQQKPGQAPVLVIYGKNNRPSGIPDRFSGSSSGNTASL
TITGAQAEDEADYYCNSRDSSGNHLVFGGGTQLTVLG SEQ ID NO: 200 is the nucleotide sequence of the mesothelin specific CAR
LTG1904 (LP-LTG1904-CD8TM-41BB-CD3zeta):
ATGCTGCTGCTGGTGACCAGCCTGCTGCTGTGCGAACTGCCGCATCCGGC
GTTTCTGCTGATTCCGGAGGTCCAGCTGGTACAGTCTGGGGGAGGCTTGG
TACAGCCTGGGGGGTCCCTGAGACTCTCCTGTGCAGCCTCTGGATTCACCT
TTGATGATTATGCCATGCACTGGGTCCGGCAAGCTCCAGGGAAGGGCCTG
GAGTGGGTCTCAGGTATTAGTTGGAATAGTGGTAGCATAGGCTATGCGGA
CTCTGTGAAGGGCCGATTCACCATCTCCAGAGACAACGCCAAGAACTCCC
TGTATCTGCAAATGAACAGTCTGAGAGCTGAGGACACGGCCTTGTATTAC
TGTGCAAAAGATTTATCGTCAGTGGCTGGACCCTTTAACTACTGGGGCCA
GGGCACCCTGGTCACCGTCTCCTCAGGAGGTGGCGGGTCTGGTGGAGGCG
GTAGCGGCGGTGGCGGATCCTCTTCTGAGCTGACTCAGGACCCTGCTGTG
TCTGTGGCCTTGGGACAGACAGTCAGGATCACATGCCAAGGAGACAGCCT
CAGAAGCTATTATGCAAGCTGGTACCAGCAGAAGCCAGGACAGGCCCCTG
TACTTGTCATCTATGGTAAAAACAACCGGCCCTCAGGGATCCCAGACCGA
TTCTCTGGCTCCAGCTCAGGAAACACAGCTTCCTTGACCATCACTGGGGCT
CAGGCGGAGGATGAGGCTGACTATTACTGTAACTCCCGGGACAGCAGTGG
TAACCATCTGGTATTCGGCGGAGGCACCCAGCTGACCGTCCTCGGTGCGG
CCGCAACTACCACCCCTGCCCCTCGGCCGCCGACTCCGGCCCCAACCATC
GCAAGCCAACCCCTCTCCTTGCGCCCCGAAGCTTGCCGCCCGGCCGCGGG
TGGAGCCGTGCATACCCGGGGCTGGACTTTGCCTGCGATATCTACATTTG
GGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGC
AGATTCCCTGAGGAGGAAGAGGGGGGATGCGAACTGCGCGTCAAGTTCTC
ACGGTCCGCCGACGCCCCCGCATATCAACGGGCCAGAATCAGCTCTACA
ACGAGCTGAACCTGGGAAGGAGAGAGGAGTACGACGTGCTGGACAAGCG
ACGCGGACGCGACCCGGAGATGGGGGGAAACCACGGCGGAAAAACCCT
CAGGAAGGACTGTACAACGAACTCCAGAAAGACAAGATGGCGGAAGCCT
ACTCAGAAATCGGGATGAAGGGAGAGCGGAGGAGGGGAAAGGGTCACG
ACGGGCTGTACCAGGGACTGAGCACCGCCACTAAGGATACCTACGATGCC
TTGCATATGCAAGCACTCCCACCCCGG SEQ ID NO: 201 amino acid sequence of the CAR LTG1904 (LP-LTG1904-CD8
TM-41BB-CD3zeta):
MLLLVTSLLLCELPHPAFLLIPEVQLVQSGGGLVQPGGSLRLSCAASGFTFDD
YAMHWVRQAPGKGLEWVSGISWNSGSIGYADSVKGRFTISRDNAKNSLYLQ
MNSLRAEDTALYYCAKDLSSVAGPFNYWGQGTLVTVSSGGGGSGGGGSGG
GGSSSELTQDPAVSVALGQTVRITCQGDSLRSYYASWYQQKPGQAPVLVIYG
KNNRPSGIPDRFSGSSSGNTASLTITGAQAEDEADYYCNSRDSSGNHLVFGGG
TQLTVLGAAATTTPAPRPPTPAPTIASQPLSLRPEACRPAAGGAVHTRGLDFA
CDIYIWAPLAGTCGVLLLSLVITLYCKRGRKKLLYIFKQPFMRPVQTTQEEDG
CSCRFPEEEEGGCELRVKFSRSADAPAYQQGQNQLYNELNLGRREEYDVLDK
RRGRDPEMGGKPRRKNPQEGLYNELQKDKMAEAYSEIGMKGERRRGKGHD
GLYQGLSTATKDTYDALHMQALPPR SEQ ID NO: 202 is the nucleotide sequence of CD33-reactive single chain binding
domain VH-4 (LTG1906):
GAGGTGCAGCTGGTGGAGTCTGGGGGAGGCTTGGTACAGCCTGGAGGGTC
CCTGAGACTCTCCTGTGCAGCCTCTGGATTCACCTTCAGTAGCTATGGCAT
GAGCTGGGTCCGCCAGGCTCCAAGACAAGGGCTTGAGTGGGTGGCCAAC
ATAAAGCAAGATGGAAGTGAGAAATACTATGCGGACTCAGTGAAGGGCC
GATTCACCATCTCCAGAGACAATTCCAAGAACACGCTGTATCTGCAAATG
AACAGCCTGAGAGCCGAGGACACAGCCACGTATTACTGTGCGAAAGAAA
ATGTGGACTGGGGCCAGGGCACCCTGGTCACCGTCTCCTCA SEQ ID NO: 203 is the amino acid sequence of CD33-reactive single chain binding
domain VH-4 (LTG1906):
EVQLVESGGGLVQPGGSLRLSCAASGFTFSSYGMSWVRQAPRQGLEWVANI
KQDGSEKYYADSVKGRFTISRDNSKNTLYLQMNSLRAEDTATYYCAKENVD
WGQGTLVTVSS SEQ ID NO: 204 is the nucleotide sequence of the CAR LTG1906 (LP-VH4-CD8
TM-41BB-CD3zeta):
ATGCTGCTGCTGGTGACCAGCCTGCTGCTGTGCGAACTGCCGCATCCGGC
GTTTCTGCTGATTCCGGAGGTGCAGCTGGTGGAGTCTGGGGGAGGCTTGG
TACAGCCTGGAGGGTCCCTGAGACTCTCCTGTGCAGCCTCTGGATTCACCT
TCAGTAGCTATGGCATGAGCTGGGTCCGCCAGGCTCCAAGACAAGGGCTT
GAGTGGGTGGCCAACATAAAGCAAGATGGAAGTGAGAAATACTATGCGG
ACTCAGTGAAGGGCCGATTCACCATCTCCAGAGACAATTCCAAGAACACG
CTGTATCTGCAAATGAACAGCCTGAGAGCCGAGGACACAGCCACGTATTA CTGTGCGAAAGAAAATGTGGACTGGGGCCAGGGCACCCTGGTCACCGTCT
CCTCAGCGGCCGCAACTACCACCCCTGCCCCTCGGCCGCCGACTCCGGCC
CCAACCATCGCAAGCCAACCCCTCTCCTTGCGCCCCGAAGCTTGCCGCCC
GGCCGCGGGTGGAGCCGTGCATACCCGGGGGCTGGACTTTGCCTGCGATA
TCTACATTTGGGCCCCGCTGGCCGGCACTTGCGGCGTGCTCCTGCTGTCGC
TGGTCATCACCCTTTACTGCAAGAGGGGCCGGAAGAAGCTGCTTTACATC
TTCAAGCAGCCGTTCATGCGGCCCGTGCAGACGACTCAGGAAGAGGACGG
ATGCTCGTGCAGATTCCCTGAGGAGGAAGAGGGGGGATGCGAACTGCGC
GTCAAGTTCTCACGGTCCGCCGACGCCCCCGCATATCAACAGGGCCAGAA
TCAGCTCTACAACGAGCTGAACCTGGGAAGGAGAGAGGAGTACGACGTG
CTGGACAAGCGACGCGGACGCGACCCGGAGATGGGGGGGAAACCACGGC
GGAAAAACCCTCAGGAAGGACTGTACAACGAACTCCAGAAAGACAAGAT
GGCGGAAGCCTACTCAGAAATCGGGATGAAGGGAGAGCGGAGGAGGGGA
AAGGGTCACGACGGGCTGTACCAGGGACTGAGCACCGCCACTAAGGATA
CCTACGATGCCTTGCATATGCAAGCACTCCCACCCCGG SEQ ID NO: 205 is the amino acid sequence of the CAR LTG1906 (LP-VH4-CD8
TM-41BB-CD3zeta):
MLLLVTSLLLCELPHPAFLLIPEVQLVESGGGLVQPGGSLRLSCAASGFTFSSY
GMSWVRQAPRQGLEWVANIKQDGSEKYYADSVKGRFTISRDNSKNTLYLQM
NSLRAEDTATYYCAKENVDWQGTLVTVSSAAATTTPAPRPPTPAPTIASQPL
SLRPEACRPAAGGAVHTRGLDFACDIYIWAPLAGTCGVLLLSLVITLYCKRGR
KKLLYIFKQPFMRPVQTTQEEDGCSCRFPEEEEGGCELRVKFSRSADAPAYQQ
GQNQLYNELNLGRREEYDVLDKRRGRDPEMGGKPRRKNPQEGLYNELQKDK
MAEAYSEIGMKGERRRGKGFIDGLYQGLSTATKDTYDALHMQALPPR

---

What is claimed is:

1. A method of treating a subject with a hematological cancer, the method comprising administering to the subject a pharmaceutical composition comprising an anti-tumor effective amount of a population of T cells, wherein each of the T cells comprise an expression control sequence operably linked to a nucleic acid sequence that encodes a chimeric antigen receptor (CAR), wherein the CAR comprises at least one extracellular antigen binding domain comprising a CD22 antigen binding domain comprising the amino acid sequence of SEQ ID NO: 2, 12, 22, 32, 42, 52, 62, 72, 82, 92, 102, 112, 122, 132, 142, 152, 162, or 172, at least one linker or spacer domain, at least one transmembrane domain, at least one intracellular signaling domain, wherein the T cells are T cells of the subject having cancer wherein the expressed CAR targets the hematological cancer.

2. The method of claim 1, wherein the at least one transmembrane domain comprises a transmembrane domain of the alpha, the beta or the zeta chain of a protein selected from a T-cell receptor, a CD8, a CD28, a CD3 epsilon, a CD45, a CD4, a CD5, a CD8, a CD9, a CD 16, a CD22, a CD33, a CD37, a CD64, a CD80, a CD86, a CD134, a CD137 or a CD154.

3. The method of 1, wherein the at least one CD22 antigen binding domain, the at least one intracellular signaling domain, or both are connected to the transmembrane domain by a linker or a spacer domain.

4. The method of claim 1, wherein the at least one linker or spacer domain is obtained derived from the extracellular domain of CD8 or CD28, and is linked to the at least one transmembrane domain.

5. The method of claim 1, wherein the encoded extracellular CD22 antigen binding domain is preceded by a leader nucleotide sequence encoding a leader peptide.

6. The method of claim 1, wherein the at least one intracellular signaling domain further comprises a CD3 zeta intracellular domain.

7. The method of claim 1, wherein the nucleic acid sequence encoding the extracellular CD22 antigen binding domain comprises a nucleic sequence comprising the nucleotide sequence of SEQ ID NO: 1, 11, 21, 31, 41, 51, 61, 71, 81, 91, 101, 111, 121, 131, 141, 151, 161, or 171.

8. The method of claim 1, wherein the at least one intracellular signaling domain comprises a costimulatory domain, a primary signaling domain, or any combination thereof.

9. The method of claim 8, wherein the at least one costimulatory domain comprises the signaling domain of 0X40, CD70, CD27, CD28, CD5, ICAM-1, LFA-1 (CD11a/CD18), ICOS (CD278), DAP10, DAP 12, or 4-1BB (CD 137).

10. The method of claim 1, wherein the hematological cancer is leukemia, lymphoma, or multiple myeloma.

11. The method of claim 10, wherein the leukemia is chronic lymphocytic leukemia (CLL), acute lymphocytic leukemia (ALL), or chronic myelogenous leukemia (CML).

12. The method of claim 10, wherein the lymphoma is mantle cell lymphoma, non-Hodgkin's lymphoma (NHL) or Hodgkin's lymphoma.

* * * * *